United States Patent
Dalmas et al.

(10) Patent No.: US 12,240,885 B2
(45) Date of Patent: Mar. 4, 2025

(54) PEPTIDE-MHC COMPACTS

(71) Applicant: ADOC SSF, LLC, South San Francisco, CA (US)

(72) Inventors: Olivier Dalmas, San Carlos, CA (US); Zheng Pan, Freemont, CA (US); Michael Bethune, Castro Valley, CA (US); Songming Peng, San Mateo, CA (US)

(73) Assignee: ADOC SSF, LLC, South San Francisco, CA (US)

( * ) Notice: Subject to any disclaimer, the term of this patent is extended or adjusted under 35 U.S.C. 154(b) by 0 days.

(21) Appl. No.: 16/951,925

(22) Filed: Nov. 18, 2020

(65) Prior Publication Data

US 2021/0070834 A1    Mar. 11, 2021

Related U.S. Application Data

(60) Division of application No. 16/679,025, filed on Nov. 8, 2019, now Pat. No. 10,875,905, which is a continuation of application No. PCT/US2019/025415, filed on Apr. 2, 2019.

(60) Provisional application No. 62/651,639, filed on Apr. 2, 2018.

(51) Int. Cl.
| | |
|---|---|
| C07K 14/74 | (2006.01) |
| C07K 14/61 | (2006.01) |
| C12N 15/10 | (2006.01) |
| G01N 33/569 | (2006.01) |

(52) U.S. Cl.
CPC ........ *C07K 14/70539* (2013.01); *C07K 14/61* (2013.01); *C12N 15/1068* (2013.01); *G01N 33/56972* (2013.01); *C07K 2319/02* (2013.01); *C07K 2319/20* (2013.01); *C07K 2319/21* (2013.01); *C07K 2319/50* (2013.01)

(58) Field of Classification Search
CPC .............. C07K 14/61; C07K 14/70539; C07K 2319/02; C07K 2319/20; C07K 2319/21; C07K 2319/50; C12N 15/1068; G01N 33/56972

See application file for complete search history.

(56) References Cited

U.S. PATENT DOCUMENTS

| | | | |
|---|---|---|---|
| 7,709,224 B2 | 5/2010 | Fang et al. | |
| 8,895,020 B2 | 11/2014 | Hansen et al. | |
| 8,992,937 B2 | 3/2015 | Hansen et al. | |

(Continued)

FOREIGN PATENT DOCUMENTS

| | | |
|---|---|---|
| AU | 2007 203 607 A1 | 8/2007 |
| WO | WO 2005/099361 A2 | 10/2005 |

(Continued)

OTHER PUBLICATIONS

Shen et al. (Scientific Reports, 2017, 7:16400) (Year: 2017).*

(Continued)

*Primary Examiner* — Jeremy C Flinders
(74) *Attorney, Agent, or Firm* — Baker Botts L.L.P.

(57) ABSTRACT

Disclosed herein are antigenic peptide-MHC molecules, termed comPACTs, and methods of producing such molecules. Also disclosed herein are methods of producing libraries of comPACT polynucleotides and polypeptides, and their exemplary use in capturing cancer neoepitope-reactive T cells.

17 Claims, 31 Drawing Sheets

Specification includes a Sequence Listing.

(56) References Cited

U.S. PATENT DOCUMENTS

| | | |
|---|---|---|
| 9,540,657 B2 | 1/2017 | Yu et al. |
| 10,584,357 B2 | 3/2020 | Jacoby et al. |
| 2004/0115775 A1 | 6/2004 | Chitlaru et al. |
| 2009/0117153 A1 | 5/2009 | Hansen et al. |
| 2015/0197771 A1 | 7/2015 | Bethune et al. |
| 2017/0003288 A1* | 1/2017 | Heath ............... G01N 33/6878 |
| 2018/0289741 A1 | 10/2018 | Nicholson et al. |
| 2019/0292263 A1* | 9/2019 | Murphy ............ C07K 16/2833 |
| 2020/0010527 A1 | 1/2020 | Gee et al. |

FOREIGN PATENT DOCUMENTS

| | | |
|---|---|---|
| WO | WO 2008/041231 A2 | 4/2008 |
| WO | WO 2014/153470 A2 | 9/2014 |
| WO | WO 2015/153969 A1 | 10/2015 |
| WO | WO 2016/069282 A1 | 5/2016 |
| WO | WO 2016/071343 A1 | 5/2016 |
| WO | WO 2017/062451 A1 | 4/2017 |
| WO | WO 2017/156484 A1 | 9/2017 |
| WO | WO 2018/165475 A1 | 9/2018 |
| WO | WO 2018/175585 A2 | 9/2018 |
| WO | WO 2019/084552 A1 | 5/2019 |

OTHER PUBLICATIONS

Truscott et al. (J. Immunol., 2007, 178(10):6280-6289) (Year: 2007).*
Bethune et al. (BioTechniques, Mar. 2017, 62(3): 123-130) (Year: 2017).*
Cunningham et al. (Biochemistry, 1973, 12(24):4811-4822) (Year: 1973).*
Altman et al. (Science, 1996, 274:94-96) (Year: 1996).*
Xu et al. (J. Microbiol. Biotechnol., 2016, 26(12), 2184-2191) (Year: 2016).*
Invitrogen Dynabeads® MyOneTM Streptavidin T1 product sheet (Year: 2011).*
U.S. Appl. No. 16/552,714 (U.S. Pat. No. 10,584,357), filed Aug. 27, 2019 (Mar. 10, 2020).
U.S. Appl. No. 16/552,786 (U.S. Pat. No. 10,550,406), filed Aug. 27, 2019 (Feb. 4, 2020).
U.S. Appl. No. 16/679,025 (US 2020/0062819), filed Nov. 8, 2019 (Feb. 27, 2020).
U.S. Appl. No. 16/782,450 (U.S. Pat. No. 10,711,283), filed Feb. 5, 2020 (Jul. 14, 2020).
U.S. Appl. No. 16/782,815 (U.S. Pat. No. 10,676,758), filed Feb. 5, 2020 (Jun. 9, 2020).
U.S. Appl. No. 16/893,166 (US 2020/0299730), filed Jun. 4, 2020 (Sep. 24, 2020).
U.S. Appl. No. 16/552,714, filed Feb. 5, 2020 Issue Fee Payment.
U.S. Appl. No. 16/552,714, filed Jan. 31, 2020 Notice of Allowance.
U.S. Appl. No. 16/552,714, filed Nov. 27, 2019 Reponse to Non-Final Office Action.
U.S. Appl. No. 16/552,714, filed Nov. 21, 2019 Applicant Initiated Interview Summary.
U.S. Appl. No. 16/552,714, filed Oct. 23, 2019 Non-Final Office Action.
U.S. Appl. No. 16/552,786, filed Dec. 20, 2019 Issue Fee Payment.
U.S. Appl. No. 16/552,786, filed Dec. 18, 2019 Notice of Allowance.
U.S. Appl. No. 16/552,786, filed Nov. 27, 2019 Response to Non-Final Office Action.
U.S. Appl. No. 16/552,786, filed Nov. 21, 2019 Applicant Initiated Interview Summary.
U.S. Appl. No. 16/552,786, filed Pct. 23, 2019 Non-Final Office Action.
U.S. Appl. No. 16/679,025, filed Nov. 12, 2020 Notice of Allowance.
U.S. Appl. No. 16/679,025, filed Aug. 14, 2020 Applicant Initiated Interview Summary.
U.S. Appl. No. 16/679,025, filed Aug. 12, 2020 Response to Non-Final Office Action.
U.S. Appl. No. 16/679,025, filed Jun. 15, 2020 Non-Final Office Action.
U.S. Appl. No. 16/679,025, filed Mar. 10, 2020 Response to Restriction Requirement.
U.S. Appl. No. 16/679,025, filed Feb. 20, 2020 Restriction Requirement.
U.S. Appl. No. 16/782,450, filed Jun. 4, 2020 Issue Fee Payment.
U.S. Appl. No. 16/782,450, filed May 6, 2020 Notice of Allowance.
U.S. Appl. No. 16/782,450, filed Apr. 27, 2020 Response to Non-Final Office Action.
U.S. Appl. No. 16/782,450, filed Nov. 21, 2019 Applicant Initiated Interview Summary.
U.S. Appl. No. 16/782,450, filed Apr. 21, 2020 Non-Final Office Action.
U.S. Appl. No. 16/893,166, filed Sep. 28, 2020 Non-Final Office Action.
U.S. Appl. No. 16/782,815, filed Apr. 27, 2020 Issue Fee Payment.
U.S. Appl. No. 16/782,815, filed Apr. 22, 2020 Notice of Allowance.
Arnau et al., "Current strategies for the use of affinity tags and tag removal for the purification of recombinant proteins," Protein Expression and Purification, 48:1-13 (2006).
Barsov et al., "Transduction of SIV-Specific TCR Genes into Rhesus Macaque CD8+ T Cells Conveys the Ability to Suppress SIV Replication," PLoS ONE, 6(8):e23703 (2011).
Bethune et al., "Preparation of Peptide-MHC and T-Cell Receptor Dextramers by Biotinylated Dextran Doping," BioTechniques 62:123-130 (2017).
Birnbaum et al., "Deconstructing the Peptide-MHC Specificity of T Cell Recognition," Cell 157:1073-1087 (2014).
Broker et al., "pUC12-STOP: An expression vector with portable translation stop signals," Appl. Microbiol. Biotechnol, 23:294-296 (1986).
Cebrian et al., "Neuronal MHC-I Expression and Its Implications in Synaptic Function, Axonal Regeneration and Parkinson's and Other Brain Diseases," Frontiers in Neuroanatomy 8(114):1-9 (2014).
Chung et al., "Functional three-domain single-chain T-cell receptors," Proc. Natl. Acad. Sci., 91:12654-12658 (1994).
Cohen et al., "Isolation of Neoantigen-Specific T Cells from Tumor and Peripheral Lymphocytes," The Journal of Clinical Investigation, 2015. 125(10): 3981-3991.
Foley et al., "Hcv T Cell Receptor Chain Modifications to Enhance Expression, Pairing, and Antigen Recognition in T Cells for Adoptive Transfer," Molecular Therapy—Oncolytics, 5:105-115 (2017).
International Search Report mailed Jul. 29, 2019 in International Application No. PCT/US19/25415.
Kitz, "Generation and analysis of T cell receptor transgenic rats to model CNS autoimmunity," PhD Dissertation 2013. Georg-August University School of Science (GAUSS) Gottingen, Germany. (125 pages).
Knipping et al., "Genome-wide Specificity of Highly Efficient TALENs and CRISPR/Cas9 for T Cell Receptor Modification," Molecular Therapy—Methods and Clinical Development, 4:213-224 (2017).
Li et al., "The Implication and Significance of Beta 2 Microglobulin: A Conservative Multifunctional Regulator," Chinese Medical Journal 129(4):448-455 (2016).
Luke (Feb. 17, 2012). Translating 2A Research into Practice, Innovations in Biotechnology, Eddy C. Agbo, IntechOpen, DOI: 10.5772/30091. p. 161-186. Available from: https://www.intechopen.com/books/innovations-in-biotechnology/translating-2a-research-into-practice.
Ohta et al., "Primordial Linkage of β2-Microglobulin to the MHC," J Immunol. 186:3563-3571 (2011).
Okamoto et al., "A Promising Vector for TCR Gene Therapy: Differential Effect of siRNA, 2A Peptide, and Disulfide Bond on the Introduced TCR Expression," Molecular Therapy—Nucleic Acids, 1:e63 (2012).
Schober et al., "Orthotopic replacement of T-cell receptor α- and β-chains with preservation of near-physiological T-cell function," Nature Biomedical Engineering, 14 pages (2019).

(56) References Cited

OTHER PUBLICATIONS

Szymczak-Workman et al. Design and Construction of 2A Peptide-linked Multicistronic Vectors. Cold Spring Harbor Protoc., 2012 Doi:10,1101/dpb.ip067876. pp. 199-204.
Extended European Search report dated Dec. 9, 2021 in Application No. EP 19782293.
Greten, et al., "Peptide-β2-microglobulin-MHC fusion molecules bind antigen-specific T cells and can be used for multivalent MHC-Ig complexes", Journal of Immunological Methods, 271:125-135 (2002).
Singapore Patent Application No. 11202009761Y, Search Report and Written Opinion mailed May 11, 2022.

\* cited by examiner

Dummy insert

Template vector   STOP   XhoI   -1STOP   -2STOP   2xSTOP                    Template vector
...GGAGGGC|TCAGACTCATGACTCGAGATAAAATGTGAATAATGA|GGATGCGGAG|GATCCGGGGG...
...CCTCCCGAGT|CGAGTCGAGCTCTATTTTACACTTATTACT|CCTACGCCTCCTAG|GCCGCC...

⬇

Neoepitope

Precut vector
...GGAGGGC                                                                                                                    Precut vector
                TCAGCATACCTGTACCACCGGGTGAGCGTGATCGGATGCGGAG                      GATCCGGGGG...
                CGTATGGACATGGTGGCCCACTGCACTAGCCTACGCCTCCTAG                      GCCGCC...
...CCTCCCGAGT

FIG. 3

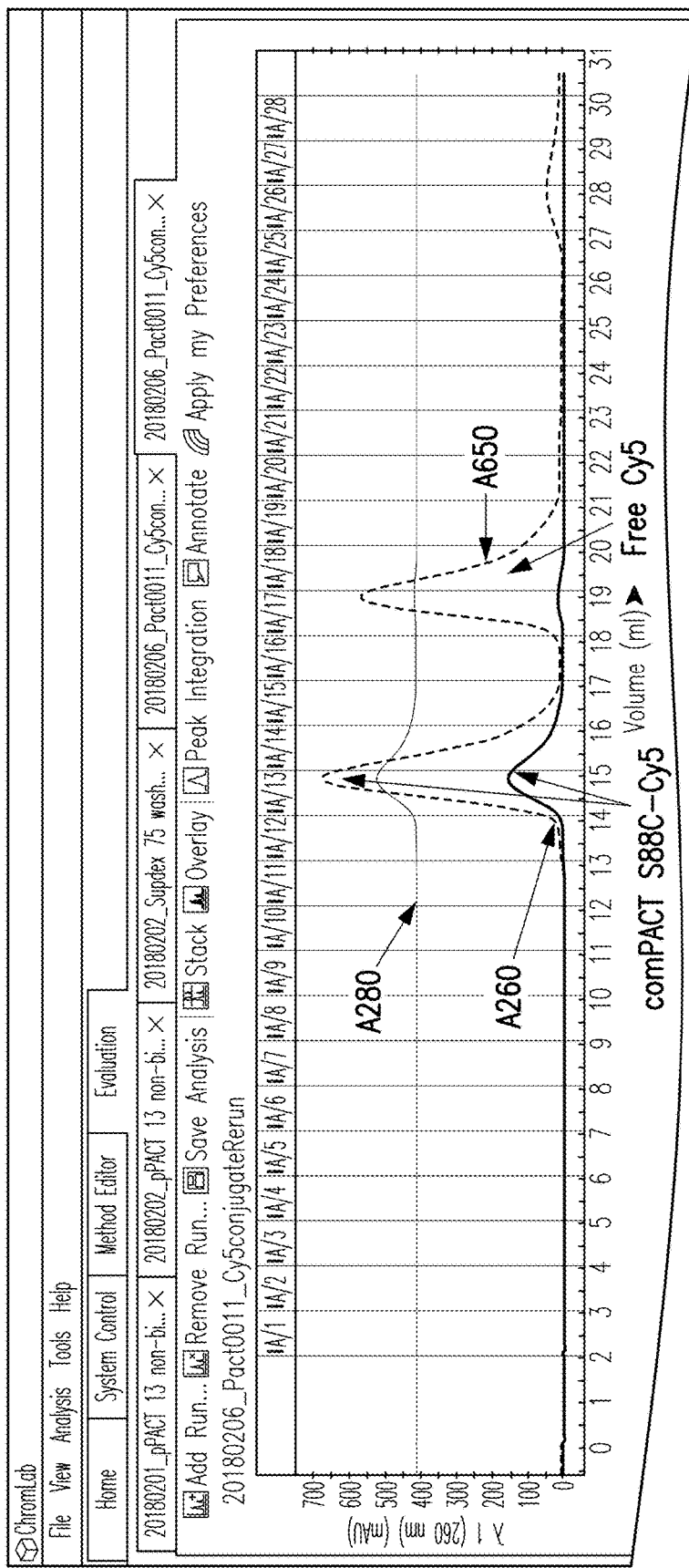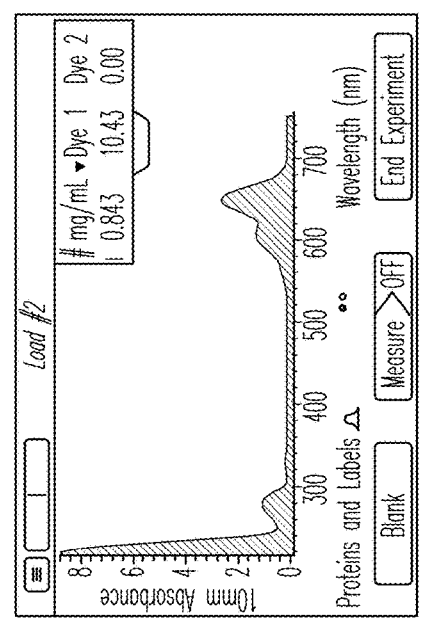
FIG. 21

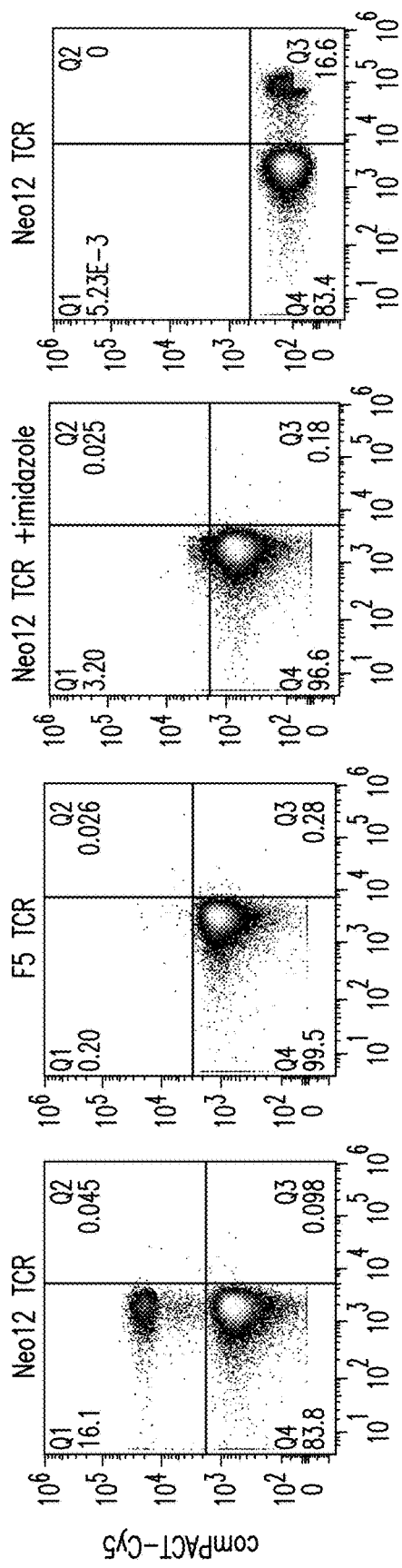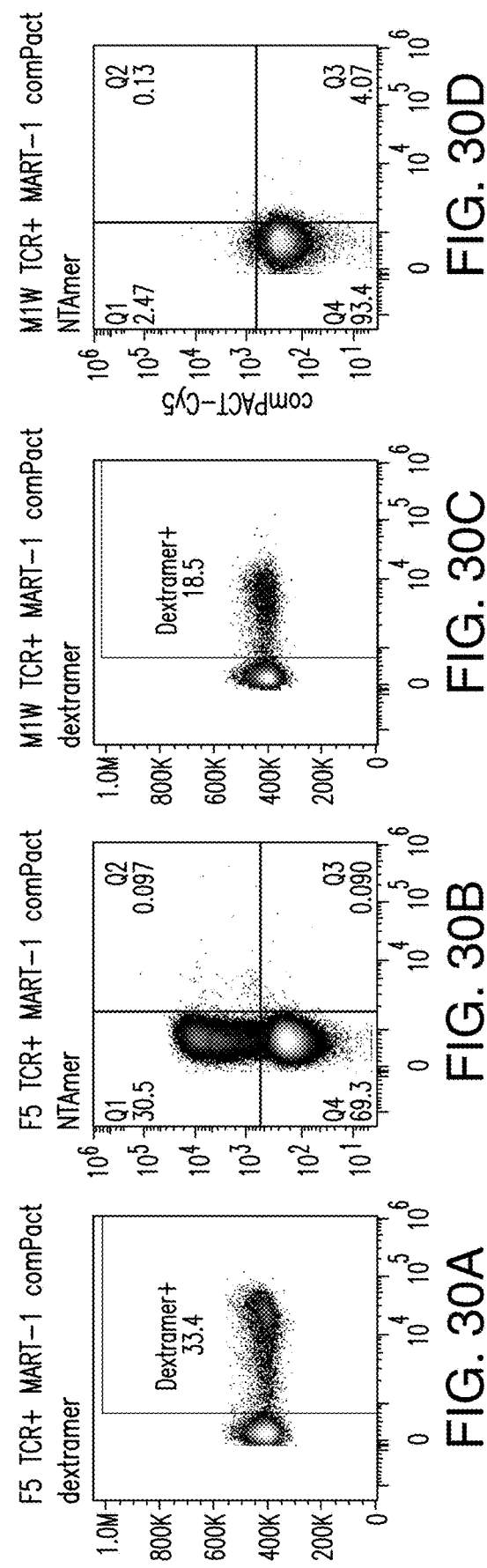

PEPTIDE-MHC COMPACTS

CROSS REFERENCE TO RELATED APPLICATIONS

This application is a Divisional of U.S. patent application Ser. No. 16/679,025, filed on Nov. 8, 2019, now allowed, which is a Continuation of International Application No. PCT/US19/25415, filed on Apr. 2, 2019, which claims the benefit of U.S. Provisional Application No. 62/651,639, filed on Apr. 2, 2018, each of which is hereby incorporated by reference in its entirety for all purposes.

SEQUENCE LISTING

The instant application contains a Sequence Listing which has been submitted via EFS-Web and is hereby incorporated herein by reference in its entirety. Said ASCII copy, created on Nov. 18, 2020, is named 0875200171SL.txt, and is 270,336 bytes in size.

BACKGROUND

T cells are the primary mediators of adaptive immunity. Directed by the specificity of each T cell's unique T cell receptor (TCR), T cells regulate autoimmunity, help activate B cells and innate effectors, and directly kill infected and cancerous cells in a precisely targeted manner. Each TCR recognizes a ligand presented by a major histocompatibility complex (MHC) molecule on target cells. Identification of relevant peptide-MHC complex ligands plays a role in understanding immune responses to tumors and pathogens. MHC complex ligands are also valuable for understanding responses to self and dietary antigens. This understanding enables clinically beneficial immunotherapies (e.g. TCR gene transfer and vaccines) that initiate, amplify, or attenuate immune responses to target antigens.

Mutated 'neoepitopes' are important targets of endogenous and engineered immune responses to cancer. Neoepitope-reactive TILs are present in the endogenous repertoire and regress tumors upon adoptive transfer. Likewise, tumor mutational burden predicts the clinical effectiveness of CTLA-4 or PD-1 blockade, suggesting these checkpoint inhibition strategies affect tumor regression by unleashing neoepitope-reactive T cells. Because neoepitopes result from somatic mutation in tumor cells, they are not generally presented by thymic epithelial cells to induce central tolerance. Thus, T cell responses directed at these neoepitopes are tumor-specific, likely high-affinity, and patient-specific (i.e. private). From a clinical standpoint, this presents an opportunity and a challenge: neoepitopes are excellent targets for immunotherapy, but TCR isolation methods should be sufficiently high-throughput to enable therapeutic application on a clinically-useful scale.

There is an unmet need for rapid and robust TCR ligand discovery technologies for both basic and translational research. Peptide-MHC multimers enable sorting of T cells according to the antigenic specificity of their TCRs, an important step in isolating tumor-specific TCRs for gene therapy. A typical current peptide-MHC production protocol begins with solid-phase synthesis of the peptide ligand(s) of interest. In parallel, the universal $\beta_2$-microglobulin and relevant MHC class I molecules are heterologously expressed in *E. coli*, yielding misfolded inclusion bodies. Each peptide is added to a refolding reaction containing $\beta$2M and the relevant MHC I molecule. Finally, the portion of ternary complex that refolds correctly can be purified and formulated for use in Peptide-MHC multimer production. To facilitate parallel production of a particular MHC molecule with many different peptide ligands, Schumacher and colleagues devised a photocleavable peptide that binds a particular MHC molecule as a conditional ligand. A single refolding reaction is performed to generate that MHC molecule bound to its conditional ligand. Upon exposure to UV light, the conditional ligand is cleaved and exchanged for a desired peptide present in excess. Many such exchange reactions can be performed in parallel, enabling the construction of a pMHC library for that particular MHC allele. Even so, this state-of-the-art technology has challenging limitations. First, the production, purification, and refolding of MHC molecules expressed in *E. coli* inclusion bodies is laborious and produces low yields of properly folded peptide-MHC complex. Second, the turnaround time (weeks) for commercial peptide synthesis is at odds with timescales optimal in the context of personalized on-demand TCR gene therapies directed at patient-specific neoepitopes. Third, many predicted ligands cannot be used to screen T cells through this approach because the biophysical properties (e.g. hydrophobicity) of the peptide precludes its synthesis or exchange. Fourth, exchange efficiency is generally poor (<50% exchange efficiency for a majority of predicted HLA-binding peptides). The resulting mixture of properly folded exchanged MHC and misfolded unliganded MHC results in multimer staining with low signal to noise, an issue that is exacerbated when screening T cells with a multiplexed pool of peptide-MHC reagents. Fifth, the design and validation of conditional ligands for each new MHC allele is a laborious and non-robust undertaking. As the MHC locus is the most multi-allelic locus in the human genome, this is a major hindrance to implementing neoepitope-targeted gene therapies across patients of diverse MHC haplotypes. Together, these limitations underscore the need for novel technologies in this field. Disclosed herein are various compositions and processes for producing peptide-MHC multimers that address these limitations.

SUMMARY

The methods and compositions described herein enable rapid identification of antigens targeted by an immune response and isolation of the T cells and thus the TCR sequences mediating that response. This rapid identification is a goal of research and drug development in the fields of infectious disease, tumor immunology, autoimmunity, and immunotherapy. The compositions may be applied to identify and to isolate antigen-specific T cells and their encoded MHC I-restricted TCRs for drug development. The identification and characterization of antigen-specific T cells may also be applied in the diagnosis, monitoring and prognosis of immune responses and disease in the context of (pre- and post-) therapeutic treatment. The comPACT approach may also be applied to identify the targets of MHC II-restricted T cell responses. Such responses are central to autoimmune disease, and are emerging as important components of cancer immunotherapy. In addition, the efficiency of comPACT protein secretion from mammalian cells expression data generated in the method described herein is potentially useful as a surrogate metric of proper protein folding and thus the affinity of each neoepitope ligand for its cognate MHC molecule. This technology may then afford the unique ability to refine the MHC binding algorithms for less-well studied MHC alleles, improving other targeted immunotherapies such as neoepitope vaccines. As such, the compositions disclosed herein will have broad application to human health and clear commercial potential.

In one aspect, disclosed herein is a polynucleotide molecule comprising, in a 5' to 3' orientation, (i) a first universal target sequence, (ii) a nucleotide sequence encoding an antigenic peptide, (iii) a second universal target sequence that is distinct from the first universal target sequence, (iv) a Beta 2 Microglobulin (β2M) sequence, and (v) a Major Histocompatibility Complex (MHC) allele sequence. In one embodiment, the polynucleotide molecule comprises, in a 5' to 3' orientation, (i) a promoter sequence, (ii) the first universal target sequence comprising the sequence shown in SEQ ID NO: 3, (iii) the nucleotide sequence encoding an antigenic peptide, wherein the antigenic peptide is a tumor neoantigen, (iv) the second universal target sequence comprising the sequence shown in SEQ ID NO: 4, (v) the β2M sequence comprising the sequence shown in SEQ ID NO: 106, (vi) the MHC allele sequence comprising a sequence selected from the group consisting of the sequences shown in SEQ ID NOs:109-174, (vii) a first affinity tag sequence comprising the sequence shown in SEQ ID NO: 29, (viii) a protease cleavage site sequence comprising the sequence shown in SEQ ID NO: 31, and (ix) a second affinity tag sequence comprising the sequence shown in SEQ ID NO: 35.

In one embodiment, the antigenic peptide is selected from the group consisting of a tumor antigen, a neoantigen, a tumor neoantigen, a viral antigen, bacterial antigen, phosphoantigen, and a microbial antigen. In another embodiment, the antigenic peptide is a neoantigen.

In some embodiments a neoantigen is selected by analyzing tumor sequencing data from a subject to identify one or more somatic mutations. In one embodiment, the analyzing is performed using an in silico predictive algorithm. In another embodiment, the predictive algorithm further comprises an MHC binding algorithm to predict binding between the neoantigen and an MHC allele.

In some embodiments, the MHC allele is a mammalian MHC allele. In some embodiments, the MHC allele is a human MHC allele. In some embodiments, the MHC allele is a class I HLA allele. In other embodiments, the HLA allele comprises an HLA-A, HLA-B, or HLA-C allele. The HLA allele is an HLA allele of the subject.

In some embodiments, the HLA allele is selected from the group consisting of: HLA-A*01:01, HLA-A*02:01, HLA-A*03:01, HLA-A*24:02, HLA-A*30:02, HLA-A*31:01, HLA-A*32:01, HLA-A*33:01, HLA-A*68:01, HLA-A*11:01, HLA-A*23:01, HLA-A*30:01, HLA-A*33:03, HLA-A*25:01, HLA-A*26:01, HLA-A*29:02, HLA-A*68:02, HLA-B*07:02, HLA-B*14:02, HLA-B*18:01, HLA-B*27:02, HLA-B*39:01, HLA-B*40:01, HLA-B*44:02, HLA-B*46:01, HLA-B*50:01, HLA-B*57:01, HLA-B*58:01, HLA-B*08:01, HLA-B*15:01, HLA-B*15:03, HLA-B*35:01, HLA-B*40:02, HLA-B*42:01, HLA-B*44:03, HLA-B*51:01, HLA-B*53:01, HLA-B*13:02, HLA-B*15:07, HLA-B*27:05, HLA-B*35:03, HLA-B*37:01, HLA-B*38:01, HLA-B*41:02, HLA-B*44:05, HLA-B*49:01, HLA-B*52:01, HLA-B*55:01, HLA-C*02:02, HLA-C*03:04, HLA-C*05:01, HLA-C*07:01, HLA-C*01:02, HLA-C*04:01, HLA-C*06:02, HLA-C*07:02, HLA-C*16:01, HLA-C*03:03, HLA-C*07:04, HLA-C*08:01, HLA-C*08:02, HLA-C*12:02, HLA-C*12:03, HLA-C*14:02, HLA-C*15:02, and HLA-C*17:01.

In some embodiments, the HLA allele comprises a sequence selected from the group consisting of SEQ ID NOs: 109-174.

In some embodiments, the β2M allele is a mammalian β2M allele. In some embodiments, the β2M allele is a human β2M allele. In some embodiments, the β2M allele comprises the sequence shown in SEQ ID NO: 106.

In some embodiments, the nucleotide sequence encoding an antigenic peptide is between 20-60, between 20-30, between 25-35, between 20-45, between 30-45, between 40-60, or between 45-60 nucleotides in length. In one embodiment, the nucleotide sequence encoding an antigenic peptide is between 20-30 nucleotides in length.

In some embodiments, the first universal target sequence is between 4-50, between 4-15, between 15-40, between 15-35, between 15-30, between 20-40, between 25-40, or between 30-40 nucleotides in length. In one embodiment, the first universal target sequence is between 25-35 nucleotides in length. In another embodiment, the first universal target sequence is at least about 15 nucleotides in length. In another embodiment, wherein the first universal target sequence is between 4-6 nucleotides in length. In some embodiments, the second universal target sequence is between 4-50, between 4-15, between 15-40, between 15-35, between 15-30, between 20-40, between 25-40, or between 30-40 nucleotides in length. In one embodiment, the second universal target sequence is between 25-35 nucleotides in length. In another embodiment, the second universal target sequence is at least about 15 nucleotides in length. In another embodiment, the second universal target sequence is between 4-6 nucleotides in length.

In some embodiments, the first and second universal target sequences comprise polymerase chain reaction (PCR) primer target sequences. In other embodiments, the first and second universal target sequences comprise restriction enzyme cleavage sites.

In some embodiments, the sequence of the first universal target comprises the sequence shown in SEQ ID NO: 3. In some embodiments, the sequence of the second universal target comprises the sequence shown in SEQ ID NO: 4.

In some embodiments, the first universal target sequence further comprises a signal sequence. In some embodiments, the signal sequence encodes a signal sequence comprising a Human Growth Hormone signal sequence, a hIG1 Kappa light chain signal sequence, a Beta 2 microglobulin signal sequence, or an IL2 signal sequence. In some embodiments, the signal sequence comprises a sequence comprising the sequence shown in SEQ ID NOs: 1, 24, 26, or 28. In one embodiment, the signal sequence encodes Human Growth Hormone (HGH). In some embodiments, the signal sequence comprises the sequence shown in SEQ ID NO: 1. In one embodiment, the signal sequence is between 40-90, 40-60, 45-70, 50-80, 60-90, 55-70, 60-80, or 70-80 nucleotides in length.

In some embodiments, the 3' end of the polynucleotide sequence further comprises, in a 5' to 3' orientation, a purification cluster sequence comprising (i) a first affinity tag sequence, (ii) a protease cleavage site sequence, and (iii) a second affinity tag sequence. In some embodiments, the first and second affinity tags are selected from the group consisting of: AviTag, streptavidin-tag, polyhistidine (His6)-tag, FLAG-tag, HA-tag, and Myc-tag. In some embodiments, the first affinity tags comprises a sequence comprising the sequence shown in SEQ ID NO: 29, and the second affinity tag comprises a sequence comprising the sequence shown in SEQ ID NO: 33.

In some embodiments, the protease cleavage site sequence is selected from the group consisting of: a TEV cleavage site sequence, a thrombin cleavage site sequence, a Factor Xa cleavage site sequence, an enteropeptidase cleavage site sequence, and a rhinovirus 3C protease cleavage site sequence. In one embodiment, the protease cleavage site sequence comprises a TEV cleavage site sequence shown in SEQ ID NO: 31. In some embodiments, the first affinity tag sequence encodes for an AviTag peptide, the protease cleavage site sequence encodes for a TEV cleavage site, and the second affinity tag encodes for a His6 peptide. In one embodiment, the first affinity tag sequence comprises the sequence shown in SEQ ID NO: 29, the protease cleavage site comprises the sequence shown in SEQ ID NO: 31, and the second affinity tag comprises the sequence shown in SEQ ID NO: 33.

In some embodiments, the second universal target sequence further comprises a first linker sequence. In one embodiment, the first linker sequence comprises the sequence shown in SEQ ID NO: 10, 14, 16, or 18.

In some embodiments, the polynucleotide further comprises a second linker sequence between the β2M sequence and the MHC allele sequence. In one embodiment, the second linker sequence comprises the sequence shown in SEQ ID NO: 10 or 20.

In some embodiments, the polynucleotide further comprises a third linker sequence between the MHC allele sequence and the first affinity tag. In one embodiment, the third linker sequence comprises the sequence shown in SEQ ID NO: 12 or 22.

The 5' end of the polynucleotide sequence may further comprise a promoter sequence linked to the 5' end of the first universal target. In some embodiments, the promoter sequence is a CMV, an EF1α, or an SV40 promoter. In one embodiment, the promoter sequence is a CMV promoter. In one embodiment, the promoter sequence is a CMV promoter sequence.

The 3' end of the polynucleotide sequence may further comprise a polyA sequence. In some embodiments, the polyA sequence is an SV40, hGH, BHG, or rbGlob polyA sequence. In one embodiment, the polyA sequence comprises a bGH polyA sequence as shown in SEQ ID NO: 179.

In one embodiment, the polynucleotide molecule comprises, in a 5' to 3' orientation, (i) a promoter sequence, (ii) a first universal target sequence, (iii) a nucleotide sequence encoding an antigenic peptide, (iv) a second universal target sequence that is distinct from the first universal target sequence, (v) a β2M sequence, (v) an MHC allele sequence, (vi) a first affinity tag sequence, (vii) a protease cleavage site sequence, and (viii) a second affinity tag sequence.

In another aspect, described herein is an expression construct comprising the polynucleotide molecule as disclosed herein. In one embodiment, the expression construct comprises a plasmid or a viral vector.

In another aspect, described herein is a host cell comprising the polynucleotide molecule or the expression construct as previously described. In one embodiment, the polynucleotide is integrated into the cell genome. In another embodiment, the polynucleotide is extrachromosomal. In some embodiments, the host cell is a mammalian cell. In some embodiments, the host cell is a human cell. In one embodiment, the cell is a stem cell, a tumor cell, an immortalized cell, or a fetal cell. In some embodiments, the host cell is a prokaryotic cell. In some embodiments, the cell is an *Escherichia coli* cell. In some embodiments, the cell expresses a BirA protein or fragment thereof.

In yet another aspect, described herein is a library comprising the polynucleotide molecule or expression construct as described herein, wherein the library comprises greater than or equal to two distinct polynucleotide molecules, wherein each distinct polynucleotide molecule comprises (i) the first universal sequence, (ii) the nucleotide sequence encoding a antigenic peptide, wherein the nucleotide sequence is not the same for each of the greater than or equal to two polynucleotide molecules (iii) the second universal target sequence, (iv) the β2M sequence, and (v) the MHC allele sequence. In one embodiment, the MHC allele sequence is not the same for each of the greater than or equal to two polynucleotide molecules. In another embodiment, the library comprises 20 to 500 distinct polynucleotide molecules. In some embodiments, the library comprises at least 66 distinct polynucleotide molecules.

In some embodiments, the library comprises at least the HLA-A*01:01, HLA-A*02:01, HLA-A*03:01, HLA-A*24:02, HLA-A*30:02, HLA-A*31:01, HLA-A*32:01, HLA-A*33:01, HLA-A*68:01, HLA-A*11:01, HLA-A*23:01, HLA-A*30:01, HLA-A*33:03, HLA-A*25:01, HLA-A*26:01, HLA-A*29:02, HLA-A*68:02, HLA-B*07:02, HLA-B*14:02, HLA-B*18:01, HLA-B*27:02, HLA-B*39:01, HLA-B*40:01, HLA-B*44:02, HLA-B*46:01, HLA-B*50:01, HLA-B*57:01, HLA-B*58:01, HLA-B*08:01, HLA-B*15:01, HLA-B*15:03, HLA-B*35:01, HLA-B*40:02, HLA-B*42:01, HLA-B*44:03, HLA-B*51:01, HLA-B*53:01, HLA-B*13:02, HLA-B*15:07, HLA-B*27:05, HLA-B*35:03, HLA-B*37:01, HLA-B*38:01, HLA-B*41:02, HLA-B*44:05, HLA-B*49:01, HLA-B*52:01, HLA-B*55:01, HLA-C*02:02, HLA-C*03:04, HLA-C*05:01, HLA-C*07:01, HLA-C*01:02, HLA-C*04:01, HLA-C*06:02, HLA-C*07:02, HLA-C*16:01, HLA-C*03:03, HLA-C*07:04, HLA-C*08:01, HLA-C*08:02, HLA-C*12:02, HLA-C*12:03, HLA-C*14:02, HLA-C*15:02, and HLA-C*17:01 alleles. In some embodiments, the library comprises at least the sequences shown in SEQ ID NOs: 109-174.

In another aspect, described herein is a polypeptide comprising, in an amino to carboxyl terminus orientation, (i) a first universal target peptide, (ii) an antigenic peptide, (iii) a second universal target peptide that is distinct from the first universal target peptide, (iv) a β2M peptide, and (v) an MHC peptide. In some embodiments, the antigenic peptide is selected from the group consisting of a tumor antigen, a neoantigen, a tumor neoantigen, a viral antigen, bacterial antigen, phosphoantigen, and a microbial antigen. In one embodiment, the antigenic peptide is a neoantigen.

In some embodiments, the polypeptide comprises in a 5' to 3' orientation, (i) a promoter peptide comprising the sequence shown in SEQ ID NO: 2, (ii) the first universal target peptide, (iii) the nucleotide sequence encoding an antigenic peptide, wherein the antigenic peptide is a tumor neoantigen, (iv) the second universal target peptide comprising the sequence shown in SEQ ID NO: 15 or 17, (v) the β2M peptide comprising the sequence shown in SEQ ID NO: 105, (vi) the MHC peptide comprising a sequence shown in SEQ ID NOs: 38-103, (vii) a first affinity peptide comprising the sequence shown in SEQ ID NO: 30, (viii) a protease cleavage site peptide comprising the sequence shown in SEQ ID NO: 32, and (ix) a second affinity peptide comprising the sequence shown in SEQ ID NO: 36.

In some embodiments the neoantigen is selected by analyzing tumor sequencing data from a subject to identify one or more somatic mutations. In one embodiment, the analyzing is performed using an in silico predictive algorithm. In another embodiment, the predictive algorithm further comprises an MHC binding algorithm to predict binding between the neoantigen and an MHC peptide.

In one embodiment, the antigenic peptide is 7-15 amino acids, 7-10, 8-9, 7, 8, 9, 10, 11, 12, 13, 14, or 15 amino acids in length.

In some embodiments, the MHC peptide is a mammalian MHC peptide. In some embodiments, the MHC peptide is a human MHC peptide. In some embodiments, the MHC peptide is a class I HLA peptide. In other embodiments, the HLA peptide comprises an HLA-A, HLA-B, or HLA-C peptide. In one embodiment, the HLA peptide is an HLA peptide of the subject. In one embodiment, the HLA peptide comprises a Y84A or a Y84C mutation.

In some embodiments, the β2M peptide is a mammalian β2M peptide. In some embodiments, the β2M peptide is a human β2M peptide. In some embodiments, the β2M peptide comprises the sequence shown in SEQ ID NO: 105. In another embodiment, the β2M peptide comprises an S88C mutation. In some embodiments, the β2M peptide comprises the sequence shown in SEQ ID NO: 107, comprising an S88C mutation at amino acid 88.

In some embodiments, the HLA peptide comprises HLA-A*01:01, HLA-A*02:01, HLA-A*03:01, HLA-A*24:02, HLA-A*30:02, HLA-A*31:01, HLA-A*32:01, HLA-A*33:01, HLA-A*68:01, HLA-A*11:01, HLA-A*23:01, HLA-A*30:01, HLA-A*33:03, HLA-A*25:01, HLA-A*26:01, HLA-A*29:02, HLA-A*68:02, HLA-B*07:02, HLA-B*14:02, HLA-B*18:01, HLA-B*27:02, HLA-B*39:01, HLA-B*40:01, HLA-B*44:02, HLA-B*46:01, HLA-B*50:01, HLA-B*57:01, HLA-B*58:01, HLA-B*08:01, HLA-B*15:01, HLA-B*15:03, HLA-B*35:01, HLA-B*40:02, HLA-B*42:01, HLA-B*44:03, HLA-B*51:01, HLA-B*53:01, HLA-B*13:02, HLA-B*15:07, HLA-B*27:05, HLA-B*35:03, HLA-B*37:01, HLA-B*38:01, HLA-B*41:02, HLA-B*44:05, HLA-B*49:01, HLA-B*52:01, HLA-B*55:01, HLA-C*02:02, HLA-C*03:04, HLA-C*05:01, HLA-C*07:01, HLA-C*01:02, HLA-C*04:01, HLA-C*06:02, HLA-C*07:02, HLA-C*16:01, HLA-C*03:03, HLA-C*07:04, HLA-C*08:01, HLA-C*08:02, HLA-C*12:02, HLA-C*12:03, HLA-C*14:02, HLA-C*15:02, or HLA-C*17:01. In some embodiments, the HLA peptide comprises a sequence selected from the group consisting of SEQ ID NOs: 38-103.

In some embodiments, the first universal target peptide further comprises a signal peptide. In one embodiment, the signal sequence is between 15-45, between 15-30, between 20-45, between 20-30, or between 30-45 amino acids in length. In one embodiment, the signal peptide comprises Human Growth Hormone. In some embodiments, the signal peptide comprising a Human Growth Hormone signal peptide, a hIG1 Kappa light chain signal peptide, a Beta 2 microglobulin signal peptide, or an IL2 signal peptide. In some embodiments, the signal peptide comprises a sequence comprising the sequence shown in SEQ ID NOs: 2, 23, 25, or 27. In some embodiments, the signal peptide comprises the Human Growth Hormone (HGH) signal peptide sequence shown in SEQ ID NO: 2. In one embodiment, the second universal target peptide comprises the sequence GGGGSGGGGSGGGGS. In one embodiment, the second universal target peptide comprising the sequence shown in SEQ ID NO: 15 or 17.

In some embodiments, the carboxyl terminus of the polypeptide may further comprise, in an amino to carboxylic terminus orientation, a purification cluster comprising (i) a first affinity peptide, (ii) a protease cleavage site, and (iii) a second affinity peptide. In some embodiments, the first and second affinity peptides are selected from the group consisting of AviTag, strep-tag, polyhistidine (His6)-tag, FLAG-tag, HA-tag, and/or Myc-tag. In some embodiments, the first affinity peptide comprises a sequence comprising SEQ ID NO: 30 and the second affinity peptide comprises a sequence comprising SEQ ID NO: 34.

In some embodiments, the protease cleavage site is a TEV cleavage site, a thrombin cleavage site, a Factor Xa cleavage site, an enteropeptidase cleavage site, or a rhinovirus 3C protease cleavage site. In some embodiments, the purification cluster comprises an AviTag epitope, a TEV cleavage site, and a His6 epitope. In some embodiments, the protease cleavage site comprises the TEV cleavage site sequence shown in SEQ ID NO: 32. In some embodiments, the purification cluster comprises the AviTag peptide sequence shown in SEQ ID NO: 30, the TEV cleavage site sequence shown in SEQ ID NO: 32, and the His6 peptide sequence shown in SEQ ID NOs: 34 or 36. In some embodiments, the purification cluster comprises two or more copies of the His6 peptide sequence shown in SEQ ID NO: 34. In some embodiments, the purification cluster comprises the sequence shown in SEQ ID NO: 37.

In some embodiments, the second universal target peptide further comprises a linker comprising the sequence shown in SEQ ID NO: 9, 11, 15, or 17.

In some embodiments, the polypeptide comprises a second linker sequence between the β2M sequence and the MHC allele sequence. In some embodiments, the second linker sequence comprises the sequence shown in SEQ ID NO: 9 or 19. In some embodiments, the polypeptide further comprising a third linker sequence between the MHC allele sequence and the first affinity tag. In some embodiments, the third linker sequence comprises the sequence shown in SEQ ID NO: 13 or 21. In some embodiments, the polypeptide is biotinylated.

In one embodiment, the polypeptide comprises in an amino to carboxyl terminus orientation, (i) the first universal target peptide, (ii) the antigenic peptide, (iii) the second universal target peptide, (iv) the β2M peptide, (v) the MHC peptide, (vi) the first affinity tag peptide, (vii) the protease cleavage site, and (viii) the second affinity tag peptide. In some embodiments, the polypeptide is biotinylated.

In another aspect, disclosed herein is a library comprises greater than or equal to two distinct polypeptide molecules, wherein the distinct polypeptide molecule comprises (i) the first universal target peptide, (ii) the antigenic peptide, wherein the antigenic peptide is not the same for each of the greater than or equal to two polypeptide molecules, (iii) the second universal target peptide that is distinct from the first universal target peptide, (iv) the β2M peptide, and (v) the MHC peptide. In one embodiment, the MHC peptide is not the same for each of the greater than or equal to two polypeptide molecules. In another embodiment, the library comprises 20 to 500 distinct polypeptide molecules. In some embodiments, the library comprises at least 66 distinct polypeptides.

In some embodiments, the library comprises HLA-A*01:01, HLA-A*02:01, HLA-A*03:01, HLA-A*24:02, HLA-A*30:02, HLA-A*31:01, HLA-A*32:01, HLA-A*33:01, HLA-A*68:01, HLA-A*11:01, HLA-A*23:01, HLA-A*30:01, HLA-A*33:03, HLA-A*25:01, HLA-A*26:01, HLA-A*29:02, HLA-A*68:02, HLA-B*07:02, HLA-B*14:02, HLA-B*18:01, HLA-B*27:02, HLA-B*39:01, HLA-B*40:01, HLA-B*44:02, HLA-B*46:01, HLA-B*50:01, HLA-B*57:01, HLA-B*58:01, HLA-B*08:01, HLA-B*15:01, HLA-B*15:03, HLA-B*35:01, HLA-B*40:02, HLA-B*42:01, HLA-B*44:03, HLA-B*51:01, HLA-B*53:01, HLA-B*13:02, HLA-B*15:07, HLA-B*27:05, HLA-B*35:03, HLA-B*37:01, HLA-B*38:01, HLA-B*41:02, HLA-B*44:05, HLA-B*49:01, HLA-B*52:01, HLA-B*55:01, HLA-C*02:02, HLA-C*03:04, HLA-C*05:01, HLA-C*07:01, HLA-C*01:02, HLA-C*04:01, HLA-C*06:02, HLA-C*07:02, HLA-C*16:01, HLA-C*03:03, HLA-C*07:04, HLA- C*08:01, HLA-C*08:02, HLA-C*12:02, HLA-C*12:03, HLA-C*14:02, HLA-C*15:02, and HLA-C*17:01 polypeptides.

In some embodiments, the polypeptide is attached to a particle, wherein the particle is a surface, a nanoparticle, a bead, or a polymer. In one embodiment, the polypeptide is attached via a linker to the particle. In one embodiment, the particle is a nanoparticle and the nanoparticle is a magnetic nanoparticle or a polystyrene nanoparticle. In one embodiment, the magnetic nanoparticle comprises magnetic iron oxide. In another embodiment, the bead is an agarose bead or a sepharose bead. In some embodiments, the polypeptide attached to the particle further comprises a fluorophore. In one embodiment, the fluorophore is attached, with or without a linker, to the particle.

In some embodiments, a library of polypeptides is attached to particles wherein the library comprises greater than or equal to two distinct polypeptide molecules, wherein the antigenic peptide is not the same for each of the greater than or equal to two polypeptide molecules, and wherein each distinct polypeptide is attached to a particle. In one embodiment, the MHC peptide is not the same for each of the greater than or equal to two polypeptide molecules. In one embodiment, the library further comprises a unique defined barcode sequence operably associated with the identity of each distinct polypeptide. In another embodiment, the library comprises 20 to 500 distinct polypeptides. In another embodiment, the library comprises at least 66 distinct polypeptides.

In another aspect, described herein is a kit comprising the composition of any of the above embodiments and instructions for use.

In another aspect, disclosed herein is a method of manufacturing a polynucleotide molecule comprising the steps of: (a) obtaining a first polynucleotide sequence comprising, in a 5' to 3' orientation, (i) a first universal target sequence comprising a restriction site, (ii) a second universal target sequence comprising a restriction site that is not the same as the first universal target sequence, (iii) a β2M sequence, and (iv) an MHC allele sequence; (b) obtaining a second polynucleotide comprising, in a 5' to 3' orientation (i) a portion of the first universal target sequence, (i) a sequence encoding an antigenic peptide, and (iii) a portion of the second universal target sequence; (c) obtaining a third polynucleotide comprising, in a 5' to 3' orientation, (i) the reverse complement of a portion of the second universal target sequence, (ii) the reverse complement of the sequence encoding an antigenic peptide, and (iii) the reverse complement of a portion of the first universal target sequence; (d) mixing the second and third polynucleotides together such that the complementary sequences anneal; (e) performing a restriction digest on the first polynucleotide sequence with at least one restriction enzyme; and (f) ligating the first and second polynucleotides together by mixing the digested first polynucleotide and annealed second and third polynucleotides together with DNA ligation reaction reagents.

In some embodiments, the method further comprises phosphorylating the 5' nucleotide of the second and third polynucleotides after the complementary sequences anneal, wherein the phosphorylating comprises incubating the first or second and third polynucleotides with an enzyme. In some embodiments, the enzyme is T4 kinase. In some embodiments, the first polynucleotide is an expression construct. In some embodiments, comprising inserting the manufactured polynucleotide into an expression construct.

In some embodiments, the first polynucleotide further comprises a promoter sequence. In one embodiment, the promoter sequence is a CMV, an EF1α, or an SV40 promoter.

In another embodiment, the 3' end of the second polynucleotide sequence further comprises, in a 5' to 3' orientation, a purification cluster sequence comprising (i) a first affinity tag sequence, (ii) a protease cleavage site sequence, and (iii) a second affinity tag sequence.

In one embodiment, the 3' end of the second polynucleotide sequence further comprises a polyA sequence.

In some embodiments, obtaining the third and fourth polynucleotide sequence steps further comprises obtaining a predictive data set of a tumor sequencing data from a subject. In one embodiment, obtaining the third and fourth polynucleotide sequence steps further comprises predicting the sequence encoding the antigenic peptide from the tumor sequencing data. In another embodiment, obtaining the third and fourth polynucleotide sequence steps further comprises synthesizing the polynucleotide encoding the antigenic peptide based on the predicted sequence.

In some embodiments, the method further comprises manufacturing a library comprising greater than or equal to two distinct polynucleotide molecules, wherein the distinct polynucleotide molecule comprises (i) the first universal target sequence, (ii) the nucleotide sequence encoding an antigenic peptide, wherein the antigenic peptide is not the same for each of the greater than or equal to two polypeptide molecules, (iii) the second universal target sequence that is distinct from the first universal target sequence, (iv) the β2M peptide, and (v) the MHC allele sequence. In one embodiment, the MHC allele is not the same for each of the greater than or equal to two polynucleotide molecules. In another embodiment, the library comprises 40 to 500 distinct polynucleotide molecules.

In some embodiments, the method further comprises inserting the manufactured polynucleotide into an expression construct. In one embodiment, the method further comprises manufacturing a library comprising greater than or equal to two expression constructs comprising distinct polynucleotide molecules, wherein the distinct polynucleotide molecule comprises (i) the first universal target sequence, (ii) the nucleotide sequence encoding an antigenic peptide, wherein the nucleotide sequence is not the same for each of the greater than or equal to two polynucleotide molecules, (iii) the second universal target sequence that is distinct from the first universal target sequence, (iv) the β2M sequence, and (v) the MHC allele sequence. In one embodiment, the MHC allele is not the same for each of the greater than or equal to two polynucleotide molecules. In another embodiment, the library comprises 20 to 500 distinct expression constructs. In some embodiments, the library comprises at least 66 distinct polynucleotide molecules. In some embodiments, the MHC allele is selected from the sequences shown in the group consisting of SEQ ID NOs: 109-174.

In some embodiments, the method further comprises expressing a polyprotein molecule from the polynucleotide molecule. In some embodiments, the polynucleotide is transfected or transduced into a cell. In one embodiment, the polynucleotide is integrated into the cell genome. In another embodiment, the polynucleotide remains extrachromosomal in the cell. In some embodiments, the host cell is a mammalian cell or a human cell. In one embodiment, the cell is a stem cell, a tumor cell, an immortalized cell, or a fetal cell. In some embodiments, the cell is a prokaryotic cell. In some embodiments, the cell is an *Escherichia coli* cell.

In one embodiment, the method further comprises quantifying the expression of the polyprotein. In some embodiments, the expressed and non-expressed polyprotein sequences are used to refine the antigenic peptide prediction analysis step of the method. In one embodiment, the method further comprises biotinylating the polyprotein.

In some embodiments, the method comprises purifying the polyprotein. The purifying step may comprise affinity chromatography. In one embodiment, the affinity chromatography comprises immobilized metal affinity chromatography, comprising a support, a chelator and a divalent metal. The chelator for the affinity chromatography can be nitrolotriacetic acid (NTA) or iminodiacetic acid (IDA). In some embodiments the divalent metal is selected from the group consisting of: Nickel (Ni), Cobalt (Co), Copper (Cu), and Iron (Fe). In one embodiment, the chelator is NTA and the divalent metal is Ni. In other embodiments, the support is selected from the group consisting of: agarose beads, sepharose beads, and magnetic beads. In some embodiments, the method further comprises quantifying the biotinylation level of the purified polyprotein.

In some embodiments the method further comprises attaching the polypeptide to a particle, wherein the particle is a surface, a nanoparticle, a bead, or a polymer. In one embodiment, the polypeptide is attached via a linker to the particle. In one embodiment, the particle is a nanoparticle and the nanoparticle is a magnetic nanoparticle or a polystyrene nanoparticle. In one embodiment, the magnetic nanoparticle comprises magnetic iron oxide. In another embodiment, the bead is an agarose bead or a sepharose bead. In some embodiments, the polypeptide attached to the particle further comprises a fluorophore. In one embodiment, the fluorophore is attached, with or without a linker, to the particle.

In another embodiment, the method further comprises producing a library comprising greater than or equal to two distinct polyproteins attached to at least one particle, wherein the distinct polypeptide comprises (i) the first universal target peptide, (ii) the antigenic peptide, wherein the antigenic peptide is not the same for each of the greater than or equal to two polypeptide molecules, (iii) the second universal target peptide that is distinct from the first universal target peptide, (iv) the β2M peptide, and (v) the MHC peptide. In one embodiment, the MHC peptide is not the same for each of the greater than or equal to two polypeptide molecules. In another embodiment, the library comprises 20 to 500 distinct single polyproteins. In another embodiment, the library comprises at least 66 distinct single polyproteins. In another embodiment, the MHC peptide is selected from the sequences shown in the group consisting of SEQ ID NO: 39-104.

In another aspect, disclosed herein is a method of manufacturing a polynucleotide molecule comprising the steps of: (a) obtaining a first polynucleotide sequence comprising, in a 5' to 3' orientation, (i) a first universal target sequence comprising a restriction site, (ii) a second universal target sequence comprising a restriction site that is not the same as the first universal target sequence, (iii) a β2M sequence, and (iv) an MHC allele sequence; (b) obtaining a second polynucleotide comprising, in a 5' to 3' orientation, (i) the first universal target sequence, (ii) a sequence encoding an antigenic peptide, and (iii) the second universal target sequence; (c) performing a restriction digest on the first polynucleotide sequence with at least one restriction enzyme; (d) performing a restriction digest on the second polynucleotide sequence with at least one restriction enzyme; and (e) ligating the first and second polynucleotides together by mixing the digested first and second polynucleotides together with DNA ligation reaction reagents.

In another aspect, described herein is a method of manufacturing a polynucleotide molecule comprising the steps of: (a) obtaining a first polynucleotide sequence comprising a first universal target sequence; (b) obtaining a second polynucleotide sequence comprising, in a 5' to 3' orientation, (i) a second universal target sequence, (ii) a β2M sequence, and (iii) an MHC allele sequence; (c) obtaining a third polynucleotide sequence comprising, in a 5' to 3' orientation, a sequence encoding an antigenic peptide and the second universal target sequence; (d) obtaining a fourth polynucleotide sequence comprising, in a 5' to 3' orientation, the reverse complement of the antigenic peptide and the reverse complement of the first universal target sequence; (e) combining the first, second, third, and fourth polynucleotides in a solution; (f) adding polymerase chain reaction (PCR) reagents; and (g) performing a PCR reaction wherein a complementary region of the second universal target sequence in the second and third polynucleotides anneal to each other and a complementary region of the first universal target sequence in the first and fourth polynucleotides anneal to each other; and wherein the annealed sequences provide priming sequences for a PCR extension and amplification reaction.

Also disclosed herein is a method for isolating an antigen specific T cell, the method comprising the steps of: (a) providing a polypeptide comprising, in an amino terminus to carboxyl terminus orientation, (i) a first universal target peptide, (ii) an antigenic peptide, (iii) a second universal target peptide that is distinct from the first universal target peptide, (iv) a β2M peptide, and (v) an MHC peptide, wherein the polypeptide is linked to one particle; (b) providing a sample known or suspected to comprise one or more T cells; (c) contacting the polypeptide with the sample, wherein the contacting comprises providing conditions sufficient for a single T cell to bind the polypeptide attached to the particle, and (d) isolating the single T cell associated with the particle.

BRIEF SUMMARY OF DRAWINGS

These and other features, aspects, and advantages of disclosed compositions and methods will become better understood with regard to the following description, and accompanying drawings, where:

FIG. 3 is a diagram of an exemplary restriction digest cloning reaction to replace the dummy insert in the MHC template with a chosen neoepitope sequence. The dummy insert (underlined, bold) contains four stop codons in different frames and a unique restriction site for destruction of uncut or re-ligated template. The restriction sites on either side of the insert are shown in boxes.

FIG. 21 shows coupling of Cy5 to S88C comPACT protein monomers.

FIGS. 29A-29D show that Neo12 NTAmers bind T cells in antigen specific manner and that the presence of imidazole prevents NTAmer binding.

FIGS. 30A-30D show that MART-1 NTAmers bind T cells in antigen specific manner.

DETAILED DESCRIPTION

Definitions

Figure 1:
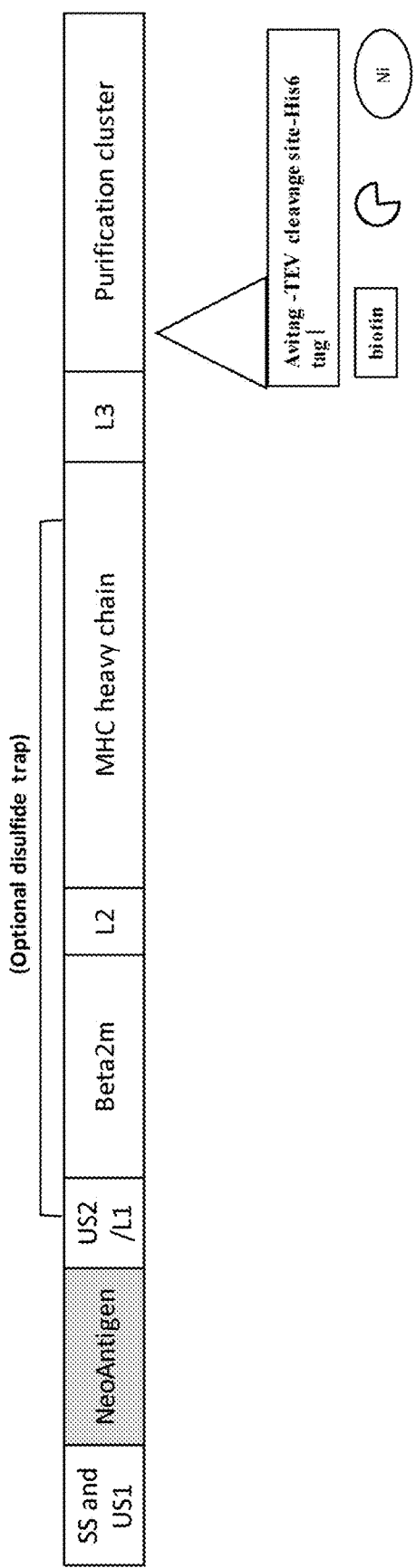
FIG. 1 shows the design of an exemplary comPACT mini-gene. SS refers to the optional signal sequence; US1 refers to the first universal target site; neoantigen refers to the antigenic peptide sequence site; US2 refers to the second universal target site; L1 refers to the optional first linker sequence; Beta2m refers to the β-2-microglobulin domain sequence; L2 refers to the optional second linker sequence; MHC heavy chain refers to the MHC heavy chain allele; L3 refers to the optional third linker sequence; and purification cluster refers to the optional purification cluster with a biotinylation sequence, a protease cleavage site, and an affinity tag sequence.

Terms used in the claims and specification are defined as set forth below unless otherwise specified.

Embodiments of the compositions and methods disclosed herein include a recombinant antigen-MHC complex that is capable of pairing with cognate T cells. As used herein, "antigen-MHC," "antigen-MHC complex," "recombinant antigen-MHC complex," "peptide MHC," and "p/MHC," are used interchangeably to refer to a major histocompatibility complex with a peptide in the antigen binding groove of MHC.

As used herein, "antigen" includes any antigen including patient-specific neoantigens. "Antigenic peptide" refers to a peptide or peptide fragment capable of binding an MHC molecule. "Neoantigen" refers to an antigen that has at least one alteration that makes the neoantigen or presentation of the neoantigen distinct from its corresponding wild-type antigen, e.g., mutations in the polypeptide sequence, differences is post-translation modifications, or differences in expression level. "Tumor neoantigens" refer to neoantigens that are derived from a tumor or a cancer, e.g., from the tumor of a patient.

As used herein, a "polynucleotide" may refer to ssDNA, dsDNA, ssRNA, dsRNA, or mRNA. One of skill in the art can understand which form is being referred to, e.g., based on the context in which the polynucleotide is being used.

The term "in vivo" refers to processes that occur in a living organism, including a cell.

The term "mammal" as used herein includes both humans and non-humans and include but is not limited to humans, non-human primates, canines, felines, murines, bovines, equines, and porcines.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

It must be noted that, as used in the specification and the appended claims, the singular forms "a," "an" and "the" include plural referents unless the context clearly dictates otherwise.

Other Interpretational Conventions

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50. For example, a sub-range of 1 to 50 can include 2-40, 5-25, and 10-20.

Nucleotide and Peptide Compositions

T-cell mediated immunity can be characterized by the activation of antigen-specific cytotoxic T cells that are able to induce death in cells that display antigen in a major histocompatibility complex (MHC) on their surface. These cells displaying an MHC complex loaded with antigen include virus-infected cells, cells with intracellular bacteria, cells that have internalized or phagocytosed extracellular sources of protein, and cancer cells displaying tumor antigens.

A natural class I MHC heavy chain comprises about 350 amino acids; a natural β2-microglobulin comprises about 100 amino acids; and a class I antigen peptide typically has a length of from about 7 to about 15 amino acids. Class I heavy chains are encoded by genes of the major histocompatibility complex, designated HLA-A, -B and -C in humans, and H-2K, D, and L in mice. The class I heavy chains and β2-microglobulin are separately encoded on different chromosomes. Antigen peptides are normally processed by cells from protein sources such as, for example, viruses, bacteria, or cancer cells. Diverse variants have been identified for the polypeptides encoded by the HLA-A, -B and -C MHC genes in humans, as well as the murine H-2K, D, and L MHC genes.

Embodiments of the method disclosed herein are directed to a method of manufacturing a single molecule in which a selected antigen (e.g., a neoantigen) is linked to an MHC complex comprising a β2-microglobulin (β2M) and an MHC heavy chain. Different MHC heavy chains can be linked to the β2M molecule to form a varying number of MHC templates. The methods disclosed herein of inserting an antigen into an MHC template via restriction digest or PCR-based assembly by utilizing universal target sequences flanking the antigen insertion site results in the ability to construct a library of different antigen-MHC complexes in a high-throughput method that can be, e.g., personalized for a given patient. These exemplary complexes are included in the term "comPACTs," and can then be, e.g., linked to a particle, barcoded particle, or surface for use in isolation and identification of patient-specific T cell populations targeted to patient-specific neoantigens. Methods of linking antigen-MHC complexes and use of such complexes are disclosed in PCT/US2018/021611, filed Mar. 8, 2018, herein incorporated by reference in its entirety.

Peptide-MHC Complex

Briefly, as used herein, "comPACTs" refer to a single polypeptide fusion including a universal target sequence, an antigen peptide, a second universal target sequence, a β2-microglobulin, and a MHC class I heavy chain comprising, e.g., the α1, α2, and α3 domains that forms an MHC display moiety. An MHC display moiety can include a recombinant MHC molecule. In certain embodiments, comPACTs can comprise disulfide traps, as described in US Publication No. 2009/0117153 and US Publication No. 2008/0219947; each of which is herein incorporated by reference. The antigen-MHC complex formed by a comPACT results in display of the antigens such that they are capable of recognition by a cognate TCR molecule. In some embodiments, the MHC complex can be an MHC Class I (MHC I) complex that pairs with CD8-positive (CD8+) T "killer" cells. In some embodiments, the MHC complex can be an MHC Class II (MHC II) complex that pairs with CD4-positive (CD4+) T cells. The MHC allele encoded in each comPACT can be easily swapped out for other MHC I or II alleles, enabling antigenic interrogation of T cells from patients of any MHC haplotype.

In some embodiments, the MHC class I heavy chain sequence of a comPACT can include one or more amino acid substitutions, additions, and/or deletions, such as a substitution of tyr-84 with a non-aromatic amino acid other than proline. In these embodiments, the amino acid substitution can be an amino acid encoded by the standard genetic code such leucine, isoleucine, valine, serine, threonine, alanine, histidine, glutamine, asparagine, lysine, aspartic acid, glutamic acid, cysteine, arginine, serine or glycine, or can be a modified or unusual amino acid. In one embodiment, the MHC class I heavy chain sequence of a comPACT comprises a tyrosine-84 to alanine substitution. In another embodiment, the MHC class I heavy chain sequence of a comPACT comprises a tyrosine-84 to cysteine substitution.

In some embodiments, the MHC allele lacks a transmembrane domain. In some embodiments, the MHC allele lacks a cytoplasmic domain. In some embodiments, the MHC allele lacks a transmembrane and a cytoplasmic domain. In some embodiments, the HLA allele lacks a transmembrane domain. In some embodiments, the HLA allele lacks a cytoplasmic domain. In some embodiments, the HLA allele lacks a transmembrane and a cytoplasmic domain.

Any MHC or HLA allele may be used in the comPACT described herein. Exemplary HLA alleles include, but are not limited to, HLA-A*01:01, HLA-A*02:01, HLA-A*03: 01, HLA-A*24:02, HLA-A*30:02, HLA-A*31:01, HLA-A*32:01, HLA-A*33:01, HLA-A*68:01, HLA-A*11:01, HLA-A*23:01, HLA-A*30:01, HLA-A*33:03, HLA-A*25: 01, HLA-A*26:01, HLA-A*29:02, HLA-A*68:02, HLA-B*07:02, HLA-B*14:02, HLA-B*18:01, HLA-B*27:02, HLA-B*39:01, HLA-B*40:01, HLA-B*44:02, HLA-B*46: 01, HLA-B*50:01, HLA-B*57:01, HLA-B*58:01, HLA-B*08:01, HLA-B*15:01, HLA-B*15:03, HLA-B*35:01, HLA-B*40:02, HLA-B*42:01, HLA-B*44:03, HLA-B*51: 01, HLA-B*53:01, HLA-B*13:02, HLA-B*15:07, HLA-B*27:05, HLA-B*35:03, HLA-B*37:01, HLA-B*38:01, HLA-B*41:02, HLA-B*44:05, HLA-B*49:01, HLA-B*52: 01, HLA-B*55:01, HLA-C*02:02, HLA-C*03:04, HLA-C*05:01, HLA-C*07:01, HLA-C*01:02, HLA-C*04:01, HLA-C*06:02, HLA-C*07:02, HLA-C*16:01, HLA-C*03: 03, HLA-C*07:04, HLA-C*08:01, HLA-C*08:02, HLA-C*12:02, HLA-C*12:03, HLA-C*14:02, HLA-C*15:02, and HLA-C*17:01. Any other suitable HLA allele known in the art may be used in the comPACT described herein.

The β2-microglobulin (β2M) may include a recombinant β2M molecule. In some embodiments, the β2M sequence can include one or more amino acid substitutions, additions, and/or deletions as described above. In one embodiment, this substitution comprises a serine-88 to cysteine substitution.

Amino acid and nucleotide sequences for an exemplary comPACT protein with a hGH signal sequence, dummy neoantigen insert, HLA*A02:01 allele, AviTag peptide, TEV cleavage site, and concatenated His tag is shown below in Table 1.

TABLE 1

| SEQ ID NO | | |
|---|---|---|
| 201 | comPACT HLA*02:01 peptide | MATGSRTSLLLAFGLLCLPWLQEGSA*LEIKCE**GCGGSGGGGSGGGGSIQRTPK IQVYSRHPAENGKSNFLNCYVSGFHPSDIEVDLLKNGERIEKVEHSDLSFSKDWSF YLLYYTEFTPTEKDEYACRVNHVTLSQPKIVKWDRDMRKVKAHSQTHRVDLGTLRG CYNQSEAGSHTVQRMYGCDVGSDWRFLRGYHQYAYDGKDYIALKEDLRSWTAADMA AQTTKHKWEAAHVAEQLRAYLEGTCVEWLRRYLENGKETLQRTDAPKTHMTHHAVS DHEATLRCWALSFYPAEITLTWQRDGEDQTQDTELVETRPAGDGTFQKWAAVVPS GQEQRYTCHVQHEGLPKPLTLRWEPGSGGSGGSAGGGLNDIFEAQKIEWHEGGGEN LYFQGGSHHHHHHGGGSGGGSGSHHHHHH |
| 202 | comPACT HLA*02:01 nucleotide | atggcgacgggttcaagaacttccctacttcttgcatttggcctgctttgtttgcc gtggttacaggagggctcagcatgactcgagataaaatgtgaataatgaggatgcg gaggatccggcggaggcgggagcggaggcggagggtcatccagcgtactccaaaga ttcaggtttactcacgtcatccagcagagaatggaaagtcaaatttcctgaattgc tatgtgtctgggtttcatccatccgacattgaagttgacttactgaagaatggaga gagaattgaaaaagtggagcattcagacttgtctttcagcaaggactggtctttct atctcttgtactacactgaattcacccccactgaaaaagatgagtatgcctgccgt gtgaaccatgtgactttgtcacagcccaagatagttaagtgggatcgagacatggg cggaggcgggagcggcggaggcgggtccggcggaggcgggtccggagggggaggca gcggctctcactccatgaggtatttcttcacatccgtgtcccggcccggccgcggg gagccccgcttcatcgcagtgggctacgtggacgacacgcagttcgtgcggttcga cagcgacgccgcgagccagaggatggagccgcgggcgccgtggatagagcaggagg gtcccgagtattgggacggggagacacggaaagtgaaggcccactcacagactcac cgagtggacctggggaccctgcgcggctgctacaaccagagcgaggccggttctca caccgtccagaggatgtatggctgcgacgtggggtcggactggcgcttcctccgcg ggtaccaccagtacgcctacgacggcaaggattacatcgccctgaaagaggacctg cgctcttggaccgcggcggacatggcagctcagaccaccaagcacaagtgggaggc ggcccatgtggcggagcagttgagagcctacctggagggcacgtgcgtggagtggc tccgcagatacctggagaacgggaaggagacgctgcagcgcacggacgcccccaaa acgcatatgactcaccacgctgtctctgaccatgaagccaccctgaggtgctggc cctgagcttctaccctgcggagatcacactgacctggcagcgggatggggaggacc agacccaggacacggagctcgtggagaccaggcctgcaggggatggaaccttccag aagtgggcggctgtggtggtgcctctggacaggagcagagatacacctgccatgt gcagcatgagggtttgcccaagccctcaccctgagatgggagccgggagcggcg gcagcggggctccgccggcggaggcctgaacgacatcttcgaagcccagaagatc gagtggcacgagggcgggagagaacctgtacttccagggcggcagccaccacca tcaccaccatggcggcggaagcggcggcgggtccggcagccaccatcaccatcacc at |

In some embodiments, the polynucleotide molecule comprises, in a 5' to 3' orientation, (i) a promoter sequence, (ii) the first universal target sequence comprising the sequence shown in SEQ ID NO: 3, (iii) the nucleotide sequence encoding an antigenic peptide, wherein the antigenic peptide is a tumor neoantigen, (iv) the second universal target sequence comprising the sequence shown in SEQ ID NO: 4, (v) the β2M sequence comprising the sequence shown in SEQ ID NO: 106, (vi) the MHC allele sequence comprising a sequence selected from the group consisting of the sequences shown in SEQ ID NOs: 109-174, (vii) a first affinity tag sequence comprising the sequence shown in SEQ ID NO: 29, (viii) a protease cleavage site sequence comprising the sequence shown in SEQ ID NO: 31, and (ix) a second affinity tag sequence comprising the sequence shown in SEQ ID NO: 35. In some embodiments, the polynucleotide molecule comprises, in a 5' to 3' orientation, (i) a promoter sequence, (ii) the first universal target sequence comprising the sequence shown in SEQ ID NO: 3, (iii) the nucleotide sequence encoding an antigenic peptide, wherein the antigenic peptide is a tumor neoantigen, (iv) the second universal target sequence comprising the sequence shown in SEQ ID NO: 4, (v) the β2M sequence comprising the sequence shown in SEQ ID NO: 106, (vi) the MHC allele sequence comprising a sequence selected from the group consisting of the sequences shown in SEQ ID NOs: 109-174. In some embodiments, the polynucleotide molecule comprises, in a 5' to 3' orientation, (i) a promoter sequence, (ii) the first universal target sequence comprising the sequence shown in SEQ ID NO: 3, (iii) the nucleotide sequence encoding an antigenic peptide, wherein the antigenic peptide is a tumor neoantigen, (iv) the second universal target sequence comprising the sequence shown in SEQ ID NO: 4, (v) the β2M sequence, (vi) the MHC allele sequence comprising a sequence selected from the group consisting of the sequences shown in SEQ ID NOs:109-174, (vii) a first affinity tag sequence, (viii) a protease cleavage site sequence, and (ix) a second affinity tag.

In some embodiments, the polypeptide comprises in a 5' to 3' orientation, (i) a promoter peptide comprising the sequence shown in SEQ ID NO: 2, (ii) the first universal target peptide, (iii) the nucleotide sequence encoding an antigenic peptide, wherein the antigenic peptide is a tumor neoantigen, (iv) the second universal target peptide, (v) the β2M peptide comprising the sequence shown in SEQ ID NO: 105, and (vi) the MHC peptide comprising a sequence shown in SEQ ID NOs: 38-103.

Universal Sequences

An antigenic peptide is generally flanked by universal target sequences or portions thereof. These sequences allow for rapid, high throughput methods for replacing or inserting the antigenic peptide encoding nucleotide in the polynucleotide MHC template. Universal sequences may comprise restriction sites for restriction digest-based cloning. Exemplary restriction sites include, but are not limited to, NotI, BamHI, BlpI, BspEI, BstBI, XbaI, HindIII, EcoRI, ApaI, NotI, and any combination thereof. In certain aspect, one or more universal target sequences are not present in the genetic material being manipulated, e.g., to reduce or eliminate off-target effects and/or to increase specificity.

Universal target sequences may be 4-100, between 4-15, between 15-40, between 15-35, between 15-30, between 20-40, between 25-40, between 30-40, between 15-75, between 50-100, between 50-75, between 75-100, between 25-50, between 40-50, between 50-60, between 60-70, between 70-80, between 80-90, or between 90-100 nucleotides in length. Universal sequences may be at least 4, at least 10, at least 15, at least 20, at least 25, at least 30, at least 35, at least 40, at least 45, at least 50, at least 60, at least 70, at least 80, at least 90, or at least 100 nucleotides in length. In some embodiments, the universal target sequence is 4-8 nucleotides in length, e.g., 4, 5, 6, 7, or 8. In other embodiments, the universal target sequence is between 25-35 nucleotides in length, e.g., 25, 26, 27, 28, 29, 30, 31, 32, 33, 34, or 35 nucleotides. In other embodiments, the universal target sequence is between 35-75 nucleotides in length, e.g., 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 nucleotides. In other embodiments, the universal target sequence is at least about 15 nucleotides in length. In some embodiments, the polynucleotide comprises at least two universal target sequences that are not the same. In some embodiments, the polynucleotide comprises at least two universal target sequences that are the same.

Exemplary universal target sequences are shown in Table 2:

TABLE 2

Universal Target Sequences

| SEQ ID NO. | Restriction Site | Sequence |
|---|---|---|
| 3 | BlpI | CGTGGTTACAGGAGGGCTCAGCA |
| 4 | BamHI | GGATGCGGAGGATCCGGCG |
| 5 | BamHI | GGAAGCGGAGGATCCGGCG |
| 6 | BamHI | GGAAGCGGAGGATCCACCAGC |

In some embodiments, the universal target sequences comprise polymerase chain reaction (PCR) primer target sequences or primer binding sites. Universal primer sequences known in the art may be used in the compositions and methods disclosed herein, or the sequences may be different than the previously described universal primer sequences.

In some embodiments, the first and/or second universal target sequences comprise restriction enzyme cleavage sites.

Linkers

In various embodiments, a comPACT can comprise a first flexible linker interposed between the antigenic peptide segment and the β2-microglobulin segment. Such linkers can extend from and connect the carboxyl terminal of the antigenic peptide segment to the amino terminal of the β2-microglobulin segment, or vice versa. Without being limited by theory, when a comPACT is expressed, the linked peptide ligand can fold into the binding groove resulting in a functional comPACT protein. In various embodiments, this linker can comprise at least about 4 amino acids, up to about 20 amino acids, e.g., 4, 5, 6, 7, 8, 9, 10, 11, 12, 13, 14, 15, 16, 17, 18, 19, or 20 amino acids.

In various embodiments, a comPACT can comprise a second flexible linker interposed between the β2-microglobulin segment and the MHC heavy chain segment. Such linkers can extend from and connect the carboxyl terminal of the β2-microglobulin segment to the amino terminal of the heavy chain segment, or vice versa. Without being limited by theory, when a comPACT is expressed, the β2-microglobulin and the heavy chain can fold into the binding groove resulting in a molecule which can function in promoting T cell expansion. In various embodiments, this linker can comprise at least about 4 amino acids, up to about 20 amino acids, e.g., 4, 5, 6, 7, 8, 9, 10, 11, 12, 13, 14, 15, 16, 17, 18, 19, or 20 amino acids.

In various embodiments, a comPACT can comprise a third flexible linker interposed between the MHC heavy chain segment and the purification cluster. Such linkers can extend from and connect the carboxyl terminal of the heavy chain segment and the amino terminus of the purification cluster, or vice versa.

Any appropriate flexible linker sequence known in the art may be used. Such linker sequences include, but are not limited to, glycine-serine sequences comprising one or more repeating units of a GS, SG, GGGGS (G$_4$S), GGGS (G$_3$S), GSGGS, or GCGGS sequence motifs. Multiple consecutive units of the linker sequence motif may be used. In some embodiments, the flexible linker sequence comprises 1, 2, 3, 4, 5, 6, 7, 8, or 10 repeating units of an appropriate linker sequence.

Linkers can also comprise cysteine residues for disulfide bonds between the linker sequence and the MHC allele sequence, such that the cysteine residues form a disulfide trap. In some embodiments, the linker sequence or second universal target peptide comprises a cysteine residue. In some embodiments, the linker sequence or second universal target peptide comprises a cysteine residue that forms a disulfide bond with the MHC allele.

Signal Sequences

In various embodiments, the comPACT polynucleotide and polypeptide may comprise a signal sequence, e.g., encoding a signal peptide in the case of a polynucleotide. The signal sequence can be a secretion signal sequence. Secretion signal sequences direct translated proteins in mammalian cells through the secretory pathway, and ensure that the translated proteins are subject to cellular quality control. Inclusion of secretory signals can ensure that the comPACT proteins are secreted into the cellular media, such that they are homogenously well-folded and more easily isolated from the media or clarified supernatant.

In one embodiment, the signal sequence is a signal sequence from Human Growth Hormone (hGH). In another embodiment, the signal sequence is a signal sequence from hIG1 Kappa light chain, Beta 2 microglobulin (β2M), or IL2 signal sequence. Additional signal sequences may also be used, including a signal sequence from β2M (e.g., human β2M) or any other eukaryotic or prokaryotic signal sequence known in the art.

The signal sequence may be between 10-100, 10-20, 10-50, 10-40, 20-40, 20-60, 40-90, 40-60, 45-70, 50-80, 60-90, 55-70, 60-80, 70-80, 50-100, 60-100, 70-100, 80-100, or 90-100 nucleotides in length. The signal peptide may be between 3-33, 3-10, 10-30, 10-20, 15-30, or 20-30 amino acids in length.

Exemplary signal sequences are shown in Table 3:

TABLE 3

| SEQ ID NO. | Signal Protein | Sequence |
|---|---|---|
| | Signal Sequence | |
| 1 | Human Growth Hormone nucleotide | ATGGCGACGGGTTCAAGAACTTCCCTA CTTCTTGCATTTGGCCTGCTTTGTTTG CCGTGGTTACAGGAGGGCTCAGCA |
| 2 | Human Growth Hormone peptide | MATGSRTSLLLAFGLLCLPWLQEGSA |

TABLE 3-continued

| SEQ ID NO. | Signal Protein | Sequence |
|---|---|---|
| | Signal Sequence | |
| 23 | hIG1 Kappa light chain, signal sequence | MDMRVPAQLLGLLLLWLSGARC |
| 24 | hIG1 Kappa light chain, signal sequence | atggatatgcgcgtgccggcgcagct gctgggcctgctgctgctgtggctga gcggcgcgcgctgc |
| 25 | B2M, signal sequence peptide | MSRSVALAVL ALLSLSGLEA |
| 26 | B2M, signal sequence | atgagccgcagcgtggcgctggcggt gctggcgctgctgagcctgagcggcc tggaagcg |
| 27 | IL2, signal sequence | MYRMQLLSCI ALSLALVTNS |
| 28 | IL2, signal sequence | atgtatcgcatgcagctgctgagctg cattgcgctgagcctggcgctggtga ccaacagc |

In some embodiments, the signal sequence comprises a sequence comprising the sequence shown in SEQ ID NOs: 1, 24, 26, or 28. In some embodiments, the signal sequence comprises a sequence comprising the sequence shown in SEQ ID NOs: 2, 23, 25, or 27. In one embodiment, the signal sequence encodes the Human Growth Hormone (HGH) signal sequence. In another embodiment, the signal sequence comprises the sequence shown in SEQ ID NO: 1. In another embodiment, the signal sequence comprises the sequence shown in SEQ ID NO: 2.

Promoters

A comPACT polynucleotide composition may further comprise a promotor, e.g., for transcription of an mRNA transcript that can be translated by a host cell. Promoters may be prokaryotic or eukaryotic (e.g., mammalian) in origin. Any appropriate promoter for gene transcription in a cell may be used, such as EF1α, cytomegalovirus (CMV), or SV40. In some embodiments, the comPACT polynucleotide comprises a CMV promoter.

In various embodiments, the 5' end of the polynucleotide sequence further comprises a promoter sequence linked to the 5' end of the first universal target. In some embodiments, the promoter sequence is selected from the group consisting of CMV, EF1α, and SV40 promoters. In one embodiment, the promoter sequence is a CMV promoter sequence. In one embodiment, the promoter sequence comprises a sequence comprising the sequence shown in SEQ ID NO: 37.

Affinity Tags

A comPACT polynucleotide composition may further comprise at least one sequence that encodes for an affinity tag or peptide. In some embodiments, the comPACT polynucleotide comprises at least two affinity tags or peptide sequences.

Any appropriate affinity tag or peptide may be used in a comPACT polynucleotide or polypeptide. Such peptides include, but are not limited to, AviTag, streptavidin-tag, polyhistidine (His6)-tag, FLAG-tag, HA-tag, and Myc-tag. The sequences in the polynucleotide comPACT gene are typically translated into peptides in the comPACT polypeptide. These epitopes may be used for affinity chromatography purification or quantification of the expressed comPACT polypeptide. For instance, the His6 tag may be used to purify the comPACT protein via Ni-NTA affinity chromatography. In some embodiments, the His6 tag may be a concatenated His6 tag, comprising multiple His6 units, with an optional linker sequence. The first and second affinity tags can be the same, i.e. both His6 tags, or both HA tags, or they can be different tags, i.e. a streptavidin-tag and a His6 tag.

In addition, the AviTag encodes a biotinylation site that is recognized by BirA enzyme. Inclusion of this peptide sequence in a protein allows for biotinylation of the sequence via enzymatic modification by BirA. Thus, a comPACT polypeptide comprising an AviTag sequence and a His6 tag may be biotinylated, purified via Ni-NTA affinity chromatography via the His6 tag, and the purity or quantity of the purified protein assessed via biotin visualization with streptavidin or other avidin reagents.

In some embodiments, the comPACT polynucleotide comprises an AviTag sequence. In some embodiments, the comPACT polypeptide comprises an AviTag peptide. In some embodiments, the comPACT polynucleotide comprises a His6 sequence. In some embodiments, the comPACT polypeptide comprises a His6 peptide. In some embodiments, the comPACT polypeptide comprises a concatenated His6 peptide. In some embodiments, the comPACT polynucleotide comprises an AviTag sequence and a His6 sequence. In some embodiments, the comPACT polynucleotide comprises an AviTag sequence and a concatenated His6 sequence. In some embodiments, the comPACT polypeptide comprises an AviTag peptide and a His6 peptide. In some embodiments, the comPACT polypeptide comprises an AviTag peptide and a concatenated His6 peptide.

In some embodiments, the first and second affinity tags are selected from the group consisting of: AviTag, streptavidin-tag, polyhistidine (His6)-tag, FLAG-tag, HA-tag, and Myc-tag.

In some embodiments, the comPACT polynucleotide comprises a FLAG sequence. In some embodiments, the comPACT polypeptide comprises a FLAG peptide. In some embodiments, the comPACT polynucleotide comprises an HA sequence. In some embodiments, the comPACT polypeptide comprises an HA peptide. In some embodiments, the comPACT polynucleotide comprises a Myc sequence. In some embodiments, the comPACT polypeptide comprises a Myc peptide. In some embodiments, the comPACT polynucleotide comprises a streptavidin sequence. In some embodiments, the comPACT polypeptide comprises a streptavidin peptide. In some embodiments, the comPACT polynucleotide comprises an AviTag sequence and a FLAG sequence. In some embodiments, the comPACT polypeptide comprises an AviTag peptide and a FLAG peptide. In some embodiments, the comPACT polynucleotide comprises an AviTag sequence and an HA sequence. In some embodiments, the comPACT polypeptide comprises an AviTag peptide and an HA peptide. In some embodiments, the comPACT polynucleotide comprises an AviTag sequence and a streptavidin sequence. In some embodiments, the comPACT polypeptide comprises an AviTag peptide and a streptavidin peptide.

In some embodiments, the first affinity tag sequence encodes for an AviTag peptide, the protease cleavage site sequence encodes for a TEV cleavage site, and the second affinity tag encodes for a FLAG peptide. In some embodiments, the purification cluster comprises an AviTag peptide, a TEV cleavage site, and a FLAG peptide. In some embodiments, the first affinity tag sequence encodes for an AviTag peptide, the protease cleavage site sequence encodes for a TEV cleavage site, and the second affinity tag encodes for an HA peptide. In some embodiments, the purification cluster comprises an AviTag peptide, a TEV cleavage site, and an HA epitope. In some embodiments, the first affinity tag sequence encodes for an AviTag peptide, the protease cleavage site sequence encodes for a TEV cleavage site, and the second affinity tag encodes for a Myc peptide. In some embodiments, the purification cluster comprises an AviTag peptide, a TEV cleavage site, and a Myc peptide. In some embodiments, the first affinity tag sequence encodes for an AviTag peptide, the protease cleavage site sequence encodes for a TEV cleavage site, and the second affinity tag encodes for a streptavidin peptide. In some embodiments, the purification cluster comprises an AviTag peptide, a TEV cleavage site, and a streptavidin peptide.

In some embodiments, the first affinity tag sequence encodes for a His peptide. In some embodiments, the first affinity tag sequence encodes for a FLAG peptide. In some embodiments, the first affinity tag sequence encodes for an HA peptide. In some embodiments, the first affinity tag sequence encodes for a Myc peptide. In some embodiments, the first affinity tag sequence encodes for a streptavidin peptide. In some embodiments, the purification cluster comprises a His peptide. In some embodiments, the purification cluster comprises a FLAG peptide. In some embodiments, the purification cluster comprises an HA peptide. In some embodiments, the purification cluster comprises a Myc peptide. In some embodiments, the purification cluster comprises a streptavidin peptide.

Protease Cleavage Sites

A comPACT polynucleotide composition may further comprises a sequence that encodes for a protease cleavage site, e.g., in the purification cluster. This cleavage site may be encoded between the first and second affinity tag sequences and allow for cleavage of the second affinity tag from the comPACT protein once the comPACT has been expressed and under gone a round of purification. Any appropriate protease cleavage site known in the art may be used, including, but not limited, cleavage sites that are recognized by TEV, thrombin, Factor Xa, enteropeptidases, and rhinovirus 3C protease, among others.

In one embodiment, the protease cleavage site sequence is a TEV cleavage site sequence, a thrombin cleavage site sequence, a Factor Xa cleavage site sequence, an enteropeptidase cleavage site sequence, and/or a rhinovirus 3C protease cleavage site sequence. In one embodiment, the protease cleavage site nucleotide sequence encodes for a TEV cleavage site. In another embodiment, the comPACT polypeptide comprises a TEV protease cleavage site, ENLYFQG. In one embodiment, the protease cleavage site nucleotide sequence encodes for a Factor Xa cleavage site. In one embodiment, the protease cleavage site nucleotide sequence encodes for a rhinovirus 3C cleavage site. In one embodiment, the protease cleavage site nucleotide sequence encodes for a enteropeptidase cleavage site. In one embodiment, the protease cleavage site nucleotide sequence encodes for a thrombin cleavage site.

In some embodiments, the first affinity tag sequence encodes for an AviTag peptide, the protease cleavage site sequence encodes for a TEV cleavage site, and the second affinity tag encodes for a His6 peptide. In some embodiments, the purification cluster comprises an AviTag epitope, a TEV cleavage site, and a His6 epitope. In some embodiments, the first affinity tag sequence encodes for an AviTag peptide, the protease cleavage site sequence encodes for a thrombin cleavage site, and the second affinity tag encodes for a His6 peptide. In some embodiments, the purification cluster comprises an AviTag epitope, a thrombin cleavage site, and a His6 epitope. In some embodiments, the first affinity tag sequence encodes for an AviTag peptide, the protease cleavage site sequence encodes for a Factor Xa cleavage site, and the second affinity tag encodes for a His6 peptide. In some embodiments, the purification cluster comprises an AviTag epitope, a Factor Xa cleavage site, and a His6 epitope. In some embodiments, the first affinity tag sequence encodes for an AviTag peptide, the protease cleavage site sequence encodes for an enteropeptidase cleavage site, and the second affinity tag encodes for a His6 peptide. In some embodiments, the purification cluster comprises an AviTag epitope, an enteropeptidase cleavage site, and a His6 epitope. In some embodiments, the first affinity tag sequence encodes for an AviTag peptide, the protease cleavage site sequence encodes for a rhinovirus 3C cleavage site, and the second affinity tag encodes for a His6 peptide. In some embodiments, the purification cluster comprises an AviTag epitope, a rhinovirus 3C cleavage site, and a His6 epitope.

PolyA Tail

A comPACT polynucleotide composition may further comprise a polyadenylation (polyA) tail. Mammalian, eukaryotic, or prokaryotic polyA sequence motifs may be used. This sequence may be included when the comPACT polynucleotide is assembled via PCR for direct transfection into a host cell (e.g., not in the context of an expression construct or vector). Any appropriate polyA tail and sequence motif may be used in the comPACT polynucleotide, including, but not limited to, SV40, hGH, bGH, and rbGlob sequences. Such sequences include the RNA sequence motif: AAUAA. In one embodiment, the polyA sequence comprises a bGH polyA sequence. In one embodiment, the polyA sequence is selected from a bGH polyA sequence, an SV40 polyA sequence, an hGH polyA sequence, and an rbGlob polyA sequence. In one embodiment, the polyA sequence comprises an SV40 polyA sequence. In one embodiment, the polyA sequence comprises an hGH polyA sequence. In one embodiment, the polyA sequence comprises an rbGlob polyA sequence.

Antigenic Sequences

Antigenic sequences may be between 5-100, between 5-10, between 10-20, between 10-30, between 10-40, between 10-50, between 10-60, between 10-70, between 10-80, between 10-90, between 10-100, between 20-100, between 30-100, between 40-100, between 50-100, between 60-100, between 70-100, between 80-100, between 90-100, between 20-40, between 20-50, between 20-60, between 20-70, between 20-80, between 20-19, between 20-100, between 20-30, between 25-35, between 20-45, between 30-45, between 30-50, between 30-60, between 30-70, between 30-80, between 30-90, between 30-100, between 40-50, between 40-60, between 45-60, between 40-70, between 40-80, between 40-90, between 40-100, between 50-60, between 50-70, between 50-80, between 50-90, between 50-100, between 60-70, between 60-80, between 60-90, between 60-100, between 70-80, between 80-90, between 80-100, or between 90-100 nucleotides in length. Antigenic sequences may be at least 5, 10, 15, 20, 25, 30, 35, 40, 45, 50, 55, 60, 65, 70, 75, 80, 85, 90, 95, or 100 nucleotides in length. The antigenic peptide may be between 3-50, between 3-10, between 5-15, between 7-15, between 5-20, between 7-20, between 10-15, between 10-20, between 15-20, between 20-25, between 20-30, between 25-35, between 30-40, or between 40-50 amino acids in length. The antigenic peptide may be 5, 6, 7, 8, 9, 10, 11, 12, 13, 14, 15, 16, 17, 18, 19, or 20 amino acids in length. The antigenic peptide may include a tumor antigen, a neoantigen, a tumor neoantigen, a viral antigen, bacterial antigen, phosphoantigen, or a microbial antigen. In one embodiment, the antigenic peptide is a neoantigen. The antigenic peptides may be selected from patient data to select antigens with one or more somatic mutations. The prediction of the antigenic peptide may include a predicative algorithm and predict binding of the antigenic peptide or neoantigen and an HMC allele. Prediction of the antigenic peptide is further discussed below.

In some embodiments, the nucleotide sequence encoding an antigenic peptide is between 20-60, between 20-30, between 25-35, between 20-45, between 30-45, between 40-60, or between 45-60 nucleotides in length. In other embodiments, the nucleotide sequence encoding an antigenic peptide is between 20-30 nucleotides in length. In some embodiments, the antigenic peptide is 7-15 amino acids, 7-10, 8-9, 7, 8, 9, 10, 11, 12, 13, 14, or 15 amino acids in length. In some embodiments, the antigenic peptide is 5, 6, 7, 8, 9, 10, 11, 12, 13, 14, 15, 16, 17, 18, 19, 20, 21, 22, 23, 24, 25, 26, 27, 28, 29, or 20 amino acids in length.

Biotinylation

The comPACT proteins described herein may further be biotinylated via any appropriate method. One such method utilizes the BirA Biotin-protein ligase and is commercially available. A specific amino acid sequence, known as the AvtiTag sequence (GLNDIFEAQKIEWHE), is encoded in the protein of interest. BirA ligase, d-biotin and ATP are added to a reaction mixture containing the protein of interest. BirA covalently ligates the biotin to the lysine in the AviTag sequence, thereby biotinylating the protein of interest. The newly biotinylated protein can then be purified and used in downstream applications. Other methods known in the art to biotinylate proteins may also be utilized.

In some embodiments, the comPACT proteins are biotinylated after protein purification with a purified BirA protein. In some embodiments, the comPACT proteins are biotinylated in cell lysate during protein purification with a purified BirA protein. Such methods using purified BirA and purified or partially purified comPACT proteins are termed "in vitro" biotinylation. In some embodiments, the comPACT proteins are biotinylated during protein production in the cell, by a cell-expressed BirA protein in the cell cytoplasm, on the cell surface, or secreted into the cell culture media. Such methods using cell-expressed BirA and unpurified comPACT proteins are termed "in vivo" biotinylation.

Expression Constructs and Vectors

The comPACT polynucleotide molecules can be inserted into expression constructs or vectors, e.g., for plasmid and protein production. The expression construct or vector can be a plasmid or a viral vector. Any suitable expression construct or vector known in the art may be used, including bacterial expression plasmids, such as *Escherichia coli* or *Bacillus subtilis* plasmids; eukaryotic expression vectors, such as *Pichia pastoris* expression vectors; or viral vectors, such as lentiviral vectors, vaccinia vectors, or baculovirus vectors. Mammalian expression vectors for use in cultured mammalian cell lines such as Chinese hamster ovary (CHO), HEK293, Expi293, or any other suitable mammalian cell line are also contemplated. Additionally, the expression construct or vector may comprise a nucleotide barcode. The nucleotide barcode can be unique for each expression construct or vector. In some embodiments, the nucleotide sequences encoding for the signal sequence, beta-2-microglobulin, and MHC allele can be ligated into an expression construct or vector with a non-coding or dummy antigen insert. This non-coding antigen insert can then be removed by an appropriate cloning technique, such as restriction digest, and a desired antigen sequence inserted via ligation or any other appropriate cloning technique.

In some aspects, provided herein are a library comprising greater than or equal to two distinct vectors encoding different MHC alleles.

Host Cells

In another aspect, provided herein are host cells comprising the polynucleotide molecule or the expression construct as described herein. The host cell can be any suitable host cell know in the art, including, but not limited to bacterial cells such as *Escherichia coli* or *Bacillus subtilis*, or eukaryotic host cells such as Chinese hamster ovary (CHO), HEK293, Expi293, HeLa, insect cell lines such as Sf9 or Sf12, or yeast cells such as *Pichia pastoris*. The host cells may also stably express the biotinylation enzyme BirA. The host cell can be a primary cell or an immortalized cell.

In some embodiments, the polynucleotide is integrated into the cell genome. In some embodiments, the polynucleotide is extrachromosomal. In some embodiments, the host cell is a mammalian cell. In some embodiments, the cell is a human cell. In some embodiments, the cell is selected from the group consisting of: a stem cell, a tumor cell, an immortalized cell, and a fetal cell. In some embodiments, the host cell is a prokaryotic cell. In some embodiments, cell is an *Escherichia coli* cell. In some embodiments, the cell expresses a BirA protein or fragment thereof.

Libraries

Also considered are libraries comprising greater than or equal to two distinct comPACT polynucleotide molecules, polypeptide molecules, or polypeptides molecules attached to particles. The library may comprise 2 to 1000 molecules. In some embodiments, the library comprises between 2-900, 2-800, 2-700, 2-600, 2-500, 2-480, 2-400, 2-300, 2-200, 2-100, 2-50, 2-66, 2-48, 2-30, 2-20, 2-19, 10-1000, 10-900, 10-800, 10-700, 10-600, 10-500, 10-480, 10-400, 10-300, 10-200, 10-100, 10-50, 10-66, 10-48, 10-30, 10-20, 20-1000, 20-900, 20-800, 20-700, 20-600, 20-500, 20-480, 20-400, 20-300, 20-200, 20-100, 20-50, 20-50, 20-66, 20-48, 20-30, 30-1000, 30-900, 30-800, 30-700, 30-600, 30-500, 30-480, 30-400, 30-300, 30-200, 30-100, 30-50, 30-50, 30-66, 30-48, 30-40, 40-1000, 40-900, 40-800, 40-700, 40-600, 40-500, 40-480, 40-400, 40-300, 40-200, 40-100, 40-60, 40-50, 40-66, 40-48, 50-1000, 50-900, 50-800, 50-700, 50-600, 50-500, 50-480, 50-400, 50-300, 50-200, 50-100, 50-60, 50-66, 60-1000, 60-900, 60-800, 60-700, 60-600, 60-500, 60-480, 60-400, 60-300, 60-200, 60-100, 70-1000, 70-900, 70-800, 70-700, 70-600, 70-500, 70-480, 70-400, 70-300, 70-200, 70-100, 70-80, 70-90, 80-1000, 80-900, 80-800, 80-700, 80-600, 80-500, 80-480, 80-400, 80-300, 80-200, 80-100 polynucleotide or polypeptide molecules. In some embodiments, the library comprises between 2-19, 48-480, between 48-66, between 66-480, between 220-240, between 40-60, between 48-66, between 50-70, or between 60-80 polynucleotide or polypeptide molecules. In some embodiments, the library comprises at least 2, 5, 10, 15, 20, 25, 30, 35, 40, 45, 48, 50, 55, 60, 65, 66, 70, 75, 80, 85, 90, 100, 110, 120, 130, 140, 150, 160, 170, 180, 190, 200, 225, 250, 275, 300, 325, 350, 375, 400, 425, 450, 475, 500, 525, 550, 600, 562, 650, 675, 700, 725, 750, 775, 800, 825, 850, 875, 900, 925, 950, 975, or 1000 comPACT polynucleotide or polypeptide molecules. In some embodiments, the library comprises 2, 10, 15, 20, 24, 48, 66, 100, 200, 300, 400, 500, 600, 700, 800, 900, or 1000 comPACT polynucleotide or polypeptide molecules. The molecules may be polynucleotides, polypeptides, or polypeptides attached to particles. In some embodiments, the greater than or equal to two polynucleotide or polypeptide molecules have distinct antigenic peptide sequences. In some embodiments, the greater than or equal to two molecules have distinct antigenic peptide sequences and distinct MHC molecules.

In some embodiments, the library comprises greater than or equal to two distinct polynucleotide molecules, wherein each distinct polynucleotide molecule comprises (i) the first universal sequence, (ii) the nucleotide sequence encoding a antigenic peptide, wherein the nucleotide sequence is not the same for each of the greater than or equal to two polynucleotide molecules (iii) the second universal target sequence, (iv) the β2M sequence, and (v) the MHC allele sequence. In some embodiments, the MHC allele sequence is not the same for each of the greater than or equal to two polynucleotide molecules.

In one embodiment, the library comprises at least two or more of the HLA-A*01:01, HLA-A*02:01, HLA-A*03:01, HLA-A*24:02, HLA-A*30:02, HLA-A*31:01, HLA-A*32:01, HLA-A*33:01, HLA-A*68:01, HLA-A*11:01, HLA-A*23:01, HLA-A*30:01, HLA-A*33:03, HLA-A*25:01, HLA-A*26:01, HLA-A*29:02, HLA-A*68:02, HLA-B*07:02, HLA-B*14:02, HLA-B*18:01, HLA-B*27:02, HLA-B*39:01, HLA-B*40:01, HLA-B*44:02, HLA-B*46:01, HLA-B*50:01, HLA-B*57:01, HLA-B*58:01, HLA-B*08:01, HLA-B*15:01, HLA-B*15:03, HLA-B*35:01, HLA-B*40:02, HLA-B*42:01, HLA-B*44:03, HLA-B*51:01, HLA-B*53:01, HLA-B*13:02, HLA-B*15:07, HLA-B*27:05, HLA-B*35:03, HLA-B*37:01, HLA-B*38:01, HLA-B*41:02, HLA-B*44:05, HLA-B*49:01, HLA-B*52:01, HLA-B*55:01, HLA-C*02:02, HLA-C*03:04, HLA-C*05:01, HLA-C*07:01, HLA-C*01:02, HLA-C*04:01, HLA-C*06:02, HLA-C*07:02, HLA-C*16:01, HLA-C*03:03, HLA-C*07:04, HLA-C*08:01, HLA-C*08:02, HLA-C*12:02, HLA-C*12:03, HLA-C*14:02, HLA-C*15:02, and HLA-C*17:01 alleles. In one embodiment, the library comprises at least HLA-A*01:01, HLA-A*02:01, HLA-A*03:01, HLA-A*24:02, HLA-A*30:02, HLA-A*31:01, HLA-A*32:01, HLA-A*33:01, HLA-A*68:01, HLA-A*11:01, HLA-A*23:01, HLA-A*30:01, HLA-A*33:03, HLA-A*25:01, HLA-A*26:01, HLA-A*29:02, HLA-A*68:02, HLA-B*07:02, HLA-B*14:02, HLA-B*18:01, HLA-B*27:02, HLA-B*39:01, HLA-B*40:01, HLA-B*44:02, HLA-B*46:01, HLA-B*50:01, HLA-B*57:01, HLA-B*58:01, HLA-B*08:01, HLA-B*15:01, HLA-B*15:03, HLA-B*35:01, HLA-B*40:02, HLA-B*42:01, HLA-B*44:03, HLA-B*51:01, HLA-B*53:01, HLA-B*13:02, HLA-B*15:07, HLA-B*27:05, HLA-B*35:03, HLA-B*37:01, HLA-B*38:01, HLA-B*41:02, HLA-B*44:05, HLA-B*49:01, HLA-B*52:01, HLA-B*55:01, HLA-C*02:02, HLA-C*03:04, HLA-C*05:01, HLA-C*07:01, HLA-C*01:02, HLA-C*04:01, HLA-C*06:02, HLA-C*07:02, HLA-C*16:01, HLA-C*03:03, HLA-C*07:04, HLA-C*08:01, HLA-C*08:02, HLA-C*12:02, HLA-C*12:03, HLA-C*14:02, HLA-C*15:02, and HLA-C*17:01 alleles.

In some embodiments, the library comprises greater than or equal to two distinct polypeptide molecules, wherein the antigenic peptide is not the same for each of the greater than or equal to two polypeptide molecules, and wherein each distinct polypeptide is attached to a particle. In some embodiments, the library further comprises a unique defined barcode sequence operably associated with the identity of each distinct polypeptide.

Embodiments can include barcoded polynucleotides comprising a defined barcode sequence. The barcoded polynucleotides can be a polynucleotide that provides a unique antigen-specific sequence for identification after T cell isolation. Therefore, each unique comPACT is attached to a particle with a unique defined barcode sequence. This allows an operative association between a given antigen and a given barcode that is unique to the pair.

The barcoded polynucleotides can be ssDNA or dsDNA. The polynucleotides comprising the barcodes can be modified at their 5' end to comprise an attachment moiety for attachment to a particle. For example, the polynucleotides comprising the barcode sequences are conjugated to a biotin molecule for binding to a streptavidin-core attached to a particle, such as dextran. However any suitable attachment moiety may be used for attachment of polynucleotides to a particle. As described herein and as understood by a person skilled in the art, suitable attachment moiety pairs are known in the art. Non-limiting examples of attachment moieties include thiol, maleimide, adamantane, cyclodextrin, amine, carboxy, azide, and alkyne.

Particles

As used herein, "nanoparticles" or alternatively "particles" refer to substrates capable of being specifically sorted or isolated, and to which other entities can be attached. In some embodiments, the nanoparticle is magnetic, e.g., for isolation using a magnet. In some embodiments, the magnetic nanoparticle comprises magnetic iron oxide. Examples of magnetic particles include, but are not limited to, Dynabeads™ (Thermo Fisher). In some embodiments, the nanoparticle is a polystyrene particle, e.g., for isolation by gravity. In other embodiments, the particle can be a surface, a bead, or a polymer. Examples of beads include, but are not limited to, agarose beads and sepharose beads. In particular embodiments, the particle or nanoparticle can be fluorescent or attached to a fluorophore directly or indirectly.

According to certain embodiments, the nanoparticle is modified with an attachment moiety for attaching additional molecules. Modification of the nanoparticle includes an attachment moiety that can pair with (e.g., covalently bind to) a corresponding cognate (e.g., complementary) attachment moiety attached to polynucleotides. Any suitable pair of attachment moieties may be used to modify the nanoparticle and the polynucleotide detection tag for attachment. Non-limiting examples of attachment moiety pairs include a streptavidin/biotin system, a thiol group (e.g., cysteine) and maleimide, adamantane and cyclodextrin, an amino group and a carboxy group, and an azido group and alkynl group. In some embodiments, the attachment moiety can comprise a cleavage moiety. In other embodiments, the attachment moiety bound to complementary cognate attachment moiety can be reversible, such as a reducible thiol group. In an exemplary embodiment, the modified nanoparticle is a streptavidin coated magnetic nanoparticle, such as 1 µm nanoparticles (e.g., Dynabeads™ MyOne™ Streptavidin T1 beads from ThermoFisher Scientific), and the polynucleotides can be biotinylated for attachment to the modified nanoparticle.

The particle can be a dextran, such as a biotinylated dextran or streptavidin coated dextran. Modified dextrans are described in further detail in Bethune et al., *BioTechniques* 62:123-130 March 2017 and US Publication No. 2015/0329617, herein incorporated by reference in its entirety. Biotinylated comPACTs can be attached to streptavidin coated dextran.

The comPACTs can also be assembled into tetramers, comprising 1, 2, 3, or 4 biotinylated comPACT proteins bound to a streptavidin core. The tetramer can also comprise a fluorophore, such as phycoerythrin (PE) or allophycocyanin (APC) bound to the streptavidin core. MHC class I and II tetramers are well known in the art. MHC class I tetramers are described in further detail in Burrow S R et al, *J Immunol* Dec. 1, 2000, 165 (11) 6229-6234 and MHC class II tetramers are described in further detail in Nepom G T, *J Immunol Mar.* 15, 2012, 188 (6) 2477-2482, both of which are herein incorporated by reference in their entirety.

ComPACT proteins can also be assembled into multimers. In some embodiments, the comPACT protein multimers can be a dimer, trimer, tetramer, pentamer, hexamer, or higher order multimer. In some embodiments, a multimer can comprise at least two or more comPACT proteins. In some embodiments, a multimer can comprise at least 2, 3, 4, 5, 6, 7, 8, 9, or 10 comPACT proteins.

Methods of Producing

Antigen Prediction

To manufacture a comPACT, one of the initial steps can include identification of the patient's tumor-specific antigens (e.g., neoantigens). The compositions produced by this method can then be utilized in a T-cell mediated immunity process, e.g., for patient-specific cancer immunotherapy. For identification of a patient's putative neoantigens (tumor or pathogen), in silico predictive algorithmic programs can be utilized that analyze the tumor, viral, or bacterial sequencing data including whole genome, whole exome, or transcriptome sequencing data, to identify one or more mutations corresponding to putatively expressed neoantigens. Additionally, human leukocyte antigen (HLA) typing can be determined from a tumor or blood sample of the patient, and this HLA information can be utilized together with the identified putative neoantigen peptide sequences in a predictive algorithm for MHC binding, as verified by Fritsch et al., 2014, *Cancer Immunol Res.*, 2:522-529, the entire contents of which are herein incorporated by reference. HLAs commonly found in the human population can also be included in neoantigen prediction algorithms, such as HLA-A*02, 24, 01; HLA-B*35, 44, 51; DRB1*11, 13, 07 in Caucasians, HLA-A*02, 03, 30; HLA-B*35, 15, 44; DRB1*13, 11, 03 in afro-Brazilians, and HLA-A*24, 02, 26; HLA-B*40, 51, 52; DRB1*04, 15, 09 in Asians. Specific pairing of HLA alleles can also be used. Common alleles found in the human population is further described in Bardi et al. (Rev Bras Hematol Hemoter. 2012; 34(1): 25-30.)

Additional examples of methods to identify neoantigens include combining sequencing with mass-spectrometry and MHC presentation prediction (e.g., US Publication No. 2017/0199961), and combining sequencing with MHC binding affinity prediction (e.g., issued U.S. Pat. No. 9,115,402). In addition, methods useful for identifying whether neoantigen specific T cells are present in a patient sample can be used in combination with the methods described here, e.g., as described in US Publication No. 2017/0003288 and PCT/US17/59598, herein incorporated by reference in their entirety. These analyses result in a ranked list of the patient's candidate neoantigen peptides which can be readily synthesized using routine methods for screening of cognate antigen-specific T cells.

Primer Annealing and Restriction Digest Assembly

In general, preparation of a comPACT polynucleotide can be accomplished by procedures disclosed herein and by recognized recombinant DNA techniques, e.g., preparation of plasmid DNA, cleavage of DNA with restriction enzymes, ligation of DNA, transformation or transfection of a host, culturing of the host, and isolation and purification of the expressed fusion complex. Such procedures are generally known and disclosed in standard references such as in Sambrook et al., supra.

In some aspects, DNA encoding an MHC class I heavy chain can be obtained from a suitable cell line such as, for example, human lymphoblastoid cells. In various configurations, a gene or cDNA encoding a class I heavy chain can be amplified by the polymerase chain reaction (PCR) or other means known in the art. In some aspects, a PCR product can also include sequences encoding linkers, and/or one or more restriction enzyme sites for ligation of such sequences.

In some embodiments, a vector encoding a comPACT polynucleotide can be prepared by ligation of sequences encoding the MHC heavy chain and the β2-microglobulin to a sequence encoding an antigen peptide. DNA encoding the antigen peptide can be obtained by isolating DNA from natural sources or by known synthetic methods, e.g., the phosphate triester method. See, e.g., Oligonucleotide Synthesis, IRL Press (M. Gait, ed., 1984). Synthetic oligonucleotides can also be prepared using commercially available automated oligonucleotide synthesizers. A DNA sequence encoding a universal target sequence as discussed herein can be interposed between a sequence encoding a signal sequence and an sequence encoding an antigenic peptide and a second universal target sequence can be interposed between the sequence encoding an antigen peptide segment and a sequence encoding a β2-microglobulin segment. In some embodiments, the segments can be joined using a ligase. In some embodiments, the sequence encoding an antigen peptide can be phosphorylated with a suitable polynucleotide kinase. In some embodiments the polynucleotide kinase is the T4 polynucleotide kinase. Any appropriate polynucleotide kinase known in the art may be used, including but not limited to T4 polynucleotide kinase, also known as T7 polynucleotide kinase.

PCR Assembly

In some aspects, the comPACT may be assembled via polymerase chain reaction (PCR) amplification. Similar to the restriction digest method, DNA encoding the MHC heavy chain and the β2-microglobulin may be obtained from a suitable source. A second DNA fragment encoding a chosen signal sequence may also be obtained from a suitable source. Both fragments of DNA may have different universal target sequences, such that primers for one universal sequence do not anneal to the second universal sequence. Two sequences encoding for a chosen antigenic peptide may be synthesized; one forward primer with the antigenic sequence at the 5' end and the complement of the universal primer sequence on the MHC DNA fragment at the 3' end; and one reverse primer with the reverse complement of the chosen antigenic sequence at the 5' end and the reverse complement of the universal primer from the signal sequence fragment at the 3' end. A PCR reaction with all four DNA fragments and primer for the 5' end of the signal sequence fragment and 3' end of the MHC allele fragment will result in amplification of two DNA fragments, one with the signal sequence at the 3' end and the antigenic sequence at the 5' end, and one with the antigenic sequence at the 3' end and the MHC allele at the 3' end. A further PCR amplification cycle will allow the overlapping antigenic peptide sequences to anneal and result in a single full-length DNA fragment. In some embodiments, the signal peptide fragment further comprises a promoter sequence. In some embodiments, the MHC fragment further comprises a purification cluster and/or a polyA tail.

Transfection, Transduction, and Genetic Modification of Host Cells

A comPACT polynucleotide may be inserted into the host cell via an appropriate method known, including, but not limited to, transfection, transduction, electroporation, lipofection, sonoporation, mechanical disruption, or viral vectors. Exemplary transfection reagents include, but are not limited to, Expifectamine, Lipofectamine, polyethylene-imine (PEI), or Fugene. In some examples, Expifectamine is used to transfect mammalian cells with the comPACT polynucleotide.

A comPACT polynucleotide may be transiently or stably expressed in the host cell. In some embodiments, the comPACT polynucleotide is integrated into the host genome. In other embodiments, the comPACT polynucleotide remains extra-chromosomal. Any appropriate genetic editing technique known in the art may also be employed to modify the host cell with the comPACT polynucleotide, including CRISPR/Cas9, zinc-finger nucleases, or TALEN nucleases.

Expression

A number of strategies can be employed to express a comPACT polyprotein. For example, the comPACT can be incorporated into a suitable vector by known methods such as by use of restriction enzymes and ligases (see, e.g., Sambrook et al., supra). A vector can be selected based on factors relating to the cloning protocol. For example, the vector can be compatible with, and have the proper replicon for the host that is being employed. Suitable host cells include eukaryotic and prokaryotic cells, and can be cells that can be easily transformed and exhibit rapid growth in culture medium. Examples of host cells include prokaryotes such as *E. coli* and *Bacillus subtilis*, and eukaryotes such as animal cells and yeasts, such as, for example, mammalian cells and human cells. Non-limiting examples of mammalian cells which can be used as hosts to express a comPACT include J558, NSO, SP2-O, 293T, Expi293, and CHO. Other examples of possible hosts include insect cells such as Sf9 or Sf12, which can be grown using conventional culturing conditions. See Sambrook, et al., supra. In various embodiments, cells expressing a comPACT polypeptide can be identified using known methods. For example, expression of a comPACT polypeptide can be determined by an ELISA or Western blot using an antibody probe directed against the MHC heavy chain portion of the comPACT, or an antibody against an affinity tag, such as His6, or a streptavidin reagent if the comPACT has been biotinylated.

In some aspects, a comPACT is expressed in mammalian cells. The benefits of expressing protein in mammalian cells instead of in *E. coli* cells are multifold. Protein expressed in *E. coli* cells must be carefully purified away from lipopolysaccharide (LPS) Expression of proteins in mammalian cells results in no LPS contamination of the purified proteins. In addition, mammalian cells are more likely to properly fold mammalian proteins since mammalian cells produce proteins with correct post-translation modifications required for proper folding, including the proper formation of disulfide bonds. In addition, mammalian cells provide the correct chaperone proteins to assist with protein folding in the endoplasmic reticulum or Golgi apparatus. This results in increased purification of homogenously well-folded proteins, as compared to proteins expressed in *E. coli* cells.

A comPACT can be substantially-free of LPS. A comPACT can be free of LPS, e.g., a comPACT can have no detectable LPS as measured using LPS-detection methods known in the art. A comPACT can be glycosylated. A comPACT can be modified via expression in a eukaryotic or mammalian cell, e.g., via one or more posttranslational modifications such as glycosylation. A comPACT can include one or more post-translational modifications. A comPACT can (1) be substantially free of LPS or free of LPS; and (2) be glycosylated.

Exemplary ComPACT Workflow Process

Figure 24:
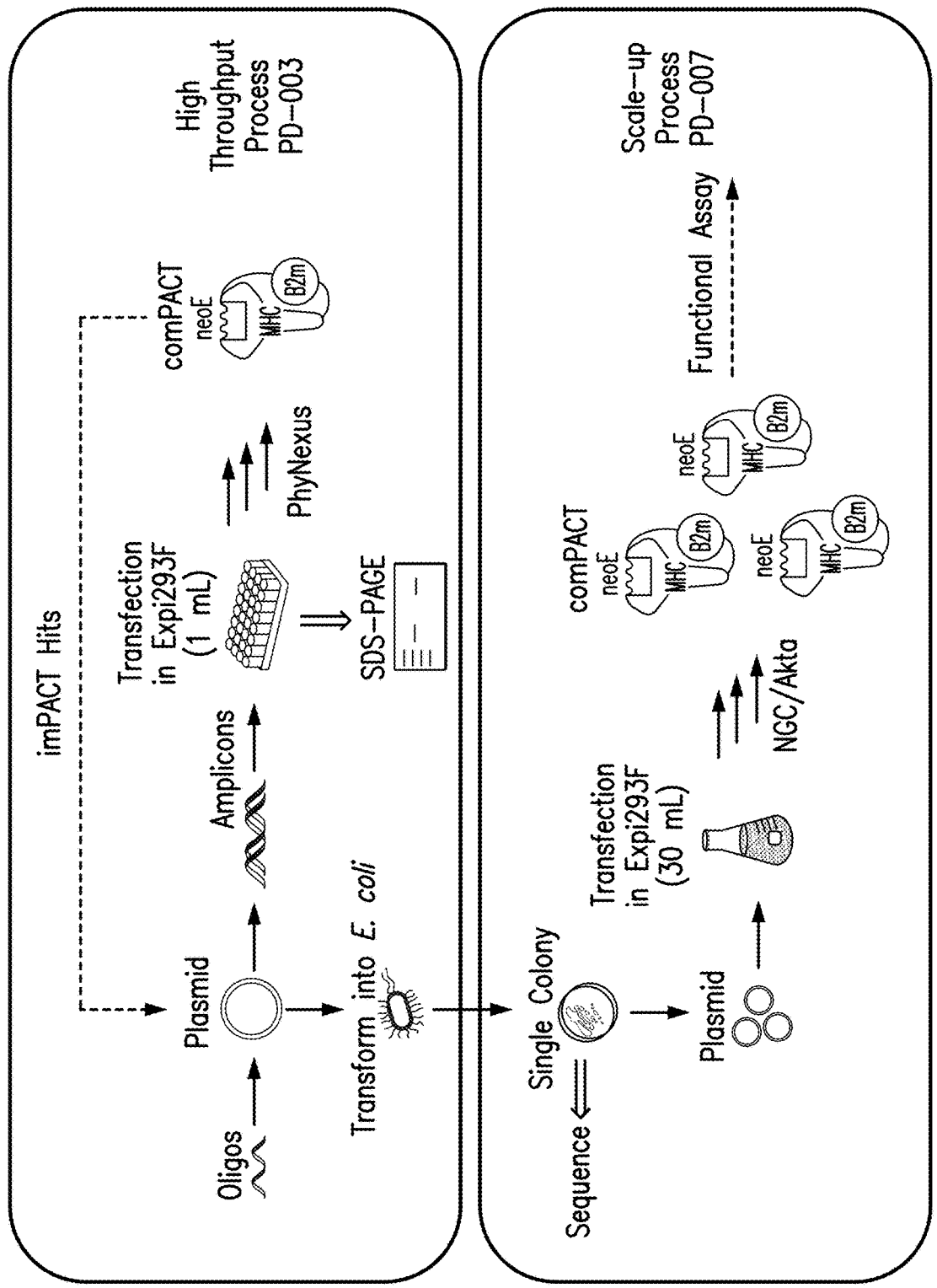
FIG. 24 provides an exemplary diagram of the work flow to manufacture comPACT polynucleotides and proteins.

FIG. 24 shows an exemplary schematic representation of the assembly and expression of a comPACT protein. Sense and antisense oligos that encode for the desired neoantigen peptide sequence are synthesized and annealed to form a double stranded oligo with overhangs at the 5' and 3' ends, which can then be ligated into a plasmid containing a β2M gene and an MHC allele. The full comPACT oligo can be amplified into a double stranded amplicon and transfected into cells for protein expression and optional biotinylation. The comPACT protein can be assessed via SDS-PAGE. ComPACTs can then be chosen for scaled up plasmid production in E. coli. Protein producer cells are transfected with the selected plasmids and the comPACTs are purified from the producer cells for use in functional assays.

Purification (Chromatography)

An expressed comPACT polypeptide can be isolated and purified by known methods. For example, a comPACT comprising a His6 affinity tag may be purified via affinity chromatography on an Ni-NTA column by procedures that are generally known and disclosed. Additionally, a comPACT containing human HLA sequences can be purified by affinity chromatography on a monoclonal antibody-Sepharose column by procedures that are generally known and disclosed.

T Cell Isolation

In another aspect, provided herein are methods of isolating an antigen specific T cell, the method comprising the steps of: (a) providing a polypeptide comprising, in an amino terminus to carboxyl terminus orientation, (i) a first universal target peptide, (ii) an antigenic peptide, (iii) a second universal target peptide that is distinct from the first universal target peptide, (iv) a β2M peptide, and (v) an MHC peptide, wherein the polypeptide is linked to one particle; (b) providing a sample known or suspected to comprise one or more T cells; (c) contacting the polypeptide with the sample, wherein the contacting comprises providing conditions sufficient for a single T cell to bind the polypeptide attached to the particle, and (d) isolating the single T cell associated with the particle.

Isolation and identification of patient-derived and antigen-specific T cells using a comPACT as described herein can include incubating the comPACT protein with patient-derived T cells. In some embodiments, a library comprising at least two comPACTs can be incubated with patient-derived T cells. T cells can be prepared using standard methods that start from a tissue such as blood, a lymph node, or a tumor.

Patient-derived T cells can be isolated from the patient's peripheral blood mononuclear cells (PBMCs) or tumor infiltrating lymphocytes (TILs). For example, both CD4+ and CD8+ T cells can be labeled and sorted from PBMCs or TILS using anti-CD4 and anti-CD8 fluorescent antibodies, with live populations of CD4+ and CD8+ single-positive cells sorted using fluorescence-activated cell sorting (FACS), to isolate only CD4+ or CD8+ cells. In some embodiments, T cells that are positive for both CD4 and CD8 can be isolated using an anti-CD3 fluorescent antibody followed by FACS. A person skilled in the art is able to determine the type of T cells to isolate for the type or types of comPACT protein being used.

Incubation of the comPACT or comPACT library with the T cell suspension allows for a complete and thorough exposure of the particle-bound antigen to the various T-cell receptors. This method may include rocking or rotation of the cells. In some embodiments, the comPACT is associated with a particle.

Following incubation of the comPACT or comPACT library and the T cells, the bound comPACT-T cell complex is selectively separated or selectively collected. T cells will likely be bound to many identical copies of identical comPACT library elements, and can be separated based on these interactions. For example, if the comPACT comprises a fluorophore, or is attached to a particle with a fluorophore, fluorescent associated cell sorting (FACS), including single-cell sorting, can be used to selectively isolate the T cells. If the comPACT is attached to a magnetic particle, applying a magnet to the suspension can allow for separation of particles complexed with antigen-paired T cells and removal of unpaired T cells. Alternatively, if the particle is a polystyrene particle, the unpaired T cells may be separated by gravity (e.g., centrifugation). After removal of unpaired T cells, in some embodiments, the separated bound particles are washed at least once to remove any non-specifically associated T cells.

ComPACT-bound T cells can be also separated by FACS into individual collection containers, such as a multi-well plate. The individual collection container can be single-cell reaction vessels. For example, components used for downstream processing and analysis can be added to each single-cell reaction vessel. The comPACT-bound T cells can be separated by FACS into a bulk collection container (e.g., every T cell isolated is collected in the same container).

ComPACT-bound T cells can also be individually isolated in droplets using a droplet generating microfluidic device (i.e., a "droplet generator"). Droplet generating devices used to encapsulate single cells are known to those skilled in the art, e.g., as described in US Publication No. 2006/0079583, US Publication No. 2006/0079584, US Publication No. 2010/0021984, US Publication No. 2015/0376609, US Publication No. 2009/0235990, and US Publication No. 2004/0180346.

After isolation of comPACT-bound T cells into single-cell reaction vessels (e.g., isolated in individual well or droplets), the nucleic acid of the comPACT-bound T cell can be further processed for downstream analysis. Specifically, the expressed TCRα and TCRβ mRNA transcripts can be first converted to cDNA by reverse transcription and the cDNA amplified for next generation sequencing (NGS) methods known to those skilled in the art, including, but not limited to, sequencing by synthesis technologies (Illumina).

EXAMPLES

Figure 2:
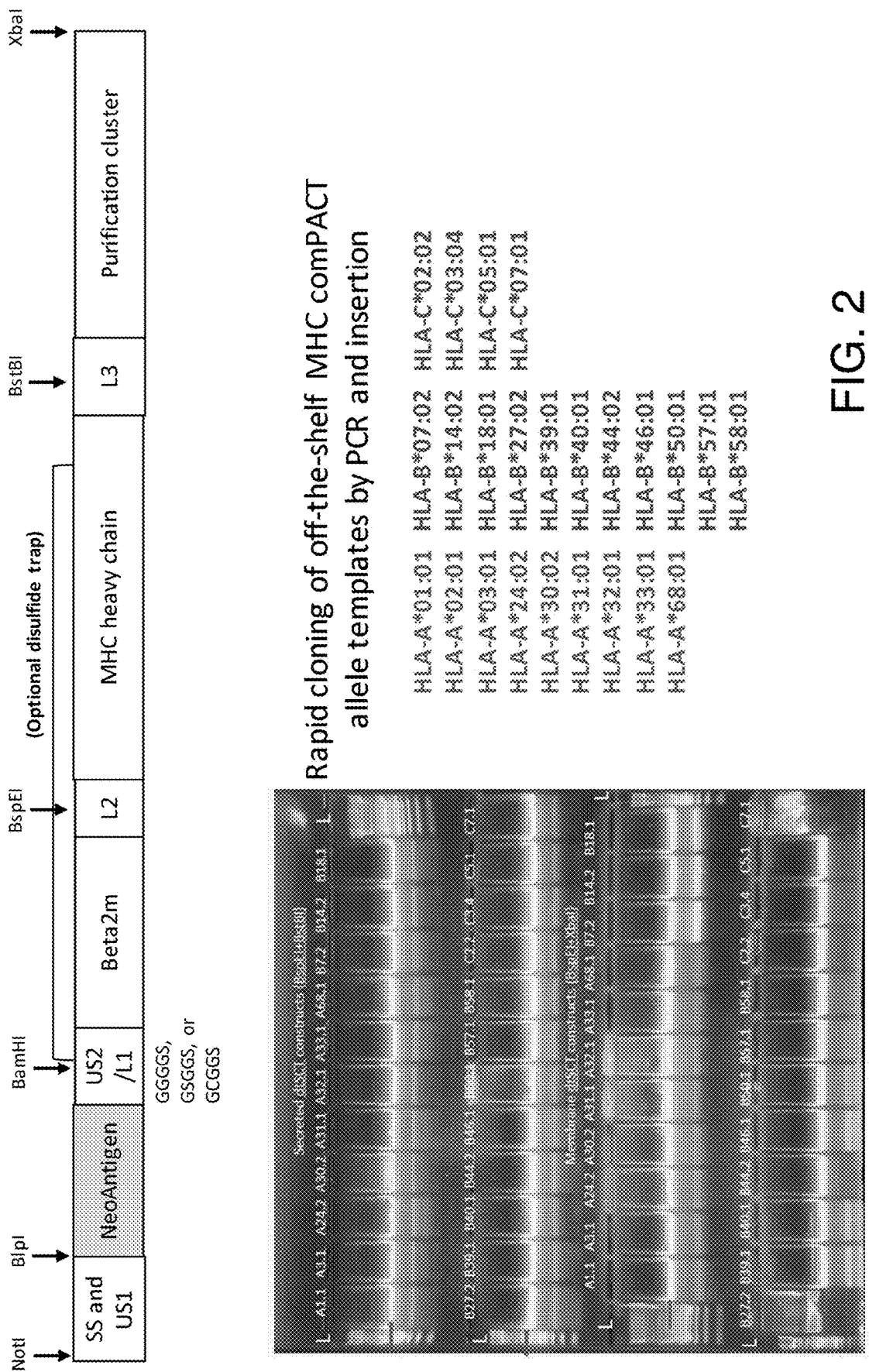
FIG. 2 shows a diagram of an exemplary modular off-the-shelf platform for rapidly assembling libraries of antigenic peptide ligands complexed with a chosen MHC allele.

Example 1: Design and Cloning of comPACT Mini-Genes Via Restriction Digest Cloning Structure of comPACT Mini-Genes for Restriction Digest:

The basic exemplary components of a comPACT mini-gene are the signal sequence that directs the secretion of the protein, universal target sequences such as restriction sites or primer binding sites, the antigenic peptide (or neoantigen, NeoE), a second universal target site, the invariant β2M, the extracellular domain of an MHC allele, and a purification cluster enabling enzymatic modification (e.g. biotinylation) and purification of the comPACT via affinity tags. The cluster may also contain a protease cleavage site and linker sequences between the peptide components. The mini-gene may also contain cysteine mutations that act as a disulfide trap. A diagram of a comPACT mini-gene is shown in FIG. 1. Additional restriction sites upstream and downstream of the MHC heavy chain sequence can be used to insert other MHC alleles to construct different MHC templates and build a library of MHC templates (FIG. 2). The DNA fragments encoding the signal sequence, universal target sequences, invariant β2M, and the extracellular domain of an MHC allele are the base MHC template.

For restriction digest cloning methods, each comPACT DNA construct is a base MHC template with a dummy antigenic sequence insert containing stop codons in three frames and a unique restriction site for destruction of uncut or re-ligated template (FIG. 3) and can be used as part of an off-the-shelf platform for rapidly assembling libraries of antigenic peptides complexed with that MHC allele. The MHC alleles may also be modified or mutated (e.g., Y84A or Y84C) to improve folding or increase binding of the antigenic peptide with the MHC protein. In addition, the β2M protein can also be mutated (e.g., S88C) to allow it to bind thiol dyes.

In this example, a comPACT mini-gene is shown with the following structure: a NotI restriction site at the 5' end; the signal sequence from human growth hormone, hGH, shown in Table 3; a restriction site Blp1 upstream of the antigenic peptide region and a BamHI restriction site downstream of the antigenic peptide sequence, shown in Table 2; a linker sequences of predominantly glycine and serine residues (i.e. Gly-Ser linkers); the β2M sequence; a second Gly-Ser linker sequence with a BspI restriction site; a MHC heavy chain; a third Gly-Ser linker sequence with a BstBI restriction site; and a purification cluster with an AviTag sequence, a TEV cleavage site, and a concatenated histidine tag.

Restriction Digest Cloning and Assembly of comPACT Mini-Gene

Figure 4:
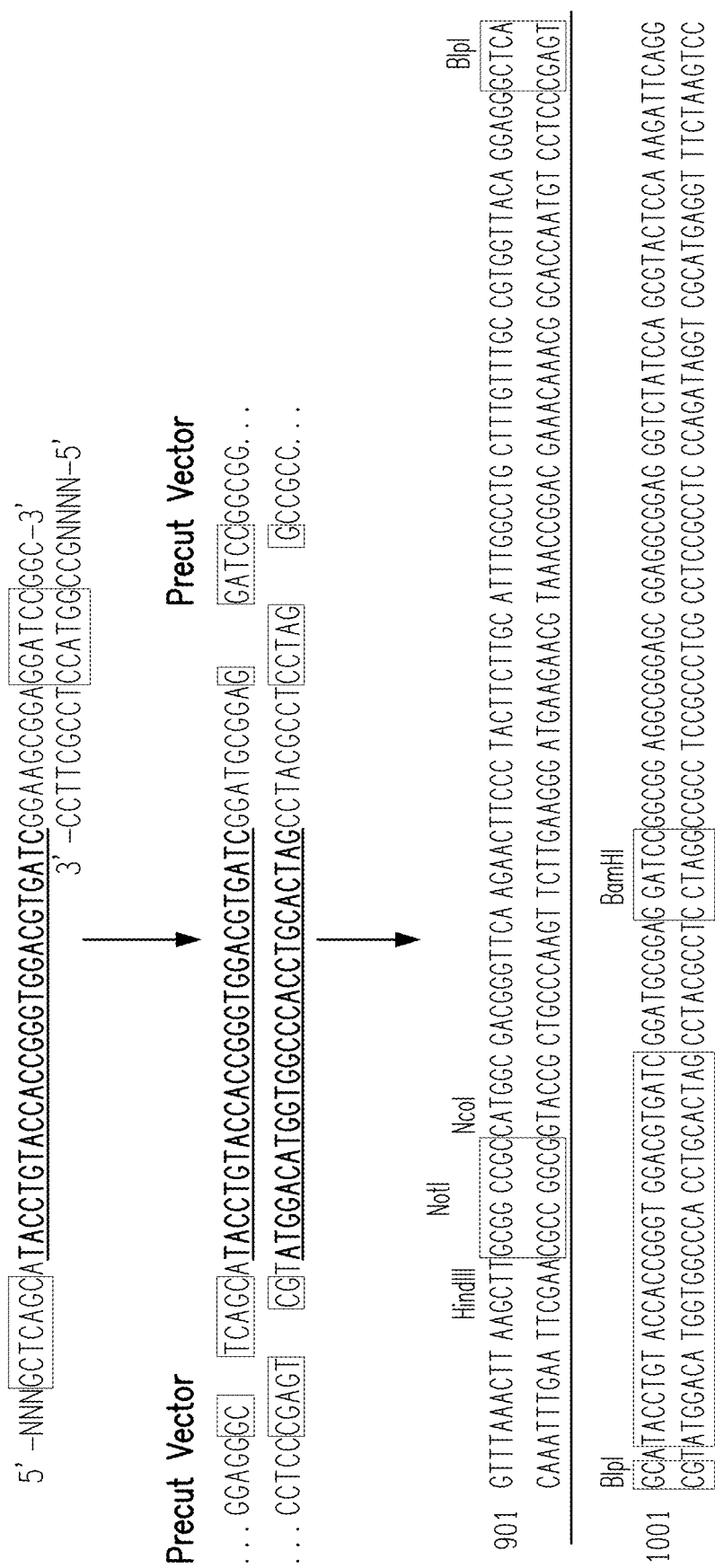
FIG. 4 is a diagram of an exemplary restriction digest cloning reaction to insert a chosen neoepitope sequence in the MHC template. The neoepitope sequence (underlined, bold) is synthesized as a primer flanked by two different restriction sites (boxed). A universal primer with the reverse complement sequence [[e]] of the 3' restriction site is used in a PCR reaction to form a double stranded primer dimer of the neoepitope sequence. Restriction digest of both the neoepitope and the MCH template vector allow for a ligation reaction to insert the chosen neoepitope sequence into the MHC template sequence. Ligation reactions are transformed into *E. coli* and plasmids prepared from transformed *E. coli* are used in mammalian producer cell transfection reactions.

Three different methods of inserting the neoantigen via restriction digest are described herein. In the first, shown as a diagram in FIG. 4, the antigenic peptide (NeoE)-encoding primer spans the first restriction site (BlpI in this example) at the 5' end and the second restriction site (BamHI in this example) at the 3' end. This primer amplifies off a universal reverse primer encoding the second restriction site, yielding a primer dimer of ~70 bp.

In the second method, the antigenic peptide-encoding primer spans the second restriction site as the 5' end and is the reverse complement of the antigen. This primer primes in reverse orientation off the template DNA encoding the signal sequence. Paired with a forward primer spanning the first restriction site sequence, this reaction yields a 70 bp product, or a ~140 bp product if a forward primer spanning a restriction site farther upstream of the antigen site is used.

In both the first and second methods, the insert is cleaned up on a commercial column, digested with appropriate restriction enzymes, cleaned again on a commercial column, and then ligated with a pre-digested MHC template in a vector. Ligation reactions are transformed into E. coli and plasmids prepared from transformed E. coli are used in mammalian producer cell transfection reactions.

Example 2: Design and Cloning of comPACT Mini-Genes Via Primer Annealing

Figure 5:
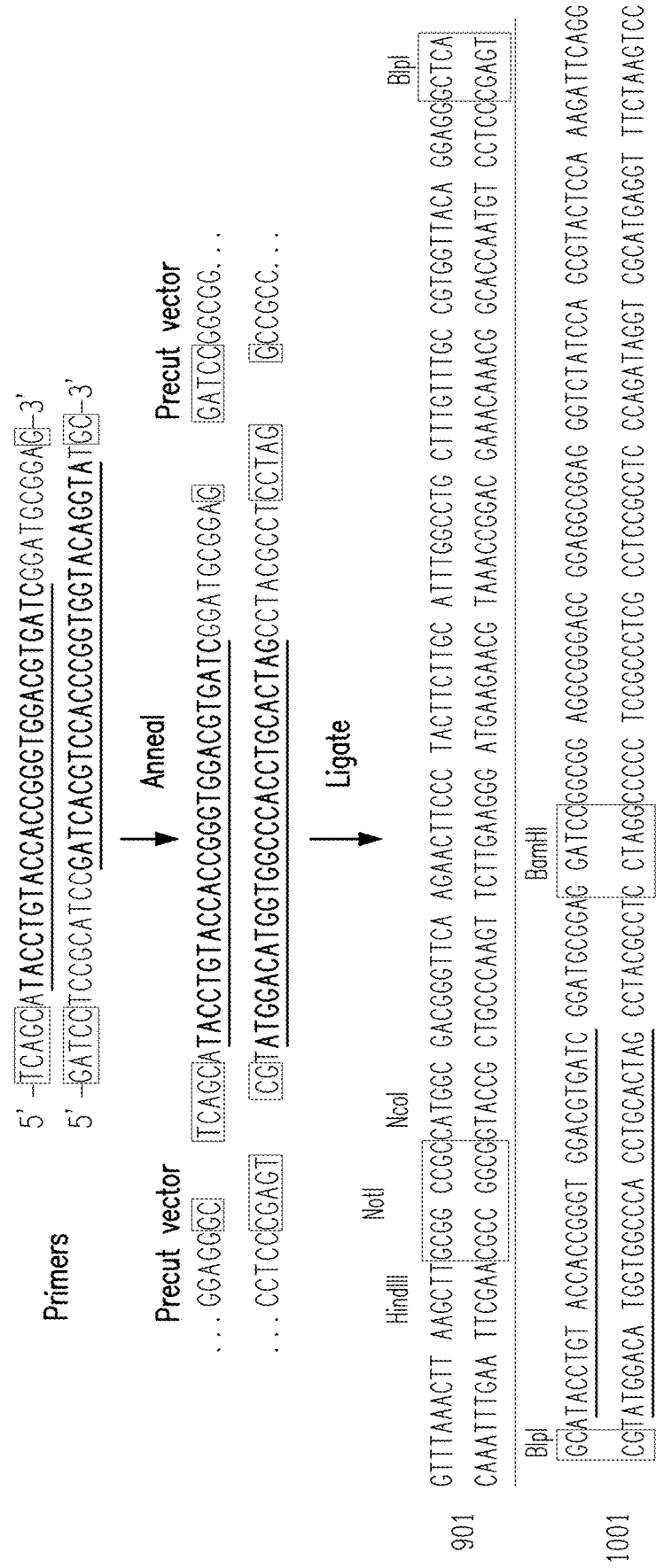
FIG. 5 is a diagram of an exemplary alternative form of a restriction digest cloning reaction to insert a chosen neoepitope sequence in the MHC template. Two complementary NeoE-encoding primers are synthesized with a portion of the 5' and 3' restriction sites. These primers are annealed and simulate the overhangs from restriction digestion. A precut vector (which critically retains 5' phosphates on its overhang ends) is then ligated with the annealed NeoE insert and the ligation product is transformed into *E. coli* for plasmid production.
Figures 22A, 22B:
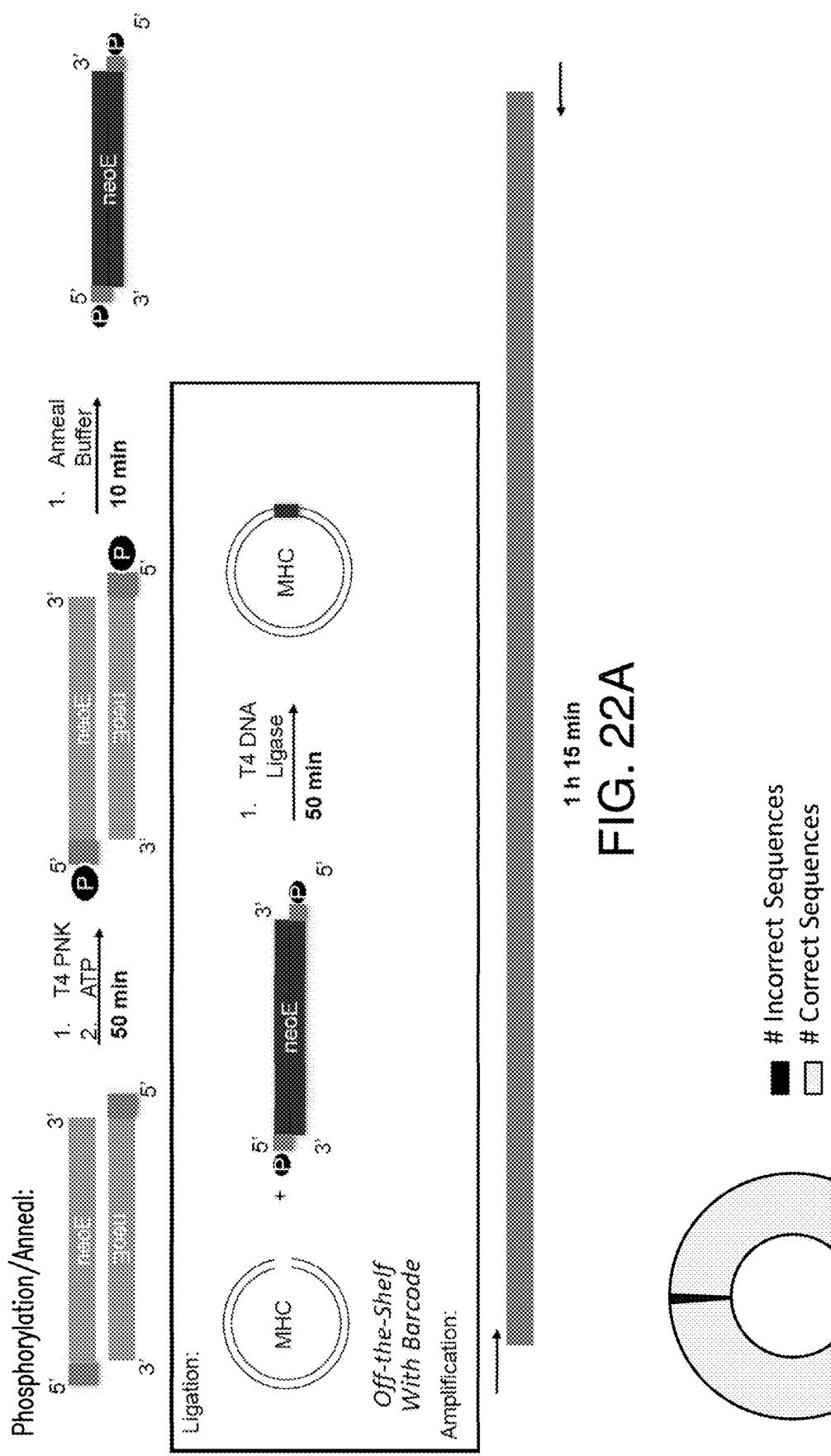
FIG. 22A shows an exemplary diagram of a cloning strategy to manufacture comPACT polynucleotides.
FIG. 22B provides sequence verification statistics obtained from 824 individual comPACT polynucleotides.

In a third variation on MHC template vector ligation, PCR and restriction digestion was bypassed by annealing two reverse complementary neoantigen-encoding primers. These primers were designed to have 5' and 3' ends that begin and terminate in complementary sequences that simulate the overhangs from restriction digestion (FIG. 5). The sense and antisense primers were incubated with T4 polynucleotide kinase and ATP to phosphorylate the 5' ends (FIG. 22A). When these primers annealed to each other, they formed a double stranded oligonucleotide sequence that has overhang nucleotides as if it had been digested with a restriction enzyme. The phosphorylated neoantigen insert was ligated into a precut MHC template in a vector. The comPACT minigene had the same structure as that described in Example 1. The ligation product was then used for PCR amplification of a linear comPACT amplicon using bookend universal primers to amplify the complete comPACT gene and sequenced. 824 comPACTs with unique neoantigen sequences were made using this method, with greater than 99% of the generated comPACTs having the correct neoantigen sequence (FIG. 22B).

Next, E. coli were transformed with the ligation product plasmids and plated onto selective agar plates containing ampicillin. Individual colonies were picked and grown overnight for plasmid purification and sequenced for full gene verification. After sequencing verification, plasmid lots were archived and propagated into larger quantities.

Alternatively, T4 kinase is not used if the precut MHC template vector retains 5' phosphates on its overhang ends. The annealed antigen insert can then be ligated with the cut MHC vector and the ligation product transformed into E. coli for plasmid production.

Example 3: Design and Cloning of comPACT Mini-Genes Via PCR Assembly

Figure 6:
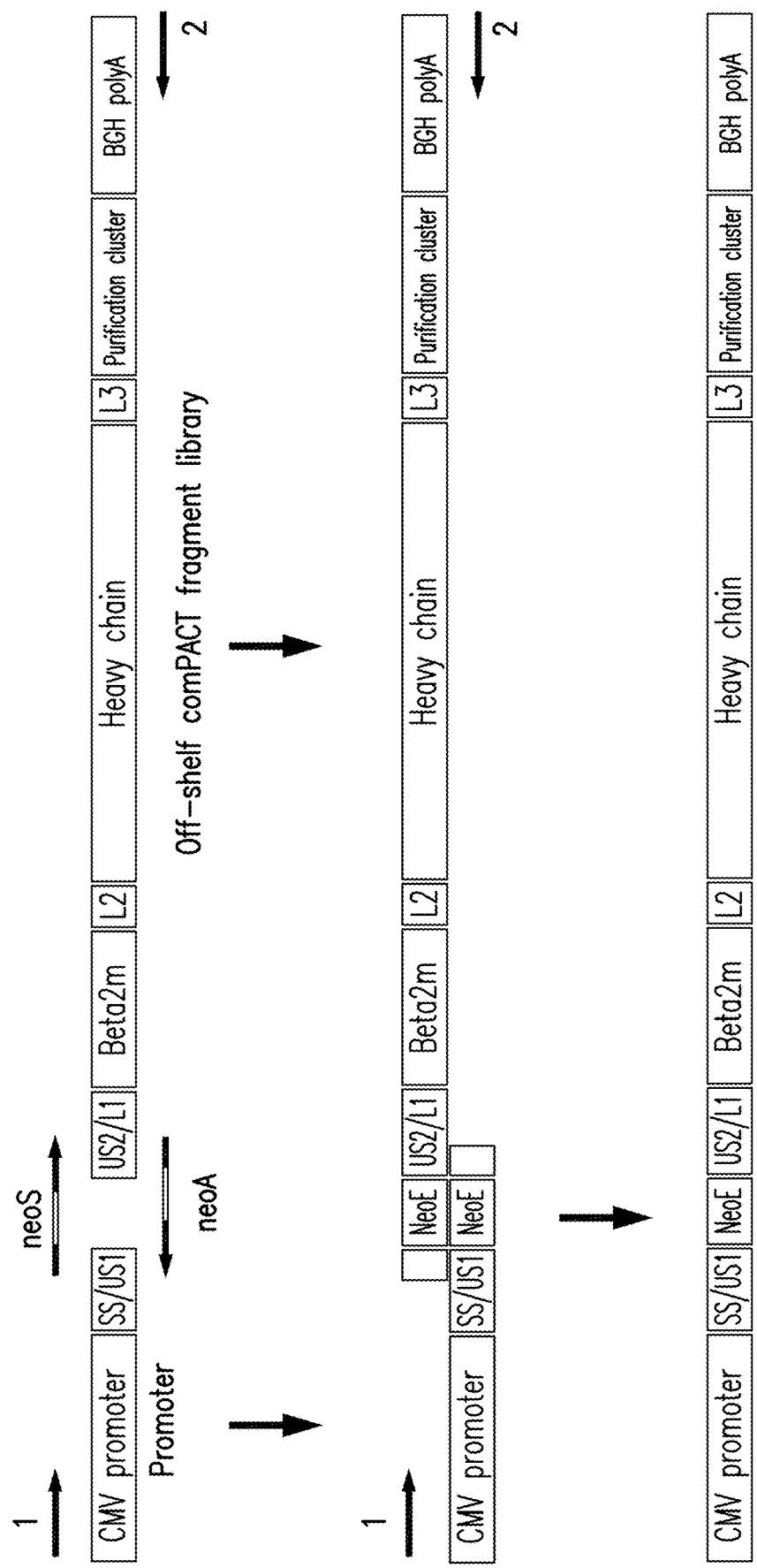
FIG. 6 is a diagram of an exemplary PCR-based method to insert a chosen neoepitope sequence in the MHC template. Two complementary NeoE-encoding primers are synthesized, the forward primer with a 3' sequence for the second universal site in the MHC template; and the reverse primer with a 3' sequence for the complementary sequence of the first universal site in the MHC template. These primers are mixed with a 5' fragment of the MHC template with the first universal sequence site, and a second fragment of the MHC template with the second universal site and remainder of the comPACT mini-gene. The first PCR amplification cycle produces two nucleotide fragments, one fragment encoding the first universal site region with downstream neoepitope and the other encoding the neoepitope followed by the remainder of the comPACT gene. These two fragments, overlapping at the unique neoepitope sequence are then assembled and the full assemble amplified and cleaned up for transfection.

Structure of comPACT Mini-Genes for PCR Assembly:

A fourth method of inserting the neoantigen may also be used. In this method, the neoantigen is inserted into the MHC template which is flanked by an upstream promoter and a downstream polyadenylation signal via polymerase chain reaction to form a 2.5 kb mini-gene. A diagram of the PCR assembly reaction is shown in FIG. 6.

In this example, a comPACT mini-gene is shown with the following structure: a promoter at the 5' end; a signal sequence with a first universal target sequence; the antigenic peptide; a second universal target sequence with a linker sequence of predominantly glycine and serine residues (i.e. GlySer linkers); the β2M sequence; a second Gly-Ser linker sequence; an MHC heavy chain allele; a third Gly-Ser linker sequence; a purification cluster; and a polyA sequence. The universal target sequences are not the same in this method.

PCR Assembly of comPACT Mini-Genes:

In this method, two primers (<60 nt) with a chosen neoantigen sequence are synthesized. The first primer has the neoantigen sequence at the 5' end followed by a stretch of the second universal target sequence at the 3' end. The second primer has the reverse complement of the neoantigen sequence at the 5' end and the reverse complement of the first universal sequence at the 3' end. These primers are mixed with a DNA fragment encoding the promoter region, signal sequence and first universal target sequence, and another DNA fragment encoding the second universal target sequence, the β2M sequence, MHC allele, purification cluster and a polyA sequence. Each antigenic peptide primer anneals to its complementary sequence and a PCR reaction is run that amplifies the neoantigen sequence onto either the promoter fragment or the MHC allele fragment. These two newly synthesized fragments now each have the neoantigen sequence. Further PCR reactions, along with primers for the 5' end of the promoter sequence and 3' end of the polyA sequence, allow the neoantigen sequences to anneal to each other and prime the assembly of a full length linear comPACT amplicon.

The fully assembled linear comPACT polynucleotide is then cleaned up for direct transfection into mammalian producer cells, bypassing the steps using E. coli and plasmid production altogether.

Example 4: Expression and Purification of comPACT Proteins from Plasmids

Expression of Protein

Neoantigen12 (neo12) was ligated into an HLA-A2 template sequence and inserted into an expression plasmid (pPACT0010) via restriction digest of the NotI and BamHI restriction sites and ligation as previously described.

Figure 7:
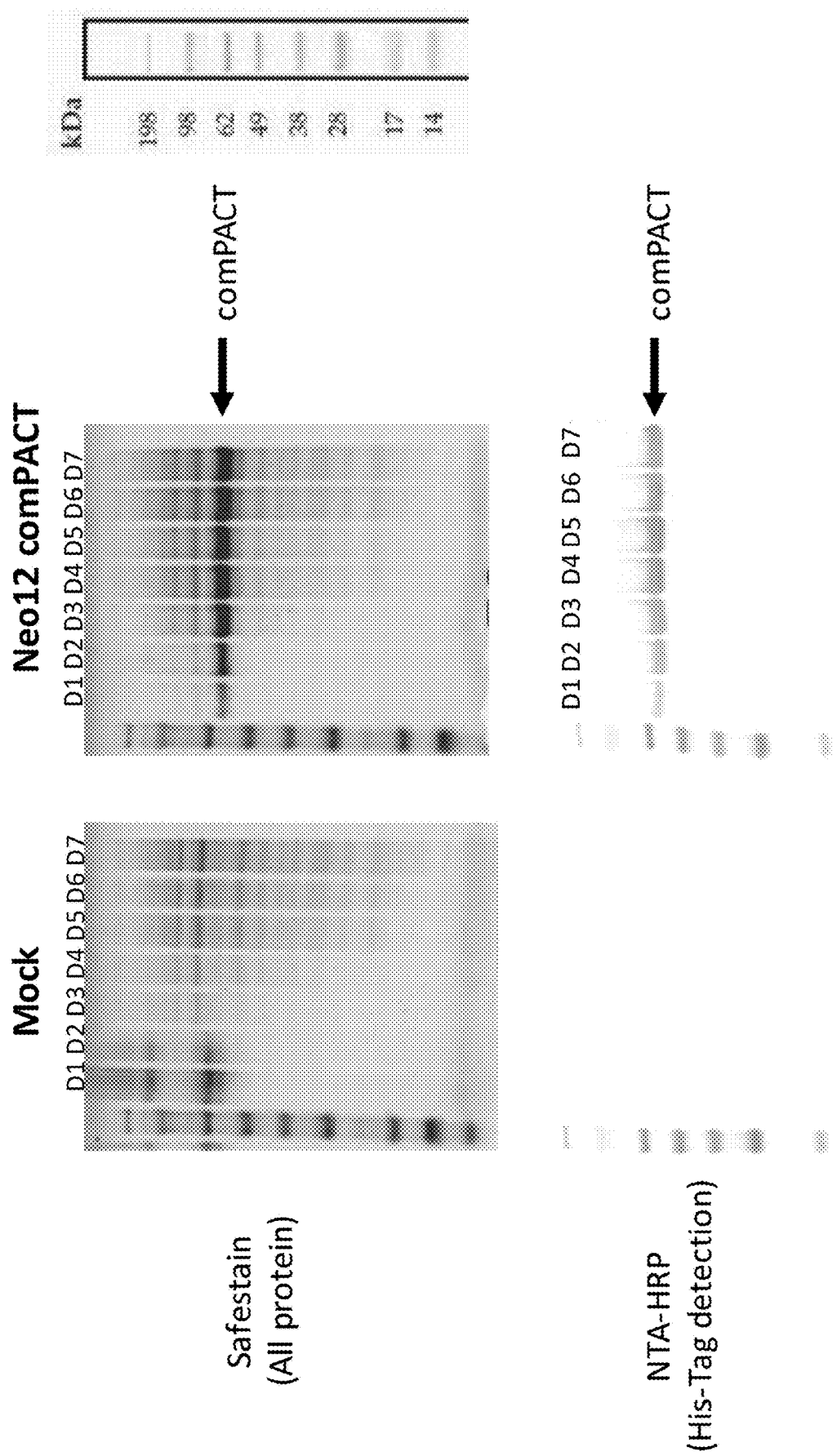
FIG. 7 shows the total protein expression in 30 mL of mammalian cells transfected with a comPACT gene (Neo12) over a seven day time course and a Western Blot using an NTA-HRP reagent that detects the His-tag.

Expi293 mammalian producer cells in a 30 mL shake flask volume were transfected with pPACT0010incubated with Expifectamine transfection reagent on day −1. Enhancers included in the Expifectamine transfection kit were added on day 0. Samples were collected from the cell supernatant on days 1 to day 7 and assessed for secreted protein via SDS-PAGE and total protein staining using Safestain (hermoFisher). Levels of secreted comPACT protein increased until day 3, at which point the protein secretion leveled off (FIG. 7). Secreted comPACT protein was initially identified by its apparent molecular weight (=53 kDa) and confirmed by a Western blot using NTA-HRP to detect the His6 affinity tag.

Purification of Protein

Figure 8:
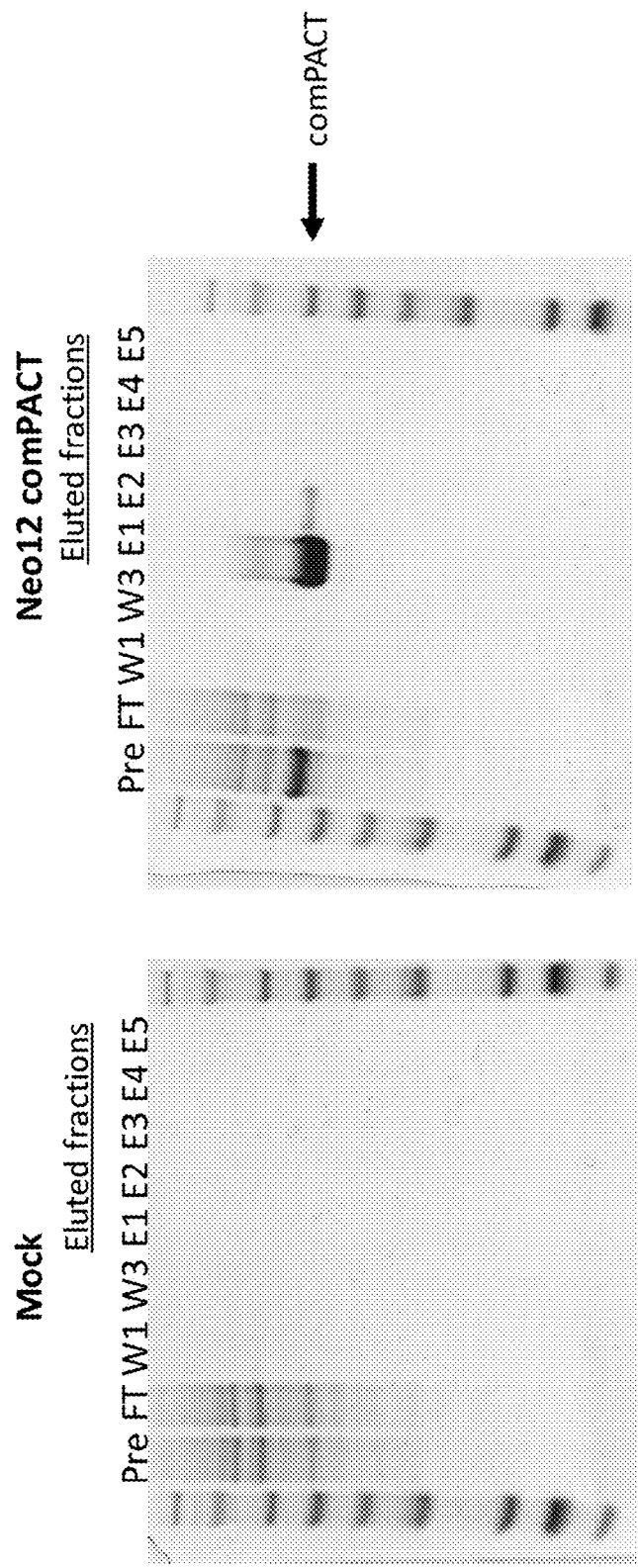
FIG. 8 shows gels of Ni-NTA affinity chromatography purification of the Neo12 comPACT protein. Pre stands for crude lysate, FT stands for Flow-through, W stands for Wash, and E stands for Eluted.

The Neo12 comPACT protein collected on day 7 was purified by Ni-NTA affinity chromatography via binding of the His6 affinity tag. Samples were assayed for total protein via SDS-PAGE and Safestain. The lack of comPACT protein in the flow-through (FT) fraction of the affinity column confirmed that the His6 tag was not cleaved during expression and purification (FIG. 8). The purified yield was >400 mg per L culture volume.

Figure 9:
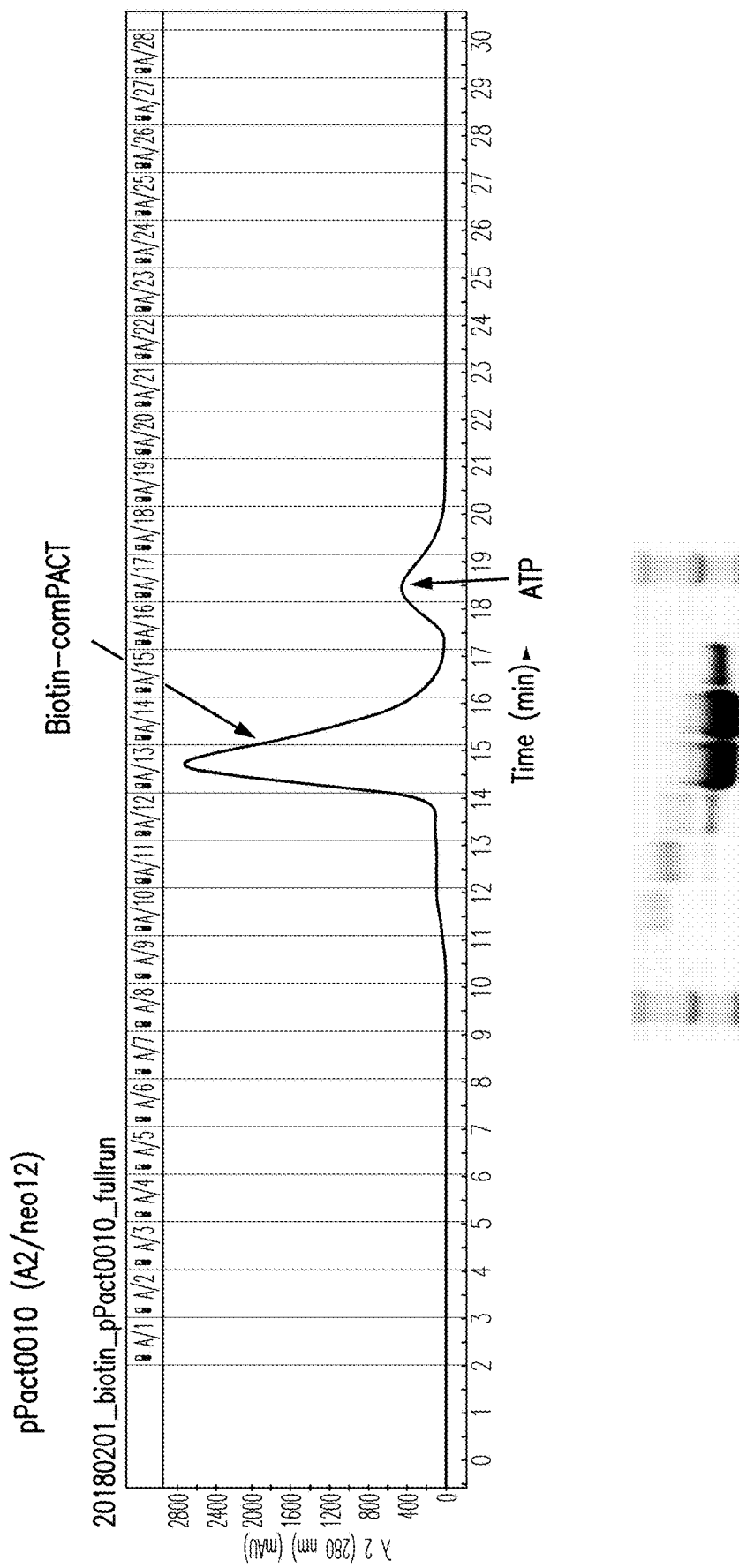
FIG. 9 shows the size exclusion chromatography spectra of the purified Neo12 protein. The major peak is the Neo12 protein, and the minor peak is ATP added during a biotinylation step.

The Neo12 comPACT protein was biotinylated (discussed below in Example 6) and further purified by size-exclusion chromatography. A singe major peak was observed, suggesting the protein was properly-folded and monomeric, with little aggregation (FIG. 9). The second peak is ATP, which was added for the BirA-catalyzed biotinylation reaction.

Optimization of Production Volume and Parallel Production

Figure 10:
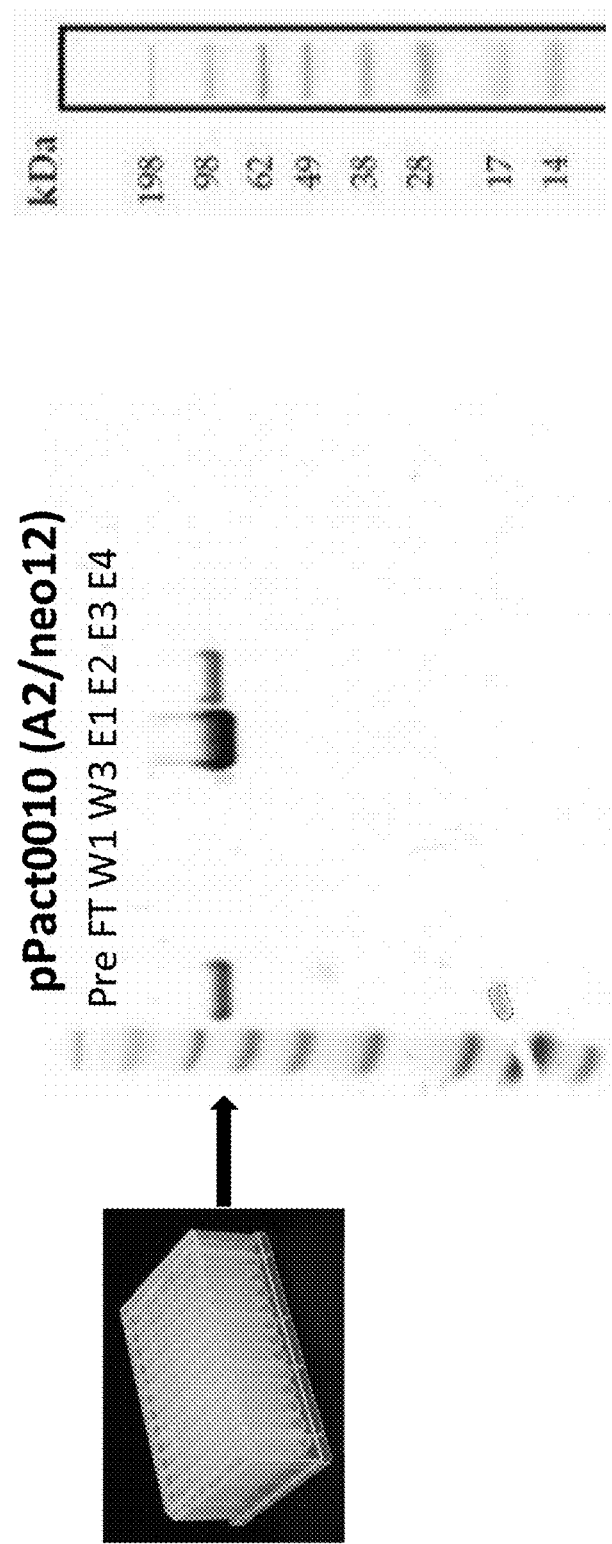
FIG. 10 shows a purification experiment similar to the one shown in FIG. 8, using a 0.7 cell culture volume.

The production of comPACTs was scaled down from a culture volume of 30 mL in a shake flask to 0.7 mL in a 96 deep-well shake block. Expi293 mammalian producer cells were transfected with plasmid DNA containing the pPACT0010 plasmid, and the secreted Neo12 comPACT protein was purified as previously described. 437 mg/L of purified Neo12 comPACT protein was collected from a 0.7 mL well volume as compared to the previously described yield of >400 mg/L from the 30 mL purification experiment (FIG. 10). The protein yield from the 0.7 mL experiment corresponds to >300 micrograms of protein, or ~1000-fold more than is typically needed for a typical flow cytometry experiment.

Figure 11:
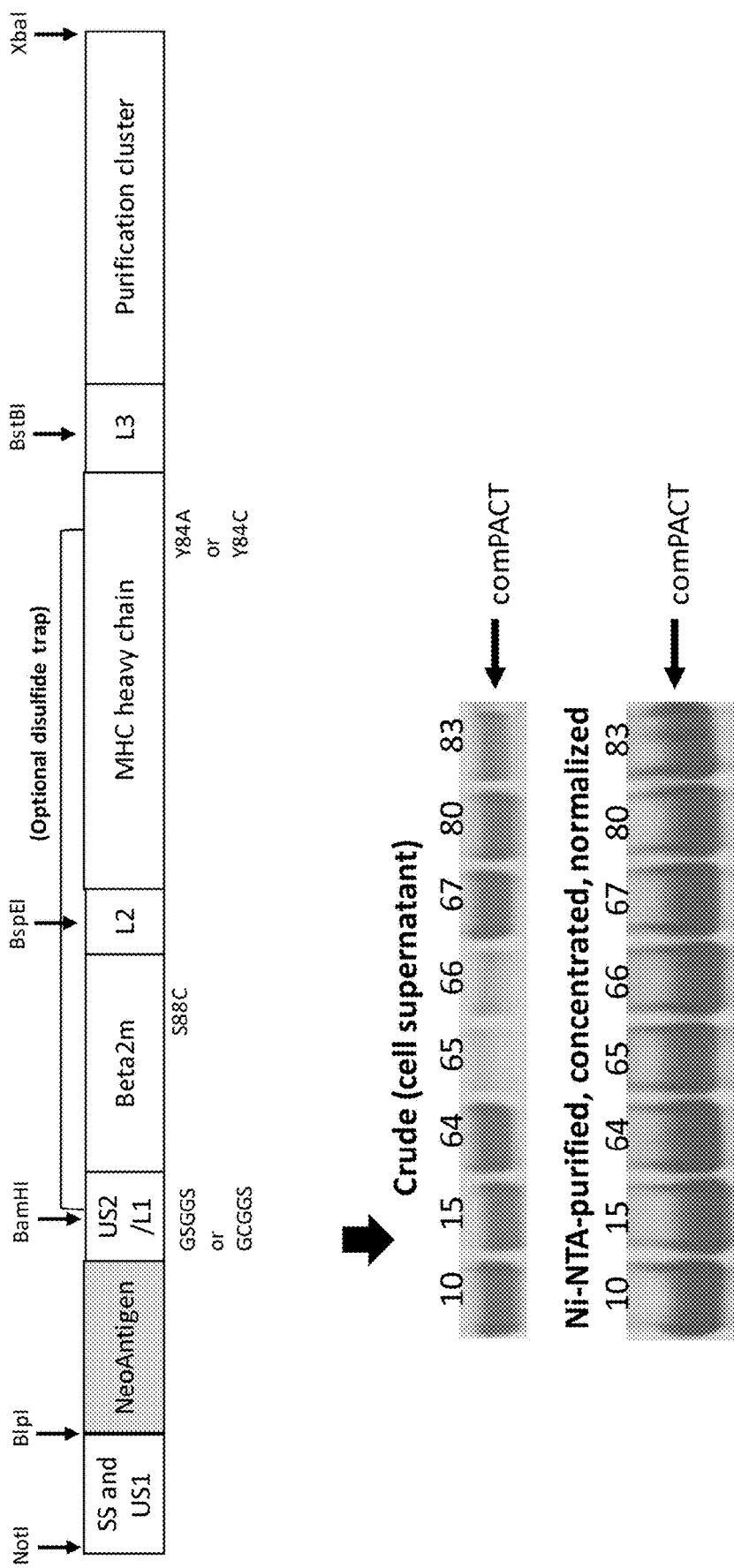
FIG. 11 shows crude and purified protein of eight different NeoE comPACT proteins, each with a different antigenic sequence.
Figure 12:
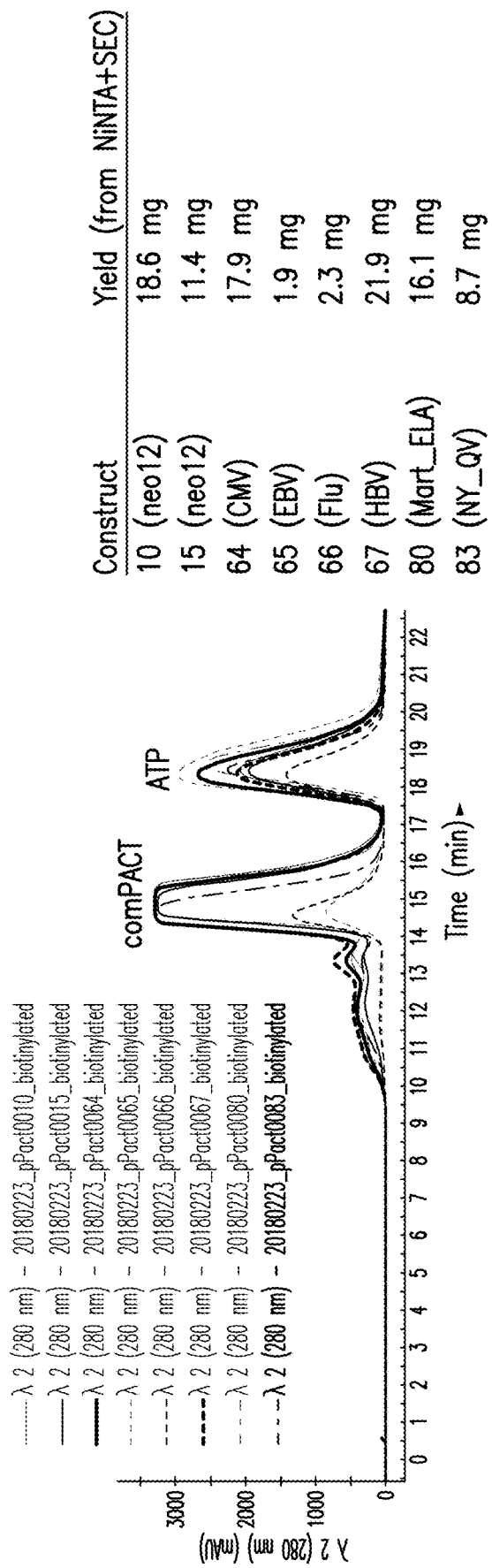
FIG. 12 shows the size exclusion chromatography spectra of the eight NeoE comPACT protein of FIG. 11.

Next, parallel expression of multiple comPACT constructs was assessed. Eight different comPACT constructs with different neoantigens (neoantigens 10, 15, 64, 65, 66, 67, 80, and 83) were expressed in 30 mL shaker flasks as a mid-throughput assay (FIG. 11). Each comPACT construct was transfected into cells as previously described where the comPACT protein was expressed and secreted into the cell supernatant. The expressed protein was purified as previously described, concentrated, and normalized. Samples of crude supernatant and concentrated proteins were assayed for total protein as previously described. The comPACT proteins were purified via size exclusion chromatography (FIG. 12). A single peak, containing 2-20 mg of protein, was seen for each protein, also suggesting that the comPACT proteins were properly-folded and monomeric.

Example 5: Expression and Purification of comPACT Proteins from Linear Amplicons In the previous examples, comPACT proteins were expressed from plasmids transfected into mammalian producer cells. As an alternative approach, linear amplicons of the neo12 comPACT mini-gene (neoantigen 12 assembled into a mini-gene with the HLA-A2 template sequence) flanked by a promoter sequence and a polyA sequence were transfected into 0.7 mL of the producer cells in a 96-deep well plate. As a control, the pPACT0010 plasmid was also transfected into separate producer cells. Protein from both samples was expressed, purified and assayed for total protein as previously described. Similar levels of expressed proteins were produced by both the linear amplicon and the plasmid (FIG. 13A), suggesting that the protein encoded by a comPACT mini-gene can be produced without the use of a plasmid intermediate. Multiple different comPACT mini-genes with different neoepitope sequences have been produced (FIG. 13B) for direct transfection of producer cells.

Figure 23:
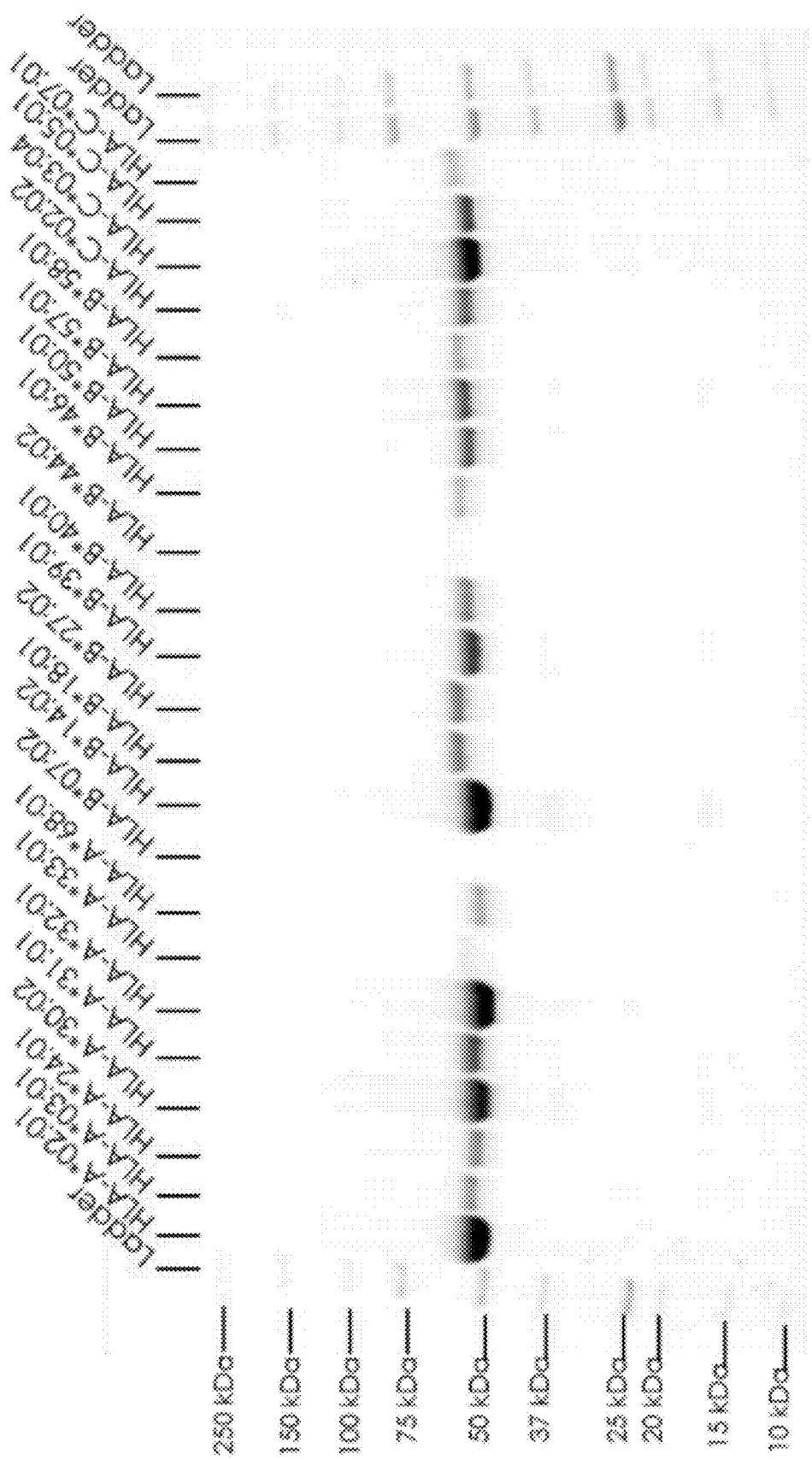
FIG. 23 shows protein expression and purification for a representative selection of comPACT proteins.

Additional comPACTs with different HLA alleles were made using the annealing and phosphorylation workflow described in Example 2. Linear amplicons were derived from the expression vector using bookend PCR and universal primers, and were transfected into Expi293F cells for comPACT protein production. FIG. 23 shows a protein gel of representative comPACT proteins made using the annealing cloning workflow. ComPACT proteins were run on an SDS-PAGE gel and stained with stained with Safestain (Thermofisher).

Example 6: Biotinylation of comPACT Proteins

In Vitro Biotinylation of comPACTs with Isolated BirA Enzyme

Figures 13A, 13B, 14:
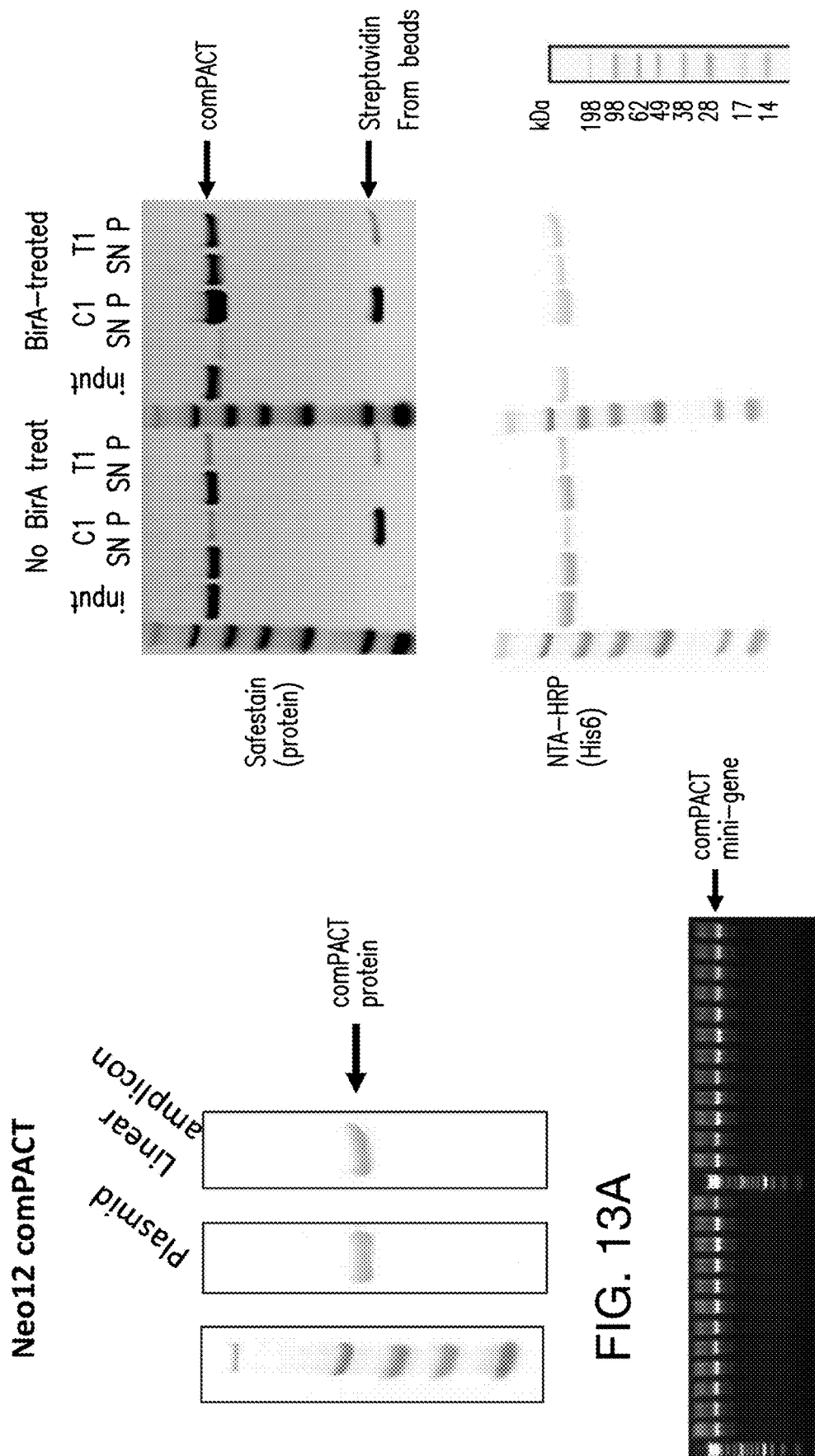
FIG. 13A shows a NeoE comPACT protein produced using the PCR assembly method described in FIG. 6 (Linear amplicon) compared to a NeoE comPACT protein produced from a plasmid (plasmid).
FIG. 13B shows a DNA gel of linear amplicons produced by the PCR assembly method. Each lane contains a comPACT mini-gene with a different neoepitope sequence.
FIG. 14 shows a streptavidin bead pulldown assay to test for complete biotinylation of the comPACT protein.

The comPACT purification cluster includes a BirA recognition sequence (Avitag) for biotinylation. Purified comPACT proteins were unbiotinylated (No BirA treat) or biotinylated with commercial BirA protein according to the manufacturer's instructions (BirA-treated). Following overnight BirA enzymatic treatment, samples were bound to two different types of magnetic streptavidin beads (C1 and T1) and incubated to allow the biotinylated protein bind to the streptavidin beads. The supernatant (SN) and beads ("pellet," P) were separated via SDS-PAGE. Samples were assayed for total protein with Safestain and the presence of comPACT protein via Western Blot with NTA-HRP (FIG. 14). In the untreated samples, the comPACT protein was mainly found in the SN fraction, confirming that it was unbiotinylated. In the biotinylated samples, the comPACT protein was found in the pellet samples of both C1 and T1 streptavidin beads, although the interaction between the biotinylated proteins and the C1 streptavidin beads was the most complete. Biotinylated comPACT protein was not detected via Western Blot in the C1 streptavidin bead-depleted supernatant, suggesting ~100% of comPACT protein was biotinylated.

Figure 15:
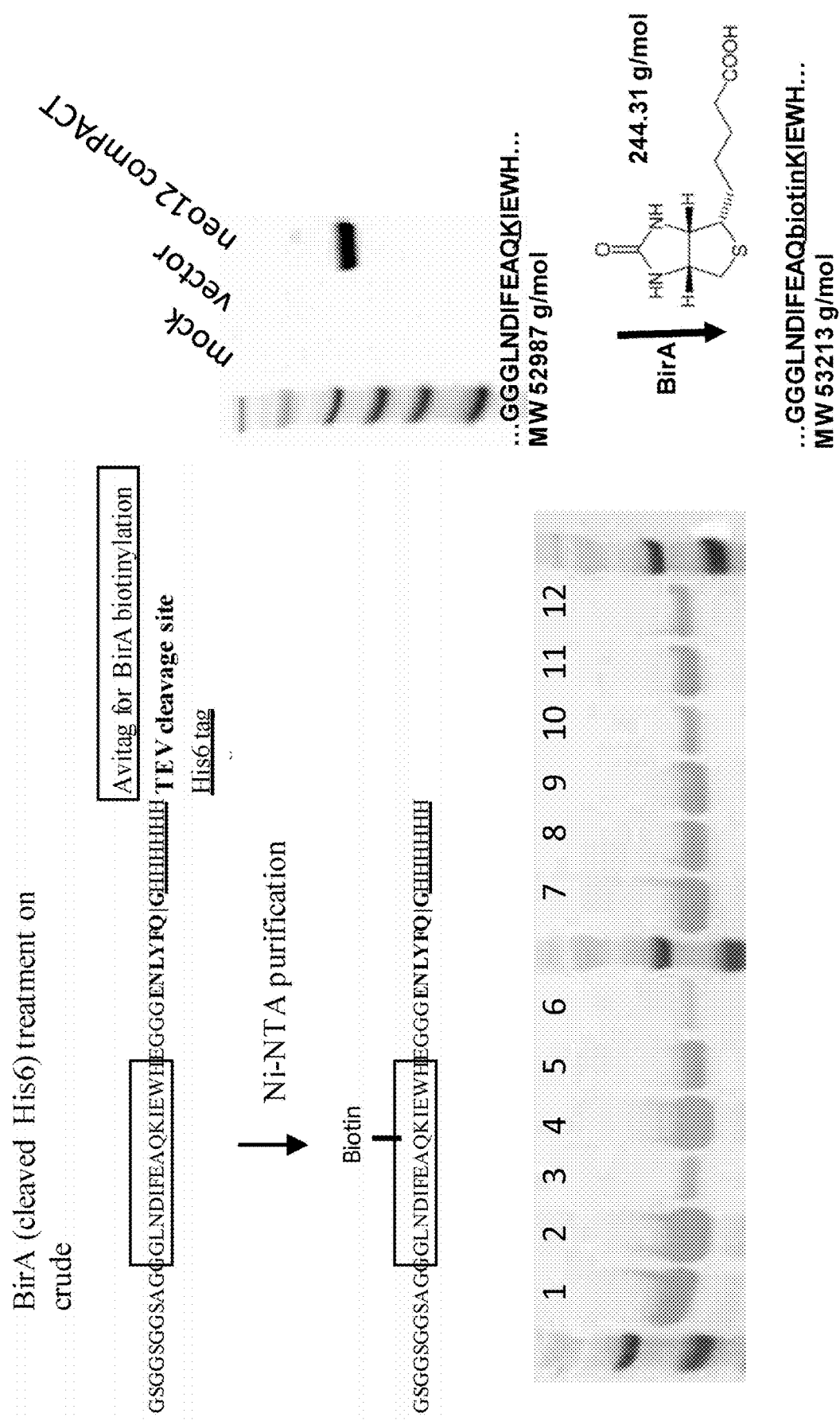
FIG. 15 shows biotinylation of different comPACT proteins in crude cell lysate, visualized via a Western Blot using streptavidin-HRP.

ComPACT proteins may also be biotinylated in the clarified supernatant, prior to purification. Multiple comPACT proteins were expressed in producer cells as previously described. The cell culture supernatant was collected and clarified via centrifugation. The clarified supernatant was treated with commercial BirA protein according to the manufacturer's instructions and then purified via Ni-NTA affinity chromatography and biotinylation was assessed via Western Blot (FIG. 15). All comPACT proteins tested were biotinylated using this method, indicating that biotinylation of comPACT proteins in clarified cell supernatants is effective.

Figures 16A, 16B, 16C:
FIGS. 16A-16C show production and purification of BirA enzyme (FIG. 16B and FIG. 16C) and TEV protease (FIG. 16A) in *E. coli*.

To produce enough BirA for high-throughput biotinylation of comPACT proteins, a BirA protein with a His6 tag was expressed in E. coli cells. This His6 tagged BirA was purified via Ni-NTA affinity chromatography (FIG. 16B) and can be used to biotinylated the comPACT proteins. A second version of BirA-His6 with a TEV-cleavable His6 tag was also expressed and purified via Ni-NTA affinity chromatography (FIG. 16C). This BirA-TEV-His6 protein can be purified via Ni-NTA, the His6 tag removed via TEV cleavage, and the tagless BirA then used to biotinylated comPACT proteins. After biotinylation of the comPACT proteins, the tagless BirA protein can then be purified away via Ni-NTA affinity chromatography. In addition, TEV protease was expressed heterologously in E. coli for use with the BirA-TEV-His6 (FIG. 16A) for use in biotinylated comPACT protein production.

Figure 17:
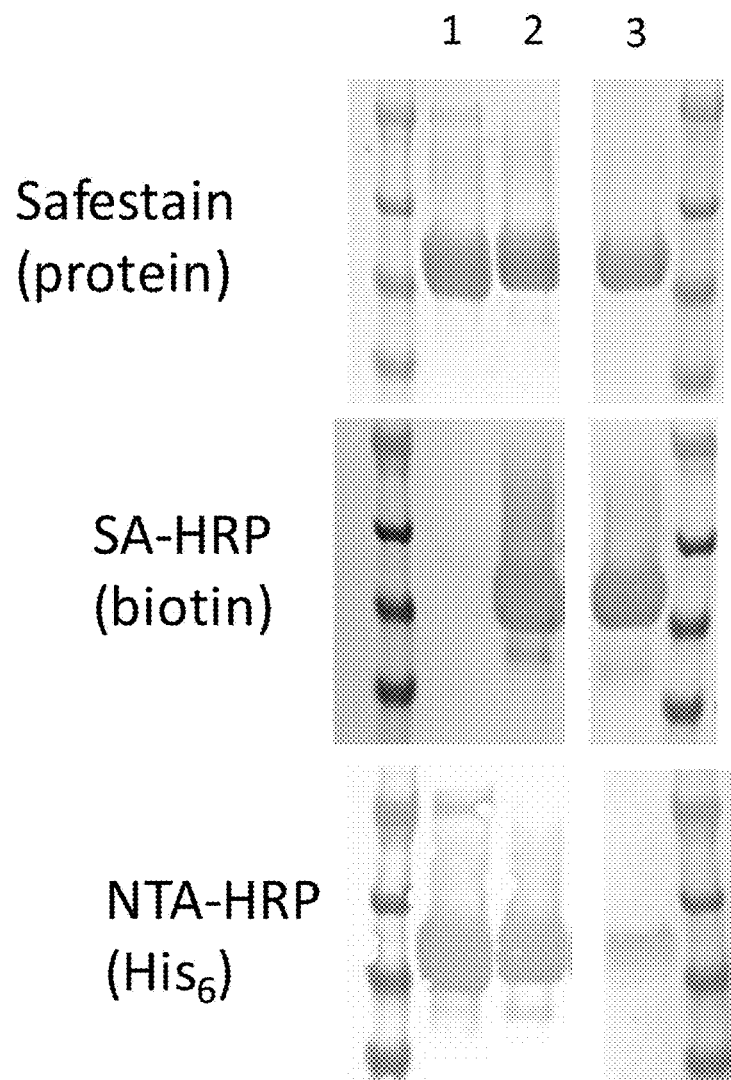
FIG. 17 shows a biotinylation of a comPACT protein using BirA (lane 2) and cleavage of the His6 tag using TEV protease (lane 3). Untreated comPACT protein is shown in lane 1.

Cleavage of the His6 tag on comPACT proteins after biotinylation was also assessed and the results shown in FIG. 17. ComPACT proteins were treated or untreated with BirA to biotinylate them as previously described (lanes 1 and 2 of FIG. 17). A third sample of comPACT protein was treated with BirA and then with TEV to cleave the His6 tag present on the protein (lane 3). Samples were separated via SDS-PAGE, and total protein was assessed via Safestain. All three samples had equal amounts of comPACT protein. Biotinylation of the comPACT proteins and cleavage of the His6 tag was assessed via Western blot using an SA-HRP reagent for the biotin signal and an NTA-HRP reagent for the His6 tag. The unbiotinylated sample did not show biotin signal, but did have a His6 signal and the biotinylated and uncleaved sample had both signals. The biotinylated and TEV cleaved sample only had the biotin signal, indicating that the His6 tag was successfully cleaved off the comPACT protein.

In Vivo Biotinylation of comPACTs in Cells Expressing BirA

Figure 18:
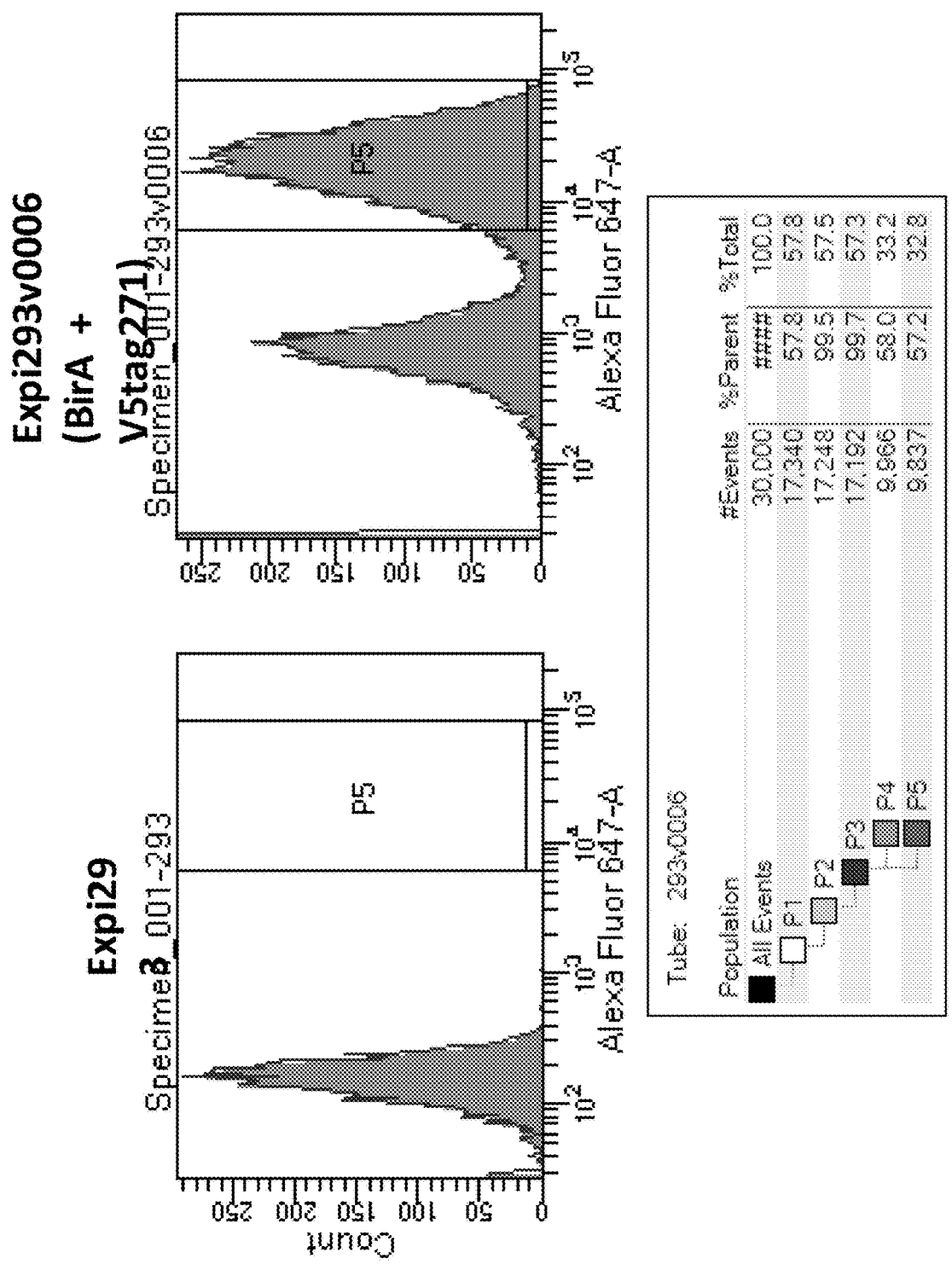
FIG. 18 shows cell sorting of cells transduced with BirA and V5 based on V5 expression.

A third approach for biotinylating the comPACTs is to express BirA in the Expi293 producer cells and biotinylate the comPACTs in vivo prior to purification. Expi293 cells were transduced with a lentiviral vector to co-express BirA flanked by V5 which acts as a cell surface transduction marker. Transduced cells sorted for V5+ also express BirA (FIG. 18). These cells can be used to produce biotinylated comPACTs in vivo before comPACT protein purification. Two cells lines were generated, which secrete BirA into the media (Expi293v0223) or express BirA on the cell surface (Expi293v0263). A third cell line expressing BirA flanked by the endoplasmic reticulum (ER) retention sequence KDEL was also made.

Figure 25:
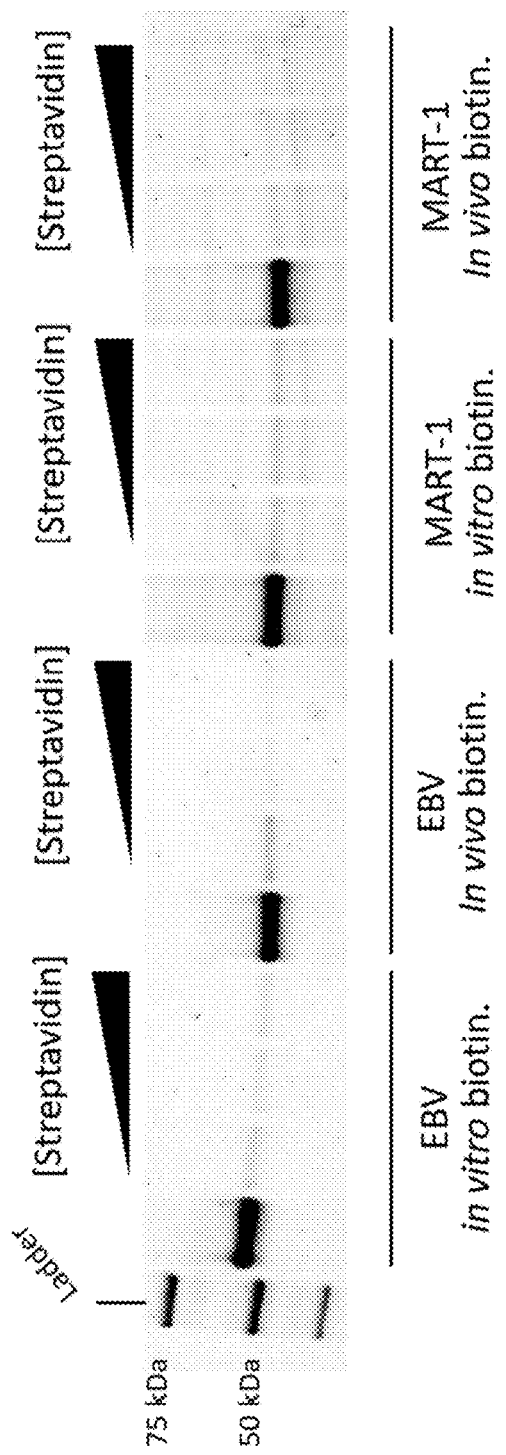
FIG. 25 shows biotinylation of EBV and MART-1 comPACT protein using BirA.

To asses biotin labeling efficiency under the in vitro or in vivo biotinylation approaches, a streptavidin pull down assay was performed. ComPACT protein (EBV or MART-1) were biotinylated either by treating the clarified media with BirA enzyme and the proper reactions components (enzymatic, in vitro) or by co-expressing the comPACT with BirA (in vivo) and incubated with increasing concentration of Streptavidin coated beads. Magnetic beads coated with Streptavidin (Dynabeads, Thermo Fisher) were added to 20 μg of the comPACT protein samples and incubated 30 min at room temperature. Magnetic beads were isolated at the bottom of the tube or well by magnetization and the protein content of the supernatant was assayed by SDS-PAGE. FIG. 25 shows the SDS-PAGE gel results. Near complete biotinylation can be achieve by adding the BirA enzyme during purification (in vitro) or by co-expressing the BirA enzyme and comPACT protein (in vivo). Samples lacking streptavidin beads had significant amounts of biotinylated protein in the supernatant, while addition of increasing amounts of streptavidin beads resulted in almost all the protein being removed from the supernatant, indicating biotinylation of the comPACT protein.

Figure 19:
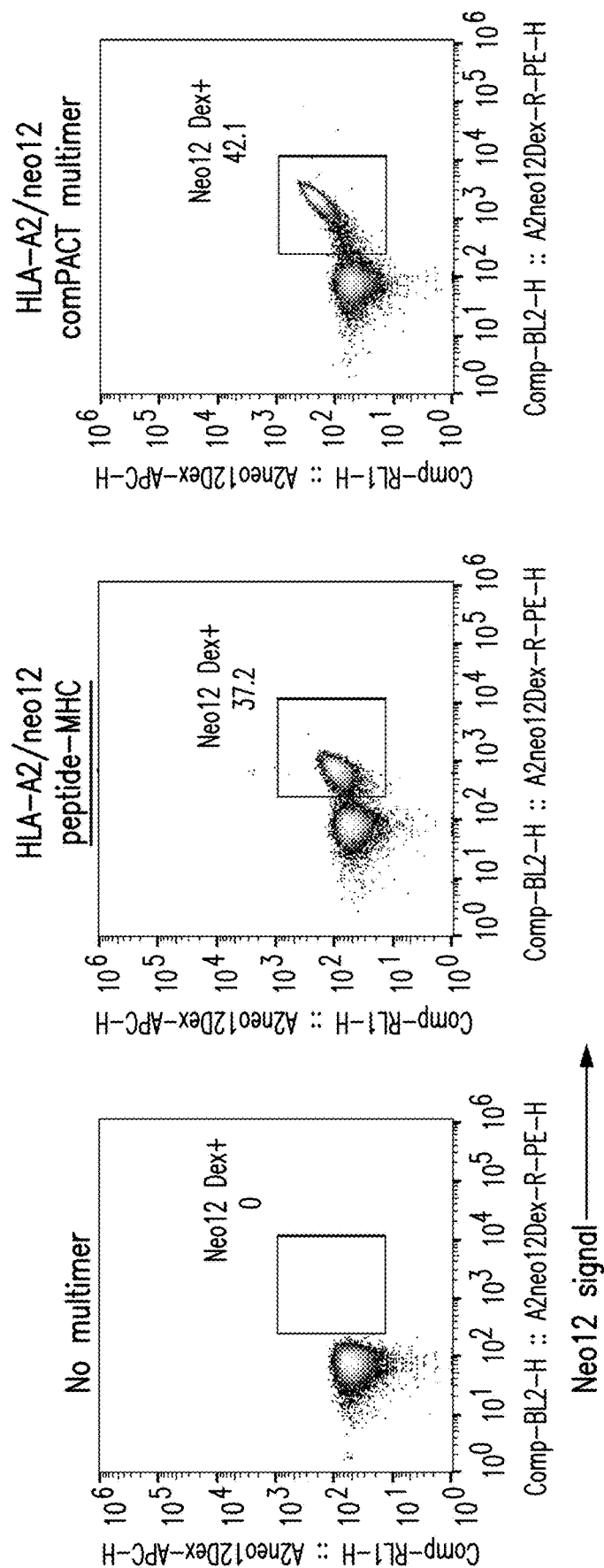
FIG. 19 shows antigen-specific capture of T cells using multimerized comPACT protein.

Example 7: Antigen-Specific T Cell Staining and Affinity Evaluation Using comPACT Proteins To compare antigen-specific T cell staining using comPACTs and conventional peptide-MHCs, comPACT dextramers were prepared according to a published protocol (Bethune, M. T., et al. BioTechniques 62, 123-130, doi: 10.2144/000114525 (2017)). T cells were engineered to express an A2/neo12-specific TCR and stained with either HLA-A2/neo12 peptide-MHC dextramers or HLA-A2/neo12 peptide comPACT dextramers. Staining with the comPACT dextramers was at least as efficient as that for peptide-MHC dextramers (FIG. 19). This data suggests that comPACT dextramers can be used to sort antigen-specific T cells for TCR sequencing.

Example 8: Functional T Cell Assays

NTAmer Binding Assay
Materials and Methods

Beyond antigen-specific capture of T cells, the modular design and ease-of-production of comPACTs facilitates their use in functional T cell assays. For example, incorporation of a mutated version (S88C) of β2M enables comPACTs to be labeled with a maleimide-dye conjugate, assembled as NTAmers, and used to measure kinetic parameters of TCR-comPACT binding. For instance, NTAmers can be used to resolve monovalent TCR-MHC I binding events in live cells. CD8 binding and multiple TCR-MHC I interactions at immune synapse allow for extended contact between T cells and antigen presenting cells. Fluorescent dye conjugated-ComPACT NTAmers are incubated with cells to allow for binding of the comPACT with the TCR. The Ni-PE particle component of the NTAmer is dissociated from the comPACT via the addition of imidazole, and the release of the fluorescent-comPACT is measured over time.

Dye Conjugation

Figure 20:
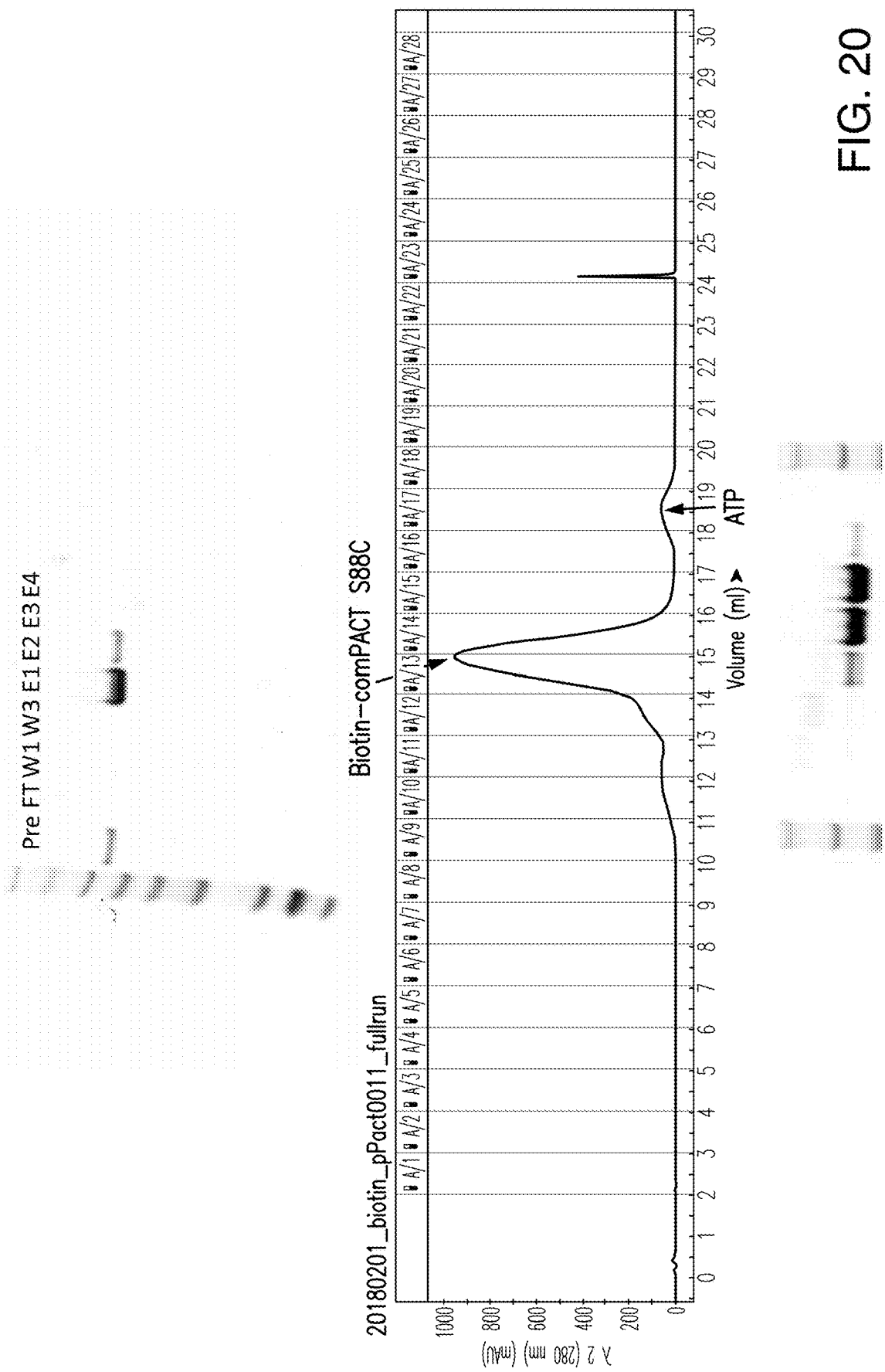
FIG. 20 shows comPACT NTAmer production using an S88C β2M comPACT protein.

S88C mutant comPACT proteins were constructed and expressed at ~150 mg/L. These mutant comPACTs exhibit similar purity and elution profiles as un-mutated comPACTs (FIG. 20). Other dyes, such as Cy5, can also be conjugated to S88C comPACTs The comPACT88C-HisTag monomer was reduced with Tris(2-carboxyethyl)phosphine hydrochloride (TCEP) and coupled with maleimide-Cy5, resulting in a comPACT88c-Cy5 labeled monomer. FIG. 21 shows the A280, A260, and A650 quantification of comPACTs labeled with Cy5. The dye to comPACT ratio was 67%.

NTAmer Assembly

The biotinylated comPACTs were bound to PE-Biotin-NTA bead by charging biotin-NTA with Nickel (Ni) (biotin-NiNTA) and then by assembling comPACT-Cy5 with biotin-NiNTA and PE-streptavidin (SA). Biotin-NiNTA was generated by mixing 5 mg biotin-NTA with 1 mL Nickel charging solution (50 mM NiSO4 in 100 mM HEPES pH7.5) to yield Ni2+NTA-biotin (7 nM). The solution was diluted with HBS to yield a 70 uM Ni2+NTA-biotin solution. The Ni2+NTA-biotin solution was combined with SA-PE (300 kDa) in 5 additions, 5 min between each addition. 20 uM Cy5-S88C comPACT was then added to NTAmer core, incubated for 10 min at room temperature in the dark and stored at 4 C. Both Neo12 and MART comPACTs were made and assembled into NTAmers. The His tag on the comPACT protein binds to the NiNTA which itself binds to the PE-streptavidin. Each NTAmer comprises multiple copies of a comPACT monomer bound to a streptavidin core with a fluorophore. Assembly of NTAmers are further discussed in Schmidt et al, *J. Biol Chem*, Dec. 2, 2011, 286 (48) 41723-41735, and Schmidt et al, Front Immunol, Jul. 30, 2013 doi: 10.3389/fimmu.2013.00218, both of which are hereby incorporated by reference in their entirety.

Biotinylated Neo12 and MART1 comPACT proteins were also assembled into PE-labeled tetramers and dextramers. Peptide-bound refolded MHC I molecules with neo12 antigenic peptides were also assembled into PE-labeled dextramers as controls. Methods of assembling peptide-MHC proteins into tetramers and dextramers are generally known in the art.

T Cell Binding

Gene edited T cells that express TCRs that bind Neo12 or MART1 neoantigens were resuspended in 1× Stain Buffer (BD Bovine serum albumin Stain Buffer, BD554657) at a density between 1-2×10$^6$ cells/mL. Cells were kept at 4° C. for duration of assay. NTAmers were added at various concentrations from 1:50-1:400 (v:v dilution) to the T cells in stain buffer and incubated for 15 min at 4° C. in the dark to allow multimerized NTAmer to bind the T cells. The T cells were washed twice in 1× stain buffer to remove unbound NTAmer and resuspended in stain buffer. To disrupt multimerized NTAmer and monitor Cy5 signal decay, imidazole disruption buffer (1.452 g imidazole and 50 mL 1× Hank's Buffered Saline) was added, mixed, and the samples were assessed via flow cytometer to monitor Cy5 signal decay. Additional antibody staining for the detection of various cellular markers was perform by incubating T cells for 15 min at 4° C. in dark, wash cells twice in 1× stain buffer. T cells were then fixed using IC Fixation Buffer (eBioscience IC Fixation Buffer, 00-8222-49).

Results

Figures 28A, 28B, 28C:
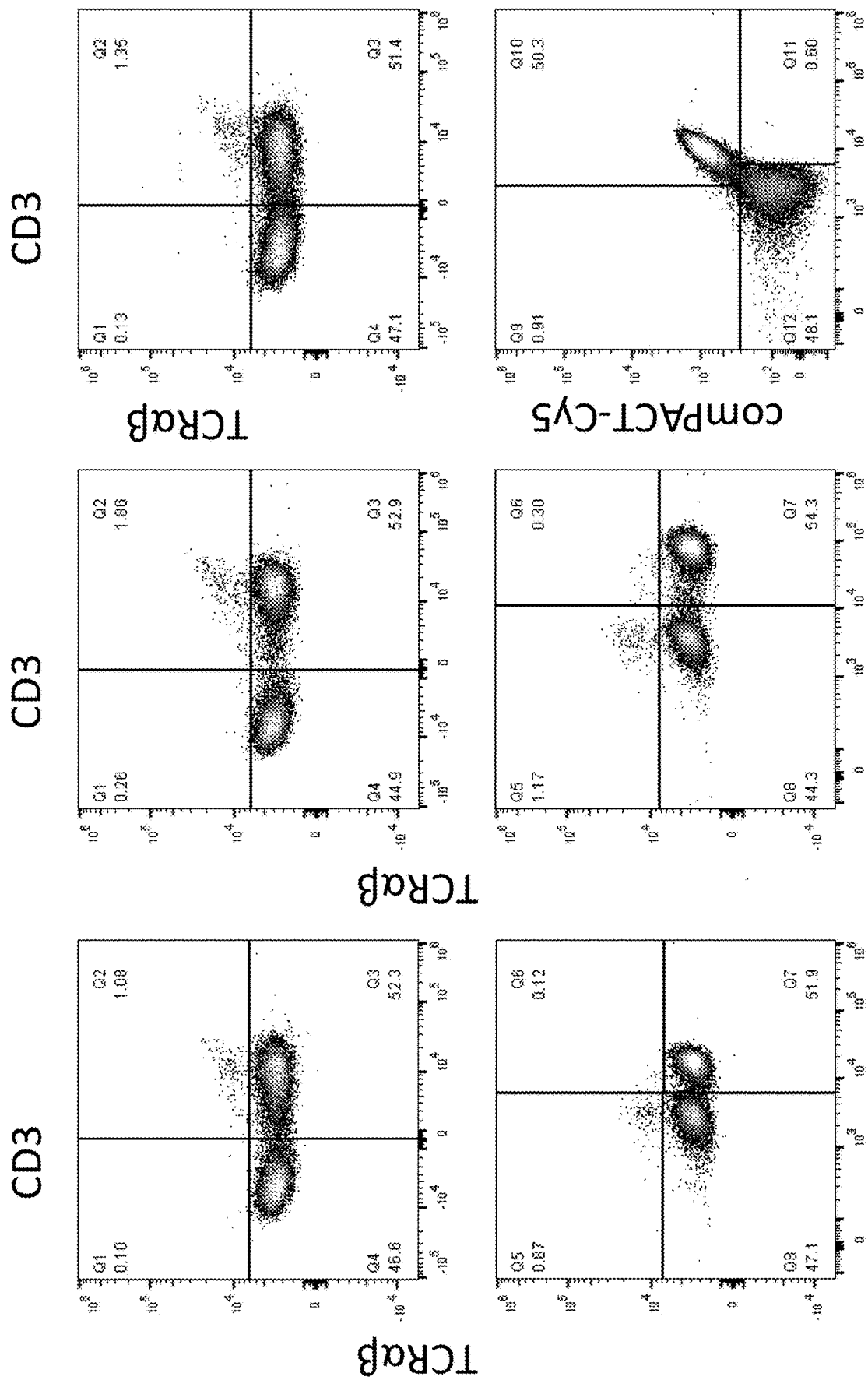
FIGS. 28A-28C show that neo12 comPACT molecules modified with Cy5 and His tags bind neo12 TCR edited T cells.

First, the ability of the biotinylated comPACT-Cy5 NTAmers to bind their cognate TCR was assessed. Neo12 peptide-bound refolded MHC I molecules, neo12 comPACT molecules, or neo12 NTAmers were assembled into dextramers and incubated with T cells expressing the neo12 TCR. Binding of each dextramer molecule to the cells was determined. FIG. 28A shows that gene edited T cells expressing neo12 TCRs demonstrated specific binding to neo12 peptide-bound refolded MHC I molecule dextramers (lower plot, x-axis is the dextramer PE signal) and this binding corresponded to the T cell population expressing CD3 at their surface (top plot, x-axis is the PE-Cy3 signal). FIG. 28B shows that gene edited T cells expressing neo12 TCR demonstrated specific binding to neo12 comPACT molecule dextramers (lower plot, x-axis is the dextramer PE signal) and this binding corresponded to the T cell population expressing CD3 at their surface (top plot, x-axis is the PE-Cy3 signal). FIG. 28C shows that gene edited T cells expressing neo12 TCR demonstrated specific binding to neo12 comPACT NTAmer dextramers (lower plot, x-axis is the dextramer PE signal) and this binding corresponded to the T cell population expressing CD3 at their surface (top plot, x-axis is the PE-Cy3 signal).

Next, the ability of the biotinylated comPACT-Cy5 NTAmers to bind TCRs in an antigen specific manner was confirmed. Neo12 or F5 TCR T cells were incubated with NTAmers with neo12 antigen. F5 TCR T cells were used as a negative control. Neo12 TCR T cells were also incubated with a dextramer composed of neo12 comPACT proteins. The bound T cells were then incubated with imidazole as described and binding of the NTAmers and dextramers was assessed as previously described. The addition of imidazole inhibited the ability of the neo12-ComPACT NTAmer to bind to neo12 T cells (FIGS. 29A-29C). Neo12 TCR T cells showed specific binding to neo12 NTAmer reagent (FIG. 29A, NTAmer Cy5 signal is the y-axis). The neo12-ComPACT NTAmer is specific to Neo12 T cells and did not bind to T cells expressing F5 TCRs (FIG. 29B). Neo12 comPACT dextramers also bound to the neo12 TCR T cells (FIG. 29D). Neo12 TCR T cells showed no binding to neo12 NTAmer reagent when incubated in the presence of imidazole (FIG. 29C) demonstrating the need for a multimerized reagent to observe Cy5 signal from S88C modified comPACT molecules.

MART-1 NTAmers were also used to show antigen specific binding of T cells edited to express F5 TCR (FIGS. 30A-30D). FIG. 30A shows binding of MART-1 comPACT dextramer to F5 TCR T cells. FIG. 30B shows binding of MART-1 comPACT dextramer to M1W TCR T cells. FIG. 30C shows binding of MART-1 comPACT NTAmers to F5 TCR T cells. FIG. 30D shows binding of MART-1 comPACT NTAmers to M1W TCR T cells. The low levels of MART-1 comPACT NTAmer binding to M1W T cells is likely due to the low affinity of the MW TCR for the cognate antigen:MHC I protein.

Figures 31A, 31B, 31C:
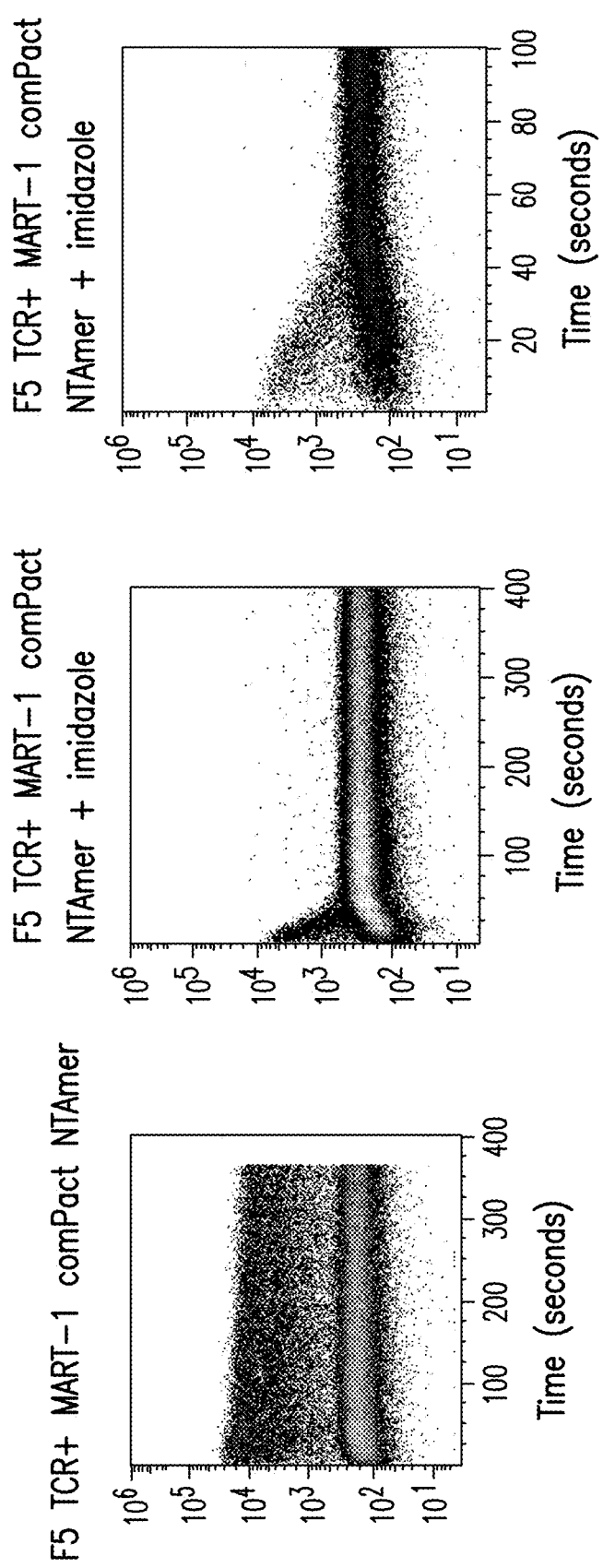
FIGS. 31A-31C show that F5 TCR edited T cells show rapid Cy5 signal decay after NTAmer disruption by imidazole.

The monomeric TCR:pMHC-Cy5 disassociation was assessed by measuring the Cy5 signal decay of two TCRs, MART-1 F5 and MW, with differential TCR:MHC I binding affinities against the same peptide:MHC I complex (HLA: A02+MART-1). Binding of MART1 NTAmers to T cells expressing F5 TCRs was stable over time in the absence of imidazole induced NTAmer disruption (FIG. 31A). However, disruption of the multimerized MART-1 NTAmers with imidazole resulted in a time dependent disassociation of monomeric MART-1 comPACT molecules to the F5 TCRs (FIG. 31). FIG. 31C shows a zoomed in view of a subset of time data from FIG. 31B.

In conclusion, Neo12 and F5 T cells demonstrate similar binding levels between NTAmers and equivalent comPACT dextramers and comPACT NTAmers are able to bind neoantigen T cells in an antigen specific manner. Neo12 and F5 T cells demonstrate similar binding levels between NTAmers and comPACT dextramers for both neo12 and MART-1 comPACTs. In addition, the NTAmer complex can be disrupted by imidazole addition and monovalent TCR:MHC I off-rates can be measured by the decay of comPACT-Cy5 signal on live T cells. This decay takes place over a tens of seconds time scale.

Example 9: comPACT Library Production

Figure 26B:
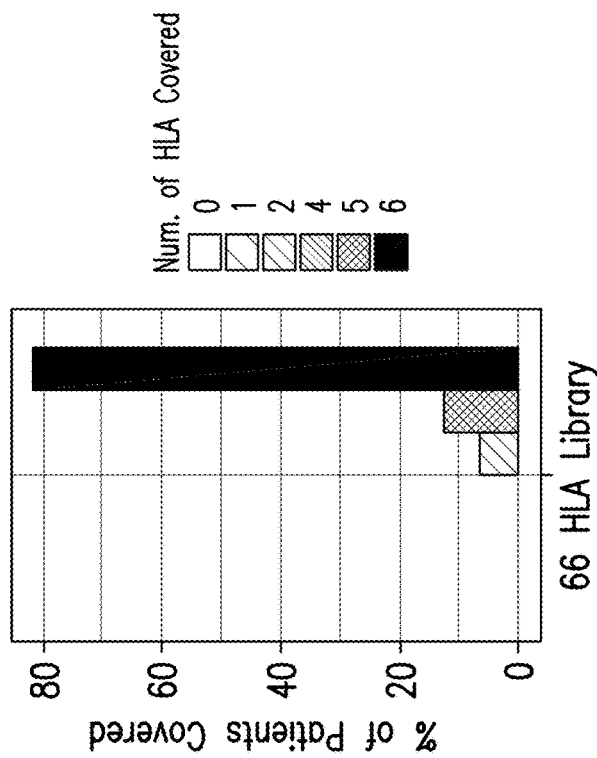
FIGS. 26A-26B show the percent of patients covered by top HLA I alleles in the United States relative to comPACT HLA repertoire size.
Figure 26A:
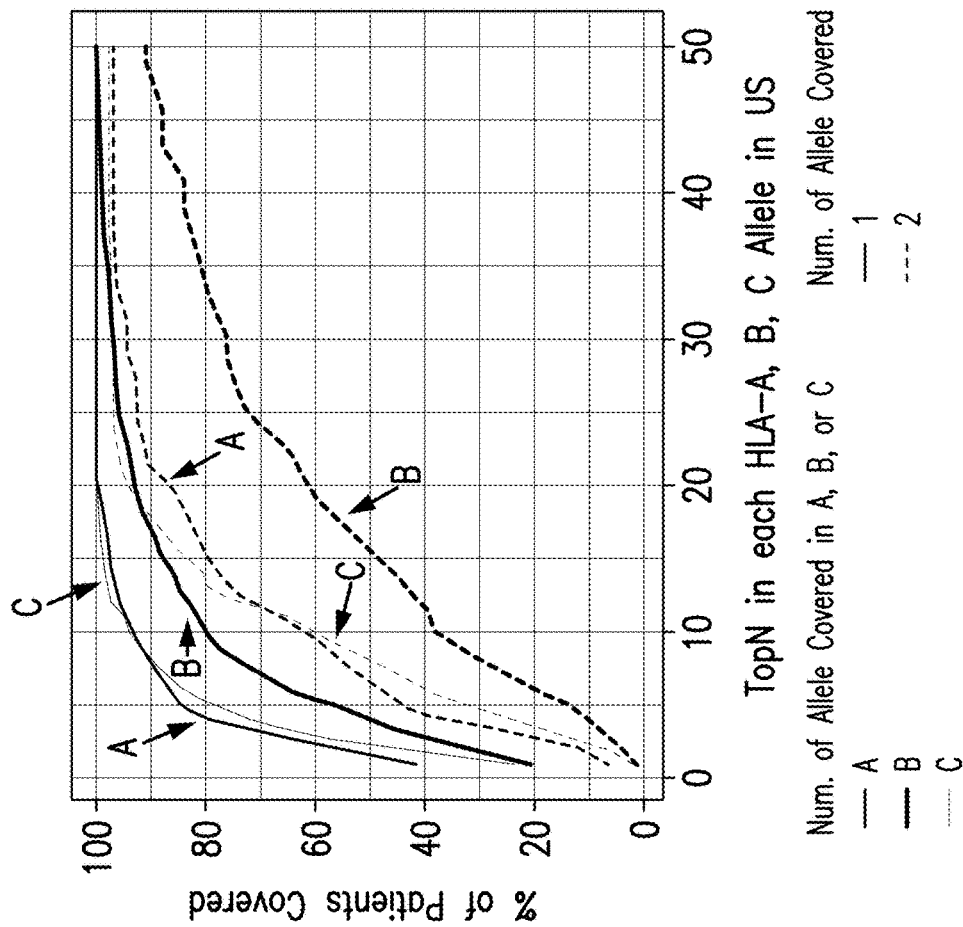

HLA allele diversity across the US human populations was analyzed from the Allele Frequency Net Database (www.allelefrequencies.net) by bioinformatics to identify the optimal number of alleles to include in the HLA repertoire to effect high coverage of subject HLA frequencies. 9736 alleles were analyzed. FIG. 26A shows the analysis of the percentage of patients in which one or both alleles from each of HLA A, B, and C loci are covered by a library of 66 HLA alleles. Solid lines indicate 1 allele is covered, while dashed lines indicate both alleles are covered. 66 alleles enable the coverage of at least 4 of 6 HLA alleles per patient in >95% of total population and 6/6 alleles in >80% of population (FIG. 26B). The most frequent HLA-I allele is HLA-A02:01 with ~50% US prevalence. HLA libraries first shown herein therefore allow the most potential for broad implementation of personalized neoTCR-T cell therapies for a global and diverse population.

Figure 27A:
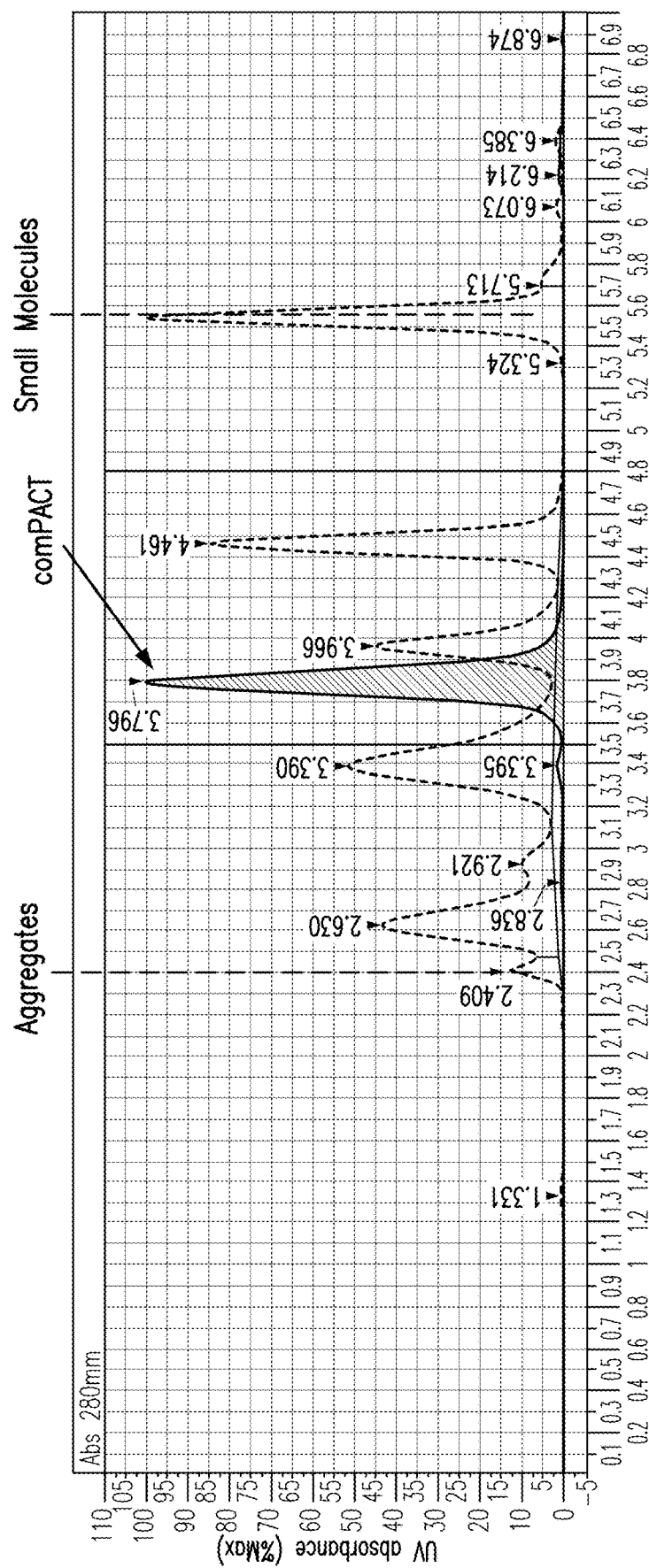
FIGS. 27A-27C show comPACT protein monodispersity, yield, and expression for a representative selection of comPACT proteins.
Figure 27B:
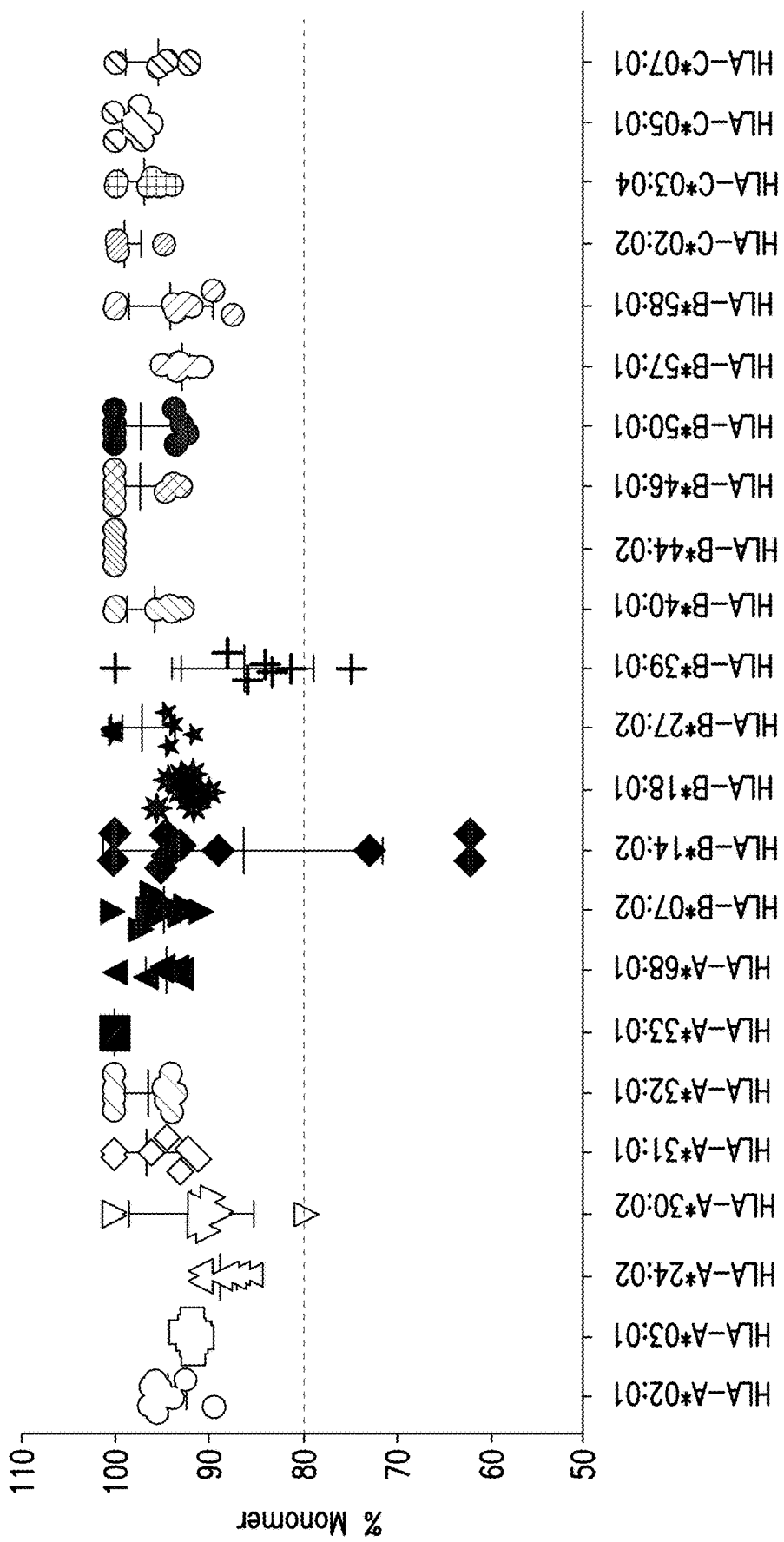
Figure 27C:
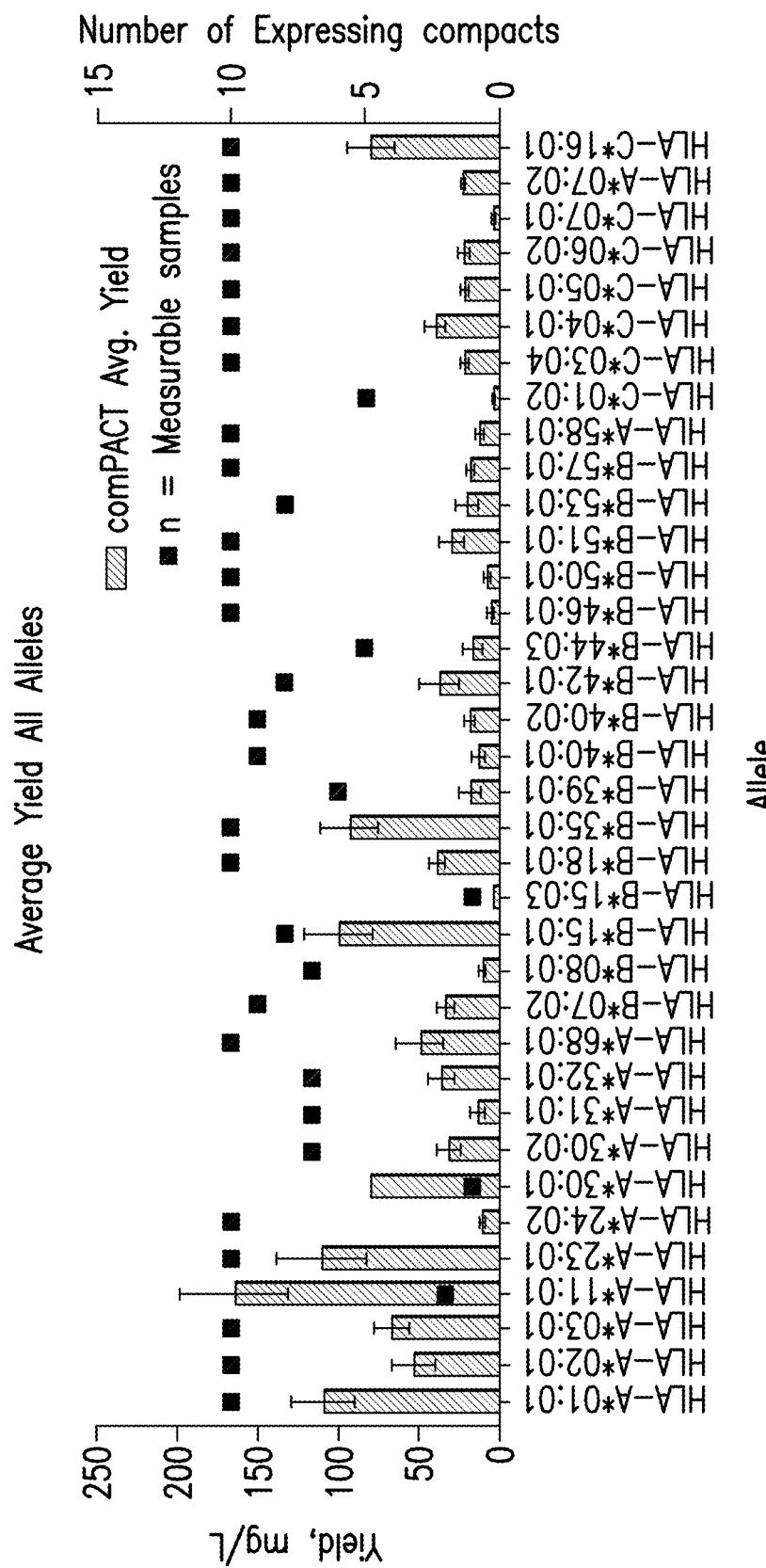

Next, a library of comPACT proteins with different neoepitopes and selected HLA alleles was made. Neoepitope candidates were chosen from the Immune Epitope Database (www.iedb.org). Full sequences for each of the 66 HLA-I alleles in the repertoire were obtained from the IMGT database and modified to include the Y84C mutation. All clones were sequence verified and banked in the database and reagent inventory. Ten neoepitope peptide were chosen from the IEDB database and inserted into a panel of 36 HLA alleles. ComPACTs of the selected neoepitopes and HLA alleles were expressed and purified via Size Exclusion Chromatography column (Agilent Sec Bio 300) connected to an Agilent Infinity II HPLC system (SEC-HPLC) according to the manufacturer's instructions. The results are shown in FIGS. 27A-27C. The comPACTs were purified as monodisperse polypeptides, as assessed via SEC-HPLC by measuring the area under the curve of the monomer peak divided by the area under the whole chromatogram (FIGS. 27A and 27B). Most comPACTs were expressed at a high titer (FIG. 27C). At least one comPACT protein for each HLA allele described has been purified and characterized via HPLC, indicating that the comPACT platform is robust and amenable to many alleles.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

SEQUENCE LISTING

| SEQ ID NO | Name | Sequence |
|---|---|---|
| 1 | hGH nucleotide | atggcgacgggttcaagaacttccctacttcttgcatttggcctgctttgtttgccgtggttacaggagggctcagca |
| 2 | hGH peptide | MATGSRTSLLLAFGLLCLPWLQEGSA |
| 3 | Universal Target 1 | cgtggttacaggagggctcagca |
| 4 | Universal Target 2 | ggatgcggaggatccggcg |
| 5 | Universal Target 3 | ggaagcggaggatccggcg |
| 6 | Universal Target 4 | ggaagcggaggatccaccagc |
| 7 | Universal Primer 1 | atgtacgggccagatatacgc |
| 8 | Universal Primer 2 | acacccgccgcgcttaatg |
| 9 | Linker peptide 1 | GGGGS |
| 10 | Linker nucleotide 1 | ggcggcggcggcagc |
| 11 | Linker peptide 2 | GSGGS |
| 12 | Linker nucleotide 2 | ggcagcggcggcagc |
| 13 | Linker peptide 3 | GCGGS |
| 14 | Linker nucleotide 3 | ggctgcggcggcagc |
| 15 | Linker L1a peptide | GCGGSGGGSGGGGS |
| 16 | Linker L1a nucleotide | ggctgcggcggcagcggcggcggcggcagcggcggcggcggcagc |
| 17 | Linker L1b peptide | GGGGSGGGSGGGGS |
| 18 | Linker L1b nucleotide | ggcggcggcggcagcggcggcggcggcagcggcggcggcggcagc |
| 19 | Linker L2 peptide | GGGGSGGGSGGGSGGGGS |
| 20 | Linker L2 nucleotide | ggcggcggcggcagcggcggcggcggcagcggcggcggcggcagcggcggcggcggcagc |
| 21 | Linker L3 peptide | GSGGSGGSAGG |
| 22 | Linker L3 nucleotide | ggcagcggcggcagcggcggcagcgcgggcggc |
| 23 | hIG1 Kappa light chain peptide | MDMRVPAQLLGLLLLWLSGARC |
| 24 | hIG1 Kappa light chain nucleotide | atggatatgcgcgtgccggcgcagctgctgggcctgctgctgctgtggctgagcggcgcgcgctgc |
| 25 | B2M, signal peptide | MSRSVALAVLALLSLSGLEA |

SEQUENCE LISTING

| SEQ ID NO | Name | Sequence |
|---|---|---|
| 26 | B2M signal nucleotide | atgagccgcagcgtggcgctggcggtgctggcgctgctgagcctgagcggcctggaagcg |
| 27 | IL2, signal peptide | MYRMQLLSCIALSLALVTNS |
| 28 | IL2, signal nucleotide | atgtatcgcatgcagctgctgagctgcattgcgctgagcctggcgctggtgaccaacagc |
| 29 | AviTag Nucleotide | GGCCTGAACGACATCTTCGAGGCTCAGAAAATCGAATGGCACGAA |
| 30 | AviTag peptide | GLNDIFEAQKIEWHE |
| 31 | TEV nucleotide | gagagaaacctgtacttccagggc |
| 32 | TEV peptide | ENLYFQG |
| 33 | His Tag nucleotide | catcatcatcatcatcat |
| 34 | His tag peptide | HHHHHH |
| 35 | Concatenated His tag | catcatcatcatcatcatggcggcggcagcggcggcggcagcggcagccatcatcatcatcatcat |
| 36 | Concatenated His tag | HHHHHHGGGSGGGSGSHHHHHH |
| 37 | Purification cluster | GLNDIFEAQKIEWHEGGGENLYFQGGSHHHHHHGGGSGGGSGSHHHHHH |
| 38 | CMV promoter | tagtaatcaattacggggtcattagttcatagcccatatatggagttccgcgttacataactta cggtaaatggcccgcctggctgaccgcccaacgacccccgcccattgacgtcaataatgacgta tgttcccatagtaacgccaatagggactttccattgacgtcaatgggtggagtatttacggtaa actgcccacttggcagtacatcaagtgtatcatatgccaagtacgccccctattgacgtcaatg acggtaaatggcccgcctggcattatgcccagtacatgaccttatgggactttcctacttggca gtacatctacgtattagtcatcgctattaccatggtgatgcggttttggcagtacatcaatggg cgtggatagcggtttgactcacggggatttccaagtctccaccccattgacgtcaatgggagtt tgttttggcaccaaaatcaacgggactttccaaaatgtcgtaacaactccgccccattgacgca aatgggcggtaggcgtgtacggtgggaggtctatataagcagagctggtttagtgaaccgtcag |
| 39 | HLA-A*01:01 | GSHSMRYFFTSVSRPGRGEPRFIAVGYVDDTQFVRFDSDAASQKMEPRAPWIEQEGPEYWDQET RNMKAHSQTDRANLGTLRGCYNQSEDGSHTIQINYGCDVGPDGRFLRGYRQDAYDGKDYIALNE DLRSWTAADMAAQITKRKWEAVHAAEQRRVYLEGRCVDGLRRYLENGKETLQRTDPPKTHMTHH PISDHEATLRCWALGFYPAEITLTWQRDGEDQTQDTELVETRPAGDGTFQKWAAVVVPSGEEQR YTCHVQHEGLPKPLTLRWEL |
| 40 | HLA-A*02:01 | GSHSMRYFFTSVSRPGRGEPRFIAVGYVDDTQFVRFDSDAASQRMEPRAPWIEQEGPEYWDGET RKVKAHSQTHRVDLGTLRGCYNQSEAGSHTVQRMYGCDVGSDWRFLRGYHQYAYDGKDYIALKE DLRSWTAADMAAQTTKHKWEAAHVAEQLRAYLEGTCVEWLRRYLENGKETLQRTDAPKTHMTHH AVSDHEATLRCWALSFYPAEITLTWQRDGEDQTQDTELVETRPAGDGTFQKWAAVVVPSGQEQR YTCHVQHEGLPKPLTLRWEP |
| 41 | HLA-A*03:01 | GSHSMRYFFTSVSRPGRGEPRFIAVGYVDDTQFVRFDSDAASQRMEPRAPWIEQEGPEYWDQET RNVKAQSQTDRVDLGTLRGCYNQSEAGSHTIQIMYGCDVGSDGRFLRGYRQDAYDGKDYIALNE DLRSWTAADMAAQITKRKWEAAHEAEQLRAYLDGTCVEWLRRYLENGKETLQRTDPPKTHMTHH PISDHEATLRCWALGFYPAEITLTWQRDGEDQTQDTELVETRPAGDGTFQKWAAVVVPSGEEQR YTCHVQHEGLPKPLTLRWEL |
| 42 | HLA-A*24:02 | GSHSMRYFSTSVSRPGRGEPRFIAVGYVDDTQFVRFDSDAASQRMEPRAPWIEQEGPEYWDEET GKVKAHSQTDRENLRIALRCYNQSEAGSHTLQMMFGCDVGSDGRFLRGYHQYAYDGKDYIALKE DLRSWTAADMAAQITKRKWEAAHVAEQQRAYLEGTCVDGLRRYLENGKETLQRTDPPKTHMTHH PISDHEATLRCWALGFYPAEITLTWQRDGEDQTQDTELVETRPAGDGTFQKWAAVVVPSGEEQR YTCHVQHEGLPKPLTLRWEP |
| 43 | HLA-A*30:02 | GSHSMRYFSTSVSRPGSGEPRFIAVGYVDDTQFVRFDSDAASQRMEPRAPWIEQERPEYWDQET RNVKAHSQTDRENLGTLRGCYNQSEAGSHTIQIMYGCDVGSDGRFLRGYEQHAYDGKDYIALNE DLRSWTAADMAAQITQRKWEAARRAEQLRAYLEGTCVEWLRRYLENGKETLQRTDPPKTHMTHH PISDHEATLRCWALGFYPAEITLTWQRDGEDQTQDTELVETRPAGDGTFQKWAAVVVPSGEEQR YTCHVQHEGLPKPLTLRWEL |
| 44 | HLA-A*31:01 | GSHSMRYFTTSVSRPGRGEPRFIAVGYVDDTQFVRFDSDAASQRMEPRAPWIEQERPEYWDQET RNVKAHSQIDRVDLGTLRGCYNQSEAGSHTIQMMYGCDVGSDGRFLRGYQQDAYDGKDYIALNE DLRSWTAADMAAQITQRKWEAARVAEQLRAYLEGTCVEWLRRYLENGKETLQRTDPPKTHMTHH AVSDHEATLRCWALSFYPAEITLTWQRDGEDQTQDTELVETRPAGDGTFQKWASVVVPSGQEQR YTCHVQHEGLPKPLTLRWEP |

SEQUENCE LISTING

| SEQ ID NO | Name | Sequence |
|---|---|---|
| 45 | HLA-A*32:01 | GSHSMRYFFTSVSRPGRGEPRFIAVGYVDDTQFVRFDSDAASQRMEPRAPWIEQEGPEYWDQET RNVKAHSQTDRESLRIALRCYNQSEAGSHTIQMMYGCDVGPDGRLLRGYQQDAYDGKDYIALNE DLRSWTAADMAAQITQRKWEAARVAEQLRAYLEGTCVEWLRRYLENGKETLQRTDAPKTHMTHH AVSDHEATLRCWALSFYPAEITLTWQRDGEDQTQDTELVETRPAGDGTFQKWASVVVPSGQEQR YTCHVQHEGLPKPLTLRWEP |
| 46 | HLA-A*33:01 | GSHSMRYFTTSVSRPGRGEPRFIAVGYVDDTQFVRFDSDAASQRMEPRAPWIEQEGPEYWDRNT RNVKAHSQIDRVDLGTLRGCYNQSEAGSHTIQMMYGCDVGSDGRFLRGYQQDAYDGKDYIALNE DLRSWTAADMAAQITQRKWEAARVAEQLRAYLEGTCVEWLRRHLENGKETLQRTDPPRTHMTHH AVSDHEATLRCWALSFYPAEITLTWQRDGEDQTQDTELVETRPAGDGTFQKWASVVVPSGQEQR YTCHVQHEGLPKPLTLRWEP |
| 47 | HLA-A*68:01 | GSHSMRYFYTSVSRPGRGEPRFIAVGYVDDTQFVRFDSDAASQRMEPRAPWIEQEGPEYWDRNT RNVKAQSQTDRVDLGTLRGCYNQSEAGSHTIQMMYGCDVGSDGRFLRGYRQDAYDGKDYIALKE DLRSWTAADMAAQTTKHKWEAAHVAEQWRAYLEGTCVEWLRRYLENGKETLQRTDAPKTHMTHH AVSDHEATLRCWALSFYPAEITLTWQRDGEDQTQDTELVETRPAGDGTFQKWVAVVVPSGQEQR YTCHVQHEGLPKPLTLRWEP |
| 48 | HLA-B*07:02 | GSHSMRYFYTSVSRPGRGEPRFISVGYVDDTQFVRFDSDAASPREEPRAPWIEQEGPEYWDRNT QIYKAQAQTDRESLRNLRGCYNQSEAGSHTLQSMYGCDVGPDGRLLRGHDQYAYDGKDYIALNE DLRSWTAADTAAQITQRKWEAAREAEQRRAYLEGECVEWLRRYLENGKDKLERADPPKTHVTHH PISDHEATLRCWALGFYPAEITLTWQRDGEDQTQDTELVETRPAGDRTFQKWAAVVVPSGEEQR YTCHVQHEGLPKPLTLRWEP |
| 49 | HLA-B*14:02 | GSHSMRYFYTAVSRPGRGEPRFISVGYVDDTQFVREDSDAASPREEPRAPWIEQEGPEYWDRNT QICKTNTQTDRESLRNLRGCYNQSEAGSHTLQWMYGCDVGPDGRLLRGYNQFAYDGKDYIALNE DLSSWTAADTAAQITQRKWEAAREAEQLRAYLEGTCVEWLRRHLENGKETLQRADPPKTHVTHH PISDHEATLRCWALGFYPAEITLTWQRDGEDQTQDTELVETRPAGDRTFQKWAAVVVPSGEEQR YTCHVQHEGLPKPLTLRWEP |
| 50 | HLA-B*18:01 | GSHSMRYFHTSVSRPGRGEPRFISVGYVDGTQFVREDSDAASPRTEPRAPWIEQEGPEYWDRNT QISKTNTQTYRESLRNLRGCYNQSEAGSHTLQRMYGCDVGPDGRLLRGHDQSAYDGKDYIALNE DLSSWTAADTAAQITQRKWEAARVAEQLRAYLEGTCVEWLRRHLENGKETLQRADPPKTHVTHH PISDHEATLRCWALGFYPAEITLTWQRDGEDQTQDTELVETRPAGDRTFQKWAAVVVPSGEEQR YTCHVQHEGLPKPLTLRWEP |
| 51 | HLA-B*27:02 | GSHSMRYFHTSVSRPGRGEPRFITVGYVDDTLEVREDSDAASPREEPRAPWIEQEGPEYWDRET QICKAKAQTDRENLRIALRCYNQSEAGSHTLQNMYGCDVGPDGRLLRGYHQDAYDGKDYIALNE DLSSWTAADTAAQITQRKWEAARVAEQLRAYLEGECVEWLRRYLENGKETLQRADPPKTHVTHH PISDHEATLRCWALGFYPAEITLTWQRDGEDQTQDTELVETRPAGDRTFQKWAAVVVPSGEEQR YTCHVQHEGLPKPLTLRWEP |
| 52 | HLA-B*39:01 | GSHSMRYFYTSVSRPGRGEPRFISVGYVDDTQFVREDSDAASPREEPRAPWIEQEGPEYWDRNT QICKTNTQTDRESLRNLRGCYNQSEAGSHTLQRMYGCDVGPDGRLLRGHNQFAYDGKDYIALNE DLSSWTAADTAAQITQRKWEAARVAEQLRTYLEGTCVEWLRRYLENGKETLQRADPPKTHVTHH PISDHEATLRCWALGFYPAEITLTWQRDGEDQTQDTELVETRPAGDRTFQKWAAVVVPSGEEQR YTCHVQHEGLPKPLTLRWEP |
| 53 | HLA-B*40:01 | GSHSMRYFHTAMSRPGRGEPRFITVGYVDDTLFVREDSDATSPRKEPRAPWIEQEGPEYWDRET QISKTNTQTYRESLRNLRGCYNQSEAGSHTLQRMYGCDVGPDGRLLRGHNQYAYDGKDYIALNE DLRSWTAADTAAQISQRKLEAARVAEQLRAYLEGECVEWLRRYLENGKDKLERADPPKTHVTHH PISDHEATLRCWALGFYPAEITLTWQRDGEDQTQDTELVETRPAGDRTFQKWAAVVVPSGEEQR YTCHVQHEGLPKPLTLRWEP |
| 54 | HLA-B*44:02 | GSHSMRYFYTAMSRPGRGEPRFITVGYVDDTLFVREDSDATSPRKEPRAPWIEQEGPEYWDRET QISKTNTQTYRENLRTALRCYNQSEAGSHIIQRMYGCDVGPDGRLLRGYDQDAYDGKDYIALNE DLSSWTAADTAAQITQRKWEAARVAEQLDRAYLEGLCVESLRRYLENGKETLQRADPPKTHVTHH PISDHEVTLRCWALGFYPAEITLTWQRDGEDQTQDTELVETRPAGDRTFQKWAAVVVPSGEEQR YTCHVQHEGLPKPLTLRWEP |
| 55 | HLA-B*46:01 | GSHSMRYFYTAMSRPGRGEPRFIAVGYVDDTQFVREDSDAASPRMAPRAPWIEQEGPEYWDRET QKYKRQAQTDRVSLRNLRGCYNQSEAGSHTLQRMYGCDVGPDGRLLRGHDQSAYDGKDYIALNE DLSSWTAADTAAQITQRKWEAAREAEQWRAYLEGLCVEWLRRYLENGKETLQRADPPKTHVTHH PISDHEATLRCWALGFYPAEITLTWQRDGEDQTQDTELVETRPAGDRTFQKWAAVVVPSGEEQR YTCHVQHEGLPKPLTLRWEP |
| 56 | HLA-B*50:01 | GSHSMRYFHTAMSRPGRGEPRFITVGYVDDTLFVREDSDATSPRKEPRAPWIEQEGPEYWDRET QISKTNTQTYRESLRNLRGCYNQSEAGSHTWQRMYGCDLGPDGRLLRGYNQLAYDGKDYIALNE DLSSWTAADTAAQITQRKWEAAREAEQLRAYLEGLCVEWLRRYLENGKETLQRADPPKTHVTHH PISDHEATLRCWALGFYPAEITLTWQRDGEDQTQDTELVETRPAGDRTFQKWAAVVVPSGEEQR YTCHVQHEGLPKPLTLRWEP |

| SEQ ID NO | Name | Sequence |
|---|---|---|
| 57 | HLA-B*57:01 | GSHSMRYFYTAMSRPGRGEPRFIAVGYVDDTQFVREDSDAASPRMAPRAPWIEQEGPEYWDGET<br>RNMKASAQTYRENLRIALRCYNQSEAGSHIIQVMYGCDVGPDGRLLRGHDQSAYDGKDYIALNE<br>DLSSWTAADTAAQITQRKWEAARVAEQLRAYLEGLCVEWLRRYLENGKETLQRADPPKTHVTHH<br>PISDHEATLRCWALGFYPAEITLTWQRDGEDQTQDTELVETRPAGDRTFQKWAAVVVPSGEEQR<br>YTCHVQHEGLPKPLTLRWEP |
| 58 | HLA-B*58:01 | GSHSMRYFYTAMSRPGRGEPRFIAVGYVDDTQFVREDSDAASPRTEPRAPWIEQEGPEYWDGET<br>RNMKASAQTYRENLRIALRCYNQSEAGSHIIQRMYGCDLGPDGRLLRGHDQSAYDGKDYIALNE<br>DLSSWTAADTAAQITQRKWEAARVAEQLRAYLEGLCVEWLRRYLENGKETLQRADPPKTHVTHH<br>PVSDHEATLRCWALGFYPAEITLTWQRDGEDQTQDTELVETRPAGDRTFQKWAAVVVPSGEEQR<br>YTCHVQHEGLPKPLTLRWEP |
| 59 | HLA-C*02:02 | CSHSMRYFYTAVSRPSRGEPHFIAVGYVDDTQFVREDSDAASPRGEPRAPWVEQEGPEYWDRET<br>QKYKRQAQTDRVNLRKLRGCYNQSEAGSHTLQRMYGCDLGPDGRLLRGYDQSAYDGKDYIALNE<br>DLRSWTAADTAAQITQRKWEAAREAEQWRAYLEGECVEWLRRYLENGKETLQRAEHPKTHVTHH<br>PVSDHEATLRCWALGFYPTEITLTWQRDGEDQTQDTELVETRPAGDTFQKWAAVVVPSGEEQR<br>YTCHVQHEGLPEPLTLRWEP |
| 60 | HLA-C*03:04 | GSHSMRYFYTAVSRPGRGEPHFIAVGYVDDTQFVREDSDAASPRGEPRAPWVEQEGPEYWDRET<br>QKYKRQAQTDRVSLRNLRGCYNQSEAGSHIIQRMYGCDLGPDGRLLRGYDQYAYDGKDYIALNE<br>DLRSWTAADTAAQITQRKWEAAREAEQLRAYLEGLCVEWLRRYLKNGKETLQRAEHPKTHVTHH<br>PVSDHEATLRCWALGFYPAEITLTWQWDGEDQTQDTELVETRPAGDGTFQKWAAVVVPSGEEQR<br>YTCHVQHEGLPEPLTLRWEP |
| 61 | HLA-C*05:01 | CSHSMRYFYTAVSRPGRGEPRFIAVGYVDDTQFVQFDSDAASPRGEPRAPWVEQEGPEYWDRET<br>QKYKRQAQTDRVNLRKLRGCYNQSEAGSHTLQRMYGCDLGPDGRLLRGYNQPAYDGKDYIALNE<br>DLRSWTAADKAAQITQRKWEAAREAEQRRAYLEGTCVEWLRRYLENGKKTLQRAEHPKTHVTHH<br>PVSDHEATLRCWALGFYPAEITLTWQRDGEDQTQDTELVETRPAGDGTFQKWAAVVVPSGEEQR<br>YTCHVQHEGLPEPLTLRWGP |
| 62 | HLA-C*07:01 | CSHSMRYFDTAVSRPGRGEPRFISVGYVDDTQFVREDSDAASPRGEPRAPWVEQEGPEYWDRET<br>QNYKRQAQADRVSLRNLRGCYNQSEDGSHTLQRMYGCDLGPDGRLLRGYDQSAYDGKDYIALNE<br>DLRSWTAADTAAQITQRKLEAARAAEQLRAYLEGTCVEWLRRYLENGKETLQRAEPPKTHVTHH<br>PLSDHEATLRCWALGFYPAEITLTWQRDGEDQTQDTELVETRPAGDTFQKWAAVVVPSGQEQR<br>YTCHMQHEGLQEPLTLSWEP |
| 63 | HLA-A*11:01 | GSHSMRYFYTSVSRPGRGEPRFIAVGYVDDTQFVREDSDAASQRMEPRAPWIEQEGPEYWDQET<br>RNVKAQSQTDRVDLGTLRGCYNQSEDGSHTIQIMYGCDVGPDGRFLRGYRQDAYDGKDYIALNE<br>DLRSWTAADMAAQITKRKWEAAHAAEQQRAYLEGRCVEWLRRYLENGKETLQRTDPPKTHMTHH<br>PISDHEATLRCWALGFYPAEITLTWQRDGEDQTQDTELVETRPAGDGTFQKWAAVVVPSGEEQR<br>YTCHVQHEGLPKPLTLRWEL |
| 64 | HLA-A*23:01 | GSHSMRYFSTSVSRPGRGEPRFIAVGYVDDTQFVREDSDAASQRMEPRAPWIEQEGPEYWDEET<br>GKVKAHSQTDRENLRIALRCYNQSEAGSHTLQMMFGCDVGSDGRFLRGYHQYAYDGKDYIALKE<br>DLRSWTAADMAAQITQRKWEAARVAEQLRAYLEGTCVDGLRRYLENGKETLQRTDPPKTHMTHH<br>PISDHEATLRCWALGFYPAEITLTWQRDGEDQTQDTELVETRPAGDGTFQKWAAVVVPSGEEQR<br>YTCHVQHEGLPKPLTLRWEP |
| 65 | HLA-A*30:01 | GSHSMRYFSTSVSRPGSGEPRFIAVGYVDDTQFVREDSDAASQRMEPRAPWIEQERPEYWDQET<br>RNVKAQSQTDRVDLGTLRGCYNQSEAGSHTIQIMYGCDVGPDGRFLRGYEQHAYDGKDYIALNE<br>DLRSWTAADMAAQITQRKWEAARWAEQLRAYLEGTCVEWLRRYLENGKETLQRTDPPKTHMTHH<br>PISDHEATLRCWALGFYPAEITLTWQRDGEDQTQDTELVETRPAGDGTFQKWAAVVVPSGEEQR<br>YTCHVQHEGLPKPLTLRWEL |
| 66 | HLA-A*33:03 | GSHSMRYFTTSVSRPGRGEPRFIAVGYVDDTQFVREDSDAASQRMEPRAPWIEQEGPEYWDRNT<br>RNVKAHSQIDRVDLGTLRGCYNQSEAGSHTIQMMYGCDVGSDGRFLRGYQQDAYDGKDYIALNE<br>DLRSWTAADMAAQITQRKWEAARVAEQLRAYLEGTCVEWLRRYLENGKETLQRTDPPKTHMTHH<br>AVSDHEATLRCWALSFYPAEITLTWQRDGEDQTQDTELVETRPAGDTFQKWASVVVPSGQEQR<br>YTCHVQHEGLPKPLTLRWEP |
| 67 | HLA-B*08:01 | GSHSMRYFDTAMSRPGRGEPRFISVGYVDDTQFVREDSDAASPREEPRAPWIEQEGPEYWDRNT<br>QIFKTNTQTDRESLRNLRGCYNQSEAGSHTLQSMYGCDVGPDGRLLRGHNQYAYDGKDYIALNE<br>DLRSWTAADTAAQITQRKWEAARVAEQDRAYLEGTCVEWLRRYLENGKDTLERADPPKTHVTHH<br>PISDHEATLRCWALGFYPAEITLTWQRDGEDQTQDTELVETRPAGDRTFQKWAAVVVPSGEEQR<br>YTCHVQHEGLPKPLTLRWEP |
| 68 | HLA-B*15:01 | GSHSMRYFYTAMSRPGRGEPRFIAVGYVDDTQFVREDSDAASPRMAPRAPWIEQEGPEYWDRET<br>QISKTNTQTYRESLRNLRGCYNQSEAGSHTLQRMYGCDVGPDGRLLRGHDQSAYDGKDYIALNE<br>DLSSWTAADTAAQITQRKWEAAREAEQWRAYLEGLCVEWLRRYLENGKETLQRADPPKTHVTHH<br>PISDHEATLRCWALGFYPAEITLTWQRDGEDQTQDTELVETRPAGDRTFQKWAAVVVPSGEEQR<br>YTCHVQHEGLPKPLTLRWEP |

| SEQ ID NO | Name | Sequence |
|---|---|---|
| 69 | HLA-B*15:03 | GSHSMRYFYTAMSRPGRGEPRFISVGYVDDTQFVREDSDAASPREEPRAPWIEQEGPEYWDRET<br>QISKTNTQTYRESLRNLRGCYNQSEAGSHTLQRMYGCDVGPDGRLLRGHDQSAYDGKDYIALNE<br>DLSSWTAADTAAQITQRKWEAAREAEQLRAYLEGLCVEWLRRYLENGKETLQRADPPKTHVTHH<br>PISDHEATLRCWALGFYPAEITLTWQRDGEDQTQDTELVETRPAGDRTFQKWAAVVVPSGEEQR<br>YTCHVQHEGLPKPLTLRWEP |
| 70 | HLA-B*35:01 | GSHSMRYFYTAMSRPGRGEPRFIAVGYVDDTQFVREDSDAASPRTEPRAPWIEQEGPEYWDRNT<br>QIFKTNTQTYRESLRNLRGCYNQSEAGSHIIQRMYGCDLGPDGRLLRGHDQSAYDGKDYIALNE<br>DLSSWTAADTAAQITQRKWEAARVAEQLRAYLEGLCVEWLRRYLENGKETLQRADPPKTHVTHH<br>PVSDHEATLRCWALGFYPAEITLTWQRDGEDQTQDTELVETRPAGDRTFQKWAAVVVPSGEEQR<br>YTCHVQHEGLPKPLTLRWEP |
| 71 | HLA-B*40:02 | GSHSMRYFHTSVSRPGRGEPRFITVGYVDDTLEVREDSDATSPRKEPRAPWIEQEGPEYWDRET<br>QISKTNTQTYRESLRNLRGCYNQSEAGSHTLQSMYGCDVGPDGRLLRGHNQYAYDGKDYIALNE<br>DLRSWTAADTAAQITQRKWEAARVAEQLRAYLEGECVEWLRRYLENGKETLQRADPPKTHVTHH<br>PISDHEATLRCWALGFYPAEITLTWQRDGEDQTQDTELVETRPAGDRTFQKWAAVVVPSGEEQR<br>YTCHVQHEGLPKPLTLRWEP |
| 72 | HLA-B*42:01 | GSHSMRYFYTSVSRPGRGEPRFISVGYVDDTQFVREDSDAASPREEPRAPWIEQEGPEYWDRNT<br>QTYKAQAQTDRESLRNLRGCYNQSEAGSHTLQSMYGCDVGPDGRLLRGHNQYAYDGKDYIALNE<br>DLRSWTAADTAAQITQRKWEAARVAEQDRAYLEGTCVEWLRRYLENGKDTLERADPPKTHVTHH<br>PISDHEATLRCWALGFYPAEITLTWQRDGEDQTQDTELVETRPAGDRTFQKWAAVVVPSGEEQR<br>YTCHVQHEGLPKPLTLRWEP |
| 73 | HLA-B*44:03 | GSHSMRYFYTAMSRPGRGEPRFITVGYVDDTLFVREDSDATSPRKEPRAPWIEQEGPEYWDRET<br>QISKTNTQTYRENLRTALRCYNQSEAGSHIIQRMYGCDVGPDGRLLRGYDQDAYDGKDYIALNE<br>DLSSWTAADTAAQITQRKWEAARVAEQLRAYLEGLCVESLRRYLENGKETLQRADPPKTHVTHH<br>PISDHEVTLRCWALGFYPAEITLTWQRDGEDQTQDTELVETRPAGDRTFQKWAAVVVPSGEEQR<br>YTCHVQHEGLPKPLTLRWEP |
| 74 | HLA-B*51:01 | GSHSMRYFYTAMSRPGRGEPRFIAVGYVDDTQFVREDSDAASPRTEPRAPWIEQEGPEYWDRNT<br>QIFKTNTQTYRENLRIALRCYNQSEAGSHTWQTMYGCDVGPDGRLLRGHNQYAYDGKDYIALNE<br>DLSSWTAADTAAQITQRKWEAAREAEQLRAYLEGLCVEWLRRHLENGKETLQRADPPKTHVTHH<br>PVSDHEATLRCWALGFYPAEITLTWQRDGEDQTQDTELVETRPAGDRTFQKWAAVVVPSGEEQR<br>YTCHVQHEGLPKPLTLRWEP |
| 75 | HLA-B*53:01 | GSHSMRYFYTAMSRPGRGEPRFIAVGYVDDTQFVREDSDAASPRTEPRAPWIEQEGPEYWDRNT<br>QIFKTNTQTYRENLRIALRCYNQSEAGSHIIQRMYGCDLGPDGRLLRGHDQSAYDGKDYIALNE<br>DLSSWTAADTAAQITQRKWEAARVAEQLRAYLEGLCVEWLRRYLENGKETLQRADPPKTHVTHH<br>PVSDHEATLRCWALGFYPAEITLTWQRDGEDQTQDTELVETRPAGDRTFQKWAAVVVPSGEEQR<br>YTCHVQHEGLPKPLTLRWEP |
| 76 | HLA-C*01:02 | CSHSMKYFFTSVSRPGRGEPRFISVGYVDDTQFVREDSDAASPRGEPRAPWVEQEGPEYWDRET<br>QKYKRQAQTDRVSLRNLRGCYNQSEAGSHTLQWMCGCDLGPDGRLLRGYDQYAYDGKDYIALNE<br>DLRSWTAADTAAQITQRKWEAAREAEQRRAYLEGTCVEWLRRYLENGKETLQRAEHPKTHVTHH<br>PVSDHEATLRCWALGFYPAEITLTWQWDGEDQTQDTELVETRPAGDGTFQKWAAVMVPSGEEQR<br>YTCHVQHEGLPEPLTLRWEP |
| 77 | HLA-C*04:01 | GSHSMRYFSTSVSWPGRGEPRFIAVGYVDDTQFVREDSDAASPRGEPREPWVEQEGPEYWDRET<br>QKYKRQAQADRVNLRKLRGCYNQSEDGSHTLQRMFGCDLGPDGRLLRGYNQPAYDGKDYIALNE<br>DLRSWTAADTAAQITQRKWEAAREAEQRRAYLEGTCVEWLRRYLENGKETLQRAEHPKTHVTHH<br>PVSDHEATLRCWALGFYPAEITLTWQWDGEDQTQDTELVETRPAGDGTFQKWAAVVVPSGEEQR<br>YTCHVQHEGLPEPLTLRWKP |
| 78 | HLA-C*06:02 | CSHSMRYFDTAVSRPGRGEPRFISVGYVDDTQFVREDSDAASPRGEPRAPWVEQEGPEYWDRET<br>QKYKRQAQADRVNLRKLRGCYNQSEDGSHTLQWMYGCDVGPDGRLLRGYDQSAYDGKDYIALNE<br>DLRSWTAADTAAQITQRKWEAAREAEQWRAYLEGTCVEWLRRYLENGKETLQRAEHPKTHVTHH<br>PVSDHEATLRCWALGFYPAEITLTWQRDGEDQTQDTELVETRPAGDGTFQKWAAVVVPSGEEQR<br>YTCHVQHEGLPEPLTLRWE |
| 79 | HLA-C*07:02 | CSHSMRYFDTAVSRPGRGEPRFISVGYVDDTQFVREDSDAASPRGEPRAPWVEQEGPEYWDRET<br>QKYKRQAQADRVSLRNLRGCYNQSEDGSHTLQRMSGCDLGPDGRLLRGYDQSAYDGKDYIALNE<br>DLRSWTAADTAAQITQRKLEAARAAEQLRAYLEGTCVEWLRRYLENGKETLQRAEPPKTHVTHH<br>PLSDHEATLRCWALGFYPAEITLTWQRDGEDQTQDTELVETRPAGDGTFQKWAAVVVPSGQEQR<br>YTCHMQHEGLQEPLTLSWEP |
| 80 | HLA-C*16:01 | CSHSMRYFYTAVSRPGRGEPRFIAVGYVDDTQFVREDSDAASPRGEPRAPWVEQEGPEYWDRET<br>QKYKRQAQTDRVSLRNLRGCYNQSEAGSHTLQWMYGCDLGPDGRLLRGYDQSAYDGKDYIALNE<br>DLRSWTAADTAAQITQRKWEAARAAEQQRAYLEGTCVEWLRRYLENGKETLQRAEHPKTHVTHH<br>LVSDHEATLRCWALGFYPAEITLTWQRDGEDQTQDTELVETRPAGDGTFQKWAAVVVPSGEEQR<br>YTCHVQHEGLPEPLTLRWEP |

| SEQ ID NO | Name | Sequence |
|---|---|---|
| 81 | HLA-A*25:01 | GSHSMRYFYTSVSRPGRGEPRFIAVGYVDDTQFVREDSDAASQRMEPRAPWIEQEGPEYWDRNT RNVKAHSQTDRESLRIALRCYNQSEDGSHTIQRMYGCDVGPDGRFLRGYQQDAYDGKDYIALNE DLRSWTAADMAAQITQRKWETAHEAEQWRAYLEGRCVEWLRRYLENGKETLQRTDAPKTHMTHH AVSDHEATLRCWALSFYPAEITLTWQRDGEDQTQDTELVETRPAGDGTFQKWASVVVPSGQEQR YTCHVQHEGLPKPLTLRWEP |
| 82 | HLA-A*26:01 | GSHSMRYFYTSVSRPGRGEPRFIAVGYVDDTQFVREDSDAASQRMEPRAPWIEQEGPEYWDRNT RNVKAHSQTDRANLGTLRGCYNQSEDGSHTIQRMYGCDVGPDGRFLRGYQQDAYDGKDYIALNE DLRSWTAADMAAQITQRKWETAHEAEQWRAYLEGRCVEWLRRYLENGKETLQRTDAPKTHMTHH AVSDHEATLRCWALSFYPAEITLTWQRDGEDQTQDTELVETRPAGDGTFQKWASVVVPSGQEQR YTCHVQHEGLPKPLTLRWEP |
| 83 | HLA-A*29:02 | GSHSMRYFTTSVSRPGRGEPRFIAVGYVDDTQFVREDSDAASQRMEPRAPWIEQEGPEYWDLQT RNVKAQSQTDRANLGTLRGCYNQSEAGSHTIQMMYGCDVGSDGRFLRGYRQDAYDGKDYIALNE DLRSWTAADMAAQITQRKWEAARVAEQLRAYLEGTCVEWLRRYLENGKETLQRTDAPKTHMTHH AVSDHEATLRCWALSFYPAEITLTWQRDGEDQTQDTELVETRPAGDGTFQKWASVVVPSGQEQR YTCHVQHEGLPKPLTLRWEP |
| 84 | HLA-A*68:02 | GSHSMRYFYTSMSRPGRGEPRFIAVGYVDDTQFVREDSDAASQRMEPRAPWIEQEGPEYWDRNT RNVKAQSQTDRVDLGTLRGCYNQSEAGSHTIQRMYGCDVGPDGRFLRGYHQYAYDGKDYIALKE DLRSWTAADMAAQTTKHKWEAAHVAEQWRAYLEGTCVEWLRRYLENGKETLQRTDAPKTHMTHH AVSDHEATLRCWALSFYPAEITLTWQRDGEDQTQDTELVETRPAGDGTFQKWVAVVVPSGQEQR YTCHVQHEGLPKPLTLRWEP |
| 85 | HLA-B*13:02 | GSHSMRYFYTAMSRPGRGEPRFITVGYVDDTQFVREDSDATSPRMAPRAPWIEQEGPEYWDRET QISKTNTQTYRENLRTALRCYNQSEAGSHTWQTMYGCDLGPDGRLLRGHNQLAYDGKDYIALNE DLSSWTAADTAAQITQLKWEAARVAEQLRAYLEGECVEWLRRYLENGKETLQRADPPKTHVTHH PISDHEATLRCWALGFYPAEITLTWQRDGEDQTQDTELVETRPAGDRTFQKWAAVVVPSGEEQR YTCHVQHEGLPKPLTLRWEP |
| 86 | HLA-B*15:07 | GSHSMRYFYTAMSRPGRGEPRFIAVGYVDDTQFVREDSDAASPRMAPRAPWIEQEGPEYWDRET QISKTNTQTYRESLRNLRGCYNQSEAGSHTLQSMYGCDVGPDGRLLRGHDQSAYDGKDYIALNE DLSSWTAADTAAQITQRKWEAAREAEQWRAYLEGLCVEWLRRYLENGKETLQRADPPKTHVTHH PISDHEATLRCWALGFYPAEITLTWQRDGEDQTQDTELVETRPAGDRTFQKWAAVVVPSGEEQR YTCHVQHEGLPKPLTLRWEP |
| 87 | HLA-B*27:05 | GSHSMRYFHTSVSRPGRGEPRFITVGYVDDTLEVREDSDAASPREEPRAPWIEQEGPEYWDRET QICKAKAQTDREDLRTLLRCYNQSEAGSHTLQNMYGCDVGPDGRLLRGYHQDAYDGKDYIALNE DLSSWTAADTAAQITQRKWEAARVAEQLRAYLEGECVEWLRRYLENGKETLQRADPPKTHVTHH PISDHEATLRCWALGFYPAEITLTWQRDGEDQTQDTELVETRPAGDRTFQKWAAVVVPSGEEQR YTCHVQHEGLPKPLTLRWEP |
| 88 | HLA-B*35:03 | GSHSMRYFYTAMSRPGRGEPRFIAVGYVDDTQFVREDSDAASPRTEPRAPWIEQEGPEYWDRNT QIFKTNTQTYRESLRNLRGCYNQSEAGSHIIQRMYGCDLGPDGRLLRGHDQPAYDGKDYIALNE DLSSWTAADTAAQITQRKWEAARVAEQLRAYLEGLCVEWLRRYLENGKETLQRADPPKTHVTHH PVSDHEATLRCWALGFYPAEITLTWQRDGEDQTQDTELVETRPAGDRTFQKWAAVVVPSGEEQR YTCHVQHEGLPKPLTLRWEP |
| 89 | HLA-B*37:01 | GSHSMRYFHTSVSRPGRGEPRFISVGYVDDTQFVREDSDAASPRTEPRAPWIEQEGPEYWDRET QISKTNTQTYREDLRTLLRCYNQSEAGSHTLQRMSGCDVGPDGRLLRGYNQFAYDGKDYIALNE DLSSWTAADTAAQITQRKWEAARVAEQDRAYLEGTCVEWLRRYLENGKETLQRADPPKTHVTHH PISDHEATLRCWALGFYPAEITLTWQRDGEDQTQDTELVETRPAGDRTFQKWAAVVVPSGEEQR YTCHVQHEGLPKPLTLRWEP |
| 90 | HLA-B*38:01 | GSHSMRYFYTSVSRPGRGEPRFISVGYVDDTQFVREDSDAASPREEPRAPWIEQEGPEYWDRNT QICKTNTQTYRENLRIALRCYNQSEAGSHTLQRMYGCDVGPDGRLLRGHNQFAYDGKDYIALNE DLSSWTAADTAAQITQRKWEAARVAEQLRTYLEGTCVEWLRRYLENGKETLQRADPPKTHVTHH PISDHEATLRCWALGFYPAEITLTWQRDGEDQTQDTELVETRPAGDRTFQKWAAVVVPSGEEQR YTCHVQHEGLPKPLTLRWEP |
| 91 | HLA-B*41:02 | GSHSMRYFHTAMSRPGRGEPRFITVGYVDDTLFVREDSDATSPRKEPRAPWIEQEGPEYWDRET QISKTNTQTYRESLRNLRGCYNQSEAGSHTLQSMYGCDVGPDGRLLRGHNQYAYDGKDYIALNE DLRSWTAADTAAQITQRKWEAARVAEQDRAYLEGTCVEWLRRYLENGKDTLERADPPKTHVTHH PISDHEATLRCWALGFYPAEITLTWQRDGEDQTQDTELVETRPAGDRTFQKWAAVVVPSGEEQR YTCHVQHEGLPKPLTLRWEP |
| 92 | HLA-B*44:05 | GSHSMRYFYTAMSRPGRGEPRFITVGYVDDTLFVREDSDATSPRKEPRAPWIEQEGPEYWDRET QISKTNTQTYRENLRTALRCYNQSEAGSHIIQRMYGCDVGPDGRLLRGYDQYAYDGKDYIALNE DLSSWTAADTAAQITQRKWEAARVAEQDRAYLEGLCVESLRRYLENGKETLQRADPPKTHVTHH PISDHEVTLRCWALGFYPAEITLTWQRDGEDQTQDTELVETRPAGDRTFQKWAAVVVPSGEEQR YTCHVQHEGLPKPLTLRWEP |

| SEQ ID NO | Name | Sequence |
|---|---|---|
| 93 | HLA-B*49:01 | GSHSMRYFHTAMSRPGRGEPRFITVGYVDDTLFVREDSDATSPRKEPRAPWIEQEGPEYWDRET QISKTNTQTYRENLRIALRCYNQSEAGSHTWQRMYGCDLGPDGRLLRGYNQLAYDGKDYIALNE DLSSWTAADTAAQITQRKWEAAREAEQLRAYLEGLCVEWLRRYLENGKETLQRADPPKTHVTHH PISDHEATLRCWALGFYPAEITLTWQRDGEDQTQDTELVETRPAGDRTFQKWAAVVVPSGEEQR YTCHVQHEGLPKPLTLRWEP |
| 94 | HLA-B*52:01 | GSHSMRYFYTAMSRPGRGEPRFIAVGYVDDTQFVREDSDAASPRTEPRAPWIEQEGPEYWDRET QISKTNTQTYRENLRIALRCYNQSEAGSHTWQTMYGCDVGPDGRLLRGHNQYAYDGKDYIALNE DLSSWTAADTAAQITQRKWEAAREAEQLRAYLEGLCVEWLRRHLENGKETLQRADPPKTHVTHH PVSDHEATLRCWALGFYPAEITLTWQRDGEDQTQDTELVETRPAGDRTFQKWAAVVVPSGEEQR YTCHVQHEGLPKPLTLRWEP |
| 95 | HLA-B*55:01 | GSHSMRYFYTAMSRPGRGEPRFIAVGYVDDTQFVREDSDAASPREEPRAPWIEQEGPEYWDRNT QTYKAQAQTDRESLRNLRGCYNQSEAGSHTWQTMYGCDLGPDGRLLRGHNQLAYDGKDYIALNE DLSSWTAADTAAQITQRKWEAAREAEQLRAYLEGTCVEWLRRYLENGKETLQRADPPKTHVTHH PISDHEATLRCWALGFYPAEITLTWQRDGEDQTQDTELVETRPAGDRTFQKWAAVVVPSGEEQR YTCHVQHEGLPKPLTLRWEP |
| 96 | HLA-C*03:03 | GSHSMRYFYTAVSRPGRGEPHFIAVGYVDDTQFVREDSDAASPRGEPRAPWVEQEGPEYWDRET QKYKRQAQTDRVSLRNLRGCYNQSEARSHIIQRMYGCDVGPDGRLLRGYDQYAYDGKDYIALNE DLRSWTAADTAAQITQRKWEAAREAEQLRAYLEGLCVEWLRRYLKNGKETLQRAEHPKTHVTHH PVSDHEATLRCWALGFYPAEITLTWQWDGEDQTQDTELVETRPAGDGTFQKWAAVVVPSGEEQR YTCHVQHEGLPEPLTLRWEP |
| 97 | HLA-C*07:04 | CSHSMRYFDTAVSRPGRGEPRFISVGYVDDTQFVREDSDAASPRGEPRAPWVEQEGPEYWDRET QKYKRQAQADRVSLRNLRGCYNQSEDGSHTFQRMYGCDLGPDGRLLRGYDQFAYDGKDYIALNE DLRSWTAADTAAQITQRKLEAARAAEQDRAYLEGTCVEWLRRYLENGKKTLQRAEPPKTHVTHH PLSDHEATLRCWALGFYPAEITLTWQRDGEDQTQDTELVETRPAGDGTFQKWAAVVVPSGQEQR YTCHMQHEGLQEPLTLSWEP |
| 98 | HLA-C*08:01 | CSHSMRYFYTAVSRPGRGEPRFIAVGYVDDTQFVQFDSDAASPRGEPRAPWVEQEGPEYWDRET QKYKRQAQTDRVSLRNLRGCYNQSEAGSHTLQRMYGCDLGPDGRLLRGYNQFAYDGKDYIALNE DLRSWTAADTAAQITQRKWEAARTAEQLRAYLEGTCVEWLRRYLENGKKTLQRAEHPKTHVTHH PVSDHEATLRCWALGFYPAEITLTWQRDGEDQTQDTELVETRPAGDGTFQKWAAVVVPSGEEQR YTCHVQHEGLPEPLTLRWGP |
| 99 | HLA-C*08:02 | CSHSMRYFYTAVSRPGRGEPRFIAVGYVDDTQFVQFDSDAASPRGEPRAPWVEQEGPEYWDRET QKYKRQAQTDRVSLRNLRGCYNQSEAGSHTLQRMYGCDLGPDGRLLRGYNQFAYDGKDYIALNE DLRSWTAADKAAQITQRKWEAAREAEQRRAYLEGTCVEWLRRYLENGKKTLQRAEHPKTHVTHH PVSDHEATLRCWALGFYPAEITLTWQRDGEDQTQDTELVETRPAGDGTFQKWAAVVVPSGEEQR YTCHVQHEGLPEPLTLRWGP |
| 100 | HLA-C*12:02 | CSHSMRYFYTAVSRPGRGEPRFIAVGYVDDTQFVREDSDAASPRGEPRAPWVEQEGPEYWDRET QKYKRQAQADRVSLRNLRGCYNQSEAGSHTLQRMYGCDLGPDGRLLRGYDQSAYDGKDYIALNE DLRSWTAADTAAQITQRKWEAAREAEQWRAYLEGTCVEWLRRYLENGKETLQRAEHPKTHVTHH PVSDHEATLRCWALGFYPAEITLTWQRDGEDQTQDTELVETRPAGDGTFQKWAAVVVPSGEEQR YTCHVQHEGLPEPLTLRWEP |
| 101 | HLA-C*12:03 | CSHSMRYFYTAVSRPGRGEPRFIAVGYVDDTQFVREDSDAASPRGEPRAPWVEQEGPEYWDRET QKYKRQAQADRVSLRNLRGCYNQSEAGSHTLQWMYGCDLGPDGRLLRGYDQSAYDGKDYIALNE DLRSWTAADTAAQITQRKWEAAREAEQWRAYLEGTCVEWLRRYLENGKETLQRAEHPKTHVTHH PVSDHEATLRCWALGFYPAEITLTWQRDGEDQTQDTELVETRPAGDGTFQKWAAVVVPSGEEQR YTCHVQHEGLPEPLTLRWEP |
| 102 | HLA-C*14:02 | CSHSMRYFSTSVSRPGRGEPRFIAVGYVDDTQFVREDSDAASPRGEPRAPWVEQEGPEYWDRET QKYKRQAQTDRVSLRNLRGCYNQSEAGSHTLQWMFGCDLGPDGRLLRGYDQSAYDGKDYIALNE DLRSWTAADTAAQITQRKWEAAREAEQRRAYLEGTCVEWLRRYLENGKETLQRAEHPKTHVTHH PVSDHEATLRCWALGFYPAEITLTWQWDGEDQTQDTELVETRPAGDGTFQKWAAVVVPSGEEQR YTCHVQHEGLPEPLTLRWEP |
| 103 | HLA-C*15:02 | CSHSMRYFYTAVSRPGRGEPHFIAVGYVDDTQFVREDSDAASPRGEPRAPWVEQEGPEYWDRET QNYKRQAQTDRVNLRKLRGCYNQSEAGSHIIQRMYGCDLGPDGRLLRGHDQLAYDGKDYIALNE DLRSWTAADTAAQITQRKWEAAREAEQLRAYLEGTCVEWLRRYLENGKETLQRAEHPKTHVTHH PVSDHEATLRCWALGFYPAEITLTWQRDGEDQTQDTELVETRPAGDGTFQKWAAVVVPSGEEQR YTCHVQHEGLPEPLTLRWEP |
| 104 | HLA-C*17:01 | GSHSMRYFYTAVSRPGRGEPRFIAVGYVDDTQFVREDSDAASPRGEPRAPWVEQEGPEYWDRET QKYKRQAQADRVNLRKLRGCYNQSEAGSHTIQRMYGCDLGPDGRLLRGYNQFAYDGKDYIALNE DLRSWTAADTAAQISQRKLEAAREAEQLRAYLEGECVEWLRGYLENGKETLQRAERPKTHVTHH PVSDHEATLRCWALGFYPAEITLTWQRDGEDQTQDTELVETRPAGDGTFQKWAAVVVPSGQEQR YTCHVQHEGLQEPCTLRWKP |

SEQUENCE LISTING

| SEQ ID NO | Name | Sequence |
|---|---|---|
| 105 | Beta 2 microglobulin protein | IQRTPKIQVYSRHPAENGKSNFLNCYVSGFHPSDIEVDLLKNGERIEKVEHSDLSFSKDWSFYL LYYTEFTPTEKDEYACRVNHVTLSQPKIVKWDRDM |
| 106 | Beta 2 microglobulin nucleotide | ATCCAGCGTACTCCAAAGATTCAGGTTTACTCACGTCATCCAGCAGAGAATGGAAAGTCAAATT TCCTGAATTGCTATGTGTCTGGGTTTCATCCATCCGACATTGAAGTTGACTTACTGAAGAATGG AGAGAGAATTGAAAAAGTGGAGCATTCAGACTTGTCTTTCAGCAAGGACTGGTCTTTCTATCTC TTGTACTACACTGAATTCACCCCCACTGAAAAAGATGAGTATGCCTGCCGTGTGAACCATGTGA CTTTGTCACAGCCCAAGATAGTTAAGTGGGATCGAGACATG |
| 107 | Beta 2 microglobulin protein S88C | IQRTPKIQVYSRHPAENGKSNFLNCYVSGFHPSDIEVDLLKNGERIEKVEHSDLSFSKDWSFYL LYYTEFTPTEKDEYACRVNHVTLCQPKIVKWDRDM |
| 108 | Beta 2 microglobulin nucleotide S88C | ATCCAGCGTACTCCAAAGATTCAGGTTTACTCACGTCATCCAGCAGAGAATGGAAAGTCAAATT TCCTGAATTGCTATGTGTCTGGGTTTCATCCATCCGACATTGAAGTTGACTTACTGAAGAATGG AGAGAGAATTGAAAAAGTGGAGCATTCAGACTTGTCTTTCAGCAAGGACTGGTCTTTCTATCTC TTGTACTACACTGAATTCACCCCCACTGAAAAAGATGAGTATGCCTGCCGTGTGAACCATGTGA CTTTGTGCCAGCCCAAGATAGTTAAGTGGGATCGAGACATG |
| 109 | HLA-A*01:01 | GGCTCCCACTCCATGAGGTATTTCTTCACATCCGTGTCCCGGCCCGGCCGCGGGGAGCCCCGCT TCATCGCCGTGGGCTACGTGGACGACACGCAGTTCGTGCGGTTCGACAGCGACGCCGCGAGCCA GAAGATGGAGCCGCGGGCGCCGTGGATAGAGCAGGAGGGGCCGGAGTATTGGGACCAGGAGACA CGGAATATGAAGGCCCACTCACAGACTGACCGAGTGGACCTGGGGACCCTGCGCGGCTGCTACA ACCAGAGCGAGGACGGTTCTCACACCATCCAGATAATGTATGGCTGCGACGTGGGGCCGGACGG GCGCTTCCTCCGCGGGTACCGGCAGGACGCCTACGACGGCAAGGATTACATCGCCCTGAACGAG GACCTGCGCTCTTGGACCGCGGCGGACATGGCAGCTCAGATCACCAAGCGCAAGTGGGAGGCGG TCCATGCGGCGGAGCAGCGGAGAGTCTACCTGGAGGGCCGGTGCGTGGACGGGCTCCGCAGATA CCTGGAGAACGGGAAGGAGACGCTGCAGCGCACGGACCCCCCCAAGACACATATGACCCACCAC CCCATCTCTGACCATGAGGCCACCCTGAGGTGCTGGGCCCTGGGCTTCTACCCTGCGGAGATCA CACTGACCTGGCAGCGGGATGGGGAGGACCAGACCCAGGACACGGAGCTCGTGGAGACCAGGCC TGCAGGGGATGGAACCTTCCAGAAGTGGGCGGCTGTGGTGGTGCCTTCTGGAGAGGAGCAGAGA TACACCTGCCATGTGCAGCATGAGGGTCTGCCCAAGCCCCTCACCCTGAGATGGGAGCTG |
| 110 | HLA-A*02:01 | GGCTCTCACTCCATGAGGTATTTCTTCACATCCGTGTCCCGGCCCGGCCGCGGGGAGCCCCGCT TCATCGCAGTGGGCTACGTGGACGACACGCAGTTCGTGCGGTTCGACAGCGACGCCGCGAGCCA GAGGATGGAGCCGCGGGCGCCGTGGATAGAGCAGGAGGGTCCGGAGTATTGGGACGAGGGAGACA CGGAAAGTGAAGGCCCACTCACAGACTCACCGAGTGGACCTGGGGACCCTGCGCGGCTGCTACA ACCAGAGCGAGGCCGGTTCTCACACCGTCCAGAGGATGTATGGCTGCGACGTGGGGTCGGACTG GCGCTTCCTCCGCGGGTACCACCAGTACGCCTACGACGGCAAGGATTACATCGCCCTGAAAGAG GACCTGCGCTCTTGGACCGCGGCGGACATGGCAGCTCAGACCACCAAGCACAAGTGGGAGGCGG CCCATGTGGCGGAGCAGTTGAGAGCCTACCTGGAGGGCACGTGCGTGGAGTGGCTCCGCAGATA CCTGGAGAACGGGAAGGAGACGCTGCAGCGCACGGACGCCCCCAAAACGCATATGACTCACCAC GCTGTCTCTGACCATGAAGCCACCCTGAGGTGCTGGGCCCTGAGCTTCTACCCTGCGGAGATCA CACTGACCTGGCAGCGGGATGGGGAGGACCAGACCCAGGACACGGAGCTCGTGGAGACCAGGCC TGCAGGGGATGGAACCTTCCAGAAGTGGGCGGCTGTGGTGGTGCCTTCTGGACAGGAGCAGAGA TACACCTGCCATGTGCAGCATGAGGGTTTGCCCAAGCCCCTCACCCTGAGATGGGAGCCG |
| 111 | HLA-A*03:01 | GGCTCCCACTCCATGAGGTATTTCTTCACATCCGTGTCCCGGCCCGGCCGCGGGGAGCCCCGCT TCATCGCCGTGGGCTACGTGGACGACACGCAGTTCGTGCGGTTCGACAGCGACGCCGCGAGCCA GAGGATGGAGCCGCGGGCGCCGTGGATAGAGCAGGAGGGGCCGGAGTATTGGGACCAGGAGACA CGGAATGTGAAGGCCCAGTCACAGACTGACCGAGTGGACCTGGGGACCCTGCGCGGCTGCTACA ACCAGAGCGAGGCCGGTTCTCACACCATCCAGATAATGTATGGCTGCGACGTGGGGTCGGACGG GCGCTTCCTCCGCGGGTACCGGCAGGACGCCTACGACGGCAAGGATTACATCGCCCTGAACGAG GACCTGCGCTCTTGGACCGCGGCGGACATGGCGGCTCAGATCACCAAGCGCAAGTGGGAGGCGG CCCATGAGGCGGAGCAGTTGAGAGCCTACCTGGATGGCACGTGCGTGGAGTGGCTCCGCAGATA CCTGGAGAACGGGAAGGAGACGCTGCAGCGCACGGACCCCCCCAAGACACATATGACCCACCAC CCCATCTCTGACCATGAGGCCACCCTGAGGTGCTGGGCCCTGGGCTTCTACCCTGCGGAGATCA CACTGACCTGGCAGCGGGATGGGGAGGACCAGACCCAGGACACGGAGCTCGTGGAGACCAGGCC TGCAGGGGATGGAACCTTCCAGAAGTGGGCGGCTGTGGTGGTGCCTTCTGGAGAGGAGCAGAGA TACACCTGCCATGTGCAGCATGAGGGTCTGCCCAAGCCCCTCACCCTGAGATGGGAGCTG |
| 112 | HLA-A*24:02 | GGCTCCCACTCCATGAGGTATTTCTCCACATCCGTGTCCCGGCCCGGCCGCGGGGAGCCCCGCT TCATCGCCGTGGGCTACGTGGACGACACGCAGTTCGTGCGGTTCGACAGCGACGCCGCGAGCCA GAGGATGGAGCCGCGGGCGCCGTGGATAGAGCAGGAGGGGCCGGAGTATTGGGACGAGGAGACA GGGAAAGTGAAGGCCCACTCACAGACTGACCGAGAGAACCTGCGGATCGCGCTCCGCTGCTACA ACCAGAGCGAGGCCGGTTCTCACACCCTCCAGATGATGTTTGGCTGCGACGTGGGGTCGGACGG GCGCTTCCTCCGCGGGTACCACCAGTACGCCTACGACGGCAAGGATTACATCGCCCTGAAAGAG GACCTGCGCTCTTGGACCGCGGCGGACATGGCGGCTCAGATCACCAAGCGCAAGTGGGAGGCGG CCCATGTGGCGGAGCAGCAGAGAGCCTACCTGGAGGGCACGTGCGTGGACGGGCTCCGCAGATA CCTGGAGAACGGGAAGGAGACGCTGCAGCGCACGGACCCCCCCAAGACACATATGACCCACCAC CCCATCTCTGACCATGAGGCCACTCTGAGATGCTGGGCCCTGGGCTTCTACCCTGCGGAGATCA CACTGACCTGGCAGCGGGATGGGGAGGACCAGACCCAGGACACGGAGCTTGTGGAGACCAGGCC |

| SEQ ID NO | Name | Sequence |
|---|---|---|
| | | TGCAGGGGATGGAACCTTCCAGAAGTGGGCAGCTGTGGTGGTACCTTCTGGAGAGGAGCAGAGA<br>TACACCTGCCATGTGCAGCATGAGGGTCTGCCCAAGCCCCTCACCCTGAGATGGGAGCCA |
| 113 | HLA-A*30:02 | GGCTCCCACTCCATGAGGTATTTCTCCACATCCGTGTCCCGGCCCGGCAGTGGAGAGCCCCGCT<br>TCATCGCAGTGGGCTACGTGGACGACACGCAGTTCGTGCGGTTCGACAGCGACGCCGCGAGCCA<br>GAGGATGGAGCCGCGGGCGCCGTGGATAGAGCAGGAGAGGCCTGAGTATTGGGACCAGGAGACA<br>CGGAATGTGAAGGCCCACTCACAGACTGACCGAGAGAACCTGGGGACCCTGCGCGGCTGCTACA<br>ACCAGAGCGAGGCCGGTTCTCACACCATCCAGATAATGTATGGCTGCGACGTGGGGTCGGACGG<br>GCGCTTCCTCCGCGGGTATGAACAGCACGCCTACGACGGCAAGGATTACATCGCCCTGAACGAG<br>GACCTGCGCTCTTGGACCGCGGCGGACATGGCGGCTCAGATCACCCAGCGCAAGTGGGAGGCGG<br>CCCGTCGGGCGGAGCAGTTGAGAGCCTACCTGGAGGGCACGTGCGTGGAGTGGCTCCGCAGATA<br>CCTGGAGAACGGGAAGGAGACGCTGCAGCGCACGGACCCCCCCAAGACACATATGACCCACCAC<br>CCCATCTCTGACCATGAGGCCACCCTGAGGTGCTGGGCCCTGGGCTTCTACCCTGCGGAGATCA<br>CACTGACCTGGCAGCGGGATGGGGAGGACCAGACCCAGGACACGGAGCTCGTGGAGACCAGGCC<br>TGCAGGGGATGGAACCTTCCAGAAGTGGGCGGCTGTGGTGGTGCCTTCTGGAGAGGAGCAGAGA<br>TACACCTGCCATGTGCAGCATGAGGGTCTGCCCAAGCCCCTCACCCTGAGATGGGAGCTG |
| 114 | HLA-A*31:01 | GGCTCCCACTCCATGAGGTATTTCACCACATCCGTGTCCCGGCCCGGCCGCGGGGAGCCCCGCT<br>TCATCGCCGTGGGCTACGTGGACGACACGCAGTTCGTGCGGTTCGACAGCGACGCCGCGAGCCA<br>GAGGATGGAGCCGCGGGCGCCGTGGATAGAGCAGGAGAGGCCTGAGTATTGGGACCAGGAGACA<br>CGGAATGTGAAGGCCCACTCACAGATTGACCGAGTGGACCTGGGGACCCTGCGCGGCTGCTACA<br>ACCAGAGCGAGGCCGGTTCTCACACCATCCAGATGATGTATGGCTGCGACGTGGGGTCGGACGG<br>GCGCTTCCTCCGCGGGTACCAGCAGGACGCCTACGACGGCAAGGATTACATCGCCTTGAACGAG<br>GACCTGCGCTCTTGGACCGCGGCGGACATGGCGGCTCAGATCACCCAGCGCAAGTGGGAGGCGG<br>CCCGTGTGGCGGAGCAGTTGAGAGCCTACCTGGAGGGCACGTGCGTGGAGTGGCTCCGCAGATA<br>CCTGGAGAACGGGAAGGAGACGCTGCAGCGCACGGACCCCCCCAAGACGCATATGACTCACCAC<br>GCTGTCTCTGACCATGAGGCCACCCTGAGGTGCTGGGCCCTGAGCTTCTACCCTGCGGAGATCA<br>CACTGACCTGGCAGCGGGATGGGGAGGACCAGACCCAGGACACGGAGCTCGTGGAGACCAGGCC<br>TGCAGGGGATGGAACCTTCCAGAAGTGGGCGTCTGTGGTGGTGCCTTCTGGACAGGAGCAGAGA<br>TACACCTGCCATGTGCAGCATGAGGGTCTCCCCAAGCCCCTCACCCTGAGATGGGAGCCG |
| 115 | HLA-A*32:01 | GGCTCCCACTCCATGAGGTATTTCTTCACATCCGTGTCCCGGCCCGGCCGCGGGGAGCCCCGCT<br>TCATCGCCGTGGGCTACGTGGACGACACGCAGTTCGTGCGGTTTGACAGCGACGCCGCGAGCCA<br>GAGGATGGAGCCGCGGGCGCCGTGGATAGAGCAGGAGGGGCCGGAGTATTGGGACCAGGAGACA<br>CGGAATGTGAAGGCCCACTCACAGACTGACCGAGAGAGCCTGCGGATCGCGCTCCGCTGCTACA<br>ACCAGAGCGAGGCCGGTTCTCACACCATCCAGATGATGTATGGCTGCGACGTGGGGCCGGACGG<br>GCGCCTCCTCCGCGGGTACCAGCAGGACGCCTACGACGGCAAGGATTACATCGCCTTGAACGAG<br>GACCTGCGCTCTTGGACCGCGGCGGACATGGCGGCTCAGATCACCCAGCGCAAGTGGGAGGCGG<br>CCCGTGTGGCGGAGCAGTTGAGAGCCTACCTGGAGGGCACGTGCGTGGAGTGGCTCCGCAGATA<br>CCTGGAGAACGGGAAGGAGACGCTGCAGCGCACGGACGCCCCCAAGACGCATATGACTCACCAC<br>GCTGTCTCTGACCATGAGGCCACCCTGAGGTGCTGGGCCCTGAGCTTCTACCCTGCGGAGATCA<br>CACTGACCTGGCAGCGGGATGGGGAGGACCAGACCCAGGACACGGAGCTTGTGGAGACCAGGCC<br>TGCAGGGGATGGAACCTTCCAGAAGTGGGCGTCTGTGGTGGTGCCTTCTGGACAGGAGCAGAGA<br>TACACCTGCCATGTGCAGCATGAGGGTCTGCCCAAGCCCCTCACCCTGAGATGGGAGCCG |
| 116 | HLA-A*33:01 | GGCTCCCACTCCATGAGGTATTTCACCACATCCGTGTCCCGGCCCGGCCGCGGGGAGCCCCGCT<br>TCATCGCCGTGGGCTACGTGGACGACACGCAGTTCGTGCGGTTCGACAGCGACGCCGCGAGCCA<br>GAGGATGGAGACCGCGGGCGCCGTGGATAGAGCAGGAGGGGCCGGAGTATTGGGACCGGAACACA<br>CGGAATGTGAAGGCCCACTCACAGATTGACCGAGTGGACCTGGGGACCCTGCGCGGCTGCTACA<br>ACCAGAGCGAGGCCGGTTCTCACACCATCCAGATGATGTATGGCTGCGACGTGGGGTCGGACGG<br>GCGCTTCCTCCGCGGGTACCAGCAGGACGCCTACGACGGCAAGGATTACATCGCCTTGAACGAG<br>GACCTGCGCTCTTGGACCGCGGCGGACATGGCGGCTCAGATCACCCAGCGCAAGTGGGAGGCGG<br>CCCGTGTGGCGGAGCAGTTGAGAGCCTACCTGGAGGGCACGTGCGTGGAGTGGCTCCGCAGACA<br>CCTGGAGAACGGGAAGGAGACGCTGCAGCGCACGGACCCCCCCAGGACGCATATGACTCACCAC<br>GCTGTCTCTGACCATGAGGCCACCCTGAGGTGCTGGGCCCTGAGCTTCTACCCTGCGGAGATCA<br>CACTGACCTGGCAGCGGGATGGGGAGGACCAGACCCAGGACACGGAGCTCGTGGAGACCAGGCC<br>TGCAGGGGATGGAACCTTCCAGAAGTGGGCGTCTGTGGTGGTGCCTTCTGGACAGGAGCAGAGA<br>TACACCTGCCATGTGCAGCATGAGGGTCTCCCCAAGCCCCTCACCCTGAGATGGGAGCCG |
| 117 | HLA-A*68:01 | GGCTCCCACTCCATGAGGTATTTCTACACCTCCGTGTCCCGGCCCGGCCGCGGGGAGCCCCGCT<br>TCATCGCCGTGGGCTACGTGGACGACACGCAGTTCGTGCGGTTCGACAGCGACGCCGCGAGCCA<br>GAGGATGGAGCCGCGGGCGCCGTGGATAGAGCAGGAGGGGCCGGAGTATTGGGACCGGAACACA<br>CGGAATGTGAAGGCCCAGTCACAGACTGACCGAGTGGACCTGGGGACCCTGCGCGGCTGCTACA<br>ACCAGAGCGAGGCCGGTTCTCACACCATCCAGATGATGTATGGCTGCGACGTGGGGTCGGACGG<br>GCGCTTCCTCCGCGGGTACCGGCAGGACGCCTACGACGGCAAGGATTACATCGCCCTGAAAGAG<br>GACCTGCGCTCTTGGACCGCGGCGGACATGGCAGCTCAGACCACCAAGCACAAGTGGGAGGCGG<br>CCCATGTGGCGGAGCAGTGAGAGCCTACCTGGAGGGCACGTGCGTGGAGTGGCTCCGCAGATA<br>CCTGGAGAACGGGAAGGAGACGCTGCAGCGCACGGACGCCCCCAAAACGCATATGACTCACCAC<br>GCTGTCTCTGACCATGAAGCCACCCTGAGGTGCTGGGCCCTGAGCTTCTACCCTGCGGAGATCA<br>CACTGACCTGGCAGCGGGATGGGGAGGACCAGACCCAGGACACGGAGCTCGTGGAGACCAGGCC<br>TGCAGGGGATGGAACCTTCCAGAAGTGGGTGGCTGTGGTGGTGCCTTCTGGACAGGAGCAGAGA<br>TACACCTGCCATGTGCAGCATGAGGGTTTGCCCAAGCCCCTCACCCTGAGATGGGAGCCG |

| SEQ ID NO | Name | Sequence |
|---|---|---|
| 118 | HLA-B*07:02 | GGCTCCCACTCCATGAGGTATTTCTACACCTCCGTGTCCCGGCCCGGCCGCGGGGAGCCCCGCT<br>TCATCTCAGTGGGCTACGTGGACGACACCCAGTTCGTGAGGTTCGACAGCGACGCCGCGAGTCC<br>GAGAGAGGAGCCGCGGGCGCCGTGGATAGAGCAGGAGGGGCCGGAGTATTGGGACCGGAACACA<br>CAGATCTACAAGGCCCAGGCACAGACTGACCGAGAGAGCCTGCGGAACCTGCGCGGCTGCTACA<br>ACCAGAGCGAGGCCGGGTCTCACACCCTCCAGAGCATGTACGGCTGCGACGTGGGGCCGGACGG<br>GCGCCTCCTCCGCGGGCATGACCAGTACGCCTACGACGGCAAGGATTACATCGCCCTGAACGAG<br>GACCTGCGCTCCTGGACCGCCGCGGACACGGCGGCTCAGATCACCCAGCGCAAGTGGGAGGCGG<br>CCCGTGAGGCGGAGCAGCGGAGAGCCTACCTGGAGGGCGAGTGCGTGGAGTGGCTCCGCAGATA<br>CCTGGAGAACGGGAAGGACAAGCTGGAGCGCGCTGACCCCCCAAAGACACACGTGACCCACCAC<br>CCCATCTCTGACCATGAGGCCACCCTGAGGTGCTGGGCCCTGGGTTTCTACCCTGCGGAGATCA<br>CACTGACCTGGCAGCGGGATGGCGAGGACCAAACTCAGGACACTGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCG |
| 119 | HLA-B*14:02 | GGCTCCCACTCCATGAGGTATTTCTACACCGCCGTGTCCCGGCCCGGCCGCGGGGAGCCCCGCT<br>TCATCTCAGTGGGCTACGTGGACGACACGCAGTTCGTGAGGTTCGACAGCGACGCCGCGAGTCC<br>GAGAGAGGAGCCGCGGGCGCCGTGGATAGAGCAGGAGGGGCCGGAATATTGGGACCGGAACACA<br>CAGATCTGCAAGACCAACACACAGACTGACCGAGAGAGCCTGCGGAACCTGCGCGGCTGCTACA<br>ACCAGAGCGAGGCCGGGTCTCACACCCTCCAGTGGATGTATGGCTGCGACGTGGGGCCGGACGG<br>GCGCCTCCTCCGCGGGTATAACCAGTTCGCCTACGACGGCAAGGATTACATCGCCCTGAACGAG<br>GACCTGAGCTCCTGGACCGCGGCGGACACCGCGGCTCAGATCACCCAGCGCAAGTGGGAGGCGG<br>CCCGTGAGGCGGAGCAGCTGAGAGCCTACCTGGAGGGCACGTGCGTGGAGTGGCTCCGCAGACA<br>CCTGGAGAACGGGAAGGAGACGCTGCAGCGCGCGGACCCCCCAAAGACACATGTGACCCACCAC<br>CCCATCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACCGAGCTTGTGGAGACCAGACC<br>AGCAGGAGACAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCA |
| 120 | HLA-B*18:01 | GGCTCCCACTCCATGAGGTATTTCCACACCTCCGTGTCCCGGCCCGGCCGCGGGGAGCCCCGCT<br>TCATCTCAGTGGGCTACGTGGACGGCACCCAGTTCGTGAGGTTCGACAGCGACGCCGCGAGTCC<br>GAGGACGGAGCCCCGGGCGCCGTGGATAGAGCAAGAGGGGCCGGAGTATTGGGACCGGAACACA<br>CAGATCTCCAAGACCAACACACAGACTTACCGAGAGAGCCTGCGGAACCTGCGCGGCTGCTACA<br>ACCAGAGCGAGGCCGGGTCTCACACCCTCCAGAGGATGTACGGCTGCGACGTGGGGCCGGACGG<br>GCGCCTCCTCCGCGGGCATGACCAGTCCGCCTACGACGGCAAGGATTACATCGCCCTGAACGAG<br>GACCTGAGCTCCTGGACCGCGGCGGACACCGCGGCTCAGATCACCCAGCGCAAGTGGGAGGCGG<br>CCCGTGTGGCGGAGCAGCTGAGAGCCTACCTGGAGGGCACGTGCGTGGAGTGGCTCCGCAGACA<br>CCTGGAGAACGGGAAGGAGACGCTGCAGCGCGCGGACCCCCCAAAGACACATGTGACCCACCAC<br>CCCATCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACCGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCA |
| 121 | HLA-B*27:02 | GGCTCCCACTCCATGAGGTATTTCCACACCTCCGTGTCCCGGCCCGGCCGCGGGGAGCCCCGCT<br>TCATCACCGTGGGCTACGTGGACGACACGCTGTTCGTGAGGTTCGACAGCGACGCCGCGAGTCC<br>GAGAGAGGAGCCGCGGGCGCCGTGGATAGAGCAGGAGGGGCCGGAGTATTGGGACCGGGAGACA<br>CAGATCTGCAAGGCCAAGGCACAGACTGACCGAGAGAACCTGCGGATCGCGCTCCGCTGCTACA<br>ACCAGAGCGAGGCCGGGTCTCACACCCTCCAGAATATGTATGGCTGCGACGTGGGGCCGGACGG<br>GCGCCTCCTCCGCGGGTACCACCAGGACGCCTACGACGGCAAGGATTACATCGCCCTGAACGAG<br>GACCTGAGCTCCTGGACCGCCGCGGACACGGCGGCTCAGATCACCCAGCGCAAGTGGGAGGCGG<br>CCCGTGTGGCGGAGCAGCTGAGAGCCTACCTGGAGGGCGAGTGCGTGGAGTGGCTCCGCAGATA<br>CCTGGAGAACGGGAAGGAGACGCTGCAGCGCGCGGACCCCCCAAAGACACACGTGACCCACCAC<br>CCCATCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACTGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCG |
| 122 | HLA-B*39:01 | GGCTCCCACTCCATGAGGTATTTCTACACCTCCGTGTCCCGGCCCGGCCGCGGGGAGCCCCGCT<br>TCATCTCAGTGGGCTACGTGGACGACACGCAGTTCGTGAGGTTCGACAGCGACGCCGCGAGTCC<br>GAGAGAGGAGCCGCGGGCGCCGTGGATAGAGCAGGAGGGGCCGGAATATTGGGACCGGAACACA<br>CAGATCTGCAAGACCAACACACAGACTGACCGAGAGAGCCTGCGGAACCTGCGCGGCTGCTACA<br>ACCAGAGCGAGGCCGGGTCTCACACCCTCCAGAGGATGTACGGCTGCGACGTGGGGCCGGACGG<br>GCGCCTCCTCCGCGGGCATAACCAGTTCGCCTACGACGGCAAGGATTACATCGCCCTGAACGAG<br>GACCTGAGCTCCTGGACCGCGGCGGACACCGCGGCTCAGATCACCCAGCGCAAGTGGGAGGCGG<br>CCCGTGTGGCGGAGCAGCTGAGAACCTACCTGGAGGGCACGTGCGTGGAGTGGCTCCGCAGATA<br>CCTGGAGAACGGGAAGGAGACGCTGCAGCGCGCGGACCCCCCAAAGACACATGTGACCCACCAC<br>CCCATCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACCGAGCTTGTGGAGACCAGACC<br>AGCAGGAGACAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCA |
| 123 | HLA-B*40:01 | GGCTCCCACTCCATGAGGTATTTCCACACCGCCATGTCCCGGCCCGGCCGCGGGGAGCCCCGCT<br>TCATCACCGTGGGCTACGTGGACGACACGCTGTTCGTGAGGTTCGACAGCGACGCCACGAGTCC<br>GAGGAAGGAGCCGCGGGCGCCATGGATAGAGCAGGAGGGGCCGGAGTATTGGGACCGGGAGACA |

| SEQ ID NO | Name | Sequence |
|---|---|---|
| | | CAGATCTCCAAGACCAACACACAGACTTACCGAGAGAGCCTGCGGAACCTGCGCGGCTGCTACA<br>ACCAGAGCGAGGCCCGGGTCTCACACCCTCCAGAGGATGTACGGCTGCGACGTGGGGCCGGACGG<br>GCGCCTCCTCCGCGGGCATAACCAGTACGCCTACGACGGCAAGGATTACATCGCCCTGAACGAG<br>GACCTGCGCTCCTGGACCGCCGCGGACACGGCGGCTCAGATCTCCCAGCGCAAGTTGGAGGCGG<br>CCCGTGTGGCGGAGCAGCTGAGAGCCTACCTGGAGGGCGAGTGCGTGGAGTGGCTCCGCAGATA<br>CCTGGAGAACGGGAAGGACAAGCTGGAGCGCGCTGACCCCCCAAAGACACACGTGACCCACCAC<br>CCCATCTCTGACCATGAGGCCACCCTGAGGTGCTGGGCCCTGGGTTTCTACCCTGCGGAGATCA<br>CACTGACCTGGCAGCGGGATGGCGAGGACCAAACTCAGGACACTGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCG |
| 124 | HLA-B*44:02 | GGCTCCCACTCCATGAGGTATTTCTACACCGCCATGTCCCGGCCCGGCCGCGGGGAGCCCCGCT<br>TCATCACCGTGGGCTACGTGGACGACACGCTGTTCGTGAGGTTCGACAGCGACGCCACGAGTCC<br>GAGGAAGGAGCCGCGGGCGCCATGGATAGAGCAGGAGGGGCCGGAGTATTGGGACCGGGAGACA<br>CAGATCTCCAAGACCAACACACAGACTTACCGAGAGAACCTGCGCACCGCGCTCCGCTGCTACA<br>ACCAGAGCGAGGCCCGGGTCTCACATCATCCAGAGGATGTACGGCTGCGACGTGGGGCCGGACGG<br>GCGCCTCCTCCGCGGGTATGACCAGGACGCCTACGACGGCAAGGATTACATCGCCCTGAACGAG<br>GACCTGAGCTCCTGGACCGCGGCGGACACCGCGGCTCAGATCACCCAGCGCAAGTGGGAGGCGG<br>CCCGTGTGGCGGAGCAGGACAGAGCCTACCTGGAGGGCCTGTGCGTGGAGTCGCTCCGCAGATA<br>CCTGGAGAACGGGAAGGAGACGCTGCAGCGCGCGGACCCCCCAAAGACACATGTGACCCACCAC<br>CCCATCTCTGACCATGAGGTCACCCTGAGGTGCTGGGCCCTGGGCTTCTACCCTGCGGAGATCA<br>CACTGACCTGGCAGCGGGATGGCGAGGACCAAACTCAGGACACCGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCG |
| 125 | HLA-B*46:01 | GGCTCCCACTCCATGAGGTATTTCTACACCGCCATGTCCCGGCCCGGCCGCGGGGAGCCCCGCT<br>TCATCGCAGTGGGCTACGTGGACGACACCCAGTTCGTGAGGTTCGACAGCGACGCCGCGAGTCC<br>GAGGATGGCGCCCCGGGCGCCATGGATAGAGCAGGAGGGGCCGGAGTATTGGGACCGGGAGACA<br>CAGAAGTACAAGCGCCAGGCACAGACTGACCGAGTGAGCCTGCGGAACCTGCGCGGCTGCTACA<br>ACCAGAGCGAGGCCCGGGTCTCACACCCTCCAGAGGATGTACGGCTGCGACGTGGGGCCGGACGG<br>GCGCCTCCTCCGCGGGCATGACCAGTCCGCCTACGACGGCAAGGATTACATCGCCCTGAACGAG<br>GACCTGAGCTCCTGGACCGCGGCGGACAACGGCGGCTCAGATCACCCAGCGCAAGTGGGAGGCGG<br>CCCGTGAGGCGGAGCAGTGGAGAGCCTACCTGGAGGGCCTGTGCGTGGAGTGGCTCCGCAGATA<br>CCTGGAGAACGGGAAGGAGACGCTGCAGCGCGCGGACCCCCCAAAGACACATGTGACCCACCAC<br>CCCATCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACCGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCA |
| 126 | HLA-B*50:01 | GGCTCCCACTCCATGAGGTATTTCCACACCGCCATGTCCCGGCCCGGCCGCGGGGAGCCCCGCT<br>TCATCACCGTGGGCTACGTGGACGACACGCTGTTCGTGAGGTTCGACAGCGACGCCACGAGTCC<br>GAGGAAGGAGCCGCGGGCGCCATGGATAGAGCAGGAGGGGCCGGAGTATTGGGACCGGGAGACA<br>CAGATCTCCAAGACCAACACACAGACTTACCGAGAGAGCCTGCGGAACCTGCGCGGCTGCTACA<br>ACCAGAGCGAGGCCCGGGTCTCACACTTGGCAGAGGATGTATGGCTGCGACCTGGGGCCCGACGG<br>GCGCCTCCTCCGCGGGTATAACCAGTTAGCCTACGACGGCAAGGATTACATCGCCCTGAACGAG<br>GACCTGAGCTCCTGGACCGCGGCGGACACCGCGGCTCAGATCACCCAGCGCAAGTGGGAGGCGG<br>CCCGTGAGGCGGAGCAGCTGAGAGCCTACCTGGAGGGCCTGTGCGTGGAGTGGCTCCGCAGATA<br>CCTGGAGAACGGGAAGGAGACGCTGCAGCGCGCGGACCCCCCAAAGACACATGTGACCCACCAC<br>CCCATCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACCGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCA |
| 127 | HLA-B*57:01 | GGCTCCCACTCCATGAGGTATTTCTACACCGCCATGTCCCGGCCCGGCCGCGGGGAGCCCCGCT<br>TCATCGCAGTGGGCTACGTGGACGACACCCAGTTCGTGAGGTTCGACAGCGACGCCGCGAGTCC<br>GAGGATGGCGCCCCGGGCGCCATGGATAGAGCAGGAGGGGCCGGAGTATTGGGACGGGGAGACA<br>CGGAACATGAAGGCCTCCGCGCAGACTTACCGAGAGAACCTGCGGATCGCGCTCCGCTGCTACA<br>ACCAGAGCGAGGCCCGGGTCTCACATCATCCAGGTGATGTATGGCTGCGACGTGGGGCCGGACGG<br>GCGCCTCCTCCGCGGGCATGACCAGTCCGCCTACGACGGCAAGGATTACATCGCCCTGAACGAG<br>GACCTGAGCTCCTGGACCGCGGCGGACACGGCGGCTCAGATCACCCAGCGCAAGTGGGAGGCGG<br>CCCGTGTGGCGGAGCAGCTGAGAGCCTACCTGGAGGGCCTGTGCGTGGAGTGGCTCCGCAGATA<br>CCTGGAGAACGGGAAGGAGACGCTGCAGCGCGCGGACCCCCCAAAGACACATGTGACCCACCAC<br>CCCATCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACCGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCAAAGCCCCTCACCCTGAGATGGGAGCCA |
| 128 | HLA-B*58:01 | GGCTCCCACTCCATGAGGTATTTCTACACCGCCATGTCCCGGCCCGGCCGCGGGGAGCCCCGCT<br>TCATCGCAGTGGGCTACGTGGACGACACCCAGTTCGTGAGGTTCGACAGCGACGCCGCGAGTCC<br>GAGGACGGAGCCCCGGGCGCCATGGATAGAGCAGGAGGGGCCGGAGTATTGGGACGGGGAGACA<br>CGGAACATGAAGGCCTCCGCGCAGACTTACCGAGAGAACCTGCGGATCGCGCTCCGCTGCTACA<br>ACCAGAGCGAGGCCCGGGTCTCACATCATCCAGAGGATGTATGGCTGCGACCTGGGGCCCGACGG<br>GCGCCTCCTCCGCGGGCATGACCAGTCCGCCTACGACGGCAAGGATTACATCGCCCTGAACGAG |

| SEQ ID NO | Name | Sequence |
|---|---|---|
| | | GACCTGAGCTCCTGGACCGCGGCGGACACCGCGGCTCAGATCACCCAGCGCAAGTGGGAGGCGG |
| | | CCCGTGTGGCGGAGCAGCTGAGAGCCTACCTGGAGGGCCTGTGCGTGGAGTGGCTCCGCAGATA |
| | | CCTGGAGAACGGGAAGGAGACGCTGCAGCGCGCGGACCCCCCAAAGACACACGTGACCCACCAC |
| | | CCCGTCTCTGACCATGAGGCCACCCTGAGGTGCTGGGCCCTGGGCTTCTACCCTGCGGAGATCA |
| | | CACTGACCTGGCAGCGGGATGGCGAGGACCAAACTCAGGACACTGAGCTTGTGGAGACCAGACC |
| | | AGCAGGAGATAGAACCTTCCAGAAGTGGGCAGCTGTGGTGGTGCCTTCTGGAGAAGAGCAGAGA |
| | | TACACATGCCATGTACAGCATGAGGGGCTGCCGAAGCCCCTCACCCTGAGATGGGAGCCA |
| 129 | HLA-C*02:02 | TGCTCCCACTCCATGAGGTATTTCTACACCGCTGTGTCCCGGCCCAGCCGCGGAGAGCCCCACT |
| | | TCATCGCAGTGGGCTACGTGGACGACACGCAGTTCGTGCGGTTCGACAGCGACGCCGCGAGTCC |
| | | AAGAGGGGAGCCGCGGGCGCCGTGGGTGGAGCAGGAGGGGCCGGAGTATTGGGACCGGGAGACA |
| | | CAGAAGTACAAGCGCCAGGCACAGACTGACCGAGTGAACCTGCGGAAACTACGCGGCTGCTACA |
| | | ACCAGAGCGAGGCCGGGTCTCACACCCTCCAGAGGATGTACGGCTGCGACCTGGGGCCCGACGG |
| | | GCGCCTCCTCCGCGGGTATGACCAGTCCGCCTACGACGGCAAGGATTACATCGCCCTGAACGAG |
| | | GACCTGCGCTCCTGGACCGCCGCGGACACAGCGGCTCAGATCACCCAGCGCAAGTGGGAGGCGG |
| | | CCCGTGAGGCGGAGCAGTGGAGAGCCTACCTGGAGGGCGAGTGCGTGGAGTGGCTCCGCAGATA |
| | | CCTGGAGAACGGGAAGGAGACGCTGCAGCGCGCGGAACACCCAAAGACACACGTGACCCACCAT |
| | | CCCGTCTCTGACCATGAGGCCACCCTGAGGTGCTGGGCCCTGGGCTTCTACCCTACGGAGATCA |
| | | CACTGACCTGGCAGCGGGATGGCGAGGACCAAACTCAGGACACCGAGCTTGTGGAGACCAGGCC |
| | | AGCAGGAGATGAACCTTCCAGAAGTGGGCAGCTGTGGTGGTGCCTTCTGGAGAAGAGCAGAGA |
| | | TACACGTGCCATGTGCAGCACGAGGGGCTGCCGGAGCCCCTCACCCTGAGATGGGAGCCA |
| 130 | HLA-C*03:04 | GGCTCCCACTCCATGAGGTATTTCTACACCGCTGTGTCCCGGCCCGGCCGCGGGGAGCCCCACT |
| | | TCATCGCAGTGGGCTACGTGGACGACACGCAGTTCGTGCGGTTCGACAGCGACGCCGCGAGTCC |
| | | GAGAGGGGAGCCGCGGGCGCCGTGGGTGGAGCAGGAGGGGCCGGAGTATTGGGACCGGGAGACA |
| | | CAGAAGTACAAGCGCCAGGCACAGACTGACCGAGTGAGCCTGCGGAACCTGCGCGGCTGCTACA |
| | | ACCAGAGCGAGGCCGGGTCTCACATCATCCAGAGGATGTATGGCTGCGACGTGGGGCCCGACGG |
| | | GCGCCTCCTCCGCGGGTATGACCAGTACGACGGCAAGGATTACATCGCCCTGAACGAG |
| | | GATCTGCGCTCCTGGACCGCCGCGGACACGGCGGCTCAGATCACCCAGCGCAAGTGGGAGGCGG |
| | | CCCGTGAGGCGGAGCAGCTGAGAGCCTACCTGGAGGGCCTGTGCGTGGAGTGGCTCCGCAGATA |
| | | CCTGAAGAATGGGAAGGAGACGCTGCAGCGCGCGGAACACCCAAAGACACACGTGACCCACCAT |
| | | CCCGTCTCTGACCATGAGGCCACCCTGAGGTGCTGGGCCCTGGGCTTCTACCCTGCGGAGATCA |
| | | CACTGACCTGGCAGTGGGATGGGGAGGACCAAACTCAGGACACTGAGCTTGTGGAGACCAGGCC |
| | | AGCAGGAGATGAACCTTCCAGAAGTGGGCAGCTGTGGTGGTGCCTTCTGGAGAAGAGCAGAGA |
| | | TACACGTGCCATGTGCAGCACGAGGGGCTGCCGGAGCCCCTCACCCTGAGATGGGAGCCG |
| 131 | HLA-C*05:01 | TGCTCCCACTCCATGAGGTATTTCTACACCGCCGTGTCCCGGCCCGGCCGCGGAGAGCCCCGCT |
| | | TCATCGCAGTGGGCTACGTGGACGACACGCAGTTCGTGCAGTTCGACAGCGACGCCGCGAGTCC |
| | | AAGAGGGGAGCCGCGGGCGCCGTGGGTGGAGCAGGAGGGGCCGGAGTATTGGGACCGGGAGACA |
| | | CAGAAGTACAAGCGCCAGGCACAGACTGACCGAGTGAACCTGCGGAAACTGCGCGGCTGCTACA |
| | | ACCAGAGCGAGGCCGGGTCTCACACCCTCCAGAGGATGTATGCTGCGACCTGGGGCCCGACGG |
| | | GCGCCTCCTCCGCGGGTATAACCAGTTCGCCTACGACGGCAAGGATTACATCGCCCTGAATGAG |
| | | GACCTGCGCTCCTGGACCGCCGCGGACAAGGCGGCTCAGATCACCCAGCGCAAGTGGGAGGCGG |
| | | CCCGTGAGGCGGAGCAGCGGAGAGCCTACCTGGAGGGCACGTGCGTGGAGTGGCTCCGCAGATA |
| | | CCTGGAGAACGGGAAGAAGACGCTGCAGCGCGCGGAACACCCAAAGACACACGTGACCCACCAT |
| | | CCCGTCTCTGACCATGAGGCCACCCTGAGGTGCTGGGCCCTGGGCTTCTACCCTGCGGAGATCA |
| | | CACTGACCTGGCAGCGGGATGGCGAGGACCAAACTCAGGACACCGAGCTTGTGGAGACCAGGCC |
| | | AGCAGGAGATGGAACCTTCCAGAAGTGGGCAGCTGTGGTGGTGCCTTCTGGAGAAGAGCAGAGA |
| | | TACACGTGCCATGTGCAGCACGAGGGGCTGCCAGAGCCCCTCACCCTGAGATGGGGGCCA |
| 132 | HLA-C*07:01 | TGCTCCCACTCCATGAGGTATTTCGACACCGCCGTGTCCCGGCCCGGCCGCGGAGAGCCCCGCT |
| | | TCATCTCAGTGGGCTACGTGGACGACACGCAGTTCGTGCGGTTCGACAGCGACGCCGCGAGTCC |
| | | GAGAGGGGAGCCGCGGGCGCCGTGGGTGGAGCAGGAGGGGCCGGAGTATTGGGACCGGGAGACA |
| | | CAGAACTACAAGCGCCAGGCACAGGCTGACCGAGTGAGCCTGCGGAACCTGCGCGGCTGCTACA |
| | | ACCAGAGCGAGGACGGGTCTCACACCCTCCAGAGGATGTATGGCTGCGACCTGGGGCCCGACGG |
| | | GCGCCTCCTCCGCGGGTATGACCAGTCCGCCTACGACGGCAAGGATTACATCGCCCTGAACGAG |
| | | GACCTGCGCTCCTGGACCGCCGCGGACACCGCGGCTCAGATCACCCAGCGCAAGTTGGAGGCGG |
| | | CCCGTGCGGCGGAGCAGCTGAGAGCCTACCTGGAGGGCACGTGCGTGGAGTGGCTCCGCAGATA |
| | | CCTGGAGAACGGGAAGGAGACGCTGCAGCGCGCAGAACCCCAAAGACACACGTGACCCACCAC |
| | | CCCCTCTCTGACCATGAGGCCACCCTGAGGTGCTGGGCCCTGGGCTTCTACCCTGCGGAGATCA |
| | | CACTGACCTGGCAGCGGGATGGGGAGGACCAGACCCAGGACACCGAGCTTGTGGAGACCAGGCC |
| | | AGCAGGAGATGAACCTTCCAGAAGTGGGCAGCTGTGGTGGTGCCTTCTGGACAAGAGCAGAGA |
| | | TACACGTGCCATATGCAGCACGAGGGGCTGCAAGAGCCCCTCACCCTGAGCTGGGAGCCA |
| 133 | HLA-A*11:01 | GGCTCCCACTCCATGAGGTATTTCTACACCTCCGTGTCCCGGCCCGGCCGCGGGGAGCCCCGCT |
| | | TCATCGCCGTGGGCTACGTGGACGACACGCAGTTCGTGCGGTTCGACAGCGACGCCGCGAGCCA |
| | | GAGGATGGAGCCGCGGGCGCCGTGGATAGAGCAGGAGGGGCCGGAGTATTGGGACCAGGAGACA |
| | | CGGAATGTGAAGGCCCAGTCACAGACTGACCGAGTGGACCTGGGGACCCTGCGCGGCTGCTACA |
| | | ACCAGAGCGAGGACGGTTCTCACACCATCCAGATAATGTATGGCTGCGACGTGGGGCCGGACGG |
| | | GCGCTTCCTCCGCGGGTACCGGCAGGACGCCTACGACGGCAAGGATTACATCGCCCTGAACGAG |
| | | GACCTGCGCTCTTGGACCGCGGCGGACATGGCAGCTCAGATCACCAAGCGCAAGTGGGAGGCGG |
| | | CCCATGCGGCGGAGCAGCAGAGAGCCTACCTGGAGGGCCGGTGCGTGGAGTGGCTCCGCAGATA |
| | | CCTGGAGAACGGGAAGGAGACGCTGCAGCGCACGGACCCCCCCAAGACACATATGACCCACCAC |

| SEQ ID NO | Name | Sequence |
|---|---|---|
| | | CCCATCTCTGACCATGAGGCCACCCTGAGGTGCTGGGCCCTGGGCTTCTACCCTGCGGAGATCA<br>CACTGACCTGGCAGCGGGATGGGGAGGACCAGACCCAGGACACGGAGCTCGTGGAGACCAGGCC<br>TGCAGGGGATGGAACCTTCCAGAAGTGGGCGGCTGTGGTGGTGCCTTCTGGAGAGGAGCAGAGA<br>TACACCTGCCATGTGCAGCATGAGGGTCTGCCCAAGCCCCTCACCCTGAGATGGGAGCTG |
| 134 | HLA-A*23:01 | GGCTCCCACTCCATGAGGTATTTCTCCACATCCGTGTCCCGGCCCGGCCGCGGGGAGCCCCGCT<br>TCATCGCCGTGGGCTACGTGGACGACACGCAGTTCGTGCGGTTCGACAGCGACGCCGCGAGCCA<br>GAGGATGGAGCCGCGGGCGCCGTGGATAGAGCAGGAGGGGCCGGAGTATTGGGACGAGGAGACA<br>GGGAAAGTGAAGGCCCACTCACAGACTGACCGAGAGAACCTGCGGATCGCGCTCCGCTGCTACA<br>ACCAGAGCGAGGCCGGTTCTCACACCCTCCAGATGATGTTTGGCTGCGACGTGGGGTCGGACGG<br>GCGCTTCCTCCGCGGGTACCACCAGTACGCCTACGACGGCAAGGATTACATCGCCCTGAAAGAG<br>GACCTGCGCTCTTGGACCGCGGCGGACATGGCGGCTCAGATCACCCAGCGCAAGTGGGAGGCGG<br>CCCGTGTGGCGGAGCAGTTGAGAGCCTACCTGGAGGGCACGTGCGTGGACGGGCTCCGCAGATA<br>CCTGGAGAACGGGAAGGAGACGCTGCAGCGCACGGACCCCCCCAAGACACATATGACCCACCAC<br>CCCATCTCTGACCATGAGGCCACTCTGAGATGCTGGGCCCTGGGCTTCTACCCTGCGGAGATCA<br>CACTGACCTGGCAGCGGGATGGGGAGGACCAGACCCAGGACACGGAGCTTGTGGAGACCAGGCC<br>TGCAGGGGATGGAACCTTCCAGAAGTGGGCAGCTGTGGTGGTACCTTCTGGAGAGGAGCAGAGA<br>TACACCTGCCATGTGCAGCATGAGGGTCTGCCCAAGCCCCTCACCCTGAGATGGGAGCCA |
| 135 | HLA-A*30:01 | GGCTCCCACTCCATGAGGTATTTCTCCACATCCGTGTCCCGGCCCGGCAGTGGAGAGCCCCGCT<br>TCATCGCAGTGGGCTACGTGGACGACACGCAGTTCGTGCGGTTCGACAGCGACGCCGCGAGCCA<br>GAGGATGGAGCCGCGGGCGCCGTGGATAGAGCAGGAGGAGGCCTGAGTATTGGGACCAGGAGACA<br>CGGAATGTGAAGGCCCAGTCACAGACTGACCGAGTGGACCTGGGGACCCTGCGCGGCTGCTACA<br>ACCAGAGCGAGGCCGGTTCTCACACCATCCAGATAATGTATGGCTGCGACGTGGGGTCGGACGG<br>GCGCTTCCTCCGCGGGTATGAACAGCACGCCTACGACGGCAAGGATTACATCGCCCTGAACGAG<br>GACCTGCGCTCTTGGACCGCGGCGGACATGGCGGCTCAGATCACCCAGCGCAAGTGGGAGGCGG<br>CCCGTTGGGCGGAGCAGTTGAGAGCCTACCTGGAGGGCACGTGCGTGGAGTGGCTCCGCAGATA<br>CCTGGAGAACGGGAAGGAGACGCTGCAGCGCACGGACCCCCCCAAGACACATATGACCCACCAC<br>CCCATCTCTGACCATGAGGCCACCCTGAGGTGCTGGGCCCTGGGCTTCTACCCTGCGGAGATCA<br>CACTGACCTGGCAGCGGGATGGGGAGGACCAGACCCAGGACACGGAGCTCGTGGAGACCAGGCC<br>TGCAGGGGATGGAACCTTCCAGAAGTGGGCGGCTGTGGTGGTGCCTTCTGGAGAGGAGCAGAGA<br>TACACCTGCCATGTGCAGCATGAGGGTCTGCCCAAGCCCCTCACCCTGAGATGGGAGCTG |
| 136 | HLA-A*33:03 | GGCTCCCACTCCATGAGGTATTTCACCACATCCGTGTCCCGGCCCGGCCGCGGGGAGCCCCGCT<br>TCATCGCCGTGGGCTACGTGGACGACACGCAGTTCGTGCGGTTCGACAGCGACGCCGCGAGCCA<br>GAGGATGGAGCCGCGGGCGCCGTGGATAGAGCAGGAGGGGCCGGAGTATTGGGACCGGAACACA<br>CGGAATGTGAAGGCCCACTCACAGATTGACCGAGTGGACCTGGGGACCCTGCGCGGCTGCTACA<br>ACCAGAGCGAGGCCGGTTCTCACACCATCCAGATGATGTATGGCTGCGACGTGGGGTCGGACGG<br>GCGCTTCCTCCGCGGGTACCAGCAGGACGCCTACGACGGCAAGGATTACATCGCCCTTGAACGAG<br>GACCTGCGCTCTTGGACCGCGGCGGACATGGCGGCTCAGATCACCCAGCGCAAGTGGGAGGCGG<br>CCCGTGTGGCGGAGCAGTTGAGAGCCTACCTGGAGGGCACGTGCGTGGAGTGGCTCCGCAGATA<br>CCTGGAGAACGGGAAGGAGACGCTGCAGCGCACGGACCCCCCCAAGACACATATGACTCACCAC<br>GCTGTCTCTGACCATGAGGCCACCCTGAGGTGCTGGGCCCTGAGCTTCTACCCTGCGGAGATCA<br>CACTGACCTGGCAGCGGGATGGGGAGGACCAGACCCAGGACACGGAGCTCGTGGAGACCAGGCC<br>TGCAGGGGATGGAACCTTCCAGAAGTGGGCGTCTGTGGTGGTGCCTTCTGGACAGGAGCAGAGA<br>TACACCTGCCATGTGCAGCATGAGGGTCTCCCCAAGCCCCTCACCCTGAGATGGGAGCCG |
| 137 | HLA-B*08:01 | GGCTCCCACTCCATGAGGTATTTCGACACCGCCATGTCCCGGCCCGGCCGCGGGGAGCCCCGCT<br>TCATCTCAGTGGGCTACGTGGACGACACGCAGTTCGTGAGGTTCGACAGCGACGCCGCGAGTCC<br>GAGAGAGGAGCCGCGGGCGCCGTGGATAGAGCAGGAGGGGCCGGAGTATTGGGACCGGAACACA<br>CAGATCTTCAAGACCAACACACAGACTGACCGAGAGAGCCTGCGGAACCTGCGCGGCTGCTACA<br>ACCAGAGCGAGGCCGGGTCTCACACCCTCCAGAGCATGTACGGCTGCGACGTGGGGCCGGACGG<br>GCGCCTCCTCCGCGGGCATAACCAGTACGCCTACGACGGCAAGGATTACATCGCCCTGAACGAG<br>GACCTGCGCTCCTGGACCGCGGCGGACACCGCGGCTCAGATCACCCAGCGCAAGTGGGAGGCGG<br>CCCGTGTGGCGGAGCAGGACAGAGCCTACCTGGAGGGCACGTGCGTGGAGTGGCTCCGCAGATA<br>CCTGGAGAACGGGAAGGACACGCTGGAGCGCGCGGACCCCCCAAAGACACACGTGACCCACCAC<br>CCCATCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACTGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCG |
| 138 | HLA-B*15:01 | GGCTCCCACTCCATGAGGTATTTCTACACCGCCATGTCCCGGCCCGGCCGCGGGGAGCCCCGCT<br>TCATCGCAGTGGGCTACGTGGACGACACCCAGTTCGTGAGGTTCGACAGCGACGCCGCGAGTCC<br>GAGGATGGCGCCCCGGGCGCCATGGATAGAGCAGGAGGGGCCGGAGTATTGGGACCGGGAGACA<br>CAGATCTCCAAGACCAACACACAGACTTACCGAGAGAGCCTGCGGAACCTGCGCGGCTGCTACA<br>ACCAGAGCGAGGCCGGGTCTCACACCCTCCAGAGGATGTACGCTGCGACGTGGGGCCGGACGG<br>GCGCCTCCTCCGCGGGCATGACCAGTCCGCCTACGACGGCAAGGATTACATCGCCCTGAACGAG<br>GACCTGAGCTCCTGGACCGCGGCGGACACGGCGGCTCAGATCACCCAGCGCAAGTGGGAGGCGG<br>CCCGTGAGGCGGAGCAGTGGAGAGCCTACCTGGAGGGCCTGTGCGTGGAGTGGCTCCGCAGATA<br>CCTGGAGAACGGGAAGGAGACGCTGCAGCGCGCGGACCCCCCAAAGACACATGTGACCCACCAC<br>CCCATCTCTGACCATGAGGCCACCCTGAGGTGCTGGGCCCTGGGCTTCTACCCTGCGGAGATCA |

| SEQ ID NO | Name | Sequence |
|---|---|---|
| | | CACTGACCTGGCAGCGGGATGGCGAGGACCAAACTCAGGACACCGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCA |
| 139 | HLA-B*15:03 | GGCTCCCACTCCATGAGGTATTTCTACACCGCCATGTCCCGGCCCGGCCGCGGGGAGCCCCGCT<br>TCATCTCAGTGGGCTACGTGGACGACACGCAGTTCGTGAGGTTCGACAGCGACGCCGCGAGTCC<br>GAGAGAGGAGCCGCGGGCGCCGTGGATAGAGCAGGAGGGGCCGGAGTATTGGGACCGGGAGACA<br>CAGATCTCCAAGACCAACACACAGACTTACCGAGAGAGCCTGCGGAACCTGCGCGGCTGCTACA<br>ACCAGAGCGAGGCCGGGTCTCACACCCTCCAGAGGATGTACGGCTGCGACGTGGGGCCGGACGG<br>GCGCCTCCTCCGCGGGCATGACCAGTCCGCCTACGACGGCAAGGATTACATCGCCCTGAACGAG<br>GACCTGAGCTCCTGGACCGCGGCGGACACGGCGGCTCAGATCACCCAGCGCAAGTGGGAGGCGG<br>CCCGTGAGGCGGAGCAGCTGAGAGCCTACCTGGAGGGCCTGTGCGTGGAGTGGCTCCGCAGATA<br>CCTGGAGAACGGGAAGGAGACGCTGCAGCGCGCGGACCCCCCAAAGACACATGTGACCCACCAC<br>CCCATCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACCGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCA |
| 140 | HLA-B*35:01 | GGCTCCCACTCCATGAGGTATTTCTACACCGCCATGTCCCGGCCCGGCCGCGGGGAGCCCCGCT<br>TCATCGCAGTGGGCTACGTGGACGACACCCAGTTCGTGAGGTTCGACAGCGACGCCGCGAGTCC<br>GAGGACGGAGCCCCGGGCGCCATGGATAGAGCAGGAGGGGCCGGAGTATTGGGACCGGAACACA<br>CAGATCTTCAAGACCAACACACAGACTTACCGAGAGAGCCTGCGGAACCTGCGCGGCTGCTACA<br>ACCAGAGCGAGGCCGGGTCTCACATCATCCAGAGGATGTATGGCTGCGACCTGGGGCCCGACGG<br>GCGCCTCCTCCGCGGGCATGACCAGTCCGCCTACGACGGCAAGGATTACATCGCCCTGAACGAG<br>GACCTGAGCTCCTGGACCGCGGCGGACACCGGGCTCAGATCACCCAGCGCAAGTGGGAGGCGG<br>CCCGTGTGGCGGAGCAGCTGAGAGCCTACCTGGAGGGCCTGTGCGTGGAGTGGCTCCGCAGATA<br>CCTGGAGAACGGGAAGGAGACGCTGCAGCGCGCGGACCCCCCAAAGACACACGTGACCCACCAC<br>CCCGTCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACTGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCA |
| 141 | HLA-B*40:02 | GGCTCCCACTCCATGAGGTATTTCCACACCTCCGTGTCCCGGCCCGGCCGCGGGGAGCCCCGCT<br>TCATCACCGTGGGCTACGTGGACGACACGCTGTTCGTGAGGTTCGACAGCGACGCCACGAGTCC<br>GAGGAAGGAGCCGCGGGCGCCATGGATAGAGCAGGAGGGGCCGGAGTATTGGGACCGGGAGACA<br>CAGATCTCCAAGACCAACACACAGACTTACCGAGAGAGCCTGCGGAACCTGCGCGGCTGCTACA<br>ACCAGAGCGAGGCCGGGTCTCACACCCTCCAGAGCATGTACGGCTGCGACGTGGGGCCGGACGG<br>GCGCCTCCTCCGCGGGCATAACCAGTACGCCTACGACGGCAAGGATTACATCGCCCTGAACGAG<br>GACCTGCGCTCCTGGACCGCCGCGGACACGGCGGCTCAGATCACCCAGCGCAAGTGGGAGGCGG<br>CCCGTGTGGCGGAGCAGCTGAGAGCCTACCTGGAGGGCGAGTGCGTGGAGTGGCTCCGCAGATA<br>CCTGGAGAACGGGAAGGAGACGCTGCAGCGCGCGGACCCCCCAAAGACACACGTGACCCACCAC<br>CCCATCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACTGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCG |
| 142 | HLA-B*42:01 | GGCTCCCACTCCATGAGGTATTTCTACACCTCCGTGTCCCGGCCCGGCCGCGGGGAGCCCCGCT<br>TCATCTCAGTGGGCTACGTGGACGACACCCAGTTCGTGAGGTTCGACAGCGACGCCGCGAGTCC<br>GAGAGAGGAGCCGCGGGCGCCGTGGATAGAGCAGGAGGGGCCGGAGTATTGGGACCGGAACACA<br>CAGATCTACAAGGCCCAGGCACAGACTGACCGAGAGAGCCTGCGGAACCTGCGCGGCTGCTACA<br>ACCAGAGCGAGGCCGGGTCTCACACCCTCCAGAGCATGTACGGCTGCGACGTGGGGCCGGACGG<br>GCGCCTCCTCCGCGGGCATAACCAGTACGCCTACGACGGCAAGGATTACATCGCCCTGAACGAG<br>GACCTGCGCTCCTGGACCGCGGCGGACACCGCGGCTCAGATCACCCAGCGCAAGTGGGAGGCGG<br>CCCGTGTGGCGGAGCAGGACAGAGCCTACCTGGAGGGCACGTGCGTGGAGTGGCTCCGCAGATA<br>CCTGGAGAACGGGAAGGACACGCTGGAGCGCGCGGACCCCCCAAAGACACACGTGACCCACCAC<br>CCCATCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACTGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCG |
| 143 | HLA-B*44:03 | GGCTCCCACTCCATGAGGTATTTCTACACCGCCATGTCCCGGCCCGGCCGCGGGGAGCCCCGCT<br>TCATCACCGTGGGCTACGTGGACGACACGCTGTTCGTGAGGTTCGACAGCGACGCCACGAGTCC<br>GAGGAAGGAGCCGCGGGCGCCATGGATAGAGCAGGAGGGGCCGGAGTATTGGGACCGGGAGACA<br>CAGATCTCCAAGACCAACACACAGACTTACCGAGAGAACCTGCGCACCGCGCTCCGCTGCTACA<br>ACCAGAGCGAGGCCGGGTCTCACATCATCCAGAGGATGTACGGCTGCGACGTGGGGCCGGACGG<br>GCGCCTCCTCCGCGGGTATGACCAGGACGCCTACGACGGCAAGGATTACATCGCCCTGAACGAG<br>GACCTGAGCTCCTGGACCGCGGCGGACACCGCGGCTCAGATCACCCAGCGCAAGTGGGAGGCGG<br>CCCGTGTGGCGGAGCAGCTGAGAGCCTACCTGGAGGGCCTGTGCGTGGAGTGGCTCTCCGCAGATA<br>CCTGGAGAACGGGAAGGAGACGCTGCAGCGCGCGGACCCCCCAAAGACACATGTGACCCACCAC<br>CCCATCTCTGACCATGAGGTCACCCTGAGGTGCTGGGCCCTGGGCTTCTACCCTGCGGAGATCA<br>CACTGACCTGGCAGCGGGATGGCGAGGACCAAACTCAGGACACCGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCG |

SEQUENCE LISTING

| SEQ ID NO | Name | Sequence |
|---|---|---|
| 144 | HLA-B*51:01 | GGCTCCCACTCCATGAGGTATTTCTACACCGCCATGTCCCGGCCCGGCCGCGGGGAGCCCCGCT<br>TCATTGCAGTGGGCTACGTGGACGACACCCAGTTCGTGAGGTTCGACAGCGACGCCGCGAGTCC<br>GAGGACGGAGCCCCGGGCGCCATGGATAGAGCAGGAGGGGCCGGAGTATTGGGACCGGAACACA<br>CAGATCTTCAAGACCAACACACAGACTTACCGAGAGAACCTGCGGATCGCGCTCCGCTGCTACA<br>ACCAGAGCGAGGCCGGGTCTCACACTTGGCAGACGATGTATGGCTGCGACGTGGGGCCGGACGG<br>GCGCCTCCTCCGCGGGCATAACCAGTACGCCTACGACGGCAAAGATTACATCGCCCTGAACGAG<br>GACCTGAGCTCCTGGACCGCGGCGGACACCGCGGCTCAGATCACCCAGCGCAAGTGGGAGGCGG<br>CCCGTGAGGCGGAGCAGCTGAGAGCCTACCTGGAGGGCCTGTGCGTGGAGTGGCTCCGCAGACA<br>CCTGGAGAACGGGAAGGAGACGCTGCAGCGCGCGGACCCCCCAAAGACACACGTGACCCACCAC<br>CCCGTCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACTGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCA |
| 145 | HLA-B*53:01 | GGCTCCCACTCCATGAGGTATTTCTACACCGCCATGTCCCGGCCCGGCCGCGGGGAGCCCCGCT<br>TCATCGCAGTGGGCTACGTGGACGACACCCAGTTCGTGAGGTTCGACAGCGACGCCGCGAGTCC<br>GAGGACGGAGCCCCGGGCGCCATGGATAGAGCAGGAGGGGCCGGAGTATTGGGACCGGAACACA<br>CAGATCTTCAAGACCAACACACAGACTTACCGAGAGAACCTGCGGATCGCGCTCCGCTGCTACA<br>ACCAGAGCGAGGCCGGGTCTCACATCATCCAGAGGATGTATGGCTGCGACCTGGGGCCCGACGG<br>GCGCCTCCTCCGCGGGCATGACCAGTCCGCCTACGACGGCAAGGATTACATCGCCCTGAACGAG<br>GACCTGAGCTCCTGGACCGCGGCGGACACCGCGGCTCAGATCACCCAGCGCAAGTGGGAGGCGG<br>CCCGTGTGGCGGAGCAGCTGAGAGCCTACCTGGAGGGCCTGTGCGTGGAGTGGCTCCGCAGATA<br>CCTGGAGAACGGGAAGGAGACGCTGCAGCGCGCGGACCCCCCAAAGACACACGTGACCCACCAC<br>CCCGTCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACTGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCA |
| 146 | HLA-C*01:02 | TGCTCCCACTCCATGAAGTATTTCTTCACATCCGTGTCCCGGCCTGGCCGCGGAGAGCCCCGCT<br>TCATCTCAGTGGGCTACGTGGACGACACGCAGTTCGTGCGGTTCGACAGCGACGCCGCGAGTCC<br>GAGAGGGGAGCCGCGGGCGCCGTGGGTGGAGCAGGAGGGGCCGGAGTATTGGGACCGGGAGACA<br>CAGAAGTACAAGCGCCAGGCACAGACTGACCGAGTGAGCCTGCGGAACCTGCGCGGCTGCTACA<br>ACCAGAGCGAGGCCGGGTCTCACACCCTCCAGTGGATGTGTGGCTGCGACCTGGGGCCCGACGG<br>GCGCCTCCTCCGCGGGTATGACCAGTACGCCTACGACGGCAAGGATTACATCGCCCTGAACGAG<br>GACCTGCGCTCCTGGACCGCCGCGGACACCGCGGCTCAGATCACCCAGCGCAAGTGGGAGGCGG<br>CCCGTGAGGCGGAGCAGCGGAGAGCCTACCTGGAGGGCACGTGCGTGGAGTGGCTCCGCAGATA<br>CCTGGAGAACGGGAAGGAGACGCTGCAGCGCGCGGAACACCCAAAGACACACGTGACCCACCAT<br>CCCGTCTCTGACCATGAGGCCACCCTGAGGTGCTGGGCCCTGGGCTTCTACCCTGCGGAGATCA<br>CACTGACCTGGCAGTGGGATGGGGAGGACCAAACTCAGGACACCGAGCTTGTGGAGACCAGGCC<br>AGCAGGAGATGAACCTTCCAGAAGTGGGCAGCTGTGATGGTGCCTTCTGGAGAAGAGCAGAGA<br>TACACGTGCCATGTGCAGCACGAGGGGCTGCCGAGCCCCTCACCCTGAGATGGGAGCCG |
| 147 | HLA-C*04:01 | GGCTCCCACTCCATGAGGTATTTCTCCACATCCGTGTCCTGGCCCGGCCGCGGGGAGCCCCGCT<br>TCATCGCAGTGGGCTACGTGGACGACACGCAGTTCGTGCGGTTCGACAGCGACGCCGCGAGTCC<br>AAGAGGGGAGCCGCGGGAGCCGTGGGTGGAGCAGGAGGGGCCGGAGTATTGGGACCGGGAGACA<br>CAGAAGTACAAGCGCCAGGCACAGGCTGACCGAGTGAACCTGCGGAAACTGCGCGGCTGCTACA<br>ACCAGAGCGAGGACGGGTCTCACACCCTCCAGAGGATGTTTGGCTGCGACCTGGGGCCGGACGG<br>GCGCCTCCTCCGCGGGTATAACCAGTTCGCCTACGACGGCAAGGATTACATCGCCCTGAACGAG<br>GATCTGCGCTCCTGGACCGCCGCGGACACGGCGGCTCAGATCACCCAGCGCAAGTGGGAGGCGG<br>CCCGTGAGGCGGAGCAGCGGAGAGCCTACCTGGAGGGCACGTGCGTGGAGTGGCTCCGCAGATA<br>CCTGGAGAACGGGAAGGAGACGCTGCAGCGCGCGGAACACCCAAAGACACACGTGACCCACCAT<br>CCCGTCTCTGACCATGAGGCCACCCTGAGGTGCTGGGCCCTGGGCTTCTACCCTGCGGAGATCA<br>CACTGACCTGGCAGTGGGATGGGGAGGACCAAACTCAGGACACCGAGCTTGTGGAGACCAGGCC<br>AGCAGGAGATGAACCTTCCAGAAGTGGGCAGCTGTGGTGGTGCCTTCTGGAGAAGAGCAGAGA<br>TACACGTGCCATGTTCAGCACGAGGGCTGCCGGAGCCCCTCACCCTGAGATGGAAGCCG |
| 148 | HLA-C*06:02 | TGCTCCCACTCCATGAGGTATTTCGACACCGCCGTGTCCCGGCCCGGCCGCGGAGAGCCCCGCT<br>TCATCTCAGTGGGCTACGTGGACGACACGCAGTTCGTGCGGTTCGACAGCGACGCCGCGAGTCC<br>GAGAGGGGAGCCCCGGGCGCCGTGGGTGGAGCAGGAGGGGCCGGAGTATTGGGACCGGGAGACA<br>CAGAAGTACAAGCGCCAGGCACAGGCTGACCGAGTGAACCTGCGGAAACTGCGCGGCTGCTACA<br>ACCAGAGCGAGGACGGGTCTCACACCCTCCAGTGGATGTATGGCTGCGACCTGGGGCCCGACGG<br>GCGCCTCCTCCGCGGGTATGACCAGTCCGCCTACGACGGCAAGGATTACATCGCCCTGAACGAG<br>GACCTGCGCTCCTGGACCGCCGCGGACACGGCGGCTCAGATCACCCAGCGCAAGTGGGAGGCGG<br>CCCGTGAGGCGGAGCAGTGGAGAGCCTACCTGGAGGGCACGTGCGTGGAGTGGCTCCGCAGATA<br>CCTGGAGAACGGGAAGGAGACGCTGCAGCGCGCGGAACACCCAAAGACACACGTGACCCACCAT<br>CCCGTCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACCGAGCTTGTGGAGACCAGGCC<br>AGCAGGAGATGAACCTTCCAGAAGTGGGCAGCTGTGGTGGTGCCTTCTGGAGAAGAGCAGAGA<br>TACACGTGCCATGTGCAGCACGAGGGGCTGCCAGAGCCCCTCACCCTGAGATGGGAGCCA |
| 149 | HLA-C*07:02 | TGCTCCCACTCCATGAGGTATTTCGACACCGCCGTGTCCCGGCCCGGCCGCGGAGAGCCCCGCT<br>TCATCTCAGTGGGCTACGTGGACGACACGCAGTTCGTGCGGTTCGACAGCGACGCCGCGAGTCC |

| SEQ ID NO | Name | Sequence |
|---|---|---|
| | | GAGAGGGGAGCCGCGGGCGCCGTGGGTGGAGCAGGAGGGGCCGGAGTATTGGGACCGGGAGACA<br>CAGAAGTACAAGCGCCAGGCACAGGCTGACCGAGTGAGCCTGCGGAACCTGCGCGGCTGCTACA<br>ACCAGAGCGAGGACGGGTCTCACACCCTCCAGAGGATGTCTGGCTGCGACCTGGGGCCCGACGG<br>GCGCCTCCTCCGCGGGTATGACCAGTCCGCCTACGACGGCAAGGATTACATCGCCCTGAACGAG<br>GACCTGCGCTCCTGGACCGCCGCGGACACCGCGGCTCAGATCACCCAGCGCAAGTTGGAGGCGG<br>CCCGTGCGGCGGAGCAGCTGAGAGCCTACCTGGAGGGCACGTGCGTGGAGTGGCTCCGCAGATA<br>CCTGGAGAACGGGAAGGAGACGCTGCAGCGCGCAGAACCCCCAAAGACACACGTGACCCACCAC<br>CCCCTCTCTGACCATGAGGCCACCCTGAGGTGCTGGGCCCTGGGCTTCTACCCTGCGGAGATCA<br>CACTGACCTGGCAGCGGGATGGGGAGGACCAGACCCAGGACACCGAGCTTGTGGAGACCAGGCC<br>AGCAGGAGATGGAACCTTCCAGAAGTGGGCAGCTGTGGTGGTGCCTTCTGGACAAGAGCAGAGA<br>TACACGTGCCATATGCAGCACGAGGGGCTGCAAGAGCCCCTCACCCTGAGCTGGGAGCCA |
| 150 | HLA-C*16:01 | TGCTCCCACTCCATGAGGTATTTCTACACCGCCGTGTCCCGGCCCGGCCGCGGAGAGCCCCGCT<br>TCATCGCAGTGGGCTACGTGGACGACACGCAGTTCGTGCGGTTCGACAGCGACGCCGCGAGTCC<br>AAGAGGGGAGCCGCGGGCGCCGTGGGTGGAGCAGGAGGGGCCGGAGTATTGGGACCGGGAGACA<br>CAGAAGTACAAGCGCCAGGCACAGACTGACCGAGTGAGCCTGCGGAACCTGCGCGGCTGCTACA<br>ACCAGAGCGAGGCCGGGTCTCACACCCTCCAGTGGATGTATGGCTGCGACCTGGGGCCCGACGG<br>GCGCCTCCTCCGCGGGTATGACCAGTCCGCCTACGACGGCAAGGATTACATCGCCCTGAACGAG<br>GACCTGCGCTCCTGGACCGCCGCGGACACGGCGGCTCAGATCACCCAGCGCAAGTGGGAGGCGG<br>CCCGTGCGGCGGAGCAGCAGAGAGCCTACCTGGAGGGCACGTGCGTGGAGTGGCTCCGCAGATA<br>CCTGGAGAACGGGAAGGAGACGCTGCAGCGCGCGGAACACCCAAAGACACACGTGACCCACCAT<br>CTCGTCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACCGAGCTTGTGGAGACCAGGCC<br>AGCAGGAGATGGAACCTTCCAGAAGTGGGCAGCTGTGGTGGTGCCTTCTGGAAGAGCAGAGA<br>TACACGTGCCATGTGCAGCACGAGGGGCTGCCGGAGCCCCTCACCCTGAGATGGGAGCCA |
| 151 | HLA-A*25:01 | GGCTCCCACTCCATGAGGTATTTCTACACCTCCGTGTCCCGGCCCGGCCGCGGGGAGCCCCGCT<br>TCATCGCCGTGGGCTACGTGGACGACACGCAGTTCGTGCGGTTCGACAGCGACGCCGCGAGCCA<br>GAGGATGGAGCCGCGGGCGCCGTGGATAGAGCAGGAGGGGCCGGAGTATTGGGACCGGAACACA<br>CGGAATGTGAAGGCCCACTCACAGACTGACCGAGAGAGCCTGCGGATCGCGCTCCGCTGCTACA<br>ACCAGAGCGAGGACGGTTCTCACACCATCCAGAGGATGTATGGCTGCGACGTGGGGCCGGACGG<br>GCGCTTCCTCCGCGGGTACCAGCAGGACGCTTACGACGGCAAGGATTACATCGCCCTGAACGAG<br>GACCTGCGCTCTTGGACCGCGGCGGACATGGCGGCTCAGATCACCCAGCGCAAGTGGGAGACGG<br>CCCATGAGGCGGAGCAGTGGAGAGCCTACCTGGAGGGCCGGTGCGTGGAGTGGCTCCGCAGATA<br>CCTGGAGAACGGGAAGGAGACGCTGCAGCGCACGGACGCCCCCAAGACGCATATGACTCACCAC<br>GCTGTCTCTGACCATGAGGCCACCCTGAGGTGCTGGGCCCTGAGCTTCTACCCTGCGGAGATCA<br>CACTGACCTGGCAGCGGGATGGGGAGGACCAGACCCAGGACACGGAGCTCGTGGAGACCAGGCC<br>TGCAGGGGATGGGACCTTCCAGAAGTGGGCGTCTGTGGTGGTGCCTTCTGGACAGGAGCAGAGA<br>TACACCTGCCATGTGCAGCATGAGGGTCTGCCCAAGCCCCTCACCCTGAGATGGGAGCCG |
| 152 | HLA-A*26:01 | GGCTCCCACTCCATGAGGTATTTCTACACCTCCGTGTCCCGGCCCGGCCGCGGGGAGCCCCGCT<br>TCATCGCCGTGGGCTACGTGGACGACACGCAGTTCGTGCGGTTCGACAGCGACGCCGCGAGCCA<br>GAGGATGGAGCCGCGGGCGCCGTGGATAGAGCAGGAGGGGCCGGAGTATTGGGACCGGAACACA<br>CGGAATGTGAAGGCCCACTCACAGACTGACCGAGCGAACCTGGGGACCCTGCGCGGCTGCTACA<br>ACCAGAGCGAGGACGGTTCTCACACCATCCAGAGGATGTATGGCTGCGACGTGGGGCCGGACGG<br>GCGCTTCCTCCGCGGGTACCAGCAGGACGCTTACGACGGCAAGGATTACATCGCCCTGAACGAG<br>GACCTGCGCTCTTGGACCGCGGCGGACATGGCGGCTCAGATCACCCAGCGCAAGTGGGAGACGG<br>CCCATGAGGCGGAGCAGTGGAGAGCCTACCTGGAGGGCCGGTGCGTGGAGTGGCTCCGCAGATA<br>CCTGGAGAACGGGAAGGAGACGCTGCAGCGCACGGACGCCCCCAAGACGCATATGACTCACCAC<br>GCTGTCTCTGACCATGAGGCCACCCTGAGGTGCTGGGCCCTGAGCTTCTACCCTGCGGAGATCA<br>CACTGACCTGGCAGCGGGATGGGGAGGACCAGACCCAGGACACGGAGCTCGTGGAGACCAGGCC<br>TGCAGGGGATGGGACCTTCCAGAAGTGGGCGTCTGTGGTGGTGCCTTCTGGACAGGAGCAGAGA<br>TACACCTGCCATGTGCAGCATGAGGGTCTGCCCAAGCCCCTCACCCTGAGATGGGAGCCG |
| 153 | HLA-A*29:02 | GGCTCCCACTCCATGAGGTATTTCACCACATCCGTGTCCCGGCCCGGCCGCGGGGAGCCCCGCT<br>TCATCGCCGTGGGCTACGTGGACGACACGCAGTTCGTGCGGTTTGACAGCGACGCCGCGAGCCA<br>GAGGATGGAGCCGCGGGCACCGTGGATAGAGCAGGAGGGGCCGGAGTATTGGGACCTGCAGACA<br>CGGAATGTGAAGGCCCAGTCACAGACTGACCGAGCGAACCTGGGGACCCTGCGCGGCTGCTACA<br>ACCAGAGCGAGGCCGGTTCTCACACCATCCAGATGATGTATGGCTGCGACGTGGGGTCGGACGG<br>GCGCTTCCTCCGCGGGTACCGGCAGGACGCCTACGACGGCAAGGATTACATCGCCTTGAACGAG<br>GACCTGCGCTCTTGGACCGCGGCGGACATGGCGGCTCAGATCACCCAGCGCAAGTGGGAGGCGG<br>CCCGTGTGGCGGAGCAGTTGAGAGCCTACCTGGAGGGCACGTGCGTGGAGTGGCTCCGCAGATA<br>CCTGGAGAACGGGAAGGAGACGCTGCAGCGCACGGACGCCCCCAAGACGCATATGACTCACCAC<br>GCTGTCTCTGACCATGAGGCCACCCTGAGGTGCTGGGCCCTGAGCTTCTACCCTGCGGAGATCA<br>CACTGACCTGGCAGCGGGATGGGGAGGACCAGACCCAGGACACGGAGCTTGTGGAGACCAGGCC<br>TGCAGGGGATGGAACCTTCCAGAAGTGGGCGTCTGTGGTGGTGCCTTCTGGACAGGAGCAGAGA<br>TACACCTGCCATGTGCAGCATGAGGGTCTGCCCAAGCCCCTCACCCTGAGATGGGAGCCG |
| 154 | HLA-A*68:02 | GGCTCCCACTCCATGAGGTATTTCTACACCTCCATGTCCCGGCCCGGCCGCGGGGAGCCCCGCT<br>TCATCGCCGTGGGCTACGTGGACGACACGCAGTTCGTGCGGTTCGACAGCGACGCCGCGAGCCA<br>GAGGATGGAGCCGCGGGCGCCGTGGATAGAGCAGGAGGGGCCGGAGTATTGGGACCGGAACACA<br>CGGAATGTGAAGGCCCAGTCACAGACTGACCGAGTGGACCTGGGGACCCTGCGCGGCTGCTACA<br>ACCAGAGCGAGGCCGGTTCTCACACCATCCAGAGGATGTATGGCTGCGACGTGGGGCCGGACGG |

SEQUENCE LISTING

| SEQ ID NO | Name | Sequence |
|---|---|---|
|  |  | GCGCTTCCTCCGCGGGTACCACCAGTACGCCTACGACGGCAAGGATTACATCGCCCTGAAAGAG<br>GACCTGCGCTCTTGGACCGCGGCGGACATGGCAGCTCAGACCACCAAGCACAAGTGGGAGGCGG<br>CCCATGTGGCGGAGCAGTGGAGAGCCTACCTGGAGGGCACGTGCGTGGAGTGGCTCCGCAGATA<br>CCTGGAGAACGGGAAGGAGACGCTGCAGCGCACGGACGCCCCCAAAACGCATATGACTCACCAC<br>GCTGTCTCTGACCATGAAGCCACCCTGAGGTGCTGGGCCCTGAGCTTCTACCCTGCGGAGATCA<br>CACTGACCTGGCAGCGGGATGGGGAGGACCAGACCCAGGACACGGAGCTCGTGGAGACCAGGCC<br>TGCAGGGGATGAACCTTCCAGAAGTGGGTGGCTGTGGTGGTGCCTTCTGGACAGGAGCAGAGA<br>TACACCTGCCATGTGCAGCATGAGGGTTTGCCCAAGCCCCTCACCCTGAGATGGGAGCCG |
| 155 | HLA-B*13:02 | GGCTCCCACTCCATGAGGTATTTCTACACCGCCATGTCCCGGCCCGGCCGCGGGGAGCCCCGCT<br>TCATCACCGTGGGCTACGTGGACGACACCCAGTTCGTGAGGTTCGACAGCGACGCCACGAGTCC<br>GAGGATGGCGCCCCGGGCGCCATGGATAGAGCAGGAGGGGCCGGAGTATTGGGACCGGGAGACA<br>CAGATCTCCAAGACCAACACACAGACTTACCGAGAGAACCTGCGCACCGCGCTCCGCTGCTACA<br>ACCAGAGCGAGGCCGGGTCTCACACTTGGCAGACGATGTATGGCTGCGACCTGGGGCCGGACGG<br>GCGCCTCCTCCGCGGGCATAACCAGTTAGCCTACGACGGCAAGGATTACATCGCCCTGAACGAG<br>GACCTGAGCTCCTGGACCGCGGCGGACACCGGCTCAGATCACCCAGCTCAAGTGGGAGGCGG<br>CCCGTGTGGCGGAGCAGCTGAGAGCCTACCTGGAGGGCGAGTGCGTGGAGTGGCTCCGCAGATA<br>CCTGGAGAACGGGAAGGAGACGCTGCAGCGCGCGGACCCCCAAAGACACACGTGACCCACCAC<br>CCCATCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACTGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCA |
| 156 | HLA-B*15:07 | GGCTCCCACTCCATGAGGTATTTCTACACCGCCATGTCCCGGCCCGGCCGCGGGGAGCCCCGCT<br>TCATCGCAGTGGGCTACGTGGACGACACCCAGTTCGTGAGGTTCGACAGCGACGCCGCGAGTCC<br>GAGGATGGCGCCCCGGGCGCCATGGATAGAGCAGGAGGGGCCGGAGTATTGGGACCGGGAGACA<br>CAGATCTCCAAGACCAACACACAGACTTACCGAGAGAGCCTGCGGAACCTGCGCGGCTGCTACA<br>ACCAGAGCGAGGCCGGGTCTCACACCCTCCAGAGCATGTACGGCTGCGACGTGGGGCCGGACGG<br>GCGCCTCCTCCGCGGGCATGACCAGTCCGCCTACGACGGCAAGGATTACATCGCCCTGAACGAG<br>GACCTGAGCTCCTGGACCGCGGCGGACACGGCGGCTCAGATCACCCAGCGCAAGTGGGAGGCG<br>CCCGTGAGGCGGAGCAGTGGAGAGCCTACCTGGAGGGCCTGTGCGTGGAGTGGCTCCGCAGATA<br>CCTGGAGAACGGGAAGGAGACGCTGCAGCGCGCGGACCCCCAAAGACACATGTGACCCACCAC<br>CCCATCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACCGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCA |
| 157 | HLA-B*27:05 | GGCTCCCACTCCATGAGGTATTTCCACACCTCCGTGTCCCGGCCCGGCCGCGGGGAGCCCCGCT<br>TCATCACCGTGGGCTACGTGGACGACACGCTGTTCGTGAGGTTCGACAGCGACGCCGCGAGTCC<br>GAGAGAGGAGCCGCGGGCGCCGTGGATAGAGCAGGAGGGGCCGGAGTATTGGGACCGGGAGACA<br>CAGATCTGCAAGGCCAAGGCACAGACTGACCGAGAGGACCTGCGGACCCTGCTCCGCTGCTACA<br>ACCAGAGCGAGGCCGGGTCTCACACCCTCCAGAATATGTATGGCTGCGACGTGGGGCCGGACGG<br>GCGCCTCCTCCGCGGGTACCACCAGGACGCCTACGACGGCAAGGATTACATCGCCCTGAACGAG<br>GACCTGAGCTCCTGGACCGCCGCGGACACGGCGGCTCAGATCACCCAGCGCAAGTGGGAGGCGG<br>CCCGTGTGGCGGAGCAGCTGAGAGCCTACCTGGAGGGCGAGTGCGTGGAGTGGCTCCGCAGATA<br>CCTGGAGAACGGGAAGGAGACGCTGCAGCGCGCGGACCCCCAAAGACACACGTGACCCACCAC<br>CCCATCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACTGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCG |
| 158 | HLA-B*35:03 | GGCTCCCACTCCATGAGGTATTTCTACACCGCCATGTCCCGGCCCGGCCGCGGGGAGCCCCGCT<br>TCATCGCAGTGGGCTACGTGGACGACACCCAGTTCGTGAGGTTCGACAGCGACGCCGCGAGTCC<br>GAGGACGGAGCCCCGGGCGCCATGGATAGAGCAGGAGGGGCCGGAGTATTGGGACCGGAACACA<br>CAGATCTTCAAGACCAACACACAGACTTACCGAGAGAGCCTGCGGAACCTGCGCGGCTGCTACA<br>ACCAGAGCGAGGCCGGGTCTCACATCATCCAGAGGATGTATGGCTGCGACCTGGGGCCCGACGG<br>GCGCCTCCTCCGCGGGCATGACCAGTTCGCCTACGACGGCAAGGATTACATCGCCCTGAACGAG<br>GACCTGAGCTCCTGGACCGCGGCGGACACCGCGGCTCAGATCACCCAGCGCAAGTGGGAGGCGG<br>CCCGTGTGGCGGAGCAGCTGAGAGCCTACCTGGAGGGCCTGTGCGTGGAGTGGCTCCGCAGATA<br>CCTGGAGAACGGGAAGGAGACGCTGCAGCGCGCGGACCCCCAAAGACACACGTGACCCACCAC<br>CCCGTCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACTGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCA |
| 159 | HLA-B*37:01 | GGCTCCCACTCCATGAGGTATTTCCACACCTCCGTGTCCCGGCCCGGCCGCGGGGAGCCCCGCT<br>TCATCTCAGTGGGCTACGTGGACGACACCCAGTTCGTGAGGTTCGACAGCGACGCCGCGAGTCC<br>GAGGACGGAGCCCCGGGCGCCGTGGATAGAGCAGGAGGGGCCGGAGTATTGGGACCGGGAGACA<br>CAGATCTCCAAGACCAACACACAGACTTACCGAGAGGACCTGCGGACCCTGCTCCGCTGCTACA<br>ACCAGAGCGAGGCCGGGTCTCACACCATCCAGAGGATGTCTGGCTGCGACGTGGGGCCGGACGG<br>GCGCCTCCTCCGCGGGTATAACCAGTTCGCCTACGACGGCAAGGATTACATCGCCCTGAACGAG<br>GACCTGAGCTCCTGGACCGCGGCGGACACCGCGGCTCAGATCACCCAGCGCAAGTGGGAGGCGG<br>CCCGTGTGGCGGAGCAGGACAGAGCCTACCTGGAGGGCACGTGCGTGGAGTGGCTCCGCAGATA |

| SEQ ID NO | Name | Sequence |
|---|---|---|
| | | CCTGGAGAACGGGAAGGAGACGCTGCAGCGCGCGGACCCCCCAAAGACACATGTGACCCACCAC<br>CCCATCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACCGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCA |
| 160 | HLA-B*38:01 | GGCTCCCACTCCATGAGGTATTTCTACACCTCCGTGTCCCGGCCCGGCCGCGGGGAGCCCCGCT<br>TCATCTCAGTGGGCTACGTGGACGACACGCAGTTCGTGAGGTTCGACAGCGACGCCGCGAGTCC<br>GAGAGAGGAGCCGCGGGCGCCGTGGATAGAGCAGGAGGGGCCGGAATATTGGGACCGGAACACA<br>CAGATCTGCAAGACCAACACACAGACTTACCGAGAGAACCTGCGGATCGCGCTCCGCTGCTACA<br>ACCAGAGCGAGGCCGGGTCTCACACCCTCCAGAGGATGTACGGCTGCGACGTGGGGCCGGACGG<br>GCGCCTCCTCCGCGGGCATAACCAGTTCGCCTACGACGGCAAGGATTACATCGCCCTGAACGAG<br>GACCTGAGCTCCTGGACCGCGGCGGACACCGCGGCTCAGATCACCCAGCGCAAGTGGGAGGCGG<br>CCCGTGTGGCGGAGCAGCTGAGAACCTACCTGGAGGGCACGTGCGTGGAGTGGCTCCGCAGATA<br>CCTGGAGAACGGGAAGGAGACGCTGCAGCGCGCGGACCCCCCAAAGACACATGTGACCCACCAC<br>CCCATCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACCGAGCTTGTGGAGACCAGACC<br>AGCAGGAGACAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCA |
| 161 | HLA-B*41:02 | GGCTCCCACTCCATGAGGTATTTCCACACCGCCATGTCCCGGCCCGGCCGCGGGGAGCCCCGCT<br>TCATCACCGTGGGCTACGTGGACGACACGCTGTTCGTGAGGTTCGACAGCGACGCCACGAGTCC<br>GAGGAAGGAGCCGCGGGCGCCATGGATAGAGCAGGAGGGGCCGGAGTATTGGGACCGGGAGACA<br>CAGATCTCCAAGACCAACACACAGACTTACCGAGAGAGCCTGCGGAACCTGCCGGCTGCTACA<br>ACCAGAGCGAGGCCGGGTCTCACACCCTCCAGAGCATGTACGGCTGCGACGTGGGGCCGGACGG<br>GCGCCTCCTCCGCGGGCATAACCAGTACGCCTACGACGGCAAGGATTACATCGCCCTGAACGAG<br>GACCTGCGCTCCTGGACCGCGGCGGACACCGCGGCTCAGATCACCCAGCGCAAGTGGGAGGCGG<br>CCCGTGTGGCGGAGCAGGACAGAGCCTACCTGGAGGGCACGTGCGTGGAGTGGCTCCGCAGATA<br>CCTGGAGAACGGGAAGGACACGCTGGAGCGCGCGGACCCCCCAAAGACACACGTGACCCACCAC<br>CCCATCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACTGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCG |
| 162 | HLA-B*44:05 | GGCTCCCACTCCATGAGGTATTTCTACACCGCCATGTCCCGGCCCGGCCGCGGGGAGCCCCGCT<br>TCATCACCGTGGGCTACGTGGACGACACGCTGTTCGTGAGGTTCGACAGCGACGCCACGAGTCC<br>GAGGAAGGAGCCGCGGGCGCCATGGATAGAGCAGGAGGGGCCGGAGTATTGGGACCGGGAGACA<br>CAGATCTCCAAGACCAACACACAGACTTACCGAGAGAACCTGCGCACCGCGCTCCGCTGCTACA<br>ACCAGAGCGAGGCCGGGTCTCACATCATCCAGAGGATGTACGGCTGCGACGTGGGGCCGGACGG<br>GCGCCTCCTCCGCGGGTATGACCAGTACGCCTACGACGGCAAGGATTACATCGCCCTGAACGAG<br>GACCTGAGCTCCTGGACCGCGGCGGACACCGCGGCTCAGATCACCCAGCGCAAGTGGGAGGCGG<br>CCCGTGTGGCGGAGCAGGACAGAGCCTACCTGGAGGGCCTGTGCGTGGAGTCGCTCCGCAGATA<br>CCTGGAGAACGGGAAGGAGACGCTGCAGCGCGCGGACCCCCCAAAGACACATGTGACCCACCAC<br>CCCATCTCTGACCATGAGGTCACCCTGAGGTGCTGGGCCCTGGGCTTCTACCCTGCGGAGATCA<br>CACTGACCTGGCAGCGGGATGGCGAGGACCAAACTCAGGACACCGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCG |
| 163 | HLA-B*49:01 | GGCTCCCACTCCATGAGGTATTTCCACACCGCCATGTCCCGGCCCGGCCGCGGGGAGCCCCGCT<br>TCATCACCGTGGGCTACGTGGACGACACGCTGTTCGTGAGGTTCGACAGCGACGCCACGAGTCC<br>GAGGAAGGAGCCGCGGGCGCCATGGATAGAGCAGGAGGGGCCGGAGTATTGGGACCGGGAGACA<br>CAGATCTCCAAGACCAACACACAGACTTACCGAGAGAACCTGCGGATCGCGCTCCGCTGCTACA<br>ACCAGAGCGAGGCCGGGTCTCACACTTGGCAGAGGATGTATGGCTGCGACCTGGGGCCCGACGG<br>GCGCCTCCTCCGCGGGTATAACCAGTTAGCCTACGACGGCAAGGATTACATCGCCCTGAACGAG<br>GACCTGAGCTCCTGGACCGCGGCGGACACCGCGGCTCAGATCACCCAGCGCAAGTGGGAGGCGG<br>CCCGTGAGGCGGAGCAGCTGAGAGCCTACCTGGAGGGCCTGTGCGTGGAGTGGCTCCGCAGATA<br>CCTGGAGAACGGGAAGGAGACGCTGCAGCGCGCGGACCCCCCAAAGACACATGTGACCCACCAC<br>CCCATCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACCGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCA |
| 164 | HLA-B*52:01 | GGCTCCCACTCCATGAGGTATTTCTACACCGCCATGTCCCGGCCCGGCCGCGGGGAGCCCCGCT<br>TCATCGCAGTGGGCTACGTGGACGACACCCAGTTCGTGAGGTTCGACAGCGACGCCGCGAGTCC<br>GAGGACGGAGCCCCGGGCGCCATGGATAGAGCAGGAGGGGCCGGAGTATTGGGACCGGGAGACA<br>CAGATCTCCAAGACCAACACACAGACTTACCGAGAGAACCTGCGGATCGCGCTCCGCTGCTACA<br>ACCAGAGCGAGGCCGGGTCTCACACTTGGCAGACGATGTATGGCTGCGACGTGGGGCCGGACGG<br>GCGCCTCCTCCGCGGGCATAACCAGTACGCCTACGACGCAAAGGATTACATCGCCCTGAACGAG<br>GACCTGAGCTCCTGGACCGCGGCGGACACCGCGGCTCAGATCACCCAGCGCAAGTGGGAGGCGG<br>CCCGTGAGGCGGAGCAGCTGAGAGCCTACCTGGAGGGCCTGTGCGTGGAGTGGCTCCGCAGACA<br>CCTGGAGAACGGGAAGGAGACGCTGCAGCGCGCGGACCCCCCAAAGACACACGTGACCCACCAC<br>CCCGTCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACTGAGCTTGTGGAGACCAGACC |

SEQUENCE LISTING

| SEQ ID NO | Name | Sequence |
|---|---|---|
| | | AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCA |
| 165 | HLA-B*55:01 | GGCTCCCACTCCATGAGGTATTTCTACACCGCCATGTCCCGGCCCGGCCGCGGGGAGCCCCGCT<br>TCATCGCAGTGGGCTACGTGGACGACACGCAGTTCGTGAGGTTCGACAGCGACGCCGCGAGTCC<br>GAGAGAGGAGCCGCGGGCGCCGTGGATAGAGCAGGAGGGGCCGGAGTATTGGGACCGGAACACA<br>CAGATCTACAAGGCCCAGGCACAGACTGACCGAGAGAGCCTGCGGAACCTGCGCGGCTGCTACA<br>ACCAGAGCGAGGCCGGGTCTCACACTTGGCAGACGATGTATGGCTGCGACCTGGGGCCGGACGG<br>GCGCCTCCTCCGCGGGCATAACCAGTTAGCCTACGACGGCAAGGATTACATCGCCCTGAACGAG<br>GACCTGAGCTCCTGGACCGCGGCGGACACCGCGGCTCAGATCACCCAGCGCAAGTGGGAGGCGG<br>CCCGTGAGGCGGAGCAGCTGAGAGCCTACCTGGAGGGCACGTGCGTGGAGTGGCTCCGCAGATA<br>CCTGGAGAACGGGAAGGAGACGCTGCAGCGCGCGGACCCCCCAAAGACACACGTGACCCACCAC<br>CCCATCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACTGAGCTTGTGGAGACCAGACC<br>AGCAGGAGATAGAACCTTCCAGAAGTGGGCAGCTGTGGTGGTGCCTTCTGGAGAAGAGCAGAGA<br>TACACATGCCATGTACAGCATGAGGGGCTGCCGAAGCCCCTCACCCTGAGATGGGAGCCA |
| 166 | HLA-C*03:03 | GGCTCCCACTCCATGAGGTATTTCTACACCGCTGTGTCCCGGCCCGGCCGCGGGGAGCCCCACT<br>TCATCGCAGTGGGCTACGTGGACGACACGCAGTTCGTGCGGTTCGACAGCGACGCCGCGAGTCC<br>GAGAGGGGAGCCGCGGGCGCCGTGGGTGGAGCAGGAGGGGCCGGAGTATTGGGACCGGGAGACA<br>CAGAAGTACAAGCGCCAGGCACAGACTGACCGAGTGAGCCTGCGGAACCTGCGCGGCTGCTACA<br>ACCAGAGCGAGGCCAGGTCTCACATCATCCAGAGGATGTATGGCTGCGACGTGGGGCCCGACGG<br>GCGCCTCCTCCGCGGGTATGACCAGTACGCCTACGACGGCAAGGATTACATCGCCCTGAACGAG<br>GATCTGCGCTCCTGGACCGCCGCGGACACGGCGGCTCAGATCACCCAGCGCAAGTGGGAGGCGG<br>CCCGTGAGGCGGAGCAGCTGAGAGCCTACCTGGAGGGCCTGTGCGTGGAGTGGCTCCGCAGATA<br>CCTGAAGAATGGGAAGGAGACGCTGCAGCGCGCGGAACACCCAAAGACACACGTGACCCACCAT<br>CCCGTCTCTGACCATGAGGCCACCCTGAGGTGCTGGGCCCTGGGCTTCTACCCTGCGGAGATCA<br>CACTGACCTGGCAGTGGGATGGGGAGGACCAAACTCAGGACACTGAGCTTGTGGAGACCAGGCC<br>AGCAGGAGATGGAACCTTCCAGAAGTGGGCAGCTGTGGTGGTGCCTTCTGGAGAAGAGCAGAGA<br>TACGTGCCATGTGCAGCACGAGGGGCTGCCGGAGCCCCTCACCCTGAGATGGGAGCCG |
| 167 | HLA-C*07:04 | TGCTCCCACTCCATGAGGTATTTCGACACCGCCGTGTCCCGGCCCGGCCGCGGAGAGCCCCGCT<br>TCATCTCAGTGGGCTACGTGGACGACACGCAGTTCGTGCGGTTCGACAGCGACGCCGCGAGTCC<br>GAGAGGGGAGCCCCGGGCGCCGTGGGTGGAGCAGGAGGGGCCGGAGTATTGGGACCGGGAGACA<br>CAGAAGTACAAGCGCCAGGCACAGGCTGACCGAGTGAGCCTGCGGAACCTGCGCGGCTGCTACA<br>ACCAGAGCGAGGACGGGTCTCACACCTTCCAGAGGATGTATGGCTGCGACCTGGGGCCCGACGG<br>GCGCCTCCTCCGCGGGTATGACCAGTTCGCCTACGACGGCAAGGATTACATCGCCCTGAACGAG<br>GACCTGCGCTCCTGGACCGCCGCGGACACCGCGGCTCAGATCACCCAGCGCAAGTTGGAGGCGG<br>CCCGTGCGGCGGAGCAGGACAGAGCCTACCTGGAGGGCACGTGCGTGGAGTGGCTCCGCAGATA<br>CCTGGAGAACGGGAAGAAGACGCTGCAGCGCGCGGAACCCCCAAAGACACACGTGACCCACCAC<br>CCCTCTCTGACCATGAGGCCACCCTGAGGTGCTGGGCCCTGGGCTTCTACCCTGCGGAGATCA<br>CACTGACCTGGCAGCGGGATGGGGAGGACCAGACCCAGGACACCGAGCTTGTGGAGACCAGGCC<br>AGCAGGAGATGGAACCTTCCAGAAGTGGGCAGCTGTGGTGGTGCCTTCTGGACAAGAGCAGAGA<br>TACGTGCCATATGCAGCACGAGGGGCTGCAAGAGCCCCTCACCCTGAGCTGGGAGCCA |
| 168 | HLA-C*08:01 | TGCTCCCACTCCATGAGGTATTTCTACACCGCCGTGTCCCGGCCCGGCCGCGGAGAGCCCCGCT<br>TCATCGCAGTGGGCTACGTGGACGACACGCAGTTCGTGCAGTTCGACAGCGACGCCGCGAGTCC<br>AAGAGGGGAGCCGCGGGCGCCGTGGGTGGAGCAGGAGGGGCCGGAGTATTGGGACCGGGAGACA<br>CAGAAGTACAAGCGCCAGGCACAGACTGACCGAGTGAGCCTGCGGAACCTGCGCGGCTGCTACA<br>ACCAGAGCGAGGCCGGGTCTCACACCCTCCAGAGGATGTATGGCTGCGACCTGGGGCCCGACGG<br>GCGCCTCCTCCGCGGGTATAACCAGTTCGCCTACGACGGCAAGGATTACATCGCCCTGAATGAG<br>GACCTGCGCTCCTGGACCGCCGCGGACACGGCGGCTCAGATCACCCAGCGCAAGTGGGAGGCGG<br>CCCGTACGGCGGAGCAGCTGAGAGCCTACCTGGAGGGCACGTGCGTGGAGTGGCTCCGCAGATA<br>CCTGGAGAACGGGAAGAAGACGCTGCAGCGCGCGGAACACCCAAAGACACACGTGACCCACCAT<br>CCCGTCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACCGAGCTTGTGGAGACCAGGCC<br>AGCAGGAGATGAACCTTCCAGAAGTGGGCAGCTGTGGTGGTGCCTTCTGGAGAAGAGCAGAGA<br>TACGTGCCATGTGCAGCACGAGGGGCTGCCAGAGCCCCTCACCCTGAGATGGGGCCA |
| 169 | HLA-C*08:02 | TGCTCCCACTCCATGAGGTATTTCTACACCGCCGTGTCCCGGCCCGGCCGCGGAGAGCCCCGCT<br>TCATCGCAGTGGGCTACGTGGACGACACGCAGTTCGTGCAGTTCGACAGCGACGCCGCGAGTCC<br>AAGAGGGGAGCCGCGGGCGCCGTGGGTGGAGCAGGAGGGGCCGGAGTATTGGGACCGGGAGACA<br>CAGAAGTACAAGCGCCAGGCACAGACTGACCGAGTGAGCCTGCGGAACCTGCGCGGCTGCTACA<br>ACCAGAGCGAGGCCGGGTCTCACACCCTCCAGAGGATGTATGGCTGCGACCTGGGGCCCGACGG<br>GCGCCTCCTCCGCGGGTATAACCAGTTCGCCTACGACGGCAAGGATTACATCGCCCTGAATGAG<br>GACCTGCGCTCCTGGACCGCCGCGGACAAGGCGGCTCAGATCACCCAGCGCAAGTGGGAGGCGG<br>CCCGTGAGGCGGAGCAGCGGAGAGCCTACCTGGAGGGCACGTGCGTGGAGTGGCTCCGCAGATA<br>CCTGGAGAACGGGAAGAAGACGCTGCAGCGCGCGGAACACCCAAAGACACACGTGACCCACCAT<br>CCCGTCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACCGAGCTTGTGGAGACCAGGCC<br>AGCAGGAGATGGAACCTTCCAGAAGTGGGCAGCTGTGGTGGTGCCTTCTGGAGAAGAGCAGAGA<br>TACGTGCCATGTGCAGCACGAGGGGCTGCCAGAGCCCCTCACCCTGAGATGGGGCCA |

SEQUENCE LISTING

| SEQ ID NO | Name | Sequence |
|---|---|---|
| 170 | HLA-C*12:02 | TGCTCCCACTCCATGAGGTATTTCTACACCGCCGTGTCCCGGCCCGGCCGCGGAGAGCCCCGCT<br>TCATCGCAGTGGGCTACGTGGACGACACGCAGTTCGTGCGGTTCGACAGCGACGCCGCGAGTCC<br>AAGAGGGGAGCCGCGGGCGCCGTGGGTGGAGCAGGAGGGGCCGGAGTATTGGGACCGGGAGACA<br>CAGAAGTACAAGCGCCAGGCACAGGCTGACCGAGTGAGCCTGCGGAACCTGCGCGGCTGCTACA<br>ACCAGAGCGAGGCCGGGTCTCACACCCTCCAGAGGATGTACGGCTGCGACCTGGGGCCCGACGG<br>GCGCCTCCTCCGCGGGTATGACCAGTCCGCCTACGACGGCAAGGATTACATCGCCCTGAACGAG<br>GACCTGCGCTCCTGGACCGCTGCGGACACGGCGGCTCAGATCACCCAGCGCAAGTGGGAGGCGG<br>CCCGTGAGGCGGAGCAGTGGAGAGCCTACCTGGAGGGCACGTGCGTGGAGTGGCTCCGCAGATA<br>CCTGGAGAACGGGAAGGAGACGCTGCAGCGCGCGAACACCCAAAGACACACGTGACCCACCAT<br>CCCGTCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACCGAGCTTGTGGAGACCAGGCC<br>AGCAGGAGATGGAACCTTCCAGAAGTGGGCAGCTGTGGTGGTGCCTTCTGGAGAAGAGCAGAGA<br>TACACGTGCCATGTGCAGCACGAGGGGCTGCCGGAGCCCCTCACCCTGAGATGGGAGCCA |
| 171 | HLA-C*12:03 | TGCTCCCACTCCATGAGGTATTTCTACACCGCCGTGTCCCGGCCCGGCCGCGGAGAGCCCCGCT<br>TCATCGCAGTGGGCTACGTGGACGACACGCAGTTCGTGCGGTTCGACAGCGACGCCGCGAGTCC<br>AAGAGGGGAGCCGCGGGCGCCGTGGGTGGAGCAGGAGGGGCCGGAGTATTGGGACCGGGAGACA<br>CAGAAGTACAAGCGCCAGGCACAGGCTGACCGAGTGAGCCTGCGGAACCTGCGCGGCTGCTACA<br>ACCAGAGCGAGGCCGGGTCTCACACCCTCCAGTGGATGTATGGCTGCGACCTGGGGCCCGACGG<br>GCGCCTCCTCCGCGGGTATGACCAGTCCGCCTACGACGGCAAGGATTACATCGCCCTGAACGAG<br>GACCTGCGCTCCTGGACTGCCGCGGACACGGCGGCTCAGATCACCCAGCGCAAGTGGGAGGCGG<br>CCCGTGAGGCGGAGCAGTGGAGAGCCTACCTGGAGGGCACGTGCGTGGAGTGGCTCCGCAGATA<br>CCTGGAGAACGGGAAGGAGACGCTGCAGCGCGCGAACACCCAAAGACACACGTGACCCACCAT<br>CCCGTCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACCGAGCTTGTGGAGACCAGGCC<br>AGCAGGAGATGGAACCTTCCAGAAGTGGGCAGCTGTGGTGGTGCCTTCTGGAGAAGAGCAGAGA<br>TACACGTGCCATGTGCAGCACGAGGGGCTGCCAGAGCCCCTCACCCTGAGATGGGAGCCA |
| 172 | HLA-C*14:02 | TGCTCCCACTCCATGAGGTATTTCTCCACATCCGTGTCCCGGCCCGGCCGCGGGGAGCCCCGCT<br>TCATCGCAGTGGGCTACGTGGACGACACGCAGTTCGTGCGGTTCGACAGCGACGCCGCGAGTCC<br>GAGAGGGGAGCCGCGGGCGCCGTGGGTGGAGCAGGAGGGGCCGGAGTATTGGGACCGGGAGACA<br>CAGAAGTACAAGCGCCAGGCACAGACTGACCGAGTGAGCCTGCGGAACCTGCGCGGCTGCTACA<br>ACCAGAGCGAGGCCGGGTCTCACACCCTCCAGTGGATGTTTGGCTGCGACCTGGGGCCCGACGG<br>GCGCCTCCTCCGCGGGTATGACCAGTCCGCCTACGACGGCAAGGATTACATCGCCCTGAACGAG<br>GATCTGCGCTCCTGGACCGCCGCGGACACGGCGGCTCAGATCACCCAGCGCAAGTGGGAGGCGG<br>CCCGTGAGGCGGAGCAGCGGAGAGCCTACCTGGAGGGCACGTGCGTGGAGTGGCTCCGCAGATA<br>CCTGGAGAACGGGAAGGAGACGCTGCAGCGCGCGAACACCCAAAGACACACGTGACCCACCAT<br>CCCGTCTCTGACCATGAGGCCACCCTGAGGTGCTGGGCCCTGGGCTTCTACCCTGCGGAGATCA<br>CACTGACCTGGCAGTGGGATGGGGAGGACCAAACTCAGGACACCGAGCTTGTGGAGACCAGGCC<br>AGCAGGAGATGGAACCTTCCAGAAGTGGGCAGCTGTGGTGGTGCCTTCTGGAGAAGAGCAGAGA<br>TACACGTGCCATGTGCAGCACGAGGGGCTGCCGGAGCCCCTCACCCTGAGATGGGAGCCG |
| 173 | HLA-C*15:02 | TGCTCCCACTCCATGAGGTATTTCTACACCGCTGTGTCCCGGCCCGGCCGCGGAGAGCCCCACT<br>TCATCGCAGTGGGCTACGTGGACGACACGCAGTTCGTGCGGTTCGACAGCGACGCCGCGAGTCC<br>AAGAGGGGAGCCGCGGGCGCCGTGGGTGGAGCAGGAGGGGCCGGAGTATTGGGACCGGGAGACA<br>CAGAACTACAAGCGCCAGGCACAGACTGACCGAGTGAACCTGCGGAAACTGCGCGGCTGCTACA<br>ACCAGAGCGAGGCCGGGTCTCACATCATCCAGAGGATGTATGGCTGCGACCTGGGGCCCGACGG<br>GCGCCTCCTCCGCGGGCATGACCAGTTAGCCTACGACGGCAAGGATTACATCGCCCTGAACGAG<br>GACCTGCGCTCCTGGACCGCCGCGGACACGGCGGCTCAGATCACCCAGCGCAAGTGGGAGGCGG<br>CCCGTGAGGCGGAGCAGCTGAGAGCCTACCTGGAGGGCACGTGCGTGGAGTGGCTCCGCAGATA<br>CCTGGAGAACGGGAAGGAGACGCTGCAGCGCGCGAACACCCAAAGACACACGTGACCCACCAT<br>CCCGTCTCTGACCATGAGGCCACCCTGAGGTGCTGGGCCCTGGGCTTCTACCCTGCGGAGATCA<br>CACTGACCTGGCAGCGGGATGGCGAGGACCAAACTCAGGACACCGAGCTTGTGGAGACCAGGCC<br>AGCAGGAGATGGAACCTTCCAGAAGTGGGCAGCTGTGGTGGTGCCTTCTGGAGAAGAGCAGAGA<br>TACACGTGCCATGTGCAGCACGAGGGGCTGCCGGAGCCCCTCACCCTGAGATGGGAGCCA |
| 174 | HLA-C*17:01 | GGCTCCCACTCCATGAGGTATTTCTACACCGCCGTGTCCCGGCCCGGCCGCGGAGAGCCCCGCT<br>TCATCGCAGTGGGCTACGTGGACGACACGCAGTTCGTGCGGTTCGACAGCGACGCCGCGAGTCC<br>GAGAGGGGAGCCGCGGGCGCCGTGGGTGGAGCAGGAGGGGCCGGAGTATTGGGACCGGGAGACA<br>CAGAAGTACAAGCGCCAGGCACAGGCTGACCGAGTGAACCTGCGGAAACTGCGCGGCTGCTACA<br>ACCAGAGCGAGGCCGGTTCTCACACCATCCAGAGGATGTATGGCTGCGACCTGGGGCCCGACGG<br>GCGCCTCCTCCGCGGGTATAACCAGTTCGCCTACGACGGCAAGGATTACATCGCCCTGAACGAG<br>GACCTGCGCTCCTGGACCGCGGCGGACACGGCGGCTCAGATCTCCCAGCGCAAGTTGGAGGCGG<br>CCCGTGAGGCGGAGCAGCTGAGAGCCTACCTGGAGGGCGAGTGCGTGGAGTGGCTCCGCGGATA<br>CCTGGAGAACGGGAAGGAGACGCTGCAGCGCGCGAACGCCCAAAGACACACGTGACCCACCAT<br>CCCGTCTCTGACCATGAGGCCACCCTGAGGTGCTGGGCCCTGGGCTTCTACCCTGCGGAGATCA<br>CACTGACCTGGCAGCGGGATGGGGAGGACCAAACTCAGGACACCGAGCTTGTGGAGACCAGGCC<br>AGCAGGAGATGGAACCTTCCAGAAGTGGGCAGCTGTGGTGGTGCCTTCTGGACAAGAACAGAGA<br>TACACGTGCCATGTGCAGCACGAGGGGCTGCAGGAGCCCTGCACCCTGAGATGGAAGCCG |

| SEQ ID NO | Name | Sequence |
|---|---|---|
| 175 | L3-purification cluster nucleotide sequence | GGCAGCGGCGGCAGCGGGGGCTCCGCCGGCGGAGGCCTGAACGACATCTTCGAAGCCCAGAAGA TCGAGTGGCACGAGGGCGGGGGAGAGAACCTGTACTTCCAGGGCGGCAGCCACCACCATCACCA CCATGGCGGCGGAAGCGGCGGCGGGTCCGGCAGCCACCATCACCATCACCAT |
| 176 | L3-purification cluster peptide sequence | GSGGSGGSAGGGLNDIFEAQKIEWHEGGGENLYFQGGSHHHHHGGGSGGGSGSHHHHHH |
| 177 | Signal sequence-universal target nucleotide sequence | ATGGCGACGGGTTCAAGAACTTCCCTACTTCTTGCATTTGGCCTGCTTTGTTTGCCGTGGTTAC AGGAGGGCTCAGCA |
| 178 | Signal sequence-universal target peptide sequence | MATGSRTSLLLAFGLLCLPWLQEGSA |
| 179 | bGH polyA | TGTGCCTTCTAGTTGCCAGCCATCTGTTGTTTGCCCCTCCCCCGTGCCTTCCTTGACCCTGGAA GGTGCCACTCCCACTGTCCTTTCCTAATAAAATGAGGAAATTGCATCGCATTGTCTGAGTAGGT GTCATTCTATTCTGGGGGGTGGGGTGGGGCAGGACAGCAAGGGGGAGGATTGGGAAGACAATAG CAGGCATGCTGGGGATGCGGTGGGCTCTATGGC |
| 180 | SV40 polyA | ACTTGTTTATTGCAGCTTATAATGGTTACAAATAAAGCAATAGCATCACAAATTTCACAAATAA AGCATTTTTTTCACTGCATTCTAGTTGTGGTTTGTCCAAACTCATCAATGTATCTTATCATGTC TGT |
| 181 | hGH polyA | ACGGGTGGCATCCCTGTGACCCCTCCCCAGTGCCTCTCCTGGCCCTGGAAGTTGCCACTCCAGT GCCCACCAGCCTTGTCCTAATAAAATTAAGTTGCATCATTTTGTCTGACTAGGTGTCCTTCTAT AATATTATGGGTGGAGGGGGGTGGTATGGAGCAAGGGGCAAGTTGGGAAGACAACCTGTAGGG CCTGCGGGGTCTATTGGGAACCAAGCTGGAGTGCAGTGGCACAATCTTGGCTCACTGCAATCTC CGCCTCCTGGGTTCAAGCGATTCTCCTGCCTCCCGAGTTGTTGGGATTCCAGGCATGC ATGACCAGGCTCAGCTAATTTTTGTTTTTTTGGTAGAGACGGGGTTTCACCATATTGGCCAGGC TGGTCTCCAACTCCTAATCTCAGGTGATCTACCCACCTTGGCCTCCCAAATTGCTGGGATTACA GGCGTGAACCACTGCTCCCTTCCCTGTCCTT |
| 182 | rbGlob polyA | TTCACTCCTCAGGTGCAGGCTGCCTATCAGAAGGTGGTGGCTGGTGTGGCCAATGCCCTGGCTC ACAAATACCACTGAGATCTTTTTCCCTCTGCCAAAAATTATGGGGACATCATGAAGCCCCTTGA GCATCTGACTTCTGGCTAATAAAGGAAATTTATTTTCATTGCAATAGTGTGTTGGAATTTTTTG TGTCTCTCACTCGGAAGGACATATGGGAGGGCAAATCATTTAAAACATCAGAATGAGTATTTGG TTTAGAGTTTGGCAACATATGCCCATATGCTGGCTGCCATGAACAAAGGTTGGCTATAAAGAGG TCATCAGTATATGAAACAGCCCCCTGCTGTCCATTCCTTATTCCATAGAAAAGCCTTGACTTGA GGTTAGATTTTTTTTATATTTTGTTTTGTGTTATTTTTTTCTTTAACATCCCTAAAATTTTCCT TACATGTTTTACTAGCCAGATTTTTCCTCCTCTCCTGACTACTCCCAGTCATAGCTGTCCCTCT TCTCTTATGGAGATC |
| 183 | thrombin cleavage site | LVPPGS |
| 184 | thrombin cleavage site | CTGGTGCCGCGCGGCAGC |
| 185 | Factor Xa site | IEGR |
| 186 | Factor Xa site | ATTGAAGGCCGC |
| 187 | rhinovirus 3C site | LEVLFQGP |
| 188 | rhinovirus 3C site | CTGGAAGTGCTGTTTCAGGGCCCG |
| 189 | Enterokinase site | DDDDK |
| 190 | Enterokinase site | GATGATGATGATAAA |
| 191 | FLAG Tag nucleotide | gattacaaggatgacgacgataag |
| 192 | FLAG Tag peptide | DYKDDDDK |
| 193 | HA Tag nucleotide | TACCCATACGATGTTCCAGATTACGCT |
| 194 | HA Tag peptide | YPYDVPDYA |
| 195 | Myc Tag nucleotide | GAACAAAAACTTATTTCTGAAGAAGATCTG |

SEQUENCE LISTING

| SEQ ID NO | Name | Sequence |
|---|---|---|
| 196 | Myc Tag peptide | EQKLISEEDL |
| 197 | Streptavidin Tag nucleotide | CGCAAGATCGTCGTTGCAGCCATCGCCGTTTCCCTGACCACGGTCTCGATTACGGCCAGCGCTT CGGCAGACCCCTCCAAGGACTCGAAGGCCCAGGTCTCGGCCGCCGAGGCCGGCATCACCGGCAC CTGGTACAACCAGCTCGGCTCGACCTTCATCGTGACCGCGGGCGCCGACGGCGCCCTGACCGGA ACCTACGAGTCGGCCGTCGGCAACGCCGAGAGCCGCTACGTCCTGACCGGTCGTTACGACAGCG CCCCGGCCACCGACGGCAGCGGCACCGCCCTCGGTTGGACGGTGGCCTGGAAGAATAACTACCG CAACGCCCACTCCGCGACCACGTGGAGCGGCCAGTACGTCGGCGGCGCCGAGGCGAGGATCAAC ACCCAGTGGCTGCTGACCTCCGGCACCACCGAGGCCAACGCCTGGAAGTCCACGCTGGTCGGCC ACGACACCTTCACCAAGGTGAAGCCGTCCGCCGCCTCCATCGACGCGGCGAAGAAGGCCGGCGT CAACAACGGCAACCCGCTCGACGCCGTTCAGCAGTAG |
| 198 | Streptavidin Tag peptide | RKIVVAAIAVSLTTVSITASASADPSKDSKAQVSAAEAGITGTWYNQLGSTFIVTAGADGALTG TYESAVGNAESRYVLTGRYDSAPATDGSGTALGWTVAWKNNYRNAHSATTWSGQYVGGAEARIN TQWLLTSGTTEANAWKSTLVGHDTFTKVKPSAASIDAAKKAGVNNGNPLDAVQQ |
| 199 | Neo12 epitope | YLYHRVDVI |
| 200 | MART1 epitope | ELAGIGILTV |

The invention claimed is:

1. A method for isolating an antigen-specific T cell, the method comprising:
   a. preparing a plurality of particles by
      i) obtaining a library comprising at least two polynucleotide, each polynucleotide comprising, from 5' to 3', a sequence insert comprising a stop codon in each of the three reading frames of the polynucleotide, a Beta 2 Microglobulin (β2M) coding sequence, and a Major Histocompatibility Complex (MHC) heavy chain coding sequence, wherein the sequence insert is flanked at its 5' or 3' by a first universal target sequence comprising a restriction site or a polymerase chain reaction (PCR) primer target site;
      ii) inserting a polynucleotide encoding an antigenic sequence into the sequence insert, to thereby obtain a polypeptide comprising, in an amino to carboxyl terminus orientation, the antigenic sequence, the Beta 2 Microglobulin (β2M) sequence, and the Major Histocompatibility Complex (MHC) heavy chain sequence;
      iii) attaching the polypeptide to a particle to obtain a plurality of particles;
   b. contacting the plurality of particles with a plurality of T cells under conditions suitable for antigen-specific binding of a T cell to a particle; and
   c. isolating the particles, to thereby isolate an antigen-specific T cell bound thereto;
   wherein the particle is a magnetic bead, an agarose bead, a styrene polymer particle, or a dextran polymer particle.

2. The method of claim 1, wherein the dextran polymer particle is streptavidin coated.

3. The method of claim 1, wherein the particle is labeled.

4. The method of claim 1, wherein the plurality of particles comprises at least two distinct particles.

5. The method of claim 1, wherein the T cells are isolated from a subject.

6. The method of claim 1, wherein the T cells are isolated from a sample comprising peripheral blood mononuclear cells or a sample comprising tumor infiltrating lymphocytes.

7. The method of claim 1, wherein the MHC heavy chain sequence is a human HLA.

8. The method of claim 7, wherein the HLA is selected from the group consisting of HLA-A*01:01, HLA-A*02:01, HLA-A*03:01, HLA-A*24:02, HLA-A*30:02, HLA-A*31:01, HLA-A*32:01, HLA-A*33:01, HLA-A*68:01, HLA-A*11:01, HLA-A*23:01, HLA-A*30:01, HLA-A*33:03, HLA-A*25:01, HLA-A*26:01, HLA-A*29:02, HLA-A*68:02, HLA-B*07:02, HLA-B*14:02, HLA-B*18:01, HLA-B*27:02, HLA-B*39:01, HLA-B*40:01, HLA-B*44:02, HLA-B*46:01, HLA-B*50:01, HLA-B*57:01, HLA-B*58:01, HLA-B*08:01, HLA-B*15:01, HLA-B*15:03, HLA-B*35:01, HLA-B*40:02, HLA-B*42:01, HLA-B*44:03, HLA-B*51:01, HLA-B*53:01, HLA-B*13:02, HLA-B*15:07, HLA-B*27:05, HLA-B*35:03, HLA-B*37:01, HLA-B*38:01, HLA-B*41:02, HLA-B*44:05, HLA-B*49:01, HLA-B*52:01, HLA-B*55:01, HLA-C*02:02, HLA-C*03:04, HLA-C*05:01, HLA-C*07:01, HLA-C*01:02, HLA-C*04:01, HLA-C*06:02, HLA-C*07:02, HLA-C*16:01, HLA-C*03:03, HLA-C*07:04, HLA-C*08:01, HLA-C*08:02, HLA-C*12:02, HLA-C*12:03, HLA-C*14:02, HLA-C*15:02, or HLA-C*17:01.

9. The method of claim 7, wherein the HLA comprises an amino acid sequence selected from the group consisting of SEQ ID NOs. 38-104.

10. The method of claim 1, wherein the polypeptide further comprises a signal peptide.

11. The method of claim 10, wherein the signal peptide is selected from the group consisting of a human growth hormone signal peptide, a hIG1 kappa light chain signal peptide, a β2M signal peptide, and an interleukin-2 (IL2) signal peptide.

12. The method of claim 11, wherein the signal peptide is a human growth hormone signal peptide.

13. The method of claim 1, wherein the β2M sequence comprises an amino acid sequence set forth in SEQ ID NO. 105 or SEQ ID NO. 107.

14. The method of claim 1, wherein the polypeptide further comprises a purification cluster.

15. The method of claim 14, wherein the purification cluster comprises at least two affinity tags and at least one protease cleavage site.

16. The method of claim 15, wherein the protease cleavage site is positioned between two affinity tags.

17. The method of claim 14, wherein the purification cluster comprises an amino acid sequence set forth in SEQ ID NO. 176.

* * * * *

SEQUENCE LISTING

<160> NUMBER OF SEQ ID NOS: 218

<210> SEQ ID NO 1
<211> LENGTH: 78
<212> TYPE: DNA
<213> ORGANISM: Homo sapiens

<400> SEQUENCE: 1
atggcgacgg gttcaagaac ttccctactt cttgcatttg gcctgctttg tttgccgtgg    60
ttacaggagg gctcagca                                                  78

<210> SEQ ID NO 2
<211> LENGTH: 26
<212> TYPE: PRT
<213> ORGANISM: Homo sapiens

<400> SEQUENCE: 2

Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25

<210> SEQ ID NO 3
<211> LENGTH: 23
<212> TYPE: DNA
<213> ORGANISM: Unknown
<220> FEATURE:
<223> OTHER INFORMATION: Description of Unknown: Universal target
      sequence

<400> SEQUENCE: 3
cgtggttaca ggagggctca gca                                            23

<210> SEQ ID NO 4
<211> LENGTH: 19
<212> TYPE: DNA
<213> ORGANISM: Unknown
<220> FEATURE:

```
<223> OTHER INFORMATION: Description of Unknown: Universal target
      sequence

<400> SEQUENCE: 4
ggatgcggag gatccggcg                                                   19

<210> SEQ ID NO 5
<211> LENGTH: 19
<212> TYPE: DNA
<213> ORGANISM: Unknown
<220> FEATURE:
<223> OTHER INFORMATION: Description of Unknown: Universal target
      sequence

<400> SEQUENCE: 5
ggaagcggag gatccggcg                                                   19

<210> SEQ ID NO 6
<211> LENGTH: 21
<212> TYPE: DNA
<213> ORGANISM: Unknown
<220> FEATURE:
<223> OTHER INFORMATION: Description of Unknown: Universal target
      sequence

<400> SEQUENCE: 6
ggaagcggag gatccaccag c                                                21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atgtacgggc cagatatacg c                                                21

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acacccgccg cgcttaatg                                                   19

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Gly Gly Ser
1               5

<210> SEQ ID NO 10
<211> LENGTH: 15
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 10
ggcggcggcg gcagc                                                    15

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Ser Gly Gly Ser
1               5

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ggcagcggcg gcagc                                                    15

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Cys Gly Gly Ser
1               5

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggctgcggcg gcagc                                                    15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Cys Gly Gly Ser Gly Gly Gly Ser Gly Gly Gly Ser
1               5                   10                  15

<210> SEQ ID NO 16
<211> LENGTH: 45
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 16
ggctgcggcg gcagcggcgg cggcggcagc ggcggcggcg gcagc                    45

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Gly Gly Ser Gly Gly Gly Gly Ser Gly Gly Gly Gly Ser
1               5                   10                  15

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ggcggcggcg gcagcggcgg cggcggcagc ggcggcggcg gcagc                    45

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Gly Gly Ser Gly Gly Gly Gly Ser Gly Gly Gly Gly Ser Gly
1               5                   10                  15

Gly Gly Gly Ser
            20

<210> SEQ ID NO 20
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ggcggcggcg gcagcggcgg cggcggcagc ggcggcggcg gcagcggcgg cggcggcagc    60

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Ser Gly Gly Ser Gly Gly Ser Ala Gly Gly
1               5                   10
```

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggcagcggcg gcagcggcgg cagcgcgggc ggc                                   33

<210> SEQ ID NO 23
<211> LENGTH: 22
<212> TYPE: PRT
<213> ORGANISM: Homo sapiens

<400> SEQUENCE: 23

Met Asp Met Arg Val Pro Ala Gln Leu Leu Gly Leu Leu Leu Leu Trp
1               5                   10                  15

Leu Ser Gly Ala Arg Cys
            20

<210> SEQ ID NO 24
<211> LENGTH: 66
<212> TYPE: DNA
<213> ORGANISM: Homo sapiens

<400> SEQUENCE: 24
atggatatgc gcgtgccggc gcagctgctg ggcctgctgc tgctgtggct gagcggcgcg     60
cgctgc                                                                66

<210> SEQ ID NO 25
<211> LENGTH: 20
<212> TYPE: PRT
<213> ORGANISM: Unknown
<220> FEATURE:
<223> OTHER INFORMATION: Description of Unknown: Beta 2 microglobulin
      sequence

<400> SEQUENCE: 25

Met Ser Arg Ser Val Ala Leu Ala Val Leu Ala Leu Leu Ser Leu Ser
1               5                   10                  15

Gly Leu Glu Ala
            20

<210> SEQ ID NO 26
<211> LENGTH: 60
<212> TYPE: DNA
<213> ORGANISM: Unknown
<220> FEATURE:
<223> OTHER INFORMATION: Description of Unknown: Beta 2 microglobulin
      sequence

<400> SEQUENCE: 26
atgagccgca gcgtggcgct ggcggtgctg gcgctgctga gcctgagcgg cctggaagcg     60

<210> SEQ ID NO 27
<211> LENGTH: 20
<212> TYPE: PRT
<213> ORGANISM: Unknown
<220> FEATURE:
<223> OTHER INFORMATION: Description of Unknown: IL2 signal sequence

<400> SEQUENCE: 27

```
Met Tyr Arg Met Gln Leu Leu Ser Cys Ile Ala Leu Ser Leu Ala Leu
1               5                   10                  15

Val Thr Asn Ser
            20

<210> SEQ ID NO 28
<211> LENGTH: 60
<212> TYPE: DNA
<213> ORGANISM: Unknown
<220> FEATURE:
<223> OTHER INFORMATION: Description of Unknown: IL2 signal sequence

<400> SEQUENCE: 28
atgtatcgca tgcagctgct gagctgcatt gcgctgagcc tggcgctggt gaccaacagc      60

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ggcctgaacg acatcttcga ggctcagaaa atcgaatggc acgaa                      45

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Leu Asn Asp Ile Phe Glu Ala Gln Lys Ile Glu Trp His Glu
1               5                   10                  15

<210> SEQ ID NO 31
<211> LENGTH: 23
<212> TYPE: DNA
<213> ORGANISM: Unknown
<220> FEATURE:
<223> OTHER INFORMATION: Description of Unknown: TEV cleavage site

<400> SEQUENCE: 31
gagagaacct gtacttccag ggc                                              23

<210> SEQ ID NO 32
<211> LENGTH: 7
<212> TYPE: PRT
<213> ORGANISM: Unknown
<220> FEATURE:
<223> OTHER INFORMATION: Description of Unknown: TEV cleavage site

<400> SEQUENCE: 32

Glu Asn Leu Tyr Phe Gln Gly
1               5

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 33
catcatcatc atcatcat                                                18

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 34

His His His His His His
1               5

<210> SEQ ID NO 35
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
catcatcatc atcatcatgg cggcggcagc ggcggcggca gcggcagcca tcatcatcat      60
catcat                                                                66

<210> SEQ ID NO 36
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

His His His His His His Gly Gly Gly Ser Gly Gly Gly Ser Gly Ser
1               5                   10                  15

His His His His His His
            20

<210> SEQ ID NO 37
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gly Leu Asn Asp Ile Phe Glu Ala Gln Lys Ile Glu Trp His Glu Gly
1               5                   10                  15

Gly Gly Glu Asn Leu Tyr Phe Gln Gly Gly Ser His His His His
            20                  25                  30

His Gly Gly Gly Ser Gly Gly Gly Ser Gly Ser His His His His
        35                  40                  45

His

<210> SEQ ID NO 38
<211> LENGTH: 576
<212> TYPE: DNA
<213> ORGANISM: Cytomegalovirus

<400> SEQUENCE: 38

```
tagtaatcaa ttacggggtc attagttcat agcccatata tggagttccg cgttacataa      60
cttacggtaa atggcccgcc tggctgaccg cccaacgacc cccgcccatt gacgtcaata     120
atgacgtatg ttcccatagt aacgccaata gggactttcc attgacgtca atgggtggag     180
tatttacggt aaactgccca cttggcagta catcaagtgt atcatatgcc aagtacgccc     240
cctattgacg tcaatgacgg taaatggccc gcctggcatt atgcccagta catgacctta     300
tgggactttc ctacttggca gtacatctac gtattagtca tcgctattac catggtgatg     360
cggttttggc agtacatcaa tgggcgtgga tagcggtttg actcacgggg atttccaagt     420
ctccacccca ttgacgtcaa tgggagtttg ttttggcacc aaaatcaacg ggactttcca     480
aaatgtcgta acaactccgc cccattgacg caaatgggcg gtaggcgtgt acggtgggag     540
gtctatataa gcagagctgg tttagtgaac cgtcag                                576
```

<210> SEQ ID NO 39
<211> LENGTH: 276
<212> TYPE: PRT
<213> ORGANISM: Homo sapiens

<400> SEQUENCE: 39

```
Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Lys Met Glu Pro Arg
        35                  40                  45

Ala Pro Trp Ile Glu Gln Glu Gly Pro Glu Tyr Trp Asp Gln Glu Thr
    50                  55                  60

Arg Asn Met Lys Ala His Ser Gln Thr Asp Arg Ala Asn Leu Gly Thr
65                  70                  75                  80

Leu Arg Gly Cys Tyr Asn Gln Ser Glu Asp Gly Ser His Thr Ile Gln
                85                  90                  95

Ile Met Tyr Gly Cys Asp Val Gly Pro Asp Gly Arg Phe Leu Arg Gly
            100                 105                 110

Tyr Arg Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Lys
    130                 135                 140

Arg Lys Trp Glu Ala Val His Ala Ala Glu Gln Arg Arg Val Tyr Leu
145                 150                 155                 160

Glu Gly Arg Cys Val Asp Gly Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
```

```
                    260                 265                 270
Arg Trp Glu Leu
        275

<210> SEQ ID NO 40
<211> LENGTH: 276
<212> TYPE: PRT
<213> ORGANISM: Homo sapiens

<400> SEQUENCE: 40

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Cys Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro
        275

<210> SEQ ID NO 41
<211> LENGTH: 276
<212> TYPE: PRT
<213> ORGANISM: Homo sapiens

<400> SEQUENCE: 41

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
```

```
                    20                  25                  30

Phe Val Arg Phe Asp Ser Asp Ala Ala Ser Gln Arg Met Glu Pro Arg
            35                  40                  45

Ala Pro Trp Ile Glu Gln Gly Pro Glu Tyr Trp Asp Gln Glu Thr
50                  55                  60

Arg Asn Val Lys Ala Gln Ser Gln Thr Asp Arg Val Asp Leu Gly Thr
65                  70                  75                  80

Leu Arg Gly Cys Tyr Asn Gln Ser Glu Ala Gly Ser His Thr Ile Gln
                85                  90                  95

Ile Met Tyr Gly Cys Asp Val Gly Ser Asp Gly Arg Phe Leu Arg Gly
            100                 105                 110

Tyr Arg Gln Asp Ala Tyr Asp Gly Lys Asp Tyr Ile Ala Leu Asn Glu
            115                 120                 125

Asp Leu Arg Ser Trp Thr Ala Ala Asp Met Ala Ala Gln Ile Thr Lys
            130                 135                 140

Arg Lys Trp Glu Ala Ala His Glu Ala Glu Gln Leu Arg Ala Tyr Leu
145                 150                 155                 160

Asp Gly Thr Cys Val Glu Trp Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
            195                 200                 205

Tyr Pro Ala Glu Ile Thr Leu Thr Trp Gln Arg Asp Gly Glu Asp Gln
            210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Leu
            275

<210> SEQ ID NO 42
<211> LENGTH: 276
<212> TYPE: PRT
<213> ORGANISM: Homo sapiens

<400> SEQUENCE: 42

Gly Ser His Ser Met Arg Tyr Phe Ser Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
            35                  40                  45

Ala Pro Trp Ile Glu Gln Glu Gly Pro Glu Tyr Trp Asp Glu Glu Thr
50                  55                  60

Gly Lys Val Lys Ala His Ser Gln Thr Asp Arg Glu Asn Leu Arg Ile
65                  70                  75                  80

Ala Leu Arg Cys Tyr Asn Gln Ser Glu Ala Gly Ser His Thr Leu Gln
                85                  90                  95

Met Met Phe Gly Cys Asp Val Gly Ser Asp Gly Arg Phe Leu Arg Gly
            100                 105                 110
```

Tyr His Gln Tyr Ala Tyr Asp Gly Lys Asp Tyr Ile Ala Leu Lys Glu
            115                 120                 125

Asp Leu Arg Ser Trp Thr Ala Ala Asp Met Ala Ala Gln Ile Thr Lys
130                 135                 140

Arg Lys Trp Glu Ala Ala His Val Ala Glu Gln Arg Ala Tyr Leu
145                 150                 155                 160

Glu Gly Thr Cys Val Asp Gly Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
            195                 200                 205

Tyr Pro Ala Glu Ile Thr Leu Thr Trp Gln Arg Asp Gly Glu Asp Gln
210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro
275

<210> SEQ ID NO 43
<211> LENGTH: 276
<212> TYPE: PRT
<213> ORGANISM: Homo sapiens

<400> SEQUENCE: 43

Gly Ser His Ser Met Arg Tyr Phe Ser Thr Ser Val Ser Arg Pro Gly
1               5                   10                  15

Ser Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Arg Pro Glu Tyr Trp Asp Gln Glu Thr
50                  55                  60

Arg Asn Val Lys Ala His Ser Gln Thr Asp Arg Glu Asn Leu Gly Thr
65                  70                  75                  80

Leu Arg Gly Cys Tyr Asn Gln Ser Glu Ala Gly Ser His Thr Ile Gln
                85                  90                  95

Ile Met Tyr Gly Cys Asp Val Gly Ser Asp Gly Arg Phe Leu Arg Gly
            100                 105                 110

Tyr Glu Gln His Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Gln
130                 135                 140

Arg Lys Trp Glu Ala Ala Arg Arg Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
            195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Leu
        275

<210> SEQ ID NO 44
<211> LENGTH: 276
<212> TYPE: PRT
<213> ORGANISM: Homo sapiens

<400> SEQUENCE: 44

Gly Ser His Ser Met Arg Tyr Phe Thr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Arg Pro Glu Tyr Trp Asp Gln Glu Thr
    50                  55                  60

Arg Asn Val Lys Ala His Ser Gln Ile Asp Arg Val Asp Leu Gly Thr
65                  70                  75                  80

Leu Arg Gly Cys Tyr Asn Gln Ser Glu Ala Gly Ser His Thr Ile Gln
                85                  90                  95

Met Met Tyr Gly Cys Asp Val Gly Ser Asp Gly Arg Phe Leu Arg Gly
            100                 105                 110

Tyr Gln Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Gln
130                 135                 140

Arg Lys Trp Glu Ala Ala Arg Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ser Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro
        275

```
<210> SEQ ID NO 45
<211> LENGTH: 276
<212> TYPE: PRT
<213> ORGANISM: Homo sapiens

<400> SEQUENCE: 45

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gln Glu Thr
    50                  55                  60

Arg Asn Val Lys Ala His Ser Gln Thr Asp Arg Glu Ser Leu Arg Ile
65                  70                  75                  80

Ala Leu Arg Cys Tyr Asn Gln Ser Glu Ala Gly Ser His Thr Ile Gln
                85                  90                  95

Met Met Tyr Gly Cys Asp Val Gly Pro Asp Gly Arg Leu Leu Arg Gly
            100                 105                 110

Tyr Gln Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ser Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro
        275

<210> SEQ ID NO 46
<211> LENGTH: 276
<212> TYPE: PRT
<213> ORGANISM: Homo sapiens

<400> SEQUENCE: 46

Gly Ser His Ser Met Arg Tyr Phe Thr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Arg Asn Thr
```

```
                  50                  55                  60

Arg Asn Val Lys Ala His Ser Gln Ile Asp Arg Val Asp Leu Gly Thr
 65                  70                  75                  80

Leu Arg Gly Cys Tyr Asn Gln Ser Glu Ala Gly Ser His Thr Ile Gln
                     85                  90                  95

Met Met Tyr Gly Cys Asp Val Gly Ser Asp Gly Arg Phe Leu Arg Gly
                100                 105                 110

Tyr Gln Gln Asp Ala Tyr Asp Gly Lys Asp Tyr Ile Ala Leu Asn Glu
            115                 120                 125

Asp Leu Arg Ser Trp Thr Ala Ala Asp Met Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Thr Cys Val Glu Trp Leu Arg Arg His Leu Glu Asn Gly Lys
                165                 170                 175

Glu Thr Leu Gln Arg Thr Asp Pro Pro Arg Thr His Met Thr His His
            180                 185                 190

Ala Val Ser Asp His Glu Ala Thr Leu Arg Cys Trp Ala Leu Ser Phe
    195                 200                 205

Tyr Pro Ala Glu Ile Thr Leu Thr Trp Gln Arg Asp Gly Glu Asp Gln
210                 215                 220

Thr Gln Asp Thr Glu Leu Val Glu Thr Arg Pro Ala Gly Asp Gly Thr
225                 230                 235                 240

Phe Gln Lys Trp Ala Ser Val Val Pro Ser Gly Gln Glu Gln Arg
                245                 250                 255

Tyr Thr Cys His Val Gln His Glu Gly Leu Pro Lys Pro Leu Thr Leu
                260                 265                 270

Arg Trp Glu Pro
        275

<210> SEQ ID NO 47
<211> LENGTH: 276
<212> TYPE: PRT
<213> ORGANISM: Homo sapiens

<400> SEQUENCE: 47

Gly Ser His Ser Met Arg Tyr Phe Tyr Thr Ser Val Ser Arg Pro Gly
 1                   5                  10                  15

Arg Gly Glu Pro Arg Phe Ile Ala Val Gly Tyr Val Asp Asp Thr Gln
                    20                  25                  30

Phe Val Arg Phe Asp Ser Asp Ala Ala Ser Gln Arg Met Glu Pro Arg
            35                  40                  45

Ala Pro Trp Ile Glu Gln Glu Gly Pro Glu Tyr Trp Asp Arg Asn Thr
    50                  55                  60

Arg Asn Val Lys Ala Gln Ser Gln Thr Asp Arg Val Asp Leu Gly Thr
 65                  70                  75                  80

Leu Arg Gly Cys Tyr Asn Gln Ser Glu Ala Gly Ser His Thr Ile Gln
                    85                  90                  95

Met Met Tyr Gly Cys Asp Val Gly Ser Asp Gly Arg Phe Leu Arg Gly
                100                 105                 110

Tyr Arg Gln Asp Ala Tyr Asp Gly Lys Asp Tyr Ile Ala Leu Lys Glu
            115                 120                 125

Asp Leu Arg Ser Trp Thr Ala Ala Asp Met Ala Ala Gln Thr Thr Lys
    130                 135                 140
```

```
His Lys Trp Glu Ala Ala His Val Ala Glu Gln Trp Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Val Ala Val Val Pro Ser Gly Gln Glu Gln Arg
                245                 250                 255

Tyr Thr Cys His Val Gln His Glu Gly Leu Pro Lys Pro Leu Thr Leu
                260                 265                 270

Arg Trp Glu Pro
            275

<210> SEQ ID NO 48
<211> LENGTH: 276
<212> TYPE: PRT
<213> ORGANISM: Homo sapiens

<400> SEQUENCE: 48

Gly Ser His Ser Met Arg Tyr Phe Tyr Thr Ser Val Ser Arg Pro Gly
1               5                   10                  15

Arg Gly Glu Pro Arg Phe Ile Ser Val Gly Tyr Val Asp Asp Thr Gln
                20                  25                  30

Phe Val Arg Phe Asp Ser Asp Ala Ala Ser Pro Arg Glu Glu Pro Arg
            35                  40                  45

Ala Pro Trp Ile Glu Gln Glu Gly Pro Glu Tyr Trp Asp Arg Asn Thr
    50                  55                  60

Gln Ile Tyr Lys Ala Gln Ala Gln Thr Asp Arg Glu Ser Leu Arg Asn
65                  70                  75                  80

Leu Arg Gly Cys Tyr Asn Gln Ser Glu Ala Gly Ser His Thr Leu Gln
                85                  90                  95

Ser Met Tyr Gly Cys Asp Val Gly Pro Asp Gly Arg Leu Leu Arg Gly
            100                 105                 110

His Asp Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Arg Arg Ala Tyr Leu
145                 150                 155                 160

Glu Gly Glu Cys Val Glu Trp Leu Arg Arg Tyr Leu Glu Asn Gly Lys
                165                 170                 175

Asp Lys Leu Glu Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240
```

Phe Gln Lys Trp Ala Ala Val Val Pro Ser Glu Glu Gln Arg
                245                 250                 255

Tyr Thr Cys His Val Gln His Glu Gly Leu Pro Lys Pro Leu Thr Leu
                260                 265                 270

Arg Trp Glu Pro
        275

<210> SEQ ID NO 49
<211> LENGTH: 276
<212> TYPE: PRT
<213> ORGANISM: Homo sapiens

<400> SEQUENCE: 49

Gly Ser His Ser Met Arg Tyr Phe Tyr Thr Ala Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Cys Lys Thr Asn Thr Gln Thr Asp Arg Glu Ser Leu Arg Asn
65                  70                  75                  80

Leu Arg Gly Cys Tyr Asn Gln Ser Glu Ala Gly Ser His Thr Leu Gln
                85                  90                  95

Trp Met Tyr Gly Cys Asp Val Gly Pro Asp Gly Arg Leu Leu Arg Gly
            100                 105                 110

Tyr Asn Gln Phe Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Glu Ala Glu Gln Leu Arg Ala Tyr Leu
145                 150                 155                 160

Glu Gly Thr Cys Val Glu Trp Leu Arg Arg His Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Pro Ser Gly Glu Glu Gln Arg
                245                 250                 255

Tyr Thr Cys His Val Gln His Glu Gly Leu Pro Lys Pro Leu Thr Leu
                260                 265                 270

Arg Trp Glu Pro
        275

<210> SEQ ID NO 50
<211> LENGTH: 276
<212> TYPE: PRT
<213> ORGANISM: Homo sapiens

<400> SEQUENCE: 50

-continued

```
Gly Ser His Ser Met Arg Tyr Phe His Thr Ser Val Ser Arg Pro Gly
1               5                   10                  15

Arg Gly Glu Pro Arg Phe Ile Ser Val Gly Tyr Val Asp Gly Thr Gln
            20                  25                  30

Phe Val Arg Phe Asp Ser Asp Ala Ala Ser Pro Arg Thr Glu Pro Arg
        35                  40                  45

Ala Pro Trp Ile Glu Gln Glu Gly Pro Glu Tyr Trp Asp Arg Asn Thr
50                  55                  60

Gln Ile Ser Lys Thr Asn Thr Gln Thr Tyr Arg Glu Ser Leu Arg Asn
65                  70                  75                  80

Leu Arg Gly Cys Tyr Asn Gln Ser Glu Ala Gly Ser His Thr Leu Gln
                85                  90                  95

Arg Met Tyr Gly Cys Asp Val Gly Pro Asp Gly Arg Leu Leu Arg Gly
                100                 105                 110

His Asp Gln Ser Ala Tyr Asp Gly Lys Asp Tyr Ile Ala Leu Asn Glu
            115                 120                 125

Asp Leu Ser Ser Trp Thr Ala Ala Asp Thr Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Thr Cys Val Glu Trp Leu Arg Arg His Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro
            275

<210> SEQ ID NO 51
<211> LENGTH: 276
<212> TYPE: PRT
<213> ORGANISM: Homo sapiens

<400> SEQUENCE: 51

Gly Ser His Ser Met Arg Tyr Phe His Thr Ser Val Ser Arg Pro Gly
1               5                   10                  15

Arg Gly Glu Pro Arg Phe Ile Thr Val Gly Tyr Val Asp Asp Thr Leu
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Glu Thr
50                  55                  60

Gln Ile Cys Lys Ala Lys Ala Gln Thr Asp Arg Glu Asn Leu Arg Ile
65                  70                  75                  80

Ala Leu Arg Cys Tyr Asn Gln Ser Glu Ala Gly Ser His Thr Leu Gln
```

```
                   85                  90                  95
Asn Met Tyr Gly Cys Asp Val Gly Pro Asp Gly Arg Leu Leu Arg Gly
               100                 105                 110

Tyr His Gln Asp Ala Tyr Asp Gly Lys Asp Tyr Ile Ala Leu Asn Glu
               115                 120                 125

Asp Leu Ser Ser Trp Thr Ala Asp Thr Ala Ala Gln Ile Thr Gln
           130                 135                 140

Arg Lys Trp Glu Ala Ala Arg Val Ala Glu Gln Leu Arg Ala Tyr Leu
145                 150                 155                 160

Glu Gly Glu Cys Val Glu Trp Leu Arg Arg Tyr Leu Glu Asn Gly Lys
               165                 170                 175

Glu Thr Leu Gln Arg Ala Asp Pro Pro Lys Thr His Val Thr His His
               180                 185                 190

Pro Ile Ser Asp His Glu Ala Thr Leu Arg Cys Trp Ala Leu Gly Phe
           195                 200                 205

Tyr Pro Ala Glu Ile Thr Leu Thr Trp Gln Arg Asp Gly Glu Asp Gln
           210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
               245                 250                 255

Tyr Thr Cys His Val Gln His Glu Gly Leu Pro Lys Pro Leu Thr Leu
               260                 265                 270

Arg Trp Glu Pro
           275

<210> SEQ ID NO 52
<211> LENGTH: 276
<212> TYPE: PRT
<213> ORGANISM: Homo sapiens

<400> SEQUENCE: 52

Gly Ser His Ser Met Arg Tyr Phe Tyr Thr Ser Val Ser Arg Pro Gly
1               5                  10                  15

Arg Gly Glu Pro Arg Phe Ile Ser Val Gly Tyr Val Asp Asp Thr Gln
               20                  25                  30

Phe Val Arg Phe Asp Ser Asp Ala Ala Ser Pro Arg Glu Glu Pro Arg
           35                  40                  45

Ala Pro Trp Ile Glu Gln Glu Gly Pro Glu Tyr Trp Asp Arg Asn Thr
       50                  55                  60

Gln Ile Cys Lys Thr Asn Thr Gln Thr Asp Arg Glu Ser Leu Arg Asn
65                  70                  75                  80

Leu Arg Gly Cys Tyr Asn Gln Ser Glu Ala Gly Ser His Thr Leu Gln
               85                  90                  95

Arg Met Tyr Gly Cys Asp Val Gly Pro Asp Gly Arg Leu Leu Arg Gly
               100                 105                 110

His Asn Gln Phe Ala Tyr Asp Gly Lys Asp Tyr Ile Ala Leu Asn Glu
           115                 120                 125

Asp Leu Ser Ser Trp Thr Ala Asp Thr Ala Ala Gln Ile Thr Gln
           130                 135                 140

Arg Lys Trp Glu Ala Ala Arg Val Ala Glu Gln Leu Arg Thr Tyr Leu
145                 150                 155                 160

Glu Gly Thr Cys Val Glu Trp Leu Arg Arg Tyr Leu Glu Asn Gly Lys
               165                 170                 175
```

-continued

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
            195                 200                 205

Tyr Pro Ala Glu Ile Thr Leu Thr Trp Gln Arg Asp Gly Glu Asp Gln
            210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
            245                 250                 255

Tyr Thr Cys His Val Gln His Glu Gly Leu Pro Lys Pro Leu Thr Leu
            260                 265                 270

Arg Trp Glu Pro
            275

<210> SEQ ID NO 53
<211> LENGTH: 276
<212> TYPE: PRT
<213> ORGANISM: Homo sapiens

<400> SEQUENCE: 53

Gly Ser His Ser Met Arg Tyr Phe His Thr Ala Met Ser Arg Pro Gly
1               5                   10                  15

Arg Gly Glu Pro Arg Phe Ile Thr Val Gly Tyr Val Asp Asp Thr Leu
            20                  25                  30

Phe Val Arg Phe Asp Ser Asp Ala Thr Ser Pro Arg Lys Glu Pro Arg
            35                  40                  45

Ala Pro Trp Ile Glu Gln Glu Gly Pro Glu Tyr Trp Asp Arg Glu Thr
    50                  55                  60

Gln Ile Ser Lys Thr Asn Thr Gln Thr Tyr Arg Glu Ser Leu Arg Asn
65                  70                  75                  80

Leu Arg Gly Cys Tyr Asn Gln Ser Glu Ala Gly Ser His Thr Leu Gln
                85                  90                  95

Arg Met Tyr Gly Cys Asp Val Gly Pro Asp Gly Arg Leu Leu Arg Gly
            100                 105                 110

His Asn Gln Tyr Ala Tyr Asp Gly Lys Asp Tyr Ile Ala Leu Asn Glu
            115                 120                 125

Asp Leu Arg Ser Trp Thr Ala Ala Asp Thr Ala Ala Gln Ile Ser Gln
            130                 135                 140

Arg Lys Leu Glu Ala Ala Arg Val Ala Glu Gln Leu Arg Ala Tyr Leu
145                 150                 155                 160

Glu Gly Glu Cys Val Glu Trp Leu Arg Arg Tyr Leu Glu Asn Gly Lys
                165                 170                 175

Asp Lys Leu Glu Arg Ala Asp Pro Pro Lys Thr His Val Thr His His
            180                 185                 190

Pro Ile Ser Asp His Glu Ala Thr Leu Arg Cys Trp Ala Leu Gly Phe
            195                 200                 205

Tyr Pro Ala Glu Ile Thr Leu Thr Trp Gln Arg Asp Gly Glu Asp Gln
            210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
            245                 250                 255

Tyr Thr Cys His Val Gln His Glu Gly Leu Pro Lys Pro Leu Thr Leu
            260                 265                 270

```
Arg Trp Glu Pro
        275

<210> SEQ ID NO 54
<211> LENGTH: 276
<212> TYPE: PRT
<213> ORGANISM: Homo sapiens

<400> SEQUENCE: 54

Gly Ser His Ser Met Arg Tyr Phe Tyr Thr Ala Met Ser Arg Pro Gly
1               5                   10                  15

Arg Gly Glu Pro Arg Phe Ile Thr Val Gly Tyr Val Asp Asp Thr Leu
            20                  25                  30

Phe Val Arg Phe Asp Ser Asp Ala Thr Ser Pro Arg Lys Glu Pro Arg
        35                  40                  45

Ala Pro Trp Ile Glu Gln Glu Gly Pro Glu Tyr Trp Asp Arg Glu Thr
    50                  55                  60

Gln Ile Ser Lys Thr Asn Thr Gln Thr Tyr Arg Glu Asn Leu Arg Thr
65                  70                  75                  80

Ala Leu Arg Cys Tyr Asn Gln Ser Glu Ala Gly Ser His Ile Ile Gln
                85                  90                  95

Arg Met Tyr Gly Cys Asp Val Gly Pro Asp Gly Arg Leu Leu Arg Gly
            100                 105                 110

Tyr Asp Gln Asp Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Val Ala Glu Gln Asp Arg Ala Tyr Leu
145                 150                 155                 160

Glu Gly Leu Cys Val Glu Ser Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Val Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro
        275

<210> SEQ ID NO 55
<211> LENGTH: 276
<212> TYPE: PRT
<213> ORGANISM: Homo sapiens

<400> SEQUENCE: 55

Gly Ser His Ser Met Arg Tyr Phe Tyr Thr Ala Met Ser Arg Pro Gly
1               5                   10                  15

Arg Gly Glu Pro Arg Phe Ile Ala Val Gly Tyr Val Asp Asp Thr Gln
            20                  25                  30
```

-continued

```
Phe Val Arg Phe Asp Ser Asp Ala Ala Ser Pro Arg Met Ala Pro Arg
            35                  40                  45

Ala Pro Trp Ile Glu Gln Glu Gly Pro Glu Tyr Trp Asp Arg Glu Thr
 50                  55                  60

Gln Lys Tyr Lys Arg Gln Ala Gln Thr Asp Arg Val Ser Leu Arg Asn
 65                  70                  75                  80

Leu Arg Gly Cys Tyr Asn Gln Ser Glu Ala Gly Ser His Thr Leu Gln
                 85                  90                  95

Arg Met Tyr Gly Cys Asp Val Gly Pro Asp Gly Arg Leu Leu Arg Gly
                100                 105                 110

His Asp Gln Ser Ala Tyr Asp Gly Lys Asp Tyr Ile Ala Leu Asn Glu
            115                 120                 125

Asp Leu Ser Ser Trp Thr Ala Ala Asp Thr Ala Ala Gln Ile Thr Gln
130                 135                 140

Arg Lys Trp Glu Ala Ala Arg Glu Ala Glu Gln Trp Arg Ala Tyr Leu
145                 150                 155                 160

Glu Gly Leu Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro
        275

<210> SEQ ID NO 56
<211> LENGTH: 276
<212> TYPE: PRT
<213> ORGANISM: Homo sapiens

<400> SEQUENCE: 56

Gly Ser His Ser Met Arg Tyr Phe His Thr Ala Met Ser Arg Pro Gly
 1               5                  10                  15

Arg Gly Glu Pro Arg Phe Ile Thr Val Gly Tyr Val Asp Asp Thr Leu
                 20                  25                  30

Phe Val Arg Phe Asp Ser Asp Ala Thr Ser Pro Arg Lys Glu Pro Arg
            35                  40                  45

Ala Pro Trp Ile Glu Gln Glu Gly Pro Glu Tyr Trp Asp Arg Glu Thr
 50                  55                  60

Gln Ile Ser Lys Thr Asn Thr Gln Thr Tyr Arg Glu Ser Leu Arg Asn
 65                  70                  75                  80

Leu Arg Gly Cys Tyr Asn Gln Ser Glu Ala Gly Ser His Thr Trp Gln
                 85                  90                  95

Arg Met Tyr Gly Cys Asp Leu Gly Pro Asp Gly Arg Leu Leu Arg Gly
                100                 105                 110

Tyr Asn Gln Leu Ala Tyr Asp Gly Lys Asp Tyr Ile Ala Leu Asn Glu
```

```
                  115                 120                 125
Asp Leu Ser Ser Trp Thr Ala Ala Asp Thr Ala Ala Gln Ile Thr Gln
    130                 135                 140

Arg Lys Trp Glu Ala Ala Arg Glu Ala Glu Gln Leu Arg Ala Tyr Leu
145                 150                 155                 160

Glu Gly Leu Cys Val Glu Trp Leu Arg Arg Tyr Leu Glu Asn Gly Lys
                    165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                    245                 250                 255

Tyr Thr Cys His Val Gln His Glu Gly Leu Pro Lys Pro Leu Thr Leu
            260                 265                 270

Arg Trp Glu Pro
        275

<210> SEQ ID NO 57
<211> LENGTH: 276
<212> TYPE: PRT
<213> ORGANISM: Homo sapiens

<400> SEQUENCE: 57

Gly Ser His Ser Met Arg Tyr Phe Tyr Thr Ala Met Ser Arg Pro Gly
1               5                   10                  15

Arg Gly Glu Pro Arg Phe Ile Ala Val Gly Tyr Val Asp Asp Thr Gln
                20                  25                  30

Phe Val Arg Phe Asp Ser Asp Ala Ala Ser Pro Arg Met Ala Pro Arg
            35                  40                  45

Ala Pro Trp Ile Glu Gln Glu Gly Pro Glu Tyr Trp Asp Gly Glu Thr
        50                  55                  60

Arg Asn Met Lys Ala Ser Ala Gln Thr Tyr Arg Glu Asn Leu Arg Ile
65                  70                  75                  80

Ala Leu Arg Cys Tyr Asn Gln Ser Glu Ala Gly Ser His Ile Ile Gln
                85                  90                  95

Val Met Tyr Gly Cys Asp Val Gly Pro Asp Gly Arg Leu Leu Arg Gly
            100                 105                 110

His Asp Gln Ser Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Leu Cys Val Glu Trp Leu Arg Arg Tyr Leu Glu Asn Gly Lys
                    165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205
```

```
Tyr Pro Ala Glu Ile Thr Leu Thr Trp Gln Arg Asp Gly Glu Asp Gln
    210                 215                 220
Thr Gln Asp Thr Glu Leu Val Glu Thr Arg Pro Ala Gly Asp Arg Thr
225                 230                 235                 240
Phe Gln Lys Trp Ala Ala Val Val Pro Ser Gly Glu Glu Gln Arg
                245                 250                 255
Tyr Thr Cys His Val Gln His Glu Gly Leu Pro Lys Pro Leu Thr Leu
                260                 265                 270
Arg Trp Glu Pro
        275

<210> SEQ ID NO 58
<211> LENGTH: 276
<212> TYPE: PRT
<213> ORGANISM: Homo sapiens

<400> SEQUENCE: 58

Gly Ser His Ser Met Arg Tyr Phe Tyr Thr Ala Met Ser Arg Pro Gly
1               5                   10                  15
Arg Gly Glu Pro Arg Phe Ile Ala Val Gly Tyr Val Asp Asp Thr Gln
            20                  25                  30
Phe Val Arg Phe Asp Ser Asp Ala Ala Ser Pro Arg Thr Glu Pro Arg
        35                  40                  45
Ala Pro Trp Ile Glu Gln Glu Gly Pro Glu Tyr Trp Asp Gly Glu Thr
    50                  55                  60
Arg Asn Met Lys Ala Ser Ala Gln Thr Tyr Arg Glu Asn Leu Arg Ile
65                  70                  75                  80
Ala Leu Arg Cys Tyr Asn Gln Ser Glu Ala Gly Ser His Ile Ile Gln
                85                  90                  95
Arg Met Tyr Gly Cys Asp Leu Gly Pro Asp Gly Arg Leu Leu Arg Gly
            100                 105                 110
His Asp Gln Ser Ala Tyr Asp Gly Lys Asp Tyr Ile Ala Leu Asn Glu
        115                 120                 125
Asp Leu Ser Ser Trp Thr Ala Ala Asp Thr Ala Ala Gln Ile Thr Gln
    130                 135                 140
Arg Lys Trp Glu Ala Ala Arg Val Ala Glu Gln Leu Arg Ala Tyr Leu
145                 150                 155                 160
Glu Gly Leu Cys Val Glu Trp Leu Arg Arg Tyr Leu Glu Asn Gly Lys
                165                 170                 175
Glu Thr Leu Gln Arg Ala Asp Pro Pro Lys Thr His Val Thr His His
            180                 185                 190
Pro Val Ser Asp His Glu Ala Thr Leu Arg Cys Trp Ala Leu Gly Phe
        195                 200                 205
Tyr Pro Ala Glu Ile Thr Leu Thr Trp Gln Arg Asp Gly Glu Asp Gln
    210                 215                 220
Thr Gln Asp Thr Glu Leu Val Glu Thr Arg Pro Ala Gly Asp Arg Thr
225                 230                 235                 240
Phe Gln Lys Trp Ala Ala Val Val Pro Ser Gly Glu Glu Gln Arg
                245                 250                 255
Tyr Thr Cys His Val Gln His Glu Gly Leu Pro Lys Pro Leu Thr Leu
                260                 265                 270
Arg Trp Glu Pro
        275

<210> SEQ ID NO 59
```

```
<211> LENGTH: 276
<212> TYPE: PRT
<213> ORGANISM: Homo sapiens

<400> SEQUENCE: 59

Cys Ser His Ser Met Arg Tyr Phe Tyr Thr Ala Val Ser Arg Pro Ser
1               5                   10                  15

Arg Gly Glu Pro His Phe Ile Ala Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Lys Tyr Lys Arg Gln Ala Gln Thr Asp Arg Val Asn Leu Arg Lys
65                  70                  75                  80

Leu Arg Gly Cys Tyr Asn Gln Ser Glu Ala Gly Ser His Thr Leu Gln
                85                  90                  95

Arg Met Tyr Gly Cys Asp Leu Gly Pro Asp Gly Arg Leu Leu Arg Gly
            100                 105                 110

Tyr Asp Gln Ser Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Trp Arg Ala Tyr Leu
145                 150                 155                 160

Glu Gly Glu Cys Val Glu Trp Leu Arg Arg Tyr Leu Glu Asn Gly Lys
                165                 170                 175

Glu Thr Leu Gln Arg Ala Glu His Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Thr Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Pro Ser Gly Glu Glu Gln Arg
                245                 250                 255

Tyr Thr Cys His Val Gln His Glu Gly Leu Pro Glu Pro Leu Thr Leu
            260                 265                 270

Arg Trp Glu Pro
            275

<210> SEQ ID NO 60
<211> LENGTH: 276
<212> TYPE: PRT
<213> ORGANISM: Homo sapiens

<400> SEQUENCE: 60

Gly Ser His Ser Met Arg Tyr Phe Tyr Thr Ala Val Ser Arg Pro Gly
1               5                   10                  15

Arg Gly Glu Pro His Phe Ile Ala Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60
```

```
Gln Lys Tyr Lys Arg Gln Ala Gln Thr Asp Arg Val Ser Leu Arg Asn
 65                  70                  75                  80

Leu Arg Gly Cys Tyr Asn Gln Ser Glu Ala Gly Ser His Ile Ile Gln
             85                  90                  95

Arg Met Tyr Gly Cys Asp Val Gly Pro Asp Gly Arg Leu Leu Arg Gly
            100                 105                 110

Tyr Asp Gln Tyr Ala Tyr Asp Gly Lys Asp Tyr Ile Ala Leu Asn Glu
            115                 120                 125

Asp Leu Arg Ser Trp Thr Ala Ala Asp Thr Ala Gln Ile Thr Gln
130                 135                 140

Arg Lys Trp Glu Ala Ala Arg Glu Ala Glu Gln Leu Arg Ala Tyr Leu
145                 150                 155                 160

Glu Gly Leu Cys Val Glu Trp Leu Arg Arg Tyr Leu Lys Asn Gly Lys
            165                 170                 175

Glu Thr Leu Gln Arg Ala Glu His Pro Lys Thr His Val Thr His His
            180                 185                 190

Pro Val Ser Asp His Glu Ala Thr Leu Arg Cys Trp Ala Leu Gly Phe
            195                 200                 205

Tyr Pro Ala Glu Ile Thr Leu Thr Trp Gln Trp Asp Gly Glu Asp Gln
210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Pro Ser Gly Glu Glu Gln Arg
            245                 250                 255

Tyr Thr Cys His Val Gln His Glu Gly Leu Pro Glu Pro Leu Thr Leu
            260                 265                 270

Arg Trp Glu Pro
            275

<210> SEQ ID NO 61
<211> LENGTH: 276
<212> TYPE: PRT
<213> ORGANISM: Homo sapiens

<400> SEQUENCE: 61

Cys Ser His Ser Met Arg Tyr Phe Tyr Thr Ala Val Ser Arg Pro Gly
 1               5                  10                  15

Arg Gly Glu Pro Arg Phe Ile Ala Val Gly Tyr Val Asp Asp Thr Gln
             20                  25                  30

Phe Val Gln Phe Asp Ser Asp Ala Ala Ser Pro Arg Gly Glu Pro Arg
         35                  40                  45

Ala Pro Trp Val Glu Gln Glu Gly Pro Glu Tyr Trp Asp Arg Glu Thr
 50                  55                  60

Gln Lys Tyr Lys Arg Gln Ala Gln Thr Asp Arg Val Asn Leu Arg Lys
 65                  70                  75                  80

Leu Arg Gly Cys Tyr Asn Gln Ser Glu Ala Gly Ser His Thr Leu Gln
             85                  90                  95

Arg Met Tyr Gly Cys Asp Leu Gly Pro Asp Gly Arg Leu Leu Arg Gly
            100                 105                 110

Tyr Asn Gln Phe Ala Tyr Asp Gly Lys Asp Tyr Ile Ala Leu Asn Glu
            115                 120                 125

Asp Leu Arg Ser Trp Thr Ala Ala Asp Lys Ala Gln Ile Thr Gln
130                 135                 140

Arg Lys Trp Glu Ala Ala Arg Glu Ala Glu Gln Arg Arg Ala Tyr Leu
```

```
                    145                 150                 155                 160
        Glu Gly Thr Cys Val Glu Trp Leu Arg Arg Tyr Leu Glu Asn Gly Lys
                        165                 170                 175

Lys Thr Leu Gln Arg Ala Glu His Pro Lys Thr His Val Thr His His
                        180                 185                 190

Pro Val Ser Asp His Glu Ala Thr Leu Arg Cys Trp Ala Leu Gly Phe
                        195                 200                 205

Tyr Pro Ala Glu Ile Thr Leu Thr Trp Gln Arg Asp Gly Glu Asp Gln
                    210                 215                 220

Thr Gln Asp Thr Glu Leu Val Glu Thr Arg Pro Ala Gly Asp Gly Thr
        225                 230                 235                 240

Phe Gln Lys Trp Ala Ala Val Val Pro Ser Gly Glu Glu Gln Arg
                        245                 250                 255

Tyr Thr Cys His Val Gln His Glu Gly Leu Pro Glu Pro Leu Thr Leu
                        260                 265                 270

Arg Trp Gly Pro
                        275

<210> SEQ ID NO 62
<211> LENGTH: 276
<212> TYPE: PRT
<213> ORGANISM: Homo sapiens

<400> SEQUENCE: 62

Cys Ser His Ser Met Arg Tyr Phe Asp Thr Ala Val Ser Arg Pro Gly
        1               5                   10                  15

Arg Gly Glu Pro Arg Phe Ile Ser Val Gly Tyr Val Asp Asp Thr Gln
                        20                  25                  30

Phe Val Arg Phe Asp Ser Asp Ala Ala Ser Pro Arg Gly Glu Pro Arg
                    35                  40                  45

Ala Pro Trp Val Glu Gln Glu Gly Pro Glu Tyr Trp Asp Arg Glu Thr
        50                  55                  60

Gln Asn Tyr Lys Arg Gln Ala Gln Ala Asp Arg Val Ser Leu Arg Asn
        65                  70                  75                  80

Leu Arg Gly Cys Tyr Asn Gln Ser Glu Asp Gly Ser His Thr Leu Gln
                        85                  90                  95

Arg Met Tyr Gly Cys Asp Leu Gly Pro Asp Gly Arg Leu Leu Arg Gly
                        100                 105                 110

Tyr Asp Gln Ser Ala Tyr Asp Gly Lys Asp Tyr Ile Ala Leu Asn Glu
                    115                 120                 125

Asp Leu Arg Ser Trp Thr Ala Ala Asp Thr Ala Ala Gln Ile Thr Gln
        130                 135                 140

Arg Lys Leu Glu Ala Ala Arg Ala Ala Glu Gln Leu Arg Ala Tyr Leu
        145                 150                 155                 160

Glu Gly Thr Cys Val Glu Trp Leu Arg Arg Tyr Leu Glu Asn Gly Lys
                        165                 170                 175

Glu Thr Leu Gln Arg Ala Glu Pro Pro Lys Thr His Val Thr His His
                        180                 185                 190

Pro Leu Ser Asp His Glu Ala Thr Leu Arg Cys Trp Ala Leu Gly Phe
                        195                 200                 205

Tyr Pro Ala Glu Ile Thr Leu Thr Trp Gln Arg Asp Gly Glu Asp Gln
                    210                 215                 220

Thr Gln Asp Thr Glu Leu Val Glu Thr Arg Pro Ala Gly Asp Gly Thr
        225                 230                 235                 240
```

```
Phe Gln Lys Trp Ala Ala Val Val Val Pro Ser Gly Gln Glu Gln Arg
                245                 250                 255

Tyr Thr Cys His Met Gln His Glu Gly Leu Gln Glu Pro Leu Thr Leu
            260                 265                 270

Ser Trp Glu Pro
        275

<210> SEQ ID NO 63
<211> LENGTH: 276
<212> TYPE: PRT
<213> ORGANISM: Homo sapiens

<400> SEQUENCE: 63

Gly Ser His Ser Met Arg Tyr Phe Tyr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gln Glu Thr
    50                  55                  60

Arg Asn Val Lys Ala Gln Ser Gln Thr Asp Arg Val Asp Leu Gly Thr
65                  70                  75                  80

Leu Arg Gly Cys Tyr Asn Gln Ser Glu Asp Gly Ser His Thr Ile Gln
                85                  90                  95

Ile Met Tyr Gly Cys Asp Val Gly Pro Asp Gly Arg Phe Leu Arg Gly
            100                 105                 110

Tyr Arg Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Lys
    130                 135                 140

Arg Lys Trp Glu Ala Ala His Ala Ala Glu Gln Gln Arg Ala Tyr Leu
145                 150                 155                 160

Glu Gly Arg Cys Val Glu Trp Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Leu
        275

<210> SEQ ID NO 64
<211> LENGTH: 276
<212> TYPE: PRT
<213> ORGANISM: Homo sapiens

<400> SEQUENCE: 64
```

Gly Ser His Ser Met Arg Tyr Phe Ser Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Glu Glu Thr
50                  55                  60

Gly Lys Val Lys Ala His Ser Gln Thr Asp Arg Glu Asn Leu Arg Ile
65                  70                  75                  80

Ala Leu Arg Cys Tyr Asn Gln Ser Glu Ala Gly Ser His Thr Leu Gln
                85                  90                  95

Met Met Phe Gly Cys Asp Val Gly Ser Asp Gly Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Ile Thr Gln
130                 135                 140

Arg Lys Trp Glu Ala Ala Arg Val Ala Glu Gln Leu Arg Ala Tyr Leu
145                 150                 155                 160

Glu Gly Thr Cys Val Asp Gly Leu Arg Arg Tyr Leu Glu Asn Gly Lys
                165                 170                 175

Glu Thr Leu Gln Arg Thr Asp Pro Pro Lys Thr His Met Thr His His
        180                 185                 190

Pro Ile Ser Asp His Glu Ala Thr Leu Arg Cys Trp Ala Leu Gly Phe
    195                 200                 205

Tyr Pro Ala Glu Ile Thr Leu Thr Trp Gln Arg Asp Gly Glu Asp Gln
210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
            245                 250                 255

Tyr Thr Cys His Val Gln His Glu Gly Leu Pro Lys Pro Leu Thr Leu
        260                 265                 270

Arg Trp Glu Pro
        275

<210> SEQ ID NO 65
<211> LENGTH: 276
<212> TYPE: PRT
<213> ORGANISM: Homo sapiens

<400> SEQUENCE: 65

Gly Ser His Ser Met Arg Tyr Phe Ser Thr Ser Val Ser Arg Pro Gly
1               5                   10                  15

Ser Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Arg Pro Glu Tyr Trp Asp Gln Glu Thr
50                  55                  60

Arg Asn Val Lys Ala Gln Ser Gln Thr Asp Arg Val Asp Leu Gly Thr
65                  70                  75                  80

Leu Arg Gly Cys Tyr Asn Gln Ser Glu Ala Gly Ser His Thr Ile Gln
                85                  90                  95

```
Ile Met Tyr Gly Cys Asp Val Gly Ser Asp Gly Arg Phe Leu Arg Gly
            100                 105                 110

Tyr Glu Gln His Ala Tyr Asp Gly Lys Asp Tyr Ile Ala Leu Asn Glu
        115                 120                 125

Asp Leu Arg Ser Trp Thr Ala Asp Met Ala Ala Gln Ile Thr Gln
    130                 135                 140

Arg Lys Trp Glu Ala Ala Arg Trp Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Leu
        275

<210> SEQ ID NO 66
<211> LENGTH: 276
<212> TYPE: PRT
<213> ORGANISM: Homo sapiens

<400> SEQUENCE: 66

Gly Ser His Ser Met Arg Tyr Phe Thr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Arg Asn Thr
    50                  55                  60

Arg Asn Val Lys Ala His Ser Gln Ile Asp Arg Val Asp Leu Gly Thr
65                  70                  75                  80

Leu Arg Gly Cys Tyr Asn Gln Ser Glu Ala Gly Ser His Thr Ile Gln
                85                  90                  95

Met Met Tyr Gly Cys Asp Val Gly Ser Asp Gly Arg Phe Leu Arg Gly
            100                 105                 110

Tyr Gln Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Pro Pro Lys Thr His Met Thr His His
```

```
                    180                 185                 190
Ala Val Ser Asp His Glu Ala Thr Leu Arg Cys Trp Ala Leu Ser Phe
            195                 200                 205

Tyr Pro Ala Glu Ile Thr Leu Thr Trp Gln Arg Asp Gly Glu Asp Gln
        210                 215                 220

Thr Gln Asp Thr Glu Leu Val Glu Thr Arg Pro Ala Gly Asp Gly Thr
225                 230                 235                 240

Phe Gln Lys Trp Ala Ser Val Val Pro Ser Gly Gln Glu Gln Arg
            245                 250                 255

Tyr Thr Cys His Val Gln His Glu Gly Leu Pro Lys Pro Leu Thr Leu
        260                 265                 270

Arg Trp Glu Pro
        275

<210> SEQ ID NO 67
<211> LENGTH: 276
<212> TYPE: PRT
<213> ORGANISM: Homo sapiens

<400> SEQUENCE: 67

Gly Ser His Ser Met Arg Tyr Phe Asp Thr Ala Met Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Phe Lys Thr Asn Thr Gln Thr Asp Arg Glu Ser Leu Arg Asn
65                  70                  75                  80

Leu Arg Gly Cys Tyr Asn Gln Ser Glu Ala Gly Ser His Thr Leu Gln
                85                  90                  95

Ser Met Tyr Gly Cys Asp Val Gly Pro Asp Gly Arg Leu Leu Arg Gly
            100                 105                 110

His Asn Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Val Ala Glu Gln Asp Arg Ala Tyr Leu
145                 150                 155                 160

Glu Gly Thr Cys Val Glu Trp Leu Arg Arg Tyr Leu Glu Asn Gly Lys
                165                 170                 175

Asp Thr Leu Glu Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Val Val Pro Ser Gly Glu Glu Gln Arg
                245                 250                 255

Tyr Thr Cys His Val Gln His Glu Gly Leu Pro Lys Pro Leu Thr Leu
        260                 265                 270
```

```
Arg Trp Glu Pro
        275

<210> SEQ ID NO 68
<211> LENGTH: 276
<212> TYPE: PRT
<213> ORGANISM: Homo sapiens

<400> SEQUENCE: 68

Gly Ser His Ser Met Arg Tyr Phe Tyr Thr Ala Met Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Met Ala Pro Arg
        35                  40                  45

Ala Pro Trp Ile Glu Gln Glu Gly Pro Glu Tyr Trp Asp Arg Glu Thr
    50                  55                  60

Gln Ile Ser Lys Thr Asn Thr Gln Thr Tyr Arg Glu Ser Leu Arg Asn
65                  70                  75                  80

Leu Arg Gly Cys Tyr Asn Gln Ser Glu Ala Gly Ser His Thr Leu Gln
                85                  90                  95

Arg Met Tyr Gly Cys Asp Val Gly Pro Asp Gly Arg Leu Leu Arg Gly
            100                 105                 110

His Asp Gln Ser Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Glu Ala Glu Gln Trp Arg Ala Tyr Leu
145                 150                 155                 160

Glu Gly Leu Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro
        275

<210> SEQ ID NO 69
<211> LENGTH: 276
<212> TYPE: PRT
<213> ORGANISM: Homo sapiens

<400> SEQUENCE: 69

Gly Ser His Ser Met Arg Tyr Phe Tyr Thr Ala Met Ser Arg Pro Gly
1               5                   10                  15

Arg Gly Glu Pro Arg Phe Ile Ser Val Gly Tyr Val Asp Asp Thr Gln
            20                  25                  30
```

```
Phe Val Arg Phe Asp Ser Asp Ala Ala Ser Pro Arg Glu Pro Arg
         35                  40                  45

Ala Pro Trp Ile Glu Gln Glu Gly Pro Glu Tyr Trp Asp Arg Glu Thr
 50                  55                  60

Gln Ile Ser Lys Thr Asn Thr Gln Thr Tyr Arg Glu Ser Leu Arg Asn
 65                  70                  75                  80

Leu Arg Gly Cys Tyr Asn Gln Ser Glu Ala Gly Ser His Thr Leu Gln
                 85                  90                  95

Arg Met Tyr Gly Cys Asp Val Gly Pro Asp Gly Arg Leu Leu Arg Gly
            100                 105                 110

His Asp Gln Ser Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
130                 135                 140

Arg Lys Trp Glu Ala Ala Arg Glu Ala Glu Gln Leu Arg Ala Tyr Leu
145                 150                 155                 160

Glu Gly Leu Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro
        275

<210> SEQ ID NO 70
<211> LENGTH: 276
<212> TYPE: PRT
<213> ORGANISM: Homo sapiens

<400> SEQUENCE: 70

Gly Ser His Ser Met Arg Tyr Phe Tyr Thr Ala Met Ser Arg Pro Gly
 1               5                  10                  15

Arg Gly Glu Pro Arg Phe Ile Ala Val Gly Tyr Val Asp Asp Thr Gln
                 20                  25                  30

Phe Val Arg Phe Asp Ser Asp Ala Ala Ser Pro Arg Thr Glu Pro Arg
            35                  40                  45

Ala Pro Trp Ile Glu Gln Glu Gly Pro Glu Tyr Trp Asp Arg Asn Thr
 50                  55                  60

Gln Ile Phe Lys Thr Asn Thr Gln Thr Tyr Arg Glu Ser Leu Arg Asn
 65                  70                  75                  80

Leu Arg Gly Cys Tyr Asn Gln Ser Glu Ala Gly Ser His Ile Ile Gln
                 85                  90                  95

Arg Met Tyr Gly Cys Asp Leu Gly Pro Asp Gly Arg Leu Leu Arg Gly
            100                 105                 110

His Asp Gln Ser Ala Tyr Asp Gly Lys Asp Tyr Ile Ala Leu Asn Glu
        115                 120                 125
```

```
Asp Leu Ser Ser Trp Thr Ala Ala Asp Thr Ala Ala Gln Ile Thr Gln
        130                 135                 140

Arg Lys Trp Glu Ala Ala Arg Val Ala Glu Gln Leu Arg Ala Tyr Leu
145                 150                 155                 160

Glu Gly Leu Cys Val Glu Trp Leu Arg Arg Tyr Leu Glu Asn Gly Lys
                165                 170                 175

Glu Thr Leu Gln Arg Ala Asp Pro Lys Thr His Val Thr His His
                180                 185                 190

Pro Val Ser Asp His Glu Ala Thr Leu Arg Cys Trp Ala Leu Gly Phe
            195                 200                 205

Tyr Pro Ala Glu Ile Thr Leu Thr Trp Gln Arg Asp Gly Glu Asp Gln
        210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Pro Ser Gly Glu Glu Gln Arg
                245                 250                 255

Tyr Thr Cys His Val Gln His Glu Gly Leu Pro Lys Pro Leu Thr Leu
                260                 265                 270

Arg Trp Glu Pro
        275

<210> SEQ ID NO 71
<211> LENGTH: 276
<212> TYPE: PRT
<213> ORGANISM: Homo sapiens

<400> SEQUENCE: 71

Gly Ser His Ser Met Arg Tyr Phe His Thr Ser Val Ser Arg Pro Gly
1               5                   10                  15

Arg Gly Glu Pro Arg Phe Ile Thr Val Gly Tyr Val Asp Asp Thr Leu
                20                  25                  30

Phe Val Arg Phe Asp Ser Asp Ala Thr Ser Pro Arg Lys Glu Pro Arg
            35                  40                  45

Ala Pro Trp Ile Glu Gln Glu Gly Pro Glu Tyr Trp Asp Arg Glu Thr
        50                  55                  60

Gln Ile Ser Lys Thr Asn Thr Gln Thr Tyr Arg Glu Ser Leu Arg Asn
65                  70                  75                  80

Leu Arg Gly Cys Tyr Asn Gln Ser Glu Ala Gly Ser His Thr Leu Gln
                85                  90                  95

Ser Met Tyr Gly Cys Asp Val Gly Pro Asp Gly Arg Leu Leu Arg Gly
                100                 105                 110

His Asn Gln Tyr Ala Tyr Asp Gly Lys Asp Tyr Ile Ala Leu Asn Glu
            115                 120                 125

Asp Leu Arg Ser Trp Thr Ala Ala Asp Thr Ala Ala Gln Ile Thr Gln
        130                 135                 140

Arg Lys Trp Glu Ala Ala Arg Val Ala Glu Gln Leu Arg Ala Tyr Leu
145                 150                 155                 160

Glu Gly Glu Cys Val Glu Trp Leu Arg Arg Tyr Leu Glu Asn Gly Lys
                165                 170                 175

Glu Thr Leu Gln Arg Ala Asp Pro Lys Thr His Val Thr His His
                180                 185                 190

Pro Ile Ser Asp His Glu Ala Thr Leu Arg Cys Trp Ala Leu Gly Phe
            195                 200                 205

Tyr Pro Ala Glu Ile Thr Leu Thr Trp Gln Arg Asp Gly Glu Asp Gln
```

Thr Gln Asp Thr Glu Leu Val Glu Thr Arg Pro Ala Gly Asp Arg Thr
225                 230                 235                 240

Phe Gln Lys Trp Ala Ala Val Val Pro Ser Gly Glu Glu Gln Arg
            245                 250                 255

Tyr Thr Cys His Val Gln His Glu Gly Leu Pro Lys Pro Leu Thr Leu
            260                 265                 270

Arg Trp Glu Pro
        275

<210> SEQ ID NO 72
<211> LENGTH: 276
<212> TYPE: PRT
<213> ORGANISM: Homo sapiens

<400> SEQUENCE: 72

Gly Ser His Ser Met Arg Tyr Phe Tyr Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Tyr Lys Ala Gln Ala Gln Thr Asp Arg Glu Ser Leu Arg Asn
65                  70                  75                  80

Leu Arg Gly Cys Tyr Asn Gln Ser Glu Ala Gly Ser His Thr Leu Gln
                85                  90                  95

Ser Met Tyr Gly Cys Asp Val Gly Pro Asp Gly Arg Leu Leu Arg Gly
            100                 105                 110

His Asn Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
130                 135                 140

Arg Lys Trp Glu Ala Ala Arg Val Ala Glu Gln Asp Arg Ala Tyr Leu
145                 150                 155                 160

Glu Gly Thr Cys Val Glu Trp Leu Arg Arg Tyr Leu Glu Asn Gly Lys
                165                 170                 175

Asp Thr Leu Glu Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Pro Ser Gly Glu Glu Gln Arg
            245                 250                 255

Tyr Thr Cys His Val Gln His Glu Gly Leu Pro Lys Pro Leu Thr Leu
            260                 265                 270

Arg Trp Glu Pro
        275

<210> SEQ ID NO 73
<211> LENGTH: 276

```
<212> TYPE: PRT
<213> ORGANISM: Homo sapiens

<400> SEQUENCE: 73

Gly Ser His Ser Met Arg Tyr Phe Tyr Thr Ala Met Ser Arg Pro Gly
1               5                   10                  15

Arg Gly Glu Pro Arg Phe Ile Thr Val Gly Tyr Val Asp Asp Thr Leu
            20                  25                  30

Phe Val Arg Phe Asp Ser Asp Ala Thr Ser Pro Arg Lys Glu Pro Arg
        35                  40                  45

Ala Pro Trp Ile Glu Gln Glu Gly Pro Glu Tyr Trp Asp Arg Glu Thr
    50                  55                  60

Gln Ile Ser Lys Thr Asn Thr Gln Thr Tyr Arg Glu Asn Leu Arg Thr
65                  70                  75                  80

Ala Leu Arg Cys Tyr Asn Gln Ser Glu Ala Gly Ser His Ile Ile Gln
                85                  90                  95

Arg Met Tyr Gly Cys Asp Val Gly Pro Asp Gly Arg Leu Leu Arg Gly
            100                 105                 110

Tyr Asp Gln Asp Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Leu Cys Val Glu Ser Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Val Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro
            275

<210> SEQ ID NO 74
<211> LENGTH: 276
<212> TYPE: PRT
<213> ORGANISM: Homo sapiens

<400> SEQUENCE: 74

Gly Ser His Ser Met Arg Tyr Phe Tyr Thr Ala Met Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Thr Glu Pro Arg
        35                  40                  45

Ala Pro Trp Ile Glu Gln Glu Gly Pro Glu Tyr Trp Asp Arg Asn Thr
    50                  55                  60
```

```
Gln Ile Phe Lys Thr Asn Thr Gln Thr Tyr Arg Glu Asn Leu Arg Ile
 65                  70                  75                  80

Ala Leu Arg Cys Tyr Asn Gln Ser Glu Ala Gly Ser His Thr Trp Gln
                 85                  90                  95

Thr Met Tyr Gly Cys Asp Val Gly Pro Asp Gly Arg Leu Leu Arg Gly
                100                 105                 110

His Asn Gln Tyr Ala Tyr Asp Gly Lys Asp Tyr Ile Ala Leu Asn Glu
            115                 120                 125

Asp Leu Ser Ser Trp Thr Ala Ala Asp Thr Ala Ala Gln Ile Thr Gln
130                 135                 140

Arg Lys Trp Glu Ala Ala Arg Glu Ala Glu Gln Leu Arg Ala Tyr Leu
145                 150                 155                 160

Glu Gly Leu Cys Val Glu Trp Leu Arg Arg His Leu Glu Asn Gly Lys
                165                 170                 175

Glu Thr Leu Gln Arg Ala Asp Pro Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro
        275

<210> SEQ ID NO 75
<211> LENGTH: 276
<212> TYPE: PRT
<213> ORGANISM: Homo sapiens

<400> SEQUENCE: 75

Gly Ser His Ser Met Arg Tyr Phe Tyr Thr Ala Met Ser Arg Pro Gly
 1               5                  10                  15

Arg Gly Glu Pro Arg Phe Ile Ala Val Gly Tyr Val Asp Asp Thr Gln
                20                  25                  30

Phe Val Arg Phe Asp Ser Asp Ala Ala Ser Pro Arg Thr Glu Pro Arg
            35                  40                  45

Ala Pro Trp Ile Glu Gln Glu Gly Pro Glu Tyr Trp Asp Arg Asn Thr
 50                 55                  60

Gln Ile Phe Lys Thr Asn Thr Gln Thr Tyr Arg Glu Asn Leu Arg Ile
 65                 70                  75                  80

Ala Leu Arg Cys Tyr Asn Gln Ser Glu Ala Gly Ser His Ile Ile Gln
                85                  90                  95

Arg Met Tyr Gly Cys Asp Leu Gly Pro Asp Gly Arg Leu Leu Arg Gly
                100                 105                 110

His Asp Gln Ser Ala Tyr Asp Gly Lys Asp Tyr Ile Ala Leu Asn Glu
            115                 120                 125

Asp Leu Ser Ser Trp Thr Ala Ala Asp Thr Ala Ala Gln Ile Thr Gln
130                 135                 140

Arg Lys Trp Glu Ala Ala Arg Val Ala Glu Gln Leu Arg Ala Tyr Leu
145                 150                 155                 160
```

```
Glu Gly Leu Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro
        275

<210> SEQ ID NO 76
<211> LENGTH: 276
<212> TYPE: PRT
<213> ORGANISM: Homo sapiens

<400> SEQUENCE: 76

Cys Ser His Ser Met Lys Tyr Phe Phe Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Gly Pro Glu Tyr Trp Asp Arg Glu Thr
    50                  55                  60

Gln Lys Tyr Lys Arg Gln Ala Gln Thr Asp Arg Val Ser Leu Arg Asn
65                  70                  75                  80

Leu Arg Gly Cys Tyr Asn Gln Ser Glu Ala Gly Ser His Thr Leu Gln
                85                  90                  95

Trp Met Cys Gly Cys Asp Leu Gly Pro Asp Gly Arg Leu Leu Arg Gly
            100                 105                 110

Tyr Asp Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Arg Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Glu His Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Trp Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Met Val Pro Ser Gly Glu Glu Gln Arg
```

```
                      245                 250                 255
Tyr Thr Cys His Val Gln His Glu Gly Leu Pro Glu Pro Leu Thr Leu
            260                 265                 270
Arg Trp Glu Pro
        275

<210> SEQ ID NO 77
<211> LENGTH: 276
<212> TYPE: PRT
<213> ORGANISM: Homo sapiens

<400> SEQUENCE: 77

Gly Ser His Ser Met Arg Tyr Phe Ser Thr Ser Val Ser Trp Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Glu Pro Trp Val Glu Gln Gly Pro Glu Tyr Trp Asp Arg Glu Thr
    50                  55                  60

Gln Lys Tyr Lys Arg Gln Ala Gln Ala Asp Arg Val Asn Leu Arg Lys
65                  70                  75                  80

Leu Arg Gly Cys Tyr Asn Gln Ser Glu Asp Gly Ser His Thr Leu Gln
                85                  90                  95

Arg Met Phe Gly Cys Asp Leu Gly Pro Asp Gly Arg Leu Leu Arg Gly
            100                 105                 110

Tyr Asn Gln Phe Ala Tyr Asp Gly Lys Asp Tyr Ile Ala Leu Asn Glu
            115                 120                 125

Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Arg Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Glu His Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Trp Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Leu Thr Leu
            260                 265                 270

Arg Trp Lys Pro
        275

<210> SEQ ID NO 78
<211> LENGTH: 275
<212> TYPE: PRT
<213> ORGANISM: Homo sapiens

<400> SEQUENCE: 78

Cys Ser His Ser Met Arg Tyr Phe Asp Thr Ala Val Ser Arg Pro Gly
```

```
            1               5                  10                 15
Arg Gly Glu Pro Arg Phe Ile Ser Val Gly Tyr Val Asp Asp Thr Gln
                20                  25                 30

Phe Val Arg Phe Asp Ser Asp Ala Ala Ser Pro Arg Gly Glu Pro Arg
                35                  40                 45

Ala Pro Trp Val Glu Gln Glu Gly Pro Glu Tyr Trp Asp Arg Glu Thr
            50                  55                 60

Gln Lys Tyr Lys Arg Gln Ala Gln Ala Asp Arg Val Asn Leu Arg Lys
65                      70                 75                 80

Leu Arg Gly Cys Tyr Asn Gln Ser Glu Asp Gly Ser His Thr Leu Gln
                    85                  90                 95

Trp Met Tyr Gly Cys Asp Leu Gly Pro Asp Gly Arg Leu Leu Arg Gly
                100                 105                110

Tyr Asp Gln Ser Ala Tyr Asp Gly Lys Asp Tyr Ile Ala Leu Asn Glu
                115                 120                125

Asp Leu Arg Ser Trp Thr Ala Ala Asp Thr Ala Ala Gln Ile Thr Gln
130                 135                 140

Arg Lys Trp Glu Ala Ala Arg Glu Ala Glu Gln Trp Arg Ala Tyr Leu
145                 150                 155                160

Glu Gly Thr Cys Val Glu Trp Leu Arg Arg Tyr Leu Glu Asn Gly Lys
                    165                 170                175

Glu Thr Leu Gln Arg Ala Glu His Pro Lys Thr His Val Thr His His
                180                 185                190

Pro Val Ser Asp His Glu Ala Thr Leu Arg Cys Trp Ala Leu Gly Phe
                195                 200                 205

Tyr Pro Ala Glu Ile Thr Leu Thr Trp Gln Arg Asp Gly Glu Asp Gln
                210                 215                 220

Thr Gln Asp Thr Glu Leu Val Glu Thr Arg Pro Ala Gly Asp Gly Thr
225                 230                 235                240

Phe Gln Lys Trp Ala Ala Val Val Val Pro Ser Gly Glu Glu Gln Arg
                    245                 250                255

Tyr Thr Cys His Val Gln His Glu Gly Leu Pro Glu Pro Leu Thr Leu
                260                 265                 270

Arg Trp Glu
            275

<210> SEQ ID NO 79
<211> LENGTH: 276
<212> TYPE: PRT
<213> ORGANISM: Homo sapiens

<400> SEQUENCE: 79

Cys Ser His Ser Met Arg Tyr Phe Asp Thr Ala Val Ser Arg Pro Gly
1               5                   10                 15

Arg Gly Glu Pro Arg Phe Ile Ser Val Gly Tyr Val Asp Asp Thr Gln
                20                  25                 30

Phe Val Arg Phe Asp Ser Asp Ala Ala Ser Pro Arg Gly Glu Pro Arg
                35                  40                 45

Ala Pro Trp Val Glu Gln Glu Gly Pro Glu Tyr Trp Asp Arg Glu Thr
            50                  55                 60

Gln Lys Tyr Lys Arg Gln Ala Gln Ala Asp Arg Val Ser Leu Arg Asn
65                      70                 75                 80

Leu Arg Gly Cys Tyr Asn Gln Ser Glu Asp Gly Ser His Thr Leu Gln
                    85                  90                 95
```

```
Arg Met Ser Gly Cys Asp Leu Gly Pro Asp Gly Arg Leu Leu Arg Gly
            100                 105                 110

Tyr Asp Gln Ser Ala Tyr Asp Gly Lys Asp Tyr Ile Ala Leu Asn Glu
            115                 120                 125

Asp Leu Arg Ser Trp Thr Ala Ala Asp Thr Ala Ala Gln Ile Thr Gln
        130                 135                 140

Arg Lys Leu Glu Ala Ala Arg Ala Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Glu Pro Pro Lys Thr His Val Thr His His
            180                 185                 190

Pro Leu Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Met Gln His Glu Gly Leu Gln Glu Pro Leu Thr Leu
            260                 265                 270

Ser Trp Glu Pro
            275

<210> SEQ ID NO 80
<211> LENGTH: 276
<212> TYPE: PRT
<213> ORGANISM: Homo sapiens

<400> SEQUENCE: 80

Cys Ser His Ser Met Arg Tyr Phe Tyr Thr Ala Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Lys Tyr Lys Arg Gln Ala Gln Thr Asp Arg Val Ser Leu Arg Asn
65                  70                  75                  80

Leu Arg Gly Cys Tyr Asn Gln Ser Glu Ala Gly Ser His Thr Leu Gln
                85                  90                  95

Trp Met Tyr Gly Cys Asp Leu Gly Pro Asp Gly Arg Leu Leu Arg Gly
            100                 105                 110

Tyr Asp Gln Ser Ala Tyr Asp Gly Lys Asp Tyr Ile Ala Leu Asn Glu
            115                 120                 125

Asp Leu Arg Ser Trp Thr Ala Ala Asp Thr Ala Ala Gln Ile Thr Gln
        130                 135                 140

Arg Lys Trp Glu Ala Ala Arg Ala Ala Glu Gln Gln Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Glu His Pro Lys Thr His Val Thr His His
            180                 185                 190
```

```
Leu Val Ser Asp His Glu Ala Thr Leu Arg Cys Trp Ala Leu Gly Phe
            195                 200                 205

Tyr Pro Ala Glu Ile Thr Leu Thr Trp Gln Arg Asp Gly Glu Asp Gln
        210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Pro Ser Gly Glu Glu Gln Arg
                245                 250                 255

Tyr Thr Cys His Val Gln His Glu Gly Leu Pro Glu Pro Leu Thr Leu
                260                 265                 270

Arg Trp Glu Pro
            275

<210> SEQ ID NO 81
<211> LENGTH: 276
<212> TYPE: PRT
<213> ORGANISM: Homo sapiens

<400> SEQUENCE: 81

Gly Ser His Ser Met Arg Tyr Phe Tyr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Arg Asn Thr
    50                  55                  60

Arg Asn Val Lys Ala His Ser Gln Thr Asp Arg Glu Ser Leu Arg Ile
65                  70                  75                  80

Ala Leu Arg Cys Tyr Asn Gln Ser Glu Asp Gly Ser His Thr Ile Gln
                85                  90                  95

Arg Met Tyr Gly Cys Asp Val Gly Pro Asp Gly Arg Phe Leu Arg Gly
            100                 105                 110

Tyr Gln Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Gln
130                 135                 140

Arg Lys Trp Glu Thr Ala His Glu Ala Glu Gln Trp Arg Ala Tyr Leu
145                 150                 155                 160

Glu Gly Arg Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ser Val Val Pro Ser Gly Gln Glu Gln Arg
                245                 250                 255

Tyr Thr Cys His Val Gln His Glu Gly Leu Pro Lys Pro Leu Thr Leu
                260                 265                 270

Arg Trp Glu Pro
```

-continued

```
              275

<210> SEQ ID NO 82
<211> LENGTH: 276
<212> TYPE: PRT
<213> ORGANISM: Homo sapiens

<400> SEQUENCE: 82

Gly Ser His Ser Met Arg Tyr Phe Tyr Thr Ser Val Ser Arg Pro Gly
1               5                   10                  15

Arg Gly Glu Pro Arg Phe Ile Ala Val Gly Tyr Val Asp Asp Thr Gln
                20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Arg Asn Thr
    50                  55                  60

Arg Asn Val Lys Ala His Ser Gln Thr Asp Arg Ala Asn Leu Gly Thr
65                  70                  75                  80

Leu Arg Gly Cys Tyr Asn Gln Ser Glu Asp Gly Ser His Thr Ile Gln
                85                  90                  95

Arg Met Tyr Gly Cys Asp Val Gly Pro Asp Gly Arg Phe Leu Arg Gly
            100                 105                 110

Tyr Gln Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Gln
    130                 135                 140

Arg Lys Trp Glu Thr Ala His Glu Ala Glu Gln Trp Arg Ala Tyr Leu
145                 150                 155                 160

Glu Gly Arg Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ser Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro
        275

<210> SEQ ID NO 83
<211> LENGTH: 276
<212> TYPE: PRT
<213> ORGANISM: Homo sapiens

<400> SEQUENCE: 83

Gly Ser His Ser Met Arg Tyr Phe Thr Thr Ser Val Ser Arg Pro Gly
1               5                   10                  15

Arg Gly Glu Pro Arg Phe Ile Ala Val Gly Tyr Val Asp Asp Thr Gln
                20                  25                  30

Phe Val Arg Phe Asp Ser Asp Ala Ala Ser Gln Arg Met Glu Pro Arg
```

```
            35                  40                  45
Ala Pro Trp Ile Glu Gln Glu Gly Pro Glu Tyr Trp Asp Leu Gln Thr
 50                  55                  60
Arg Asn Val Lys Ala Gln Ser Gln Thr Asp Arg Ala Asn Leu Gly Thr
 65                  70                  75                  80
Leu Arg Gly Cys Tyr Asn Gln Ser Glu Ala Gly Ser His Thr Ile Gln
                 85                  90                  95
Met Met Tyr Gly Cys Asp Val Gly Ser Asp Gly Arg Phe Leu Arg Gly
                100                 105                 110
Tyr Arg Gln Asp Ala Tyr Asp Gly Lys Asp Tyr Ile Ala Leu Asn Glu
            115                 120                 125
Asp Leu Arg Ser Trp Thr Ala Ala Asp Met Ala Ala Gln Ile Thr Gln
        130                 135                 140
Arg Lys Trp Glu Ala Ala Arg Val Ala Glu Gln Leu Arg Ala Tyr Leu
145                 150                 155                 160
Glu Gly Thr Cys Val Glu Trp Leu Arg Arg Tyr Leu Glu Asn Gly Lys
                165                 170                 175
Glu Thr Leu Gln Arg Thr Asp Ala Pro Lys Thr His Met Thr His His
            180                 185                 190
Ala Val Ser Asp His Glu Ala Thr Leu Arg Cys Trp Ala Leu Ser Phe
        195                 200                 205
Tyr Pro Ala Glu Ile Thr Leu Thr Trp Gln Arg Asp Gly Glu Asp Gln
210                 215                 220
Thr Gln Asp Thr Glu Leu Val Glu Thr Arg Pro Ala Gly Asp Gly Thr
225                 230                 235                 240
Phe Gln Lys Trp Ala Ser Val Val Pro Ser Gly Gln Glu Gln Arg
                245                 250                 255
Tyr Thr Cys His Val Gln His Glu Gly Leu Pro Lys Pro Leu Thr Leu
            260                 265                 270
Arg Trp Glu Pro
        275

<210> SEQ ID NO 84
<211> LENGTH: 276
<212> TYPE: PRT
<213> ORGANISM: Homo sapiens

<400> SEQUENCE: 84

Gly Ser His Ser Met Arg Tyr Phe Tyr Thr Ser Met Ser Arg Pro Gly
 1               5                  10                  15
Arg Gly Glu Pro Arg Phe Ile Ala Val Gly Tyr Val Asp Asp Thr Gln
             20                  25                  30
Phe Val Arg Phe Asp Ser Asp Ala Ala Ser Gln Arg Met Glu Pro Arg
         35                  40                  45
Ala Pro Trp Ile Glu Gln Glu Gly Pro Glu Tyr Trp Asp Arg Asn Thr
 50                  55                  60
Arg Asn Val Lys Ala Gln Ser Gln Thr Asp Arg Val Asp Leu Gly Thr
 65                  70                  75                  80
Leu Arg Gly Cys Tyr Asn Gln Ser Glu Ala Gly Ser His Thr Ile Gln
                 85                  90                  95
Arg Met Tyr Gly Cys Asp Val Gly Pro Asp Gly Arg Phe Leu Arg Gly
                100                 105                 110
Tyr His Gln Tyr Ala Tyr Asp Gly Lys Asp Tyr Ile Ala Leu Lys Glu
            115                 120                 125
```

```
Asp Leu Arg Ser Trp Thr Ala Ala Asp Met Ala Ala Gln Thr Thr Lys
    130                 135                 140

His Lys Trp Glu Ala Ala His Val Ala Glu Gln Trp Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
210                 215                 220

Thr Gln Asp Thr Glu Leu Val Glu Thr Arg Pro Ala Gly Asp Gly Thr
225                 230                 235                 240

Phe Gln Lys Trp Val Ala Val Val Pro Ser Gly Gln Glu Gln Arg
                245                 250                 255

Tyr Thr Cys His Val Gln His Glu Gly Leu Pro Lys Pro Leu Thr Leu
                260                 265                 270

Arg Trp Glu Pro
            275

<210> SEQ ID NO 85
<211> LENGTH: 276
<212> TYPE: PRT
<213> ORGANISM: Homo sapiens

<400> SEQUENCE: 85

Gly Ser His Ser Met Arg Tyr Phe Tyr Thr Ala Met Ser Arg Pro Gly
1               5                   10                  15

Arg Gly Glu Pro Arg Phe Ile Thr Val Gly Tyr Val Asp Asp Thr Gln
            20                  25                  30

Phe Val Arg Phe Asp Ser Asp Ala Thr Ser Pro Arg Met Ala Pro Arg
        35                  40                  45

Ala Pro Trp Ile Glu Gln Glu Gly Pro Glu Tyr Trp Asp Arg Glu Thr
    50                  55                  60

Gln Ile Ser Lys Thr Asn Thr Gln Thr Tyr Arg Glu Asn Leu Arg Thr
65                  70                  75                  80

Ala Leu Arg Cys Tyr Asn Gln Ser Glu Ala Gly Ser His Thr Trp Gln
                85                  90                  95

Thr Met Tyr Gly Cys Asp Leu Gly Pro Asp Gly Arg Leu Leu Arg Gly
                100                 105                 110

His Asn Gln Leu Ala Tyr Asp Gly Lys Asp Tyr Ile Ala Leu Asn Glu
            115                 120                 125

Asp Leu Ser Ser Trp Thr Ala Asp Thr Ala Ala Gln Ile Thr Gln
    130                 135                 140

Leu Lys Trp Glu Ala Ala Arg Val Ala Glu Gln Leu Arg Ala Tyr Leu
145                 150                 155                 160

Glu Gly Glu Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
210                 215                 220
```

Thr Gln Asp Thr Glu Leu Val Glu Thr Arg Pro Ala Gly Asp Arg Thr
225                 230                 235                 240

Phe Gln Lys Trp Ala Ala Val Val Pro Ser Gly Glu Glu Gln Arg
            245                 250                 255

Tyr Thr Cys His Val Gln His Glu Gly Leu Pro Lys Pro Leu Thr Leu
                260                 265                 270

Arg Trp Glu Pro
        275

<210> SEQ ID NO 86
<211> LENGTH: 276
<212> TYPE: PRT
<213> ORGANISM: Homo sapiens

<400> SEQUENCE: 86

Gly Ser His Ser Met Arg Tyr Phe Tyr Thr Ala Met Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Met Ala Pro Arg
        35                  40                  45

Ala Pro Trp Ile Glu Gln Glu Gly Pro Glu Tyr Trp Asp Arg Glu Thr
    50                  55                  60

Gln Ile Ser Lys Thr Asn Thr Gln Thr Tyr Arg Glu Ser Leu Arg Asn
65                  70                  75                  80

Leu Arg Gly Cys Tyr Asn Gln Ser Glu Ala Gly Ser His Thr Leu Gln
                85                  90                  95

Ser Met Tyr Gly Cys Asp Val Gly Pro Asp Gly Arg Leu Leu Arg Gly
            100                 105                 110

His Asp Gln Ser Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Glu Ala Glu Gln Trp Arg Ala Tyr Leu
145                 150                 155                 160

Glu Gly Leu Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Pro Ser Gly Glu Glu Gln Arg
            245                 250                 255

Tyr Thr Cys His Val Gln His Glu Gly Leu Pro Lys Pro Leu Thr Leu
                260                 265                 270

Arg Trp Glu Pro
        275

<210> SEQ ID NO 87
<211> LENGTH: 276
<212> TYPE: PRT

<213> ORGANISM: Homo sapiens

<400> SEQUENCE: 87

```
Gly Ser His Ser Met Arg Tyr Phe His Thr Ser Val Ser Arg Pro Gly
1               5                   10                  15
Arg Gly Glu Pro Arg Phe Ile Thr Val Gly Tyr Val Asp Asp Thr Leu
            20                  25                  30
Phe Val Arg Phe Asp Ser Asp Ala Ala Ser Pro Arg Glu Glu Pro Arg
        35                  40                  45
Ala Pro Trp Ile Glu Gln Gly Pro Glu Tyr Trp Asp Arg Glu Thr
    50                  55                  60
Gln Ile Cys Lys Ala Lys Ala Gln Thr Asp Arg Glu Asp Leu Arg Thr
65                  70                  75                  80
Leu Leu Arg Cys Tyr Asn Gln Ser Glu Ala Gly Ser His Thr Leu Gln
                85                  90                  95
Asn Met Tyr Gly Cys Asp Val Gly Pro Asp Gly Arg Leu Leu Arg Gly
            100                 105                 110
Tyr His Gln Asp Ala Tyr Asp Gly Lys Asp Tyr Ile Ala Leu Asn Glu
        115                 120                 125
Asp Leu Ser Ser Trp Thr Ala Ala Asp Thr Ala Ala Gln Ile Thr Gln
130                 135                 140
Arg Lys Trp Glu Ala Ala Arg Val Ala Glu Gln Leu Arg Ala Tyr Leu
145                 150                 155                 160
Glu Gly Glu Cys Val Glu Trp Leu Arg Arg Tyr Leu Glu Asn Gly Lys
                165                 170                 175
Glu Thr Leu Gln Arg Ala Asp Pro Pro Lys Thr His Val Thr His His
            180                 185                 190
Pro Ile Ser Asp His Glu Ala Thr Leu Arg Cys Trp Ala Leu Gly Phe
        195                 200                 205
Tyr Pro Ala Glu Ile Thr Leu Thr Trp Gln Arg Asp Gly Glu Asp Gln
    210                 215                 220
Thr Gln Asp Thr Glu Leu Val Glu Thr Arg Pro Ala Gly Asp Arg Thr
225                 230                 235                 240
Phe Gln Lys Trp Ala Ala Val Val Val Pro Ser Gly Glu Glu Gln Arg
                245                 250                 255
Tyr Thr Cys His Val Gln His Glu Gly Leu Pro Lys Pro Leu Thr Leu
            260                 265                 270
Arg Trp Glu Pro
        275
```

<210> SEQ ID NO 88
<211> LENGTH: 276
<212> TYPE: PRT
<213> ORGANISM: Homo sapiens

<400> SEQUENCE: 88

```
Gly Ser His Ser Met Arg Tyr Phe Tyr Thr Ala Met Ser Arg Pro Gly
1               5                   10                  15
Arg Gly Glu Pro Arg Phe Ile Ala Val Gly Tyr Val Asp Asp Thr Gln
            20                  25                  30
Phe Val Arg Phe Asp Ser Asp Ala Ala Ser Pro Arg Thr Glu Pro Arg
        35                  40                  45
Ala Pro Trp Ile Glu Gln Glu Gly Pro Glu Tyr Trp Asp Arg Asn Thr
    50                  55                  60
Gln Ile Phe Lys Thr Asn Thr Gln Thr Tyr Arg Glu Ser Leu Arg Asn
```

-continued

```
                65                  70                  75                  80
Leu Arg Gly Cys Tyr Asn Gln Ser Glu Ala Gly Ser His Ile Ile Gln
                    85                  90                  95

Arg Met Tyr Gly Cys Asp Leu Gly Pro Asp Gly Arg Leu Leu Arg Gly
                    100                 105                 110

His Asp Gln Phe Ala Tyr Asp Gly Lys Asp Tyr Ile Ala Leu Asn Glu
                    115                 120                 125

Asp Leu Ser Ser Trp Thr Ala Asp Thr Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Leu Cys Val Glu Trp Leu Arg Arg Tyr Leu Glu Asn Gly Lys
                    165                 170                 175

Glu Thr Leu Gln Arg Ala Asp Pro Pro Lys Thr His Val Thr His His
                    180                 185                 190

Pro Val Ser Asp His Glu Ala Thr Leu Arg Cys Trp Ala Leu Gly Phe
                    195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                    245                 250                 255

Tyr Thr Cys His Val Gln His Glu Gly Leu Pro Lys Pro Leu Thr Leu
                    260                 265                 270

Arg Trp Glu Pro
            275

<210> SEQ ID NO 89
<211> LENGTH: 276
<212> TYPE: PRT
<213> ORGANISM: Homo sapiens

<400> SEQUENCE: 89

Gly Ser His Ser Met Arg Tyr Phe His Thr Ser Val Ser Arg Pro Gly
1               5                   10                  15

Arg Gly Glu Pro Arg Phe Ile Ser Val Gly Tyr Val Asp Asp Thr Gln
                    20                  25                  30

Phe Val Arg Phe Asp Ser Asp Ala Ala Ser Pro Arg Thr Glu Pro Arg
                    35                  40                  45

Ala Pro Trp Ile Glu Gln Glu Gly Pro Glu Tyr Trp Asp Arg Glu Thr
    50                  55                  60

Gln Ile Ser Lys Thr Asn Thr Gln Thr Tyr Arg Glu Asp Leu Arg Thr
65                  70                  75                  80

Leu Leu Arg Cys Tyr Asn Gln Ser Glu Ala Gly Ser His Thr Ile Gln
                    85                  90                  95

Arg Met Ser Gly Cys Asp Val Gly Pro Asp Gly Arg Leu Leu Arg Gly
                    100                 105                 110

Tyr Asn Gln Phe Ala Tyr Asp Gly Lys Asp Tyr Ile Ala Leu Asn Glu
                    115                 120                 125

Asp Leu Ser Ser Trp Thr Ala Asp Thr Ala Ala Gln Ile Thr Gln
    130                 135                 140

Arg Lys Trp Glu Ala Ala Arg Val Ala Glu Gln Asp Arg Ala Tyr Leu
145                 150                 155                 160
```

```
Glu Gly Thr Cys Val Glu Trp Leu Arg Arg Tyr Leu Glu Asn Gly Lys
                165                 170                 175
Glu Thr Leu Gln Arg Ala Asp Pro Pro Lys Thr His Val Thr His His
            180                 185                 190
Pro Ile Ser Asp His Glu Ala Thr Leu Arg Cys Trp Ala Leu Gly Phe
        195                 200                 205
Tyr Pro Ala Glu Ile Thr Leu Thr Trp Gln Arg Asp Gly Glu Asp Gln
    210                 215                 220
Thr Gln Asp Thr Glu Leu Val Glu Thr Arg Pro Ala Gly Asp Arg Thr
225                 230                 235                 240
Phe Gln Lys Trp Ala Ala Val Val Val Pro Ser Gly Glu Glu Gln Arg
                245                 250                 255
Tyr Thr Cys His Val Gln His Glu Gly Leu Pro Lys Pro Leu Thr Leu
                260                 265                 270
Arg Trp Glu Pro
        275

<210> SEQ ID NO 90
<211> LENGTH: 276
<212> TYPE: PRT
<213> ORGANISM: Homo sapiens

<400> SEQUENCE: 90

Gly Ser His Ser Met Arg Tyr Phe Tyr Thr Ser Val Ser Arg Pro Gly
1               5                   10                  15
Arg Gly Glu Pro Arg Phe Ile Ser Val Gly Tyr Val Asp Asp Thr Gln
            20                  25                  30
Phe Val Arg Phe Asp Ser Asp Ala Ala Ser Pro Arg Glu Glu Pro Arg
        35                  40                  45
Ala Pro Trp Ile Glu Gln Glu Gly Pro Glu Tyr Trp Asp Arg Asn Thr
    50                  55                  60
Gln Ile Cys Lys Thr Asn Thr Gln Thr Tyr Arg Glu Asn Leu Arg Ile
65                  70                  75                  80
Ala Leu Arg Cys Tyr Asn Gln Ser Glu Ala Gly Ser His Thr Leu Gln
                85                  90                  95
Arg Met Tyr Gly Cys Asp Val Gly Pro Asp Gly Arg Leu Leu Arg Gly
                100                 105                 110
His Asn Gln Phe Ala Tyr Asp Gly Lys Asp Tyr Ile Ala Leu Asn Glu
            115                 120                 125
Asp Leu Ser Ser Trp Thr Ala Ala Asp Thr Ala Ala Gln Ile Thr Gln
        130                 135                 140
Arg Lys Trp Glu Ala Ala Arg Val Ala Glu Gln Leu Arg Thr Tyr Leu
145                 150                 155                 160
Glu Gly Thr Cys Val Glu Trp Leu Arg Arg Tyr Leu Glu Asn Gly Lys
                165                 170                 175
Glu Thr Leu Gln Arg Ala Asp Pro Pro Lys Thr His Val Thr His His
            180                 185                 190
Pro Ile Ser Asp His Glu Ala Thr Leu Arg Cys Trp Ala Leu Gly Phe
        195                 200                 205
Tyr Pro Ala Glu Ile Thr Leu Thr Trp Gln Arg Asp Gly Glu Asp Gln
    210                 215                 220
Thr Gln Asp Thr Glu Leu Val Glu Thr Arg Pro Ala Gly Asp Arg Thr
225                 230                 235                 240
Phe Gln Lys Trp Ala Ala Val Val Val Pro Ser Gly Glu Glu Gln Arg
                245                 250                 255
```

-continued

```
Tyr Thr Cys His Val Gln His Glu Gly Leu Pro Lys Pro Leu Thr Leu
            260                 265                 270

Arg Trp Glu Pro
        275

<210> SEQ ID NO 91
<211> LENGTH: 276
<212> TYPE: PRT
<213> ORGANISM: Homo sapiens

<400> SEQUENCE: 91

Gly Ser His Ser Met Arg Tyr Phe His Thr Ala Met Ser Arg Pro Gly
1               5                   10                  15

Arg Gly Glu Pro Arg Phe Ile Thr Val Gly Tyr Val Asp Asp Thr Leu
            20                  25                  30

Phe Val Arg Phe Asp Ser Asp Ala Thr Ser Pro Arg Lys Glu Pro Arg
        35                  40                  45

Ala Pro Trp Ile Glu Gln Glu Gly Pro Glu Tyr Trp Asp Arg Glu Thr
    50                  55                  60

Gln Ile Ser Lys Thr Asn Thr Gln Thr Tyr Arg Glu Ser Leu Arg Asn
65                  70                  75                  80

Leu Arg Gly Cys Tyr Asn Gln Ser Glu Ala Gly Ser His Thr Leu Gln
                85                  90                  95

Ser Met Tyr Gly Cys Asp Val Gly Pro Asp Gly Arg Leu Leu Arg Gly
            100                 105                 110

His Asn Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Val Ala Glu Gln Asp Arg Ala Tyr Leu
145                 150                 155                 160

Glu Gly Thr Cys Val Glu Trp Leu Arg Arg Tyr Leu Glu Asn Gly Lys
                165                 170                 175

Asp Thr Leu Glu Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro
        275

<210> SEQ ID NO 92
<211> LENGTH: 276
<212> TYPE: PRT
<213> ORGANISM: Homo sapiens

<400> SEQUENCE: 92

Gly Ser His Ser Met Arg Tyr Phe Tyr Thr Ala Met Ser Arg Pro Gly
1               5                   10                  15
```

```
Arg Gly Glu Pro Arg Phe Ile Thr Val Gly Tyr Val Asp Asp Thr Leu
             20                  25                  30

Phe Val Arg Phe Asp Ser Asp Ala Thr Ser Pro Arg Lys Glu Pro Arg
         35                  40                  45

Ala Pro Trp Ile Glu Gln Glu Gly Pro Glu Tyr Trp Asp Arg Glu Thr
     50                  55                  60

Gln Ile Ser Lys Thr Asn Thr Gln Thr Tyr Arg Glu Asn Leu Arg Thr
 65                  70                  75                  80

Ala Leu Arg Cys Tyr Asn Gln Ser Glu Ala Gly Ser His Ile Ile Gln
                 85                  90                  95

Arg Met Tyr Gly Cys Asp Val Gly Pro Asp Gly Arg Leu Leu Arg Gly
            100                 105                 110

Tyr Asp Gln Tyr Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
130                 135                 140

Arg Lys Trp Glu Ala Ala Arg Val Ala Glu Gln Asp Arg Ala Tyr Leu
145                 150                 155                 160

Glu Gly Leu Cys Val Glu Ser Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Val Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro
        275

<210> SEQ ID NO 93
<211> LENGTH: 276
<212> TYPE: PRT
<213> ORGANISM: Homo sapiens

<400> SEQUENCE: 93

Gly Ser His Ser Met Arg Tyr Phe His Thr Ala Met Ser Arg Pro Gly
 1               5                  10                  15

Arg Gly Glu Pro Arg Phe Ile Thr Val Gly Tyr Val Asp Asp Thr Leu
             20                  25                  30

Phe Val Arg Phe Asp Ser Asp Ala Thr Ser Pro Arg Lys Glu Pro Arg
         35                  40                  45

Ala Pro Trp Ile Glu Gln Glu Gly Pro Glu Tyr Trp Asp Arg Glu Thr
     50                  55                  60

Gln Ile Ser Lys Thr Asn Thr Gln Thr Tyr Arg Glu Asn Leu Arg Ile
 65                  70                  75                  80

Ala Leu Arg Cys Tyr Asn Gln Ser Glu Ala Gly Ser His Thr Trp Gln
                 85                  90                  95

Arg Met Tyr Gly Cys Asp Leu Gly Pro Asp Gly Arg Leu Leu Arg Gly
```

-continued

```
                100             105             110
Tyr Asn Gln Leu Ala Tyr Asp Gly Lys Asp Tyr Ile Ala Leu Asn Glu
            115                 120                 125
Asp Leu Ser Ser Trp Thr Ala Asp Thr Ala Gln Ile Thr Gln
    130                 135                 140
Arg Lys Trp Glu Ala Ala Arg Glu Ala Glu Gln Leu Arg Ala Tyr Leu
145                 150                 155                 160
Glu Gly Leu Cys Val Glu Trp Leu Arg Arg Tyr Leu Glu Asn Gly Lys
                165                 170                 175
Glu Thr Leu Gln Arg Ala Asp Pro Pro Lys Thr His Val Thr His His
            180                 185                 190
Pro Ile Ser Asp His Glu Ala Thr Leu Arg Cys Trp Ala Leu Gly Phe
            195                 200                 205
Tyr Pro Ala Glu Ile Thr Leu Thr Trp Gln Arg Asp Gly Glu Asp Gln
            210                 215                 220
Thr Gln Asp Thr Glu Leu Val Glu Thr Arg Pro Ala Gly Asp Arg Thr
225                 230                 235                 240
Phe Gln Lys Trp Ala Ala Val Val Pro Ser Gly Glu Glu Gln Arg
                245                 250                 255
Tyr Thr Cys His Val Gln His Glu Gly Leu Pro Lys Pro Leu Thr Leu
            260                 265                 270
Arg Trp Glu Pro
        275

<210> SEQ ID NO 94
<211> LENGTH: 276
<212> TYPE: PRT
<213> ORGANISM: Homo sapiens

<400> SEQUENCE: 94

Gly Ser His Ser Met Arg Tyr Phe Tyr Thr Ala Met Ser Arg Pro Gly
1               5                   10                  15
Arg Gly Glu Pro Arg Phe Ile Ala Val Gly Tyr Val Asp Asp Thr Gln
            20                  25                  30
Phe Val Arg Phe Asp Ser Asp Ala Ala Ser Pro Arg Thr Glu Pro Arg
        35                  40                  45
Ala Pro Trp Ile Glu Gln Glu Gly Pro Glu Tyr Trp Asp Arg Glu Thr
    50                  55                  60
Gln Ile Ser Lys Thr Asn Thr Gln Thr Tyr Arg Glu Asn Leu Arg Ile
65                  70                  75                  80
Ala Leu Arg Cys Tyr Asn Gln Ser Glu Ala Gly Ser His Thr Trp Gln
                85                  90                  95
Thr Met Tyr Gly Cys Asp Val Gly Pro Asp Gly Arg Leu Leu Arg Gly
                100                 105                 110
His Asn Gln Tyr Ala Tyr Asp Gly Lys Asp Tyr Ile Ala Leu Asn Glu
            115                 120                 125
Asp Leu Ser Ser Trp Thr Ala Asp Thr Ala Gln Ile Thr Gln
    130                 135                 140
Arg Lys Trp Glu Ala Ala Arg Glu Ala Glu Gln Leu Arg Ala Tyr Leu
145                 150                 155                 160
Glu Gly Leu Cys Val Glu Trp Leu Arg Arg His Leu Glu Asn Gly Lys
                165                 170                 175
Glu Thr Leu Gln Arg Ala Asp Pro Pro Lys Thr His Val Thr His His
            180                 185                 190
```

```
Pro Val Ser Asp His Glu Ala Thr Leu Arg Cys Trp Ala Leu Gly Phe
            195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro
        275

<210> SEQ ID NO 95
<211> LENGTH: 276
<212> TYPE: PRT
<213> ORGANISM: Homo sapiens

<400> SEQUENCE: 95

Gly Ser His Ser Met Arg Tyr Phe Tyr Thr Ala Met Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Tyr Lys Ala Gln Ala Gln Thr Asp Arg Glu Ser Leu Arg Asn
65                  70                  75                  80

Leu Arg Gly Cys Tyr Asn Gln Ser Glu Ala Gly Ser His Thr Trp Gln
                85                  90                  95

Thr Met Tyr Gly Cys Asp Leu Gly Pro Asp Gly Arg Leu Leu Arg Gly
            100                 105                 110

His Asn Gln Leu Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Glu Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro
        275
```

<210> SEQ ID NO 96
<211> LENGTH: 276
<212> TYPE: PRT
<213> ORGANISM: Homo sapiens

<400> SEQUENCE: 96

```
Gly Ser His Ser Met Arg Tyr Phe Tyr Thr Ala Val Ser Arg Pro Gly
1               5                   10                  15

Arg Gly Glu Pro His Phe Ile Ala Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Lys Tyr Lys Arg Gln Ala Gln Thr Asp Arg Val Ser Leu Arg Asn
65                  70                  75                  80

Leu Arg Gly Cys Tyr Asn Gln Ser Glu Ala Arg Ser His Ile Ile Gln
                85                  90                  95

Arg Met Tyr Gly Cys Asp Val Gly Pro Asp Gly Arg Leu Leu Arg Gly
            100                 105                 110

Tyr Asp Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Leu Arg Ala Tyr Leu
145                 150                 155                 160

Glu Gly Leu Cys Val Glu Trp Leu Arg Arg Tyr Leu Lys Asn Gly Lys
                165                 170                 175

Glu Thr Leu Gln Arg Ala Glu His Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Trp Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Leu Thr Leu
            260                 265                 270

Arg Trp Glu Pro
        275
```

<210> SEQ ID NO 97
<211> LENGTH: 276
<212> TYPE: PRT
<213> ORGANISM: Homo sapiens

<400> SEQUENCE: 97

```
Cys Ser His Ser Met Arg Tyr Phe Asp Thr Ala Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Gly Glu Pro Arg
        35                  40                  45
```

Ala Pro Trp Val Glu Gln Gly Pro Glu Tyr Trp Asp Arg Glu Thr
 50                  55                  60

Gln Lys Tyr Lys Arg Gln Ala Gln Ala Asp Arg Val Ser Leu Arg Asn
 65                  70                  75                  80

Leu Arg Gly Cys Tyr Asn Gln Ser Glu Asp Gly Ser His Thr Phe Gln
                 85                  90                  95

Arg Met Tyr Gly Cys Asp Leu Gly Pro Asp Gly Arg Leu Leu Arg Gly
                100                 105                 110

Tyr Asp Gln Phe Ala Tyr Asp Gly Lys Asp Tyr Ile Ala Leu Asn Glu
            115                 120                 125

Asp Leu Arg Ser Trp Thr Ala Ala Asp Thr Ala Ala Gln Ile Thr Gln
130                 135                 140

Arg Lys Leu Glu Ala Ala Arg Ala Ala Glu Gln Asp Arg Ala Tyr Leu
145                 150                 155                 160

Glu Gly Thr Cys Val Glu Trp Leu Arg Arg Tyr Leu Glu Asn Gly Lys
                165                 170                 175

Lys Thr Leu Gln Arg Ala Glu Pro Pro Lys Thr His Val Thr His His
            180                 185                 190

Pro Leu Ser Asp His Glu Ala Thr Leu Arg Cys Trp Ala Leu Gly Phe
            195                 200                 205

Tyr Pro Ala Glu Ile Thr Leu Thr Trp Gln Arg Asp Gly Glu Asp Gln
210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Met Gln His Glu Gly Leu Gln Glu Pro Leu Thr Leu
                260                 265                 270

Ser Trp Glu Pro
            275

<210> SEQ ID NO 98
<211> LENGTH: 276
<212> TYPE: PRT
<213> ORGANISM: Homo sapiens

<400> SEQUENCE: 98

Cys Ser His Ser Met Arg Tyr Phe Tyr Thr Ala Val Ser Arg Pro Gly
1               5                   10                  15

Arg Gly Glu Pro Arg Phe Ile Ala Val Gly Tyr Val Asp Asp Thr Gln
                20                  25                  30

Phe Val Gln Phe Asp Ser Asp Ala Ala Ser Pro Arg Gly Glu Pro Arg
            35                  40                  45

Ala Pro Trp Val Glu Gln Gly Pro Glu Tyr Trp Asp Arg Glu Thr
 50                  55                  60

Gln Lys Tyr Lys Arg Gln Ala Gln Thr Asp Arg Val Ser Leu Arg Asn
 65                  70                  75                  80

Leu Arg Gly Cys Tyr Asn Gln Ser Glu Ala Gly Ser His Thr Leu Gln
                 85                  90                  95

Arg Met Tyr Gly Cys Asp Leu Gly Pro Asp Gly Arg Leu Leu Arg Gly
                100                 105                 110

Tyr Asn Gln Phe Ala Tyr Asp Gly Lys Asp Tyr Ile Ala Leu Asn Glu
            115                 120                 125

Asp Leu Arg Ser Trp Thr Ala Ala Asp Thr Ala Ala Gln Ile Thr Gln

```
                130                 135                 140
Arg Lys Trp Glu Ala Ala Arg Thr Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Lys Thr Leu Gln Arg Ala Glu His Pro Lys Thr His Val Thr His His
                180                 185                 190

Pro Val Ser Asp His Glu Ala Thr Leu Arg Cys Trp Ala Leu Gly Phe
                195                 200                 205

Tyr Pro Ala Glu Ile Thr Leu Thr Trp Gln Arg Asp Gly Glu Asp Gln
            210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Leu Thr Leu
                260                 265                 270

Arg Trp Gly Pro
            275

<210> SEQ ID NO 99
<211> LENGTH: 276
<212> TYPE: PRT
<213> ORGANISM: Homo sapiens

<400> SEQUENCE: 99

Cys Ser His Ser Met Arg Tyr Phe Tyr Thr Ala Val Ser Arg Pro Gly
1               5                   10                  15

Arg Gly Glu Pro Arg Phe Ile Ala Val Gly Tyr Val Asp Asp Thr Gln
                20                  25                  30

Phe Val Gln Phe Asp Ser Asp Ala Ala Ser Pro Arg Gly Glu Pro Arg
            35                  40                  45

Ala Pro Trp Val Glu Gln Glu Gly Pro Glu Tyr Trp Asp Arg Glu Thr
        50                  55                  60

Gln Lys Tyr Lys Arg Gln Ala Gln Thr Asp Arg Val Ser Leu Arg Asn
65                  70                  75                  80

Leu Arg Gly Cys Tyr Asn Gln Ser Glu Ala Gly Ser His Thr Leu Gln
                85                  90                  95

Arg Met Tyr Gly Cys Asp Leu Gly Pro Asp Gly Arg Leu Leu Arg Gly
                100                 105                 110

Tyr Asn Gln Phe Ala Tyr Asp Gly Lys Asp Tyr Ile Ala Leu Asn Glu
            115                 120                 125

Asp Leu Arg Ser Trp Thr Ala Ala Asp Lys Ala Ala Gln Ile Thr Gln
130                 135                 140

Arg Lys Trp Glu Ala Ala Arg Glu Ala Glu Gln Arg Arg Ala Tyr Leu
145                 150                 155                 160

Glu Gly Thr Cys Val Glu Trp Leu Arg Arg Tyr Leu Glu Asn Gly Lys
                165                 170                 175

Lys Thr Leu Gln Arg Ala Glu His Pro Lys Thr His Val Thr His His
                180                 185                 190

Pro Val Ser Asp His Glu Ala Thr Leu Arg Cys Trp Ala Leu Gly Phe
                195                 200                 205

Tyr Pro Ala Glu Ile Thr Leu Thr Trp Gln Arg Asp Gly Glu Asp Gln
            210                 215                 220
```

```
Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
            245                 250                 255

Tyr Thr Cys His Val Gln His Glu Gly Leu Pro Glu Pro Leu Thr Leu
                260                 265                 270

Arg Trp Gly Pro
        275

<210> SEQ ID NO 100
<211> LENGTH: 276
<212> TYPE: PRT
<213> ORGANISM: Homo sapiens

<400> SEQUENCE: 100

Cys Ser His Ser Met Arg Tyr Phe Tyr Thr Ala Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Lys Tyr Lys Arg Gln Ala Gln Ala Asp Arg Val Ser Leu Arg Asn
65                  70                  75                  80

Leu Arg Gly Cys Tyr Asn Gln Ser Glu Ala Gly Ser His Thr Leu Gln
                85                  90                  95

Arg Met Tyr Gly Cys Asp Leu Gly Pro Asp Gly Arg Leu Leu Arg Gly
            100                 105                 110

Tyr Asp Gln Ser Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Trp Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Glu His Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
            245                 250                 255

Tyr Thr Cys His Val Gln His Glu Gly Leu Pro Glu Pro Leu Thr Leu
                260                 265                 270

Arg Trp Glu Pro
        275

<210> SEQ ID NO 101
<211> LENGTH: 276
<212> TYPE: PRT
<213> ORGANISM: Homo sapiens
```

<400> SEQUENCE: 101

Cys Ser His Ser Met Arg Tyr Phe Tyr Thr Ala Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Lys Tyr Lys Arg Gln Ala Gln Ala Asp Arg Val Ser Leu Arg Asn
65                  70                  75                  80

Leu Arg Gly Cys Tyr Asn Gln Ser Glu Ala Gly Ser His Thr Leu Gln
                85                  90                  95

Trp Met Tyr Gly Cys Asp Leu Gly Pro Asp Gly Arg Leu Leu Arg Gly
                100                 105                 110

Tyr Asp Gln Ser Ala Tyr Asp Gly Lys Asp Tyr Ile Ala Leu Asn Glu
            115                 120                 125

Asp Leu Arg Ser Trp Thr Ala Ala Asp Thr Ala Ala Gln Ile Thr Gln
130                 135                 140

Arg Lys Trp Glu Ala Ala Arg Glu Ala Glu Gln Trp Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Glu His Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Leu Thr Leu
            260                 265                 270

Arg Trp Glu Pro
            275

<210> SEQ ID NO 102
<211> LENGTH: 276
<212> TYPE: PRT
<213> ORGANISM: Homo sapiens

<400> SEQUENCE: 102

Cys Ser His Ser Met Arg Tyr Phe Ser Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Lys Tyr Lys Arg Gln Ala Gln Thr Asp Arg Val Ser Leu Arg Asn
65                  70                  75                  80

```
Leu Arg Gly Cys Tyr Asn Gln Ser Glu Ala Gly Ser His Thr Leu Gln
                85                  90                  95

Trp Met Phe Gly Cys Asp Leu Gly Pro Asp Gly Arg Leu Leu Arg Gly
            100                 105                 110

Tyr Asp Gln Ser Ala Tyr Asp Gly Lys Asp Tyr Ile Ala Leu Asn Glu
        115                 120                 125

Asp Leu Arg Ser Trp Thr Ala Asp Thr Ala Ala Gln Ile Thr Gln
    130                 135                 140

Arg Lys Trp Glu Ala Ala Arg Glu Ala Glu Gln Arg Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Glu His Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Trp Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Leu Thr Leu
            260                 265                 270

Arg Trp Glu Pro
        275

<210> SEQ ID NO 103
<211> LENGTH: 276
<212> TYPE: PRT
<213> ORGANISM: Homo sapiens

<400> SEQUENCE: 103

Cys Ser His Ser Met Arg Tyr Phe Tyr Thr Ala Val Ser Arg Pro Gly
1               5                   10                  15

Arg Gly Glu Pro His Phe Ile Ala Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Asn Tyr Lys Arg Gln Ala Gln Thr Asp Arg Val Asn Leu Arg Lys
65                  70                  75                  80

Leu Arg Gly Cys Tyr Asn Gln Ser Glu Ala Gly Ser His Ile Ile Gln
                85                  90                  95

Arg Met Tyr Gly Cys Asp Leu Gly Pro Asp Gly Arg Leu Leu Arg Gly
            100                 105                 110

His Asp Gln Leu Ala Tyr Asp Gly Lys Asp Tyr Ile Ala Leu Asn Glu
        115                 120                 125

Asp Leu Arg Ser Trp Thr Ala Asp Thr Ala Ala Gln Ile Thr Gln
    130                 135                 140

Arg Lys Trp Glu Ala Ala Arg Glu Ala Glu Gln Leu Arg Ala Tyr Leu
145                 150                 155                 160

Glu Gly Thr Cys Val Glu Trp Leu Arg Arg Tyr Leu Glu Asn Gly Lys
```

```
                165                 170                 175
Glu Thr Leu Gln Arg Ala Glu His Pro Lys Thr His Val Thr His His
                180                 185                 190

Pro Val Ser Asp His Glu Ala Thr Leu Arg Cys Trp Ala Leu Gly Phe
                195                 200                 205

Tyr Pro Ala Glu Ile Thr Leu Thr Trp Gln Arg Asp Gly Glu Asp Gln
                210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Leu Thr Leu
                260                 265                 270

Arg Trp Glu Pro
                275

<210> SEQ ID NO 104
<211> LENGTH: 276
<212> TYPE: PRT
<213> ORGANISM: Homo sapiens

<400> SEQUENCE: 104

Gly Ser His Ser Met Arg Tyr Phe Tyr Thr Ala Val Ser Arg Pro Gly
1               5                   10                  15

Arg Gly Glu Pro Arg Phe Ile Ala Val Gly Tyr Val Asp Asp Thr Gln
                20                  25                  30

Phe Val Arg Phe Asp Ser Asp Ala Ala Ser Pro Arg Gly Glu Pro Arg
            35                  40                  45

Ala Pro Trp Val Glu Gln Glu Gly Pro Glu Tyr Trp Asp Arg Glu Thr
        50                  55                  60

Gln Lys Tyr Lys Arg Gln Ala Gln Ala Asp Arg Val Asn Leu Arg Lys
65                  70                  75                  80

Leu Arg Gly Cys Tyr Asn Gln Ser Glu Ala Gly Ser His Thr Ile Gln
                85                  90                  95

Arg Met Tyr Gly Cys Asp Leu Gly Pro Asp Gly Arg Leu Leu Arg Gly
                100                 105                 110

Tyr Asn Gln Phe Ala Tyr Asp Gly Lys Asp Tyr Ile Ala Leu Asn Glu
            115                 120                 125

Asp Leu Arg Ser Trp Thr Ala Ala Asp Thr Ala Ala Gln Ile Ser Gln
130                 135                 140

Arg Lys Leu Glu Ala Ala Arg Glu Ala Glu Gln Leu Arg Ala Tyr Leu
145                 150                 155                 160

Glu Gly Glu Cys Val Glu Trp Leu Arg Gly Tyr Leu Glu Asn Gly Lys
                165                 170                 175

Glu Thr Leu Gln Arg Ala Glu Arg Pro Lys Thr His Val Thr His His
                180                 185                 190

Pro Val Ser Asp His Glu Ala Thr Leu Arg Cys Trp Ala Leu Gly Phe
                195                 200                 205

Tyr Pro Ala Glu Ile Thr Leu Thr Trp Gln Arg Asp Gly Glu Asp Gln
                210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255
```

Tyr Thr Cys His Val Gln His Glu Gly Leu Gln Glu Pro Cys Thr Leu
              260                 265                 270

Arg Trp Lys Pro
        275

<210> SEQ ID NO 105
<211> LENGTH: 99
<212> TYPE: PRT
<213> ORGANISM: Unknown
<220> FEATURE:
<223> OTHER INFORMATION: Description of Unknown: Beta 2 microglobulin
      sequence

<400> SEQUENCE: 105

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met

<210> SEQ ID NO 106
<211> LENGTH: 297
<212> TYPE: DNA
<213> ORGANISM: Unknown
<220> FEATURE:
<223> OTHER INFORMATION: Description of Unknown: Beta 2 microglobulin
      sequence

<400> SEQUENCE: 106
atccagcgta ctccaaagat tcaggtttac tcacgtcatc cagcagagaa tggaaagtca     60
aatttcctga attgctatgt gtctgggttt catccatccg acattgaagt tgacttactg    120
aagaatggag agagaattga aaaagtggag cattcagact tgtctttcag caaggactgg    180
tctttctatc tcttgtacta cactgaattc accccactg aaaaagatga gtatgcctgc     240
cgtgtgaacc atgtgacttt gtcacagccc aagatagtta agtgggatcg agacatg       297

<210> SEQ ID NO 107
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu

```
            50                  55                  60
Leu Tyr Tyr Thr Glu Phe Thr Pro Thr Glu Lys Asp Glu Tyr Ala Cys
 65                  70                  75                  80

Arg Val Asn His Val Thr Leu Cys Gln Pro Lys Ile Val Lys Trp Asp
                 85                  90                  95

Arg Asp Met

<210> SEQ ID NO 108
<211> LENGTH: 297
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
atccagcgta ctccaaagat tcaggtttac tcacgtcatc cagcagagaa tggaaagtca      60
aatttcctga attgctatgt gtctgggttt catccatccg acattgaagt tgacttactg    120
aagaatggag agagaattga aaaagtggag cattcagact tgtctttcag caaggactgg    180
tctttctatc tcttgtacta cactgaattc accccactg aaaaagatga gtatgcctgc     240
cgtgtgaacc atgtgacttt gtgccagccc aagatagtta agtgggatcg agacatg       297

<210> SEQ ID NO 109
<211> LENGTH: 828
<212> TYPE: DNA
<213> ORGANISM: Homo sapiens

<400> SEQUENCE: 109
ggctcccact ccatgaggta tttcttcaca tccgtgtccc ggcccggccg cggggagccc      60
cgcttcatcg ccgtgggcta cgtggacgac acgcagttcg tgcggttcga cagcgacgcc    120
gcgagccaga gatggagcc gcgggcgccg tggatagagc aggaggggcc ggagtattgg    180
gaccaggaga cacggaatat gaaggcccac tcacagactg accgagcgaa cctggggacc    240
ctgcgcggct gctacaacca gagcgaggac ggttctcaca ccatccagat aatgtatggc    300
tgcgacgtgg ggccggacgg gcgcttcctc cgcgggtacc ggcaggacgc ctacgacggc    360
aaggattaca tcgccctgaa cgaggacctg cgctcttgga ccgcggcgga catggcagct    420
cagatcacca agcgcaagtg ggaggcggtc atgcgcgcgg agcagcggag agtctacctg    480
gagggccggt gcgtggacgg gctccgcaga tacctggaga cgggaagga cgcgctgcag    540 cgcacggacc cccccaagac acatatgacc caccacccca tctctgacca tgaggccacc    600
ctgaggtgct gggccctggg cttctaccct gcggagatca cactgacctg gcagcgggat    660
ggggaggacc agacccagga cacggagctc gtggagacca ggcctgcagg ggatggaacc    720
ttccagaagt gggcggctgt ggtggtgcct tctggagagg agcagagata cacctgccat    780
gtgcagcatg agggtctgcc caagcccctc accctgagat gggagctg                 828

<210> SEQ ID NO 110
<211> LENGTH: 828
<212> TYPE: DNA
<213> ORGANISM: Homo sapiens

<400> SEQUENCE: 110
ggctctcact ccatgaggta tttcttcaca tccgtgtccc ggcccggccg cggggagccc      60
cgcttcatcg cagtgggcta cgtggacgac acgcagttcg tgcggttcga cagcgacgcc    120
```

| | |
|---|---|
| gcgagccaga ggatggagcc gcgggcgccg tggatagagc aggagggtcc cgagtattgg | 180 |
| gacggggaga cacggaaagt gaaggcccac tcacagactc accgagtgga cctggggacc | 240 |
| ctgcgcggct gctacaacca gagcgaggcc ggttctcaca ccgtccagag gatgtatggc | 300 |
| tgcgacgtgg ggtcggactg gcgcttcctc cgcgggtacc accagtacgc ctacgacggc | 360 |
| aaggattaca tcgccctgaa agaggacctg cgctcttgga ccgcggcgga catggcagct | 420 |
| cagaccacca agcacaagtg ggaggcggcc catgtggcgg agcagttgag agcctacctg | 480 |
| gagggcacgt gcgtggagtg gctccgcaga tacctggaga cgggaagga gacgctgcag | 540 |
| cgcacggacg ccccaaaac gcatatgact caccacgctg tctctgacca tgaagccacc | 600 |
| ctgaggtgct gggccctgag cttctaccct gcggagatca cactgacctg gcagcgggat | 660 |
| ggggaggacc agacccagga cacggagctc gtggagacca ggcctgcagg ggatggaacc | 720 |
| ttccagaagt gggcggctgt ggtggtgcct tctggacagg agcagagata cacctgccat | 780 |
| gtgcagcatg agggtttgcc caagcccctc accctgagat gggagccg | 828 |

<210> SEQ ID NO 111
<211> LENGTH: 828
<212> TYPE: DNA
<213> ORGANISM: Homo sapiens

<400> SEQUENCE: 111

| | |
|---|---|
| ggctcccact ccatgaggta tttcttcaca tccgtgtccc ggcccggccg cggggagccc | 60 |
| cgcttcatcg ccgtgggcta cgtggacgac acgcagttcg tgcggttcga cagcgacgcc | 120 |
| gcgagccaga ggatggagcc gcgggcgccg tggatagagc aggaggggcc ggagtattgg | 180 |
| gaccaggaga cacggaatgt gaaggcccag tcacagactg accgagtgga cctggggacc | 240 |
| ctgcgcggct gctacaacca gagcgaggcc ggttctcaca ccatccagat aatgtatggc | 300 |
| tgcgacgtgg ggtcggacgg gcgcttcctc cgcgggtacc ggcaggacgc ctacgacggc | 360 |
| aaggattaca tcgccctgaa cgaggacctg cgctcttgga ccgcggcgga catggcggct | 420 |
| cagatcacca agcgcaagtg ggaggcggcc catgaggcgg agcagttgag agcctacctg | 480 |
| gatggcacgt gcgtggagtg gctccgcaga tacctggaga cgggaagga gacgctgcag | 540 |
| cgcacggacc ccccaagac acatatgacc caccaccca tctctgacca tgaggccacc | 600 |
| ctgaggtgct gggccctggg cttctaccct gcggagatca cactgacctg gcagcgggat | 660 |
| ggggaggacc agacccagga cacggagctc gtggagacca ggcctgcagg ggatggaacc | 720 |
| ttccagaagt gggcggctgt ggtggtgcct tctggagagg agcagagata cacctgccat | 780 |
| gtgcagcatg agggtctgcc caagcccctc accctgagat gggagctg | 828 |

<210> SEQ ID NO 112
<211> LENGTH: 828
<212> TYPE: DNA
<213> ORGANISM: Homo sapiens

<400> SEQUENCE: 112

| | |
|---|---|
| ggctcccact ccatgaggta tttctccaca tccgtgtccc ggcccggccg cggggagccc | 60 |
| cgcttcatcg ccgtgggcta cgtggacgac acgcagttcg tgcggttcga cagcgacgcc | 120 |
| gcgagccaga ggatggagcc gcgggcgccg tggatagagc aggaggggcc ggagtattgg | 180 |
| gacgaggaga cagggaaagt gaaggcccac tcacagactg accgagagaa cctgcggatc | 240 |
| gcgctccgct gctacaacca gagcgaggcc ggttctcaca ccctccagat gatgtttggc | 300 |
| tgcgacgtgg ggtcggacgg gcgcttcctc cgcgggtacc accagtacgc ctacgacggc | 360 |

```
aaggattaca tcgccctgaa agaggacctg cgctcttgga ccgcggcgga catggcggct    420
cagatcacca agcgcaagtg ggaggcggcc catgtggcgg agcagcagag agcctacctg    480
gagggcacgt gcgtggacgg gctccgcaga tacctggaga cgggaaggga gacgctgcag    540
cgcacggacc cccccaagac acatatgacc caccacccca tctctgacca tgaggccact    600
ctgagatgct gggccctggg cttctaccct gcggagatca cactgacctg gcagcgggat    660
ggggaggacc agacccagga cacggagctt gtggagacca ggcctgcagg ggatggaacc    720
ttccagaagt gggcagctgt ggtggtacct tctggagagg agcagagata cacctgccat    780
gtgcagcatg agggtctgcc caagcccctc accctgagat gggagcca              828

<210> SEQ ID NO 113
<211> LENGTH: 828
<212> TYPE: DNA
<213> ORGANISM: Homo sapiens

<400> SEQUENCE: 113
ggctcccact ccatgaggta tttctccaca tccgtgtccc ggcccggcag tggagagccc     60
cgcttcatcg cagtgggcta cgtggacgac acgcagttcg tgcggttcga cagcgacgcc    120
gcgagccaga ggatggagcc gcgggcgccg tggatagagc aggagaggcc tgagtattgg    180
gaccaggaga cacggaatgt gaaggccac tcacagactg accgagagaa cctggggacc    240
ctgcgcggct gctacaacca gagcgaggcc ggttctcaca ccatccagat aatgtatggc    300
tgcgacgtgg ggtcggacgg gcgcttcctc cgcgggtatg aacagcacgc ctacgacggc    360
aaggattaca tcgccctgaa cgaggacctg cgctcttgga ccgcggcgga catggcggct    420
cagatcaccc agcgcaagtg ggaggcggcc cgtcgggcgg agcagttgag agcctacctg    480
gagggcacgt gcgtggagtg gctccgcaga tacctggaga cgggaaggga gacgctgcag    540
cgcacggacc cccccaagac acatatgacc caccacccca tctctgacca tgaggccacc    600
ctgaggtgct gggccctggg cttctaccct gcggagatca cactgacctg gcagcgggat    660
ggggaggacc agacccagga cacggagctc gtggagacca ggcctgcagg ggatggaacc    720
ttccagaagt gggcggctgt ggtggtgcct tctggagagg agcagagata cacctgccat    780
gtgcagcatg agggtctgcc caagcccctc accctgagat gggagctg                828

<210> SEQ ID NO 114
<211> LENGTH: 828
<212> TYPE: DNA
<213> ORGANISM: Homo sapiens

<400> SEQUENCE: 114
ggctcccact ccatgaggta tttcaccaca tccgtgtccc ggcccggccg cggggagccc     60
cgcttcatcg ccgtgggcta cgtggacgac acgcagttcg tgcggttcga cagcgacgcc    120
gcgagccaga ggatggagcc gcgggcgccg tggatagagc aggagaggcc tgagtattgg    180
gaccaggaga cacggaatgt gaaggcccac tcacagattg accgagtgga cctggggacc    240
ctgcgcggct gctacaacca gagcgaggcc ggttctcaca ccatccagat gatgtatggc    300
tgcgacgtgg ggtcggacgg gcgcttcctc cgcgggtacc agcaggacgc ctacgacggc    360
aaggattaca tcgccttgaa cgaggacctg cgctcttgga ccgcggcgga catggcggct    420
cagatcaccc agcgcaagtg ggaggcggcc cgtgtggcgg agcagttgag agcctacctg    480
gagggcacgt gcgtggagtg gctccgcaga tacctggaga cgggaaggga gacgctgcag    540
```

| | |
|---|---|
| cgcacggacc cccccaagac gcatatgact caccacgctg tctctgacca tgaggccacc | 600 |
| ctgaggtgct gggccctgag cttctaccct gcggagatca cactgacctg gcagcgggat | 660 |
| ggggaggacc agacccagga cacggagctc gtggagacca ggcctgcagg ggatggaacc | 720 |
| ttccagaagt gggcgtctgt ggtggtgcct tctggacagg agcagagata cacctgccat | 780 |
| gtgcagcatg agggtctccc caagcccctc accctgagat gggagccg | 828 |

<210> SEQ ID NO 115
<211> LENGTH: 828
<212> TYPE: DNA
<213> ORGANISM: Homo sapiens

<400> SEQUENCE: 115

| | |
|---|---|
| ggctcccact ccatgaggta tttcttcaca tccgtgtccc ggcccggccg cggggagccc | 60 |
| cgcttcatcg ccgtgggcta cgtggacgac acgcagttcg tgcggtttga cagcgacgcc | 120 |
| gcgagccaga ggatggagcc gcgggcgccg tggatagagc aggagggggcc ggagtattgg | 180 |
| gaccaggaga cacggaatgt gaaggccac tcacagactg accgagagag cctgcggatc | 240 |
| gcgctccgct gctacaacca gagcgaggcc ggttctcaca ccatccagat gatgtatggc | 300 |
| tgcgacgtgg ggccggacgg gcgcctcctc cgcgggtacc agcaggacgc ctacgacggc | 360 |
| aaggattaca tcgccttgaa cgaggacctg cgctcttgga ccgcggcgga catggcggct | 420 |
| cagatcaccc agcgcaagtg ggaggcggcc cgtgtggcgg agcagttgag agcctacctg | 480 |
| gagggcacgt gcgtggagtg gctccgcaga tacctggaga cgggaaggaa gacgctgcag | 540 |
| cgcacggacg cccccaagac gcatatgact caccacgctg tctctgacca tgaggccacc | 600 |
| ctgaggtgct gggccctgag cttctaccct gcggagatca cactgacctg gcagcgggat | 660 |
| ggggaggacc agacccagga cacggagctt gtggagacca ggcctgcagg ggatggaacc | 720 |
| ttccagaagt gggcgtctgt ggtggtgcct tctggacagg agcagagata cacctgccat | 780 |
| gtgcagcatg agggtctgcc caagcccctc accctgagat gggagccg | 828 |

<210> SEQ ID NO 116
<211> LENGTH: 828
<212> TYPE: DNA
<213> ORGANISM: Homo sapiens

<400> SEQUENCE: 116

| | |
|---|---|
| ggctcccact ccatgaggta tttcaccaca tccgtgtccc ggcccggccg cggggagccc | 60 |
| cgcttcatcg ccgtgggcta cgtggacgac acgcagttcg tgcggttcga cagcgacgcc | 120 |
| gcgagccaga ggatggagcc gcgggcgccg tggatagagc aggagggggcc ggagtattgg | 180 |
| gaccggaaca cacggaatgt gaaggccac tcacagattg accgagtgga cctgggggacc | 240 |
| ctgcgcggct gctacaacca gagcgaggcc ggttctcaca ccatccagat gatgtatggc | 300 |
| tgcgacgtgg ggtcggacgg gcgcttcctc cgcgggtacc agcaggacgc ctacgacggc | 360 |
| aaggattaca tcgccttgaa cgaggacctg cgctcttgga ccgcggcgga catggcggct | 420 |
| cagatcaccc agcgcaagtg ggaggcggcc cgtgtggcgg agcagttgag agcctacctg | 480 |
| gagggcacgt gcgtggagtg gctccgcaga cacctggaga cgggaaggaa gacgctgcag | 540 |
| cgcacggacc cccccaggac gcatatgact caccacgctg tctctgacca tgaggccacc | 600 |
| ctgaggtgct gggccctgag cttctaccct gcggagatca cactgacctg gcagcgggat | 660 |
| ggggaggacc agacccagga cacggagctc gtggagacca ggcctgcagg ggatggaacc | 720 |
| ttccagaagt gggcgtctgt ggtggtgcct tctggacagg agcagagata cacctgccat | 780 | gtgcagcatg agggtctccc caagcccctc accctgagat gggagccg          828

<210> SEQ ID NO 117
<211> LENGTH: 828
<212> TYPE: DNA
<213> ORGANISM: Homo sapiens

<400> SEQUENCE: 117
ggctcccact ccatgaggta tttctacacc tccgtgtccc ggcccggccg cggggagccc      60
cgcttcatcg ccgtgggcta cgtggacgac acgcagttcg tgcggttcga cagcgacgcc     120
gcgagccaga ggatggagcc gcgggcgccg tggatagagc aggaggggcc ggagtattgg     180
gaccggaaca cacggaatgt gaaggcccag tcacagactg accgagtgga cctggggacc     240
ctgcgcggct gctacaacca gagcgaggcc ggttctcaca ccatccagat gatgtatggc     300
tgcgacgtgg ggtcggacgg gcgcttcctc cgcgggtacc ggcaggacgc ctacgacggc     360
aaggattaca tcgccctgaa agaggacctg cgctcttgga ccgcggcgga catggcagct     420
cagaccacca agcacaagtg ggaggcggcc catgtggcgg agcagtggag agcctacctg     480
gagggcacgt gcgtggagtg gctccgcaga tacctggaga cgggaagga gacgctgcag     540
cgcacggacg cccccaaaac gcatatgact caccacgctg tctctgacca tgaagccacc     600
ctgaggtgct gggccctgag cttctaccct gcggagatca cactgacctg gcagcgggat     660
ggggaggacc agacccagga cacggagctc gtggagacca ggcctgcagg ggatggaacc     720
ttccagaagt gggtggctgt ggtggtgcct tctggacagg agcagagata cacctgccat     780
gtgcagcatg agggtttgcc caagcccctc accctgagat gggagccg              828

<210> SEQ ID NO 118
<211> LENGTH: 828
<212> TYPE: DNA
<213> ORGANISM: Homo sapiens

<400> SEQUENCE: 118
ggctcccact ccatgaggta tttctacacc tccgtgtccc ggcccggccg cggggagccc      60
cgcttcatct cagtgggcta cgtggacgac acccagttcg tgaggttcga cagcgacgcc     120
gcgagtccga gagaggagcc gcgggcgccg tggatagagc aggaggggcc ggagtattgg     180
gaccggaaca cacagatcta caaggcccag gcacagactg accgagagag cctgcgaaac     240
ctgcgcggct gctacaacca gagcgaggcc gggtctcaca ccctccagag catgtacggc     300
tgcgacgtgg ggccggacgg gcgcctcctc cgcgggcatg accagtacgc ctacgacggc     360
aaggattaca tcgccctgaa cgaggacctg cgctcctgga ccgccgcgga cacggcggct     420
cagatcaccc agcgcaagtg ggaggcggcc cgtgaggcgg agcagcggag agcctacctg     480
gagggcgagt gcgtggagtg gctccgcaga tacctggaga cgggaagga caagctggag     540
cgcgctgacc cccaaagac acacgtgacc caccaccca tctctgacca tgaggccacc     600
ctgaggtgct gggccctggg tttctaccct gcggagatca cactgacctg gcagcgggat     660
ggcgaggacc aaaactcagga cactgagctt gtggagacca gaccagcagg agatagaacc     720
ttccagaagt gggcagctgt ggtggtgcct tctggagaag agcagagata cacatgccat     780
gtacagcatg aggggctgcc gaagcccctc accctgagat gggagccg              828

<210> SEQ ID NO 119
<211> LENGTH: 828
<212> TYPE: DNA

<213> ORGANISM: Homo sapiens

<400> SEQUENCE: 119

| | | | | | |
|---|---|---|---|---|---|
| ggctcccact | ccatgaggta | tttctacacc | gccgtgtccc | ggcccggccg | cggggagccc | 60 |
| cgcttcatct | cagtgggcta | cgtggacgac | acgcagttcg | tgaggttcga | cagcgacgcc | 120 |
| gcgagtccga | gagaggagcc | gcgggcgccg | tggatagagc | aggaggggcc | ggaatattgg | 180 |
| gaccggaaca | cacagatctg | caagaccaac | acacagactg | accgagagag | cctgcggaac | 240 |
| ctgcgcggct | gctacaacca | gagcgaggcc | gggtctcaca | ccctccagtg | gatgtatggc | 300 |
| tgcgacgtgg | ggccggacgg | gcgcctcctc | cgcgggtata | accagttcgc | ctacgacggc | 360 |
| aaggattaca | tcgccctgaa | cgaggacctg | agctcctgga | ccgcggcgga | caccgcggct | 420 |
| cagatcaccc | agcgcaagtg | ggaggcggcc | cgtgaggcgg | agcagctgag | agcctacctg | 480 |
| gagggcacgt | gcgtggagtg | gctccgcaga | cacctggaga | acgggaagga | gacgctgcag | 540 |
| cgcgcggacc | ccccaaagac | acatgtgacc | caccacccca | tctctgacca | tgaggccacc | 600 |
| ctgaggtgct | gggccctggg | cttctaccct | gcggagatca | cactgacctg | gcagcgggat | 660 |
| ggcgaggacc | aaaactcagga | caccgagctt | gtggagacca | gaccagcagg | agacagaacc | 720 |
| ttccagaagt | gggcagctgt | ggtggtgcct | tctggagaag | agcagagata | cacatgccat | 780 |
| gtacagcatg | aggggctgcc | gaagcccctc | accctgagat | gggagcca | | 828 |

<210> SEQ ID NO 120
<211> LENGTH: 828
<212> TYPE: DNA
<213> ORGANISM: Homo sapiens

<400> SEQUENCE: 120

| | | | | | |
|---|---|---|---|---|---|
| ggctcccact | ccatgaggta | tttccacacc | tccgtgtccc | ggcccggccg | cggggagccc | 60 |
| cgcttcatct | cagtgggcta | cgtggacggc | acccagttcg | tgaggttcga | cagcgacgcc | 120 |
| gcgagtccga | ggacggagcc | ccgggcgccg | tggatagagc | aagagggggcc | ggagtattgg | 180 |
| gaccggaaca | cacagatctc | caagaccaac | acacagactt | accgagagag | cctgcggaac | 240 |
| ctgcgcggct | gctacaacca | gagcgaggcc | gggtctcaca | ccctccagag | gatgtacggc | 300 |
| tgcgacgtgg | ggccggacgg | gcgcctcctc | cgcgggcatg | accagtccgc | ctacgacggc | 360 |
| aaggattaca | tcgccctgaa | cgaggacctg | agctcctgga | ccgcggcgga | caccgcggct | 420 |
| cagatcaccc | agcgcaagtg | ggaggcggcc | cgtgtggcgg | agcagctgag | agcctacctg | 480 |
| gagggcacgt | gcgtggagtg | gctccgcaga | cacctggaga | acgggaagga | gacgctgcag | 540 |
| cgcgcggacc | ccccaaagac | acatgtgacc | caccacccca | tctctgacca | tgaggccacc | 600 |
| ctgaggtgct | gggccctggg | cttctaccct | gcggagatca | cactgacctg | gcagcgggat | 660 |
| ggcgaggacc | aaaactcagga | caccgagctt | gtggagacca | gaccagcagg | agatagaacc | 720 |
| ttccagaagt | gggcagctgt | ggtggtgcct | tctggagaag | agcagagata | cacatgccat | 780 |
| gtacagcatg | aggggctgcc | gaagcccctc | accctgagat | gggagcca | | 828 |

<210> SEQ ID NO 121
<211> LENGTH: 828
<212> TYPE: DNA
<213> ORGANISM: Homo sapiens

<400> SEQUENCE: 121

| | | | | | |
|---|---|---|---|---|---|
| ggctcccact | ccatgaggta | tttccacacc | tccgtgtccc | ggcccggccg | cggggagccc | 60 |
| cgcttcatca | ccgtgggcta | cgtggacgac | acgctgttcg | tgaggttcga | cagcgacgcc | 120 |

```
gcgagtccga gagaggagcc gcgggcgccg tggatagagc aggaggggcc ggagtattgg    180
gaccgggaga cacagatctg caaggccaag gcacagactg accgagagaa cctgcggatc    240
gcgctccgct gctacaacca gagcgaggcc gggtctcaca ccctccagaa tatgtatggc    300
tgcgacgtgg ggccggacgg gcgcctcctc cgcgggtacc accaggacgc ctacgacggc    360
aaggattaca tcgccctgaa cgaggacctg agctcctgga ccgccgcgga cacggcggct    420
cagatcaccc agcgcaagtg ggaggcggcc cgtgtggcgg agcagctgag agcctacctg    480
gagggcgagt gcgtggagtg gctccgcaga tacctggaga cgggaagga dacgctgcag    540 cgcgcggacc cccaaagac acacgtgacc caccacccca tctctgacca tgaggccacc    600
ctgaggtgct gggccctggg cttctaccct gcggagatca cactgacctg gcagcgggat    660
ggcgaggacc aaactcagga cactgagctt gtggagacca gaccagcagg agatagaacc    720
ttccagaagt gggcagctgt ggtggtgcct tctggagaag agcagagata cacatgccat    780
gtacagcatg aggggctgcc gaagcccctc accctgagat gggagccg              828

<210> SEQ ID NO 122
<211> LENGTH: 828
<212> TYPE: DNA
<213> ORGANISM: Homo sapiens

<400> SEQUENCE: 122
ggctcccact ccatgaggta tttctacacc tccgtgtccc ggcccggccg cggggagccc     60
cgcttcatct cagtgggcta cgtggacgac acgcagttcg tgaggttcga cagcgacgcc    120
gcgagtccga gagaggagcc gcgggcgccg tggatagagc aggaggggcc ggaatattgg    180
gaccggaaca cacagatctg caagaccaac acacagactg accgagagag cctgcggaac    240
ctgcgcggct gctacaacca gagcgaggcc gggtctcaca ccctccagag gatgtacggc    300
tgcgacgtgg ggccggacgg gcgcctcctc cgcgggcata accagttcgc ctacgacggc    360
aaggattaca tcgccctgaa cgaggacctg agctcctgga ccgcggcgga caccgcggct    420
cagatcaccc agcgcaagtg ggaggcggcc cgtgtggcgg agcagctgag aacctacctg    480
gagggcacgt gcgtggagtg gctccgcaga tacctggaga cgggaagga dacgctgcag    540 cgcgcggacc cccaaagac acatgtgacc caccacccca tctctgacca tgaggccacc    600
ctgaggtgct gggccctggg cttctaccct gcggagatca cactgacctg gcagcgggat    660
ggcgaggacc aaactcagga caccgagctt gtggagacca gaccagcagg agacagaacc    720
ttccagaagt gggcagctgt ggtggtgcct tctggagaag agcagagata cacatgccat    780
gtacagcatg aggggctgcc gaagcccctc accctgagat gggagcca               828

<210> SEQ ID NO 123
<211> LENGTH: 828
<212> TYPE: DNA
<213> ORGANISM: Homo sapiens

<400> SEQUENCE: 123
ggctcccact ccatgaggta tttccacacc gccatgtccc ggcccggccg cggggagccc     60
cgcttcatca ccgtgggcta cgtggacgac acgctgttcg tgaggttcga cagcgacgcc    120
acgagtccga ggaaggagcc gcgggcgcca tggatagagc aggaggggcc ggagtattgg    180
gaccgggaga cacagatctc caagaccaac acacagactt accgagagag cctgcggaac    240
ctgcgcggct gctacaacca gagcgaggcc gggtctcaca ccctccagag gatgtacggc    300
```

| | |
|---|---|
| tgcgacgtgg ggccggacgg gcgcctcctc cgcgggcata accagtacgc ctacgacggc | 360 |
| aaggattaca tcgccctgaa cgaggacctg cgctcctgga ccgccgcgga cacggcggct | 420 |
| cagatctccc agcgcaagtt ggaggcggcc cgtgtggcgg agcagctgag agcctacctg | 480 |
| gagggcgagt gcgtggagtg gctccgcaga tacctggaga cgggaagga caagctggag | 540 |
| cgcgctgacc ccccaaagac acacgtgacc caccaccca tctctgacca tgaggccacc | 600 |
| ctgaggtgct gggccctggg tttctaccct gcggagatca cactgacctg gcagcgggat | 660 |
| ggcgaggacc aaactcagga cactgagctt gtggagacca gccagcagg agatagaacc | 720 |
| ttccagaagt gggcagctgt ggtggtgcct tctggagaag agcagagata cacatgccat | 780 |
| gtacagcatg aggggctgcc gaagcccctc accctgagat gggagccg | 828 |

<210> SEQ ID NO 124
<211> LENGTH: 828
<212> TYPE: DNA
<213> ORGANISM: Homo sapiens

<400> SEQUENCE: 124

| | |
|---|---|
| ggctcccact ccatgaggta tttctacacc gccatgtccc ggcccggccg cggggagccc | 60 |
| cgcttcatca ccgtgggcta cgtggacgac acgctgttcg tgaggttcga cagcgacgcc | 120 |
| acgagtccga ggaaggagcc gcgggcgcca tggatagagc aggaggggcc ggagtattgg | 180 |
| gaccgggaga cacagatctc caagaccaac acacagactt accgagagaa cctgcgcacc | 240 |
| gcgctccgct gctacaacca gagcgaggcc gggtctcaca tcatccagag gatgtacggc | 300 |
| tgcgacgtgg ggccggacgg gcgcctcctc cgcgggtatg accaggacgc ctacgacggc | 360 |
| aaggattaca tcgccctgaa cgaggacctg agctcctgga ccgcggcgga caccgcggct | 420 |
| cagatcaccc agcgcaagtg ggaggcggcc cgtgtggcgg agcaggacag agcctacctg | 480 |
| gagggcctgt gcgtggagtc gctccgcaga tacctggaga cgggaagga gacgctgcag | 540 |
| cgcgcggacc ccccaaagac acatgtgacc caccaccca tctctgacca tgaggtcacc | 600 |
| ctgaggtgct gggccctggg cttctaccct gcggagatca cactgacctg gcagcgggat | 660 |
| ggcgaggacc aaactcagga caccgagctt gtggagacca gccagcagg agatagaacc | 720 |
| ttccagaagt gggcagctgt ggtggtgcct tctggagaag agcagagata cacatgccat | 780 |
| gtacagcatg aggggctgcc gaagcccctc accctgagat gggagccg | 828 |

<210> SEQ ID NO 125
<211> LENGTH: 828
<212> TYPE: DNA
<213> ORGANISM: Homo sapiens

<400> SEQUENCE: 125

| | |
|---|---|
| ggctcccact ccatgaggta tttctacacc gccatgtccc ggcccggccg cggggagccc | 60 |
| cgcttcatcg cagtgggcta cgtggacgac acccagttcg tgaggttcga cagcgacgcc | 120 |
| gcgagtccga ggatggcgcc ccgggcgcca tggatagagc aggaggggcc ggagtattgg | 180 |
| gaccgggaga cacagaagta caagcgccag gcacagactg accgagtgag cctgcggaac | 240 |
| ctgcgcggct gctacaacca gagcgaggcc gggtctcaca ccctccagag gatgtacggc | 300 |
| tgcgacgtgg ggccggacgg gcgcctcctc cgcgggcatg accagtccgc ctacgacggc | 360 |
| aaggattaca tcgccctgaa cgaggacctg agctcctgga ccgcggcgga cacggcggct | 420 |
| cagatcaccc agcgcaagtg ggaggcggcc cgtgaggcgg agcagtggag agcctacctg | 480 |
| gagggcctgt gcgtggagtg gctccgcaga tacctggaga cgggaagga gacgctgcag | 540 |

| cgcgcggacc ccccaaagac acatgtgacc caccaccca tctctgacca tgaggccacc | 600 |
| ctgaggtgct gggccctggg cttctaccct gcggagatca cactgacctg gcagcgggat | 660 |
| ggcgaggacc aaactcagga caccgagctt gtggagacca gaccagcagg agatagaacc | 720 |
| ttccagaagt gggcagctgt ggtggtgcct tctggagaag agcagagata cacatgccat | 780 |
| gtacagcatg aggggctgcc gaagcccctc accctgagat gggagcca | 828 |

<210> SEQ ID NO 126
<211> LENGTH: 828
<212> TYPE: DNA
<213> ORGANISM: Homo sapiens

<400> SEQUENCE: 126

| ggctcccact ccatgaggta tttccacacc gccatgtccc ggcccggccg cggggagccc | 60 |
| cgcttcatca ccgtgggcta cgtggacgac acgctgttcg tgaggttcga cagcgacgcc | 120 |
| acgagtccga ggaaggagcc gcgggcgcca tggatagagc aggaggggcc ggagtattgg | 180 |
| gaccgggaga cacagatctc caagaccaac acacagactt accgagagag cctgcggaac | 240 |
| ctgcgcggct gctacaacca gagcgaggcc gggtctcaca cttggcagag gatgtatggc | 300 |
| tgcgacctgg ggcccgacgg gcgcctcctc cgcgggtata accagttagc ctacgacggc | 360 |
| aaggattaca tcgccctgaa cgaggacctg agctcctgga ccgcggcgga caccgcggct | 420 |
| cagatcaccc agcgcaagtg ggaggcggcc cgtgaggcgg agcagctgag agcctacctg | 480 |
| gagggcctgt gcgtggagtg gctccgcaga tacctggaga cgggaaagga gacgctgcag | 540 |
| cgcgcggacc ccccaaagac acatgtgacc caccaccca tctctgacca tgaggccacc | 600 |
| ctgaggtgct gggccctggg cttctaccct gcggagatca cactgacctg gcagcgggat | 660 |
| ggcgaggacc aaactcagga caccgagctt gtggagacca gaccagcagg agatagaacc | 720 |
| ttccagaagt gggcagctgt ggtggtgcct tctggagaag agcagagata cacatgccat | 780 |
| gtacagcatg aggggctgcc gaagcccctc accctgagat gggagcca | 828 |

<210> SEQ ID NO 127
<211> LENGTH: 828
<212> TYPE: DNA
<213> ORGANISM: Homo sapiens

<400> SEQUENCE: 127

| ggctcccact ccatgaggta tttctacacc gccatgtccc ggcccggccg cggggagccc | 60 |
| cgcttcatcg cagtgggcta cgtggacgac acccagttcg tgaggttcga cagcgacgcc | 120 |
| gcgagtccga ggatggcgcc ccgggcgcca tggatagagc aggaggggcc ggagtattgg | 180 |
| gacgggggaga cacggaacat gaaggcctcc gcgcagactt accgagagaa cctgcggatc | 240 |
| gcgctccgct gctacaacca gagcgaggcc gggtctcaca tcatccaggt gatgtatggc | 300 |
| tgcgacgtgg ggccggacgg gcgcctcctc cgcgggcatg accagtccgc ctacgacggc | 360 |
| aaggattaca tcgccctgaa cgaggacctg agctcctgga ccgcggcgga caccgcggct | 420 |
| cagatcaccc agcgcaagtg ggaggcggcc cgtgtggcgg agcagctgag agcctacctg | 480 |
| gagggcctgt gcgtggagtg gctccgcaga tacctggaga cgggaaagga gacgctgcag | 540 |
| cgcgcggacc ccccaaagac acatgtgacc caccaccca tctctgacca tgaggccacc | 600 |
| ctgaggtgct gggccctggg cttctaccct gcggagatca cactgacctg gcagcgggat | 660 |
| ggcgaggacc aaactcagga caccgagctt gtggagacca gaccagcagg agatagaacc | 720 |

| ttccagaagt gggcagctgt ggtggtgcct tctggagaag agcagagata cacatgccat | 780 |
| gtacagcatg aggggctgcc aaagcccctc accctgagat gggagcca | 828 |

<210> SEQ ID NO 128
<211> LENGTH: 828
<212> TYPE: DNA
<213> ORGANISM: Homo sapiens

<400> SEQUENCE: 128

| ggctcccact ccatgaggta tttctacacc gccatgtccc ggcccggccg cggggagccc | 60 |
| cgcttcatcg cagtgggcta cgtggacgac acccagttcg tgaggttcga cagcgacgcc | 120 |
| gcgagtccga ggacggagcc ccgggcgcca tggatagagc aggaggggcc ggagtattgg | 180 |
| gacggggaga cacggaacat gaaggcctcc gcgcagactt accgagagaa cctgcggatc | 240 |
| gcgctccgct gctacaacca gagcgaggcc gggtctcaca tcatccagag gatgtatggc | 300 |
| tgcgacctgg ggcccgacgg gcgcctcctc cgcgggcatg accagtccgc ctacgacggc | 360 |
| aaggattaca tcgccctgaa cgaggacctg agctcctgga ccgcggcgga caccgcggct | 420 |
| cagatcaccc agcgcaagtg ggaggcggcc cgtgtggcgg agcagctgag agcctacctg | 480 |
| gagggcctgt gcgtggagtg gctccgcaga tacctggaga cgggaaggga gacgctgcag | 540 |
| cgcgcggacc ccccaaagac acacgtgacc caccacccg tctctgacca tgaggccacc | 600 |
| ctgaggtgct gggccctggg cttctaccct gcggagatca cactgacctg gcagcgggat | 660 |
| ggcgaggacc aaactcagga cactgagctt gtggagacca ccagcagg agatagaacc | 720 |
| ttccagaagt gggcagctgt ggtggtgcct tctggagaag agcagagata cacatgccat | 780 |
| gtacagcatg aggggctgcc gaagcccctc accctgagat gggagcca | 828 |

<210> SEQ ID NO 129
<211> LENGTH: 828
<212> TYPE: DNA
<213> ORGANISM: Homo sapiens

<400> SEQUENCE: 129

| tgctcccact ccatgaggta tttctacacc gctgtgtccc ggcccagccg cggagagccc | 60 |
| cacttcatcg cagtgggcta cgtggacgac acgcagttcg tgcggttcga cagcgacgcc | 120 |
| gcgagtccaa gaggggagcc gcgggcgccg tgggtggagc aggaggggcc ggagtattgg | 180 |
| gaccgggaga cacagaagta caagcgccag gcacagactg accgagtgaa cctgcggaaa | 240 |
| ctacgcggct gctacaacca gagcgaggcc gggtctcaca ccctccagag gatgtacggc | 300 |
| tgcgacctgg ggcccgacgg gcgcctcctc cgcgggtatg accagtccgc ctacgacggc | 360 |
| aaggattaca tcgccctgaa cgaggacctg cgctcctgga ccgccgcgga cacagcggct | 420 |
| cagatcaccc agcgcaagtg ggaggcggcc cgtgaggcgg agcagtggag agcctacctg | 480 |
| gagggcgagt gcgtggagtg gctccgcaga tacctggaga cgggaaggga gacgctgcag | 540 |
| cgcgcggaac acccaaagac acacgtgacc caccatcccg tctctgacca tgaggccacc | 600 |
| ctgaggtgct gggccctggg cttctaccct acggagatca cactgacctg gcagcgggat | 660 |
| ggcgaggacc aaactcagga caccgagctt gtggagacca ggccagcagg agatggaacc | 720 |
| ttccagaagt gggcagctgt ggtggtgcct tctggagaag agcagagata cacgtgccat | 780 |
| gtgcagcacg aggggctgcc ggagcccctc accctgagat gggagcca | 828 |

<210> SEQ ID NO 130
<211> LENGTH: 828

```
<212> TYPE: DNA
<213> ORGANISM: Homo sapiens

<400> SEQUENCE: 130
ggctcccact ccatgaggta tttctacacc gctgtgtccc ggcccggccg cggggagccc      60
cacttcatcg cagtgggcta cgtggacgac acgcagttcg tgcggttcga cagcgacgcc     120
gcgagtccga gaggggagcc gcgggcgccg tgggtggagc aggaggggcc ggagtattgg     180
gaccgggaga cacagaagta caagcgccag gcacagactg accgagtgag cctgcgaaac     240
ctgcgcggct gctacaacca gagcgaggcc gggtctcaca tcatccagag gatgtatggc     300
tgcgacgtgg ggcccgacgg gcgcctcctc cgcgggtatg accagtacgc ctacgacggc     360
aaggattaca tcgccctgaa cgaggatctg cgctcctgga ccgccgcgga cacggcggct     420
cagatcaccc agcgcaagtg ggaggcggcc cgtgaggcgg agcagctgag agcctacctg     480
gagggcctgt gcgtggagtg gctccgcaga tacctgaaga atgggaagga gacgctgcag     540
cgcgcggaac acccaaagac acacgtgacc caccatcccg tctctgacca tgaggccacc     600
ctgaggtgct gggccctggg cttctaccct gcggagatca cactgacctg gcagtgggat     660
ggggaggacc aaaactcagga cactgagctt gtggagacca ggccagcagg agatggaacc     720
ttccagaagt gggcagctgt ggtggtgcct tctggagaag agcagagata cacgtgccat     780
gtgcagcacg aggggctgcc ggagcccctc accctgagat gggagccg                  828

<210> SEQ ID NO 131
<211> LENGTH: 828
<212> TYPE: DNA
<213> ORGANISM: Homo sapiens

<400> SEQUENCE: 131
tgctcccact ccatgaggta tttctacacc gccgtgtccc ggcccggccg cggagagccc      60
cgcttcatcg cagtgggcta cgtggacgac acgcagttcg tgcagttcga cagcgacgcc     120
gcgagtccaa gaggggagcc gcgggcgccg tgggtggagc aggaggggcc ggagtattgg     180
gaccgggaga cacagaagta caagcgccag gcacagactg accgagtgaa cctgcggaaa     240
ctgcgcggct gctacaacca gagcgaggcc gggtctcaca ccctccagag gatgtatggc     300
tgcgacctgg ggcccgacgg gcgcctcctc cgcgggtata accagttcgc ctacgacggc     360
aaggattaca tcgccctgaa tgaggacctg cgctcctgga ccgccgcgga caaggcggct     420
cagatcaccc agcgcaagtg ggaggcggcc cgtgaggcgg agcagcggag agcctacctg     480
gagggcacgt gcgtggagtg gctccgcaga tacctggaga cgggaagaa gacgctgcag     540 cgcgcggaac acccaaagac acacgtgacc caccatcccg tctctgacca tgaggccacc     600
ctgaggtgct gggccctggg cttctaccct gcggagatca cactgacctg gcagcgggat     660
ggcgaggacc aaaactcagga caccgagctt gtggagacca ggccagcagg agatggaacc     720
ttccagaagt gggcagctgt ggtggtgcct tctggagaag agcagagata cacgtgccat     780
gtgcagcacg aggggctgcc agagcccctc accctgagat gggggcca                  828

<210> SEQ ID NO 132
<211> LENGTH: 828
<212> TYPE: DNA
<213> ORGANISM: Homo sapiens

<400> SEQUENCE: 132
tgctcccact ccatgaggta tttcgacacc gccgtgtccc ggcccggccg cggagagccc      60
```

| | |
|---|---|
| cgcttcatct cagtgggcta cgtggacgac acgcagttcg tgcggttcga cagcgacgcc | 120 |
| gcgagtccga gagggagcc gcgggcgccg tgggtggagc aggagggcc ggagtattgg | 180 |
| gaccgggaga cacagaacta caagcgccag gcacaggctg accgagtgag cctgcggaac | 240 |
| ctgcgcggct gctacaacca gagcgaggac gggtctcaca ccctccagag gatgtatggc | 300 |
| tgcgacctgg ggcccgacgg gcgcctcctc cgcgggtatg accagtccgc ctacgacggc | 360 |
| aaggattaca tcgccctgaa cgaggacctg cgctcctgga ccgccgcgga cacccgcggct | 420 |
| cagatcaccc agcgcaagtt ggaggcggcc cgtgcggcgg agcagctgag agcctacctg | 480 |
| gagggcacgt gcgtggagtg gctccgcaga tacctggaga cgggaagga gacgctgcag | 540 |
| cgcgcagaac ccccaaagac acacgtgacc caccaccccc tctctgacca tgaggccacc | 600 |
| ctgaggtgct gggccctggg cttctaccct gcggagatca cactgacctg gcagcgggat | 660 |
| ggggaggacc agacccagga caccgagctt gtggagacca ggccagcagg agatggaacc | 720 |
| ttccagaagt gggcagctgt ggtggtgcct tctggacaag agcagagata cacgtgccat | 780 |
| atgcagcacg aggggctgca agagcccctc accctgagct gggagcca | 828 |

<210> SEQ ID NO 133
<211> LENGTH: 828
<212> TYPE: DNA
<213> ORGANISM: Homo sapiens

<400> SEQUENCE: 133

| | |
|---|---|
| ggctcccact ccatgaggta tttctacacc tccgtgtccc ggcccggccg cggggagccc | 60 |
| cgcttcatcg ccgtgggcta cgtggacgac acgcagttcg tgcggttcga cagcgacgcc | 120 |
| gcgagccaga ggatggagcc gcgggcgccg tggatagagc aggagggcc ggagtattgg | 180 |
| gaccaggaga cacggaatgt gaaggcccag tcacagactg accgagtgga cctggggacc | 240 |
| ctgcgcggct gctacaacca gagcgaggac ggttctcaca ccatccagat aatgtatggc | 300 |
| tgcgacgtgg ggccggacgg gcgcttcctc cgcgggtacc ggcaggacgc ctacgacggc | 360 |
| aaggattaca tcgccctgaa cgaggacctg cgctcttgga ccgcggcgga catggcagct | 420 |
| cagatcacca agcgcaagtg ggaggcggcc catgcggcgg agcagcagag agcctacctg | 480 |
| gagggccggt gcgtggagtg gctccgcaga tacctggaga cgggaagga gacgctgcag | 540 |
| cgcacggacc ccccaagac acatatgacc caccacccca tctctgacca tgaggccacc | 600 |
| ctgaggtgct gggccctggg cttctaccct gcggagatca cactgacctg gcagcgggat | 660 |
| ggggaggacc agacccagga cacggagctc gtggagacca ggcctgcagg ggatggaacc | 720 |
| ttccagaagt gggcggctgt ggtggtgcct tctggagagg agcagagata cacctgccat | 780 |
| gtgcagcatg agggtctgcc caagcccctc accctgagat gggagctg | 828 |

<210> SEQ ID NO 134
<211> LENGTH: 828
<212> TYPE: DNA
<213> ORGANISM: Homo sapiens

<400> SEQUENCE: 134

| | |
|---|---|
| ggctcccact ccatgaggta tttctccaca tccgtgtccc ggcccggccg cggggagccc | 60 |
| cgcttcatcg ccgtgggcta cgtggacgac acgcagttcg tgcggttcga cagcgacgcc | 120 |
| gcgagccaga ggatggagcc gcgggcgccg tggatagagc aggagggcc ggagtattgg | 180 |
| gacgaggaga cagggaaagt gaaggcccac tcacagactg accgagagaa cctgcggatc | 240 |
| gcgctccgct gctacaacca gagcgaggcc ggttctcaca ccctccagat gatgtttggc | 300 |

```
tgcgacgtgg ggtcggacgg gcgcttcctc cgcgggtacc accagtacgc ctacgacggc    360
aaggattaca tcgccctgaa agaggacctg cgctcttgga ccgcggcgga catggcggct    420
cagatcaccc agcgcaagtg ggaggcggcc cgtgtggcgg agcagttgag agcctacctg    480
gagggcacgt gcgtggacgg gctccgcaga tacctggaga cgggaaagga gacgctgcag    540
cgcacggacc cccccaagac acatatgacc caccaccccca tctctgacca tgaggccact    600
ctgagatgct gggccctggg cttctaccct gcggagatca cactgacctg gcagcgggat    660
ggggaggacc agacccagga cacggagctt gtggagacca ggcctgcagg ggatggaacc    720
ttccagaagt gggcagctgt ggtggtacct tctggagagg agcagagata cacctgccat    780
gtgcagcatg agggtctgcc caagcccctc accctgagat gggagcca              828
```

<210> SEQ ID NO 135
<211> LENGTH: 828
<212> TYPE: DNA
<213> ORGANISM: Homo sapiens

<400> SEQUENCE: 135

```
ggctcccact ccatgaggta tttctccaca tccgtgtccc ggcccggcag tggagagccc     60
cgcttcatcg cagtgggcta cgtggacgac acgcagttcg tgcggttcga cagcgacgcc    120
gcgagccaga ggatggagcc gcgggcgccg tggatagagc aggagaggcc tgagtattgg    180
gaccaggaga cacggaatgt gaaggcccag tcacagactg accgagtgga cctggggacc    240
ctgcgcggct gctacaacca gagcgaggcc ggttctcaca ccatccagat aatgtatggc    300
tgcgacgtgg ggtcggacgg gcgcttcctc cgcgggtatg aacagcacgc ctacgacggc    360
aaggattaca tcgccctgaa cgaggacctg cgctcttgga ccgcggcgga catggcggct    420
cagatcaccc agcgcaagtg ggaggcggcc cgttgggcgg agcagttgag agcctacctg    480
gagggcacgt gcgtggagtg gctccgcaga tacctggaga cgggaaagga gacgctgcag    540
cgcacggacc cccccaagac acatatgacc caccaccccca tctctgacca tgaggccacc    600
ctgaggtgct gggccctggg cttctaccct gcggagatca cactgacctg gcagcgggat    660
ggggaggacc agacccagga cacggagctc gtggagacca ggcctgcagg ggatggaacc    720
ttccagaagt gggcggctgt ggtggtgcct tctggagagg agcagagata cacctgccat    780
gtgcagcatg agggtctgcc caagcccctc accctgagat gggagctg                 828
```

<210> SEQ ID NO 136
<211> LENGTH: 828
<212> TYPE: DNA
<213> ORGANISM: Homo sapiens

<400> SEQUENCE: 136

```
ggctcccact ccatgaggta tttcaccaca tccgtgtccc ggcccggccg cggggagccc     60
cgcttcatcg ccgtgggcta cgtggacgac acgcagttcg tgcggttcga cagcgacgcc    120
gcgagccaga ggatggagcc gcgggcgccg tggatagagc aggaggggcc ggagtattgg    180
gaccggaaca cacggaatgt gaaggcccac tcacagattg accgagtgga cctggggacc    240
ctgcgcggct gctacaacca gagcgaggcc ggttctcaca ccatccagat gatgtatggc    300
tgcgacgtgg ggtcggacgg gcgcttcctc cgcgggtacc agcaggacgc ctacgacggc    360
aaggattaca tcgccttgaa cgaggacctg cgctcttgga ccgcggcgga catggcggct    420
cagatcaccc agcgcaagtg ggaggcggcc cgtgtggcgg agcagttgag agcctacctg    480
```

```
gagggcacgt gcgtggagtg gctccgcaga tacctggaga acgggaagga gacgctgcag    540
cgcacggacc cccccaagac gcatatgact caccacgctg tctctgacca tgaggccacc    600
ctgaggtgct gggccctgag cttctaccct gcggagatca cactgacctg gcagcgggat    660
ggggaggacc agacccagga cacggagctc gtggagacca ggcctgcagg ggatggaacc    720
ttccagaagt gggcgtctgt ggtggtgcct tctggacagg agcagagata cacctgccat    780
gtgcagcatg agggtctccc caagcccctc accctgagat gggagccg                828
```

<210> SEQ ID NO 137
<211> LENGTH: 828
<212> TYPE: DNA
<213> ORGANISM: Homo sapiens

<400> SEQUENCE: 137

```
ggctcccact ccatgaggta tttcgacacc gccatgtccc ggcccggccg cggggagccc     60
cgcttcatct cagtgggcta cgtggacgac acgcagttcg tgaggttcga cagcgacgcc    120
gcgagtccga gagaggagcc gcgggcgccg tggatagagc aggaggggcc ggagtattgg    180
gaccggaaca cacagatctt caagaccaac acacagactg accgagagag cctgcggaac    240
ctgcgcggct gctacaacca gagcgaggcc gggtctcaca ccctccagag catgtacggc    300
tgcgacgtgg ggccggacgg gcgcctcctc cgcgggcata accagtacgc ctacgacggc    360
aaggattaca tcgccctgaa cgaggacctg cgctcctgga ccgcggcgga caccgcggct    420
cagatcaccc agcgcaagtg ggaggcggcc cgtgtggcgg agcaggacag agcctacctg    480
gagggcacgt gcgtggagtg gctccgcaga tacctggaga acgggaagga cacgctggag    540
cgcgcggacc cccaaagac acacgtgacc caccaccca tctctgacca tgaggccacc    600
ctgaggtgct gggccctggg cttctaccct gcggagatca cactgacctg gcagcgggat    660
ggcgaggacc aaactcagga cactgagctt gtggagacca gccagcagg agatagaacc    720 ttccagaagt gggcagctgt ggtggtgcct tctggagaag agcagagata cacatgccat    780
gtacagcatg aggggctgcc gaagcccctc accctgagat gggagccg                828
```

<210> SEQ ID NO 138
<211> LENGTH: 828
<212> TYPE: DNA
<213> ORGANISM: Homo sapiens

<400> SEQUENCE: 138

```
ggctcccact ccatgaggta tttctacacc gccatgtccc ggcccggccg cggggagccc     60
cgcttcatcg cagtgggcta cgtggacgac acccagttcg tgaggttcga cagcgacgcc    120
gcgagtccga ggatggcgcc ccgggcgcca tggatagagc aggaggggcc ggagtattgg    180
gaccgggaga cacagatctc caagaccaac acacagactt accgagagag cctgcggaac    240
ctgcgcggct gctacaacca gagcgaggcc gggtctcaca ccctccagag gatgtacggc    300
tgcgacgtgg ggccggacgg gcgcctcctc cgcgggcatg accagtccgc ctacgacggc    360
aaggattaca tcgccctgaa cgaggacctg agctcctgga ccgcggcgga cacggcggct    420
cagatcaccc agcgcaagtg ggaggcggcc cgtgaggcgg agcagtggag agcctacctg    480
gagggcctgt gcgtggagtg gctccgcaga tacctggaga acgggaagga gacgctgcag    540
cgcgcggacc cccaaagac acatgtgacc caccaccca tctctgacca tgaggccacc    600
ctgaggtgct gggccctggg cttctaccct gcggagatca cactgacctg gcagcgggat    660
ggcgaggacc aaactcagga caccgagctt gtggagacca gccagcagg agatagaacc    720
```

| | |
|---|---|
| ttccagaagt gggcagctgt ggtggtgcct tctggagaag agcagagata cacatgccat | 780 |
| gtacagcatg aggggctgcc gaagcccctc accctgagat gggagcca | 828 |

<210> SEQ ID NO 139
<211> LENGTH: 828
<212> TYPE: DNA
<213> ORGANISM: Homo sapiens

<400> SEQUENCE: 139

| | |
|---|---|
| ggctcccact ccatgaggta tttctacacc gccatgtccc ggcccggccg cggggagccc | 60 |
| cgcttcatct cagtgggcta cgtggacgac acgcagttcg tgaggttcga cagcgacgcc | 120 |
| gcgagtccga gagaggagcc gcgggcgccg tggatagagc aggaggggcc ggagtattgg | 180 |
| gaccgggaga cacagatctc caagaccaac acacagactt accgagagag cctgcgaac | 240 |
| ctgcgcggct gctacaacca gagcgaggcc gggtctcaca ccctccagag gatgtacggc | 300 |
| tgcgacgtgg ggccgacgg gcgcctcctc cgcgggcatg accagtccgc ctacgacggc | 360 |
| aaggattaca tcgccctgaa cgaggacctg agctcctgga ccgcggcgga cacggcggct | 420 |
| cagatcaccc agcgcaagtg ggaggcggcc cgtgaggcgg agcagctgag agcctacctg | 480 |
| gagggcctgt gcgtggagtg gctccgcaga tacctggaga acgggaagga gacgctgcag | 540 |
| cgcgcggacc ccccaaagac acatgtgacc caccaccca tctctgacca tgaggccacc | 600 |
| ctgaggtgct gggccctggg cttctaccct gcggagatca cactgacctg gcagcgggat | 660 |
| ggcgaggacc aaactcagga caccgagctt gtggagacca gaccagcagg agatagaacc | 720 |
| ttccagaagt gggcagctgt ggtggtgcct tctggagaag agcagagata cacatgccat | 780 |
| gtacagcatg aggggctgcc gaagcccctc accctgagat gggagcca | 828 |

<210> SEQ ID NO 140
<211> LENGTH: 828
<212> TYPE: DNA
<213> ORGANISM: Homo sapiens

<400> SEQUENCE: 140

| | |
|---|---|
| ggctcccact ccatgaggta tttctacacc gccatgtccc ggcccggccg cggggagccc | 60 |
| cgcttcatcg cagtgggcta cgtggacgac acccagttcg tgaggttcga cagcgacgcc | 120 |
| gcgagtccga ggacggagcc ccgggcgcca tggatagagc aggaggggcc ggagtattgg | 180 |
| gaccggaaca cacagatctt caagaccaac acacagactt accgagagag cctgcggaac | 240 |
| ctgcgcggct gctacaacca gagcgaggcc gggtctcaca tcatccagag gatgtatggc | 300 |
| tgcgacctgg ggcccgacgg gcgcctcctc cgcgggcatg accagtccgc ctacgacggc | 360 |
| aaggattaca tcgccctgaa cgaggacctg agctcctgga ccgcggcgga caccgcggct | 420 |
| cagatcaccc agcgcaagtg ggaggcggcc cgtgtggcgg agcagctgag agcctacctg | 480 |
| gagggcctgt gcgtggagtg gctccgcaga tacctggaga acgggaagga gacgctgcag | 540 |
| cgcgcggacc ccccaaagac acacgtgacc caccacccg tctctgacca tgaggccacc | 600 |
| ctgaggtgct gggccctggg cttctaccct gcggagatca cactgacctg gcagcgggat | 660 |
| ggcgaggacc aaactcagga cactgagctt gtggagacca gaccagcagg agatagaacc | 720 |
| ttccagaagt gggcagctgt ggtggtgcct tctggagaag agcagagata cacatgccat | 780 |
| gtacagcatg aggggctgcc gaagcccctc accctgagat gggagcca | 828 |

<210> SEQ ID NO 141

```
<211> LENGTH: 828
<212> TYPE: DNA
<213> ORGANISM: Homo sapiens

<400> SEQUENCE: 141
ggctcccact ccatgaggta tttccacacc tccgtgtccc ggcccggccg cggggagccc      60
cgcttcatca ccgtgggcta cgtggacgac acgctgttcg tgaggttcga cagcgacgcc     120
acgagtccga ggaaggagcc gcgggcgcca tggatagagc aggaggggcc ggagtattgg     180
gaccgggaga cacagatctc caagaccaac acacagactt accgagagag cctgcggaac     240
ctgcgcggct gctacaacca gagcgaggcc gggtctcaca ccctccagag catgtacggc     300
tgcgacgtgg ggccggacgg gcgcctcctc cgcgggcata accagtacgc ctacgacggc     360
aaggattaca tcgccctgaa cgaggacctg cgctcctgga ccgccgcgga cacggcggct     420
cagatcaccc agcgcaagtg ggaggcggcc cgtgtggcgg agcagctgag agcctacctg     480
gagggcgagt gcgtggagtg gctccgcaga tacctggaga cgggaagga  gacgctgcag     540
cgcgcggacc cccaaagac acacgtgacc caccacccca tctctgacca tgaggccacc     600
ctgaggtgct gggccctggg cttctaccct gcggagatca cactgacctg gcagcgggat     660
ggcgaggacc aaactcagga cactgagctt gtggagacca gccagcagg agatagaacc     720
ttccagaagt gggcagctgt ggtggtgcct tctggagaag agcagagata cacatgccat     780
gtacagcatg aggggctgcc gaagcccctc accctgagat gggagccg                  828

<210> SEQ ID NO 142
<211> LENGTH: 828
<212> TYPE: DNA
<213> ORGANISM: Homo sapiens

<400> SEQUENCE: 142
ggctcccact ccatgaggta tttctacacc tccgtgtccc ggcccggccg cggggagccc      60
cgcttcatct cagtgggcta cgtggacgac acccagttcg tgaggttcga cagcgacgcc     120
gcgagtccga gagaggagcc gcgggcgccg tggatagagc aggaggggcc ggagtattgg     180
gaccggaaca cacagatcta caaggcccag gcacagactg accgagagag cctgcggaac     240
ctgcgcggct gctacaacca gagcgaggcc gggtctcaca ccctccagag catgtacggc     300
tgcgacgtgg ggccggacgg gcgcctcctc cgcgggcata accagtacgc ctacgacggc     360
aaggattaca tcgccctgaa cgaggacctg cgctcctgga ccgcggcgga caccgcggct     420
cagatcaccc agcgcaagtg ggaggcggcc cgtgtggcgg agcaggacag agcctacctg     480
gagggcacgt gcgtggagtg gctccgcaga tacctggaga cgggaagga  cacgctggag     540
cgcgcggacc cccaaagac acacgtgacc caccacccca tctctgacca tgaggccacc     600
ctgaggtgct gggccctggg cttctaccct gcggagatca cactgacctg gcagcgggat     660
ggcgaggacc aaactcagga cactgagctt gtggagacca gccagcagg agatagaacc     720
ttccagaagt gggcagctgt ggtggtgcct tctggagaag agcagagata cacatgccat     780
gtacagcatg aggggctgcc gaagcccctc accctgagat gggagccg                  828

<210> SEQ ID NO 143
<211> LENGTH: 828
<212> TYPE: DNA
<213> ORGANISM: Homo sapiens

<400> SEQUENCE: 143
ggctcccact ccatgaggta tttctacacc gccatgtccc ggcccggccg cggggagccc      60
```

```
cgcttcatca ccgtgggcta cgtggacgac acgctgttcg tgaggttcga cagcgacgcc    120
acgagtccga ggaaggagcc gcgggcgcca tggatagagc aggaggggcc ggagtattgg    180
gaccgggaga cacagatctc caagaccaac acacagactt accgagagaa cctgcgcacc    240
gcgctccgct gctacaacca gagcgaggcc gggtctcaca tcatccagag gatgtacggc    300
tgcgacgtgg ggccggacgg gcgcctcctc cgcgggtatg accaggacgc ctacgacggc    360
aaggattaca tcgccctgaa cgaggacctg agctcctgga ccgcggcgga caccgcggct    420
cagatcaccc agcgcaagtg ggaggcggcc cgtgtggcgg agcagctgag agcctacctg    480
gagggcctgt gcgtggagtc gctccgcaga tacctggaga cgggaagga  gacgctgcag    540 cgcgcggacc ccccaaagac acatgtgacc caccacccca tctctgacca tgaggtcacc    600
ctgaggtgct gggccctggg cttctaccct gcggagatca cactgacctg gcagcgggat    660
ggcgaggacc aaactcagga caccgagctt gtggagacca gaccagcagg agatagaacc    720
ttccagaagt gggcagctgt ggtggtgcct tctggagaag agcagagata cacatgccat    780
gtacagcatg agggctgcc  gaagcccctc accctgagat gggagccg               828

<210> SEQ ID NO 144
<211> LENGTH: 828
<212> TYPE: DNA
<213> ORGANISM: Homo sapiens

<400> SEQUENCE: 144
ggctcccact ccatgaggta tttctacacc gccatgtccc ggcccggccg cggggagccc     60
cgcttcattg cagtgggcta cgtggacgac acccagttcg tgaggttcga cagcgacgcc    120
gcgagtccga ggacggagcc ccgggcgcca tggatagagc aggaggggcc ggagtattgg    180
gaccggaaca cacagatctt caagaccaac acacagactt accgagagaa cctgcggatc    240
gcgctccgct gctacaacca gagcgaggcc gggtctcaca cttggcagac gatgtatggc    300
tgcgacgtgg ggccggacgg gcgcctcctc cgcgggcata accagtacgc ctacgacggc    360
aaagattaca tcgccctgaa cgaggacctg agctcctgga ccgcggcgga caccgcggct    420
cagatcaccc agcgcaagtg ggaggcggcc cgtgaggcgg agcagctgag agcctacctg    480
gagggcctgt gcgtggagtg gctccgcaga cacctggaga cgggaagga  gacgctgcag    540 cgcgcggacc ccccaaagac acacgtgacc caccaccccg tctctgacca tgaggccacc    600
ctgaggtgct gggccctggg cttctaccct gcggagatca cactgacctg gcagcgggat    660
ggcgaggacc aaactcagga cactgagctt gtggagacca gaccagcagg agatagaacc    720
ttccagaagt gggcagctgt ggtggtgcct tctggagaag agcagagata cacatgccat    780
gtacagcatg agggctgcc  gaagcccctc accctgagat gggagcca                828

<210> SEQ ID NO 145
<211> LENGTH: 828
<212> TYPE: DNA
<213> ORGANISM: Homo sapiens

<400> SEQUENCE: 145
ggctcccact ccatgaggta tttctacacc gccatgtccc ggcccggccg cggggagccc     60
cgcttcatcg cagtgggcta cgtggacgac acccagttcg tgaggttcga cagcgacgcc    120
gcgagtccga ggacggagcc ccgggcgcca tggatagagc aggaggggcc ggagtattgg    180
gaccggaaca cacagatctt caagaccaac acacagactt accgagagaa cctgcggatc    240
```

| | |
|---|---|
| gcgctccgct gctacaacca gagcgaggcc gggtctcaca tcatccagag gatgtatggc | 300 |
| tgcgacctgg ggcccgacgg gcgcctcctc cgcgggcatg accagtccgc ctacgacggc | 360 |
| aaggattaca tcgccctgaa cgaggacctg agctcctgga ccgcggcgga caccgcggct | 420 |
| cagatcaccc agcgcaagtg ggaggcggcc cgtgtggcgg agcagctgag agcctacctg | 480 |
| gagggcctgt gcgtggagtg gctccgcaga tacctggaga cgggaagga dacgctgcag | 540 |
| cgcgcggacc ccccaaagac acacgtgacc caccacccg tctctgacca tgaggccacc | 600 |
| ctgaggtgct gggccctggg cttctaccct gcggagatca cactgacctg gcagcgggat | 660 |
| ggcgaggacc aaactcagga cactgagctt gtggagacca gaccagcagg agatagaacc | 720 |
| ttccagaagt gggcagctgt ggtggtgcct tctggagaag agcagagata cacatgccat | 780 |
| gtacagcatg aggggctgcc gaagcccctc accctgagat gggagcca | 828 |

<210> SEQ ID NO 146
<211> LENGTH: 828
<212> TYPE: DNA
<213> ORGANISM: Homo sapiens

<400> SEQUENCE: 146

| | |
|---|---|
| tgctcccact ccatgaagta tttcttcaca tccgtgtccc ggcctggccg cggagagccc | 60 |
| cgcttcatct cagtgggcta cgtggacgac acgcagttcg tgcggttcga cagcgacgcc | 120 |
| gcgagtccga gagggagcc gcgggcgccg tgggtggagc aggaggggcc ggagtattgg | 180 |
| gaccgggaga cacagaagta caagcgccag gcacagactg accgagtgag cctgcggaac | 240 |
| ctgcgcggct gctacaacca gagcgaggcc gggtctcaca ccctccagtg gatgtgtggc | 300 |
| tgcgacctgg ggcccgacgg gcgcctcctc cgcgggtatg accagtacgc ctacgacggc | 360 |
| aaggattaca tcgccctgaa cgaggacctg cgctcctgga ccgccgcgga caccgcggct | 420 |
| cagatcaccc agcgcaagtg ggaggcggcc cgtgaggcgg agcagcggag agcctacctg | 480 |
| gagggcacgt gcgtggagtg gctccgcaga tacctggaga cgggaagga dacgctgcag | 540 |
| cgcgcggaac acccaaagac acacgtgacc caccatcccg tctctgacca tgaggccacc | 600 |
| ctgaggtgct gggccctggg cttctaccct gcggagatca cactgacctg gcagtgggat | 660 |
| ggggaggacc aaactcagga caccgagctt gtggagacca ggccagcagg agatggaacc | 720 |
| ttccagaagt gggcagctgt gatggtgcct tctggagaag agcagagata cacgtgccat | 780 |
| gtgcagcacg aggggctgcc ggagcccctc accctgagat gggagccg | 828 |

<210> SEQ ID NO 147
<211> LENGTH: 828
<212> TYPE: DNA
<213> ORGANISM: Homo sapiens

<400> SEQUENCE: 147

| | |
|---|---|
| ggctcccact ccatgaggta tttctccaca tccgtgtcct ggcccggccg cggggagccc | 60 |
| cgcttcatcg cagtgggcta cgtggacgac acgcagttcg tgcggttcga cagcgacgcc | 120 |
| gcgagtccaa gagggagcc gcgggagccg tgggtggagc aggaggggcc ggagtattgg | 180 |
| gaccgggaga cacagaagta caagcgccag gcacaggctg accgagtgaa cctgcggaaa | 240 |
| ctgcgcggct gctacaacca gagcgaggac gggtctcaca ccctccagag gatgtttggc | 300 |
| tgcgacctgg ggccggacgg gcgcctcctc cgcgggtata accagttcgc ctacgacggc | 360 |
| aaggattaca tcgccctgaa cgaggatctg cgctcctgga ccgccgcgga cacggcggct | 420 |
| cagatcaccc agcgcaagtg ggaggcggcc cgtgaggcgg agcagcggag agcctacctg | 480 |

| | | |
|---|---|---|
| gagggcacgt gcgtggagtg gctccgcaga tacctggaga acgggaagga gacgctgcag | 540 | |
| cgcgcggaac acccaaagac acacgtgacc caccatcccg tctctgacca tgaggccacc | 600 | |
| ctgaggtgct gggccctggg cttctaccct gcggagatca cactgacctg gcagtgggat | 660 | |
| ggggaggacc aaaactcagga caccgagctt gtggagacca ggccagcagg agatggaacc | 720 | |
| ttccagaagt gggcagctgt ggtggtgcct tctggagaag agcagagata cacgtgccat | 780 | |
| gttcagcacg aggggctgcc ggagcccctc accctgagat ggaagccg | 828 | |

<210> SEQ ID NO 148
<211> LENGTH: 828
<212> TYPE: DNA
<213> ORGANISM: Homo sapiens

<400> SEQUENCE: 148

| | | |
|---|---|---|
| tgctcccact ccatgaggta tttcgacacc gccgtgtccc ggcccggccg cggagagccc | 60 | |
| cgcttcatct cagtgggcta cgtggacgac acgcagttcg tgcggttcga cagcgacgcc | 120 | |
| gcgagtccga gagggagcc ccgggcgccg tgggtggagc aggaggggcc ggagtattgg | 180 | |
| gaccgggaga cacagaagta caagcgccag gcacaggctg accgagtgaa cctgcggaaa | 240 | |
| ctgcgcggct gctacaacca gagcgaggac gggtctcaca ccctccagtg gatgtatggc | 300 | |
| tgcgacctgg ggcccgacgg gcgcctcctc cgcgggtatg accagtccgc ctacgacggc | 360 | |
| aaggattaca tcgccctgaa cgaggacctg cgctcctgga ccgccgcgga caccgcggct | 420 | |
| cagatcaccc agcgcaagtg ggaggcggcc cgtgaggcgg agcagtggag agcctacctg | 480 | |
| gagggcacgt gcgtggagtg gctccgcaga tacctggaga acgggaagga gacgctgcag | 540 | |
| cgcgcggaac acccaaagac acacgtgacc caccatcccg tctctgacca tgaggccacc | 600 | |
| ctgaggtgct gggccctggg cttctaccct gcggagatca cactgacctg gcagcgggat | 660 | |
| ggcgaggacc aaaactcagga caccgagctt gtggagacca ggccagcagg agatggaacc | 720 | |
| ttccagaagt gggcagctgt ggtggtgcct tctggagaag agcagagata cacgtgccat | 780 | |
| gtgcagcacg aggggctgcc agagcccctc accctgagat gggagcca | 828 | |

<210> SEQ ID NO 149
<211> LENGTH: 828
<212> TYPE: DNA
<213> ORGANISM: Homo sapiens

<400> SEQUENCE: 149

| | | |
|---|---|---|
| tgctcccact ccatgaggta tttcgacacc gccgtgtccc ggcccggccg cggagagccc | 60 | |
| cgcttcatct cagtgggcta cgtggacgac acgcagttcg tgcggttcga cagcgacgcc | 120 | |
| gcgagtccga gagggagcc gcgggcgccg tgggtggagc aggaggggcc ggagtattgg | 180 | |
| gaccgggaga cacagaagta caagcgccag gcacaggctg accgagtgag cctgcggaac | 240 | |
| ctgcgcggct gctacaacca gagcgaggac gggtctcaca ccctccagag gatgtctggc | 300 | |
| tgcgacctgg ggcccgacgg gcgcctcctc cgcgggtatg accagtccgc ctacgacggc | 360 | |
| aaggattaca tcgccctgaa cgaggacctg cgctcctgga ccgccgcgga caccgcggct | 420 | |
| cagatcaccc agcgcaagtt ggaggcggcc cgtgcgcgg agcagctgag agcctacctg | 480 | |
| gagggcacgt gcgtggagtg gctccgcaga tacctggaga acgggaagga gacgctgcag | 540 | |
| cgcgcagaac ccccaaagac acacgtgacc caccacccccc tctctgacca tgaggccacc | 600 | |
| ctgaggtgct gggccctggg cttctaccct gcggagatca cactgacctg gcagcgggat | 660 | |

```
ggggaggacc agacccagga caccgagctt gtggagacca ggccagcagg agatggaacc    720
ttccagaagt gggcagctgt ggtggtgcct tctggacaag agcagagata cacgtgccat    780
atgcagcacg aggggctgca agagcccctc accctgagct gggagcca                 828
```

<210> SEQ ID NO 150
<211> LENGTH: 828
<212> TYPE: DNA
<213> ORGANISM: Homo sapiens

<400> SEQUENCE: 150

```
tgctcccact ccatgaggta tttctacacc gccgtgtccc ggcccggccg cggagagccc     60
cgcttcatcg cagtgggcta cgtggacgac acgcagttcg tgcggttcga cagcgacgcc   120
gcgagtccaa gaggggagcc gcgggcgccg tgggtggagc aggaggggcc ggagtattgg   180
gaccgggaga cacagaagta caagcgccag gcacagactg accgagtgag cctgcggaac   240
ctgcgcggct gctacaacca gagcgaggcc gggtctcaca ccctccagtg gatgtatggc   300
tgcgacctgg ggcccgacgg gcgcctcctc cgcgggtatg accagtccgc ctacgacggc   360
aaggattaca tcgccctgaa cgaggacctg cgctcctgga ccgccgcgga cacggcggct   420
cagatcaccc agcgcaagtg ggaggcggcc cgtgcggcgg agcagcagag agcctacctg   480
gagggcacgt gcgtggagtg gctccgcaga tacctggaga cgggaagga dacgctgcag   540 cgcgcggaac acccaaagac acacgtgacc caccatctcg tctctgacca tgaggccacc   600
ctgaggtgct gggccctggg cttctaccct gcggagatca cactgacctg cagcgggat    660 ggcgaggacc aaactcagga caccgagctt gtggagacca ggccagcagg agatggaacc   720
ttccagaagt gggcagctgt ggtggtgcct tctggagaag agcagagata cacgtgccat   780
gtgcagcacg aggggctgcc ggagcccctc accctgagat gggagcca                828
```

<210> SEQ ID NO 151
<211> LENGTH: 828
<212> TYPE: DNA
<213> ORGANISM: Homo sapiens

<400> SEQUENCE: 151

```
ggctcccact ccatgaggta tttctacacc tccgtgtccc ggcccggccg cggggagccc     60
cgcttcatcg ccgtgggcta cgtggacgac acgcagttcg tgcggttcga cagcgacgcc   120
gcgagccaga ggatggagcc gcgggcgccg tggatagagc aggaggggcc ggagtattgg   180
gaccggaaca cacggaatgt gaaggccac tcacagactg accgagagag cctgcggatc   240
gcgctccgct gctacaacca gagcgaggac ggttctcaca ccatccagag gatgtatggc   300
tgcgacgtgg ggccggacgg gcgcttcctc cgcgggtacc agcaggacgc ttacgacggc   360
aaggattaca tcgccctgaa cgaggacctg cgctcttgga ccgcggcgga catggcggct   420
cagatcaccc agcgcaagtg ggagacggcc catgaggcgg agcagtggag agcctacctg   480
gagggccggt gcgtggagtg gctccgcaga tacctggaga cgggaagga dacgctgcag   540 cgcacggacg ccccaagac gcatatgact caccacgctg tctctgacca tgaggccacc   600
ctgaggtgct gggccctgag cttctaccct gcggagatca cactgacctg cagcgggat    660 ggggaggacc agacccagga caccggagctc gtggagacca ggcctgcagg ggatgggacc   720
ttccagaagt gggcgtctgt ggtggtgcct tctggacagg agcagagata cacctgccat   780
gtgcagcatg agggtctgcc caagcccctc accctgagat gggagccg                 828
```

```
<210> SEQ ID NO 152
<211> LENGTH: 828
<212> TYPE: DNA
<213> ORGANISM: Homo sapiens

<400> SEQUENCE: 152
ggctcccact ccatgaggta tttctacacc tccgtgtccc ggcccggccg cggggagccc      60
cgcttcatcg ccgtgggcta cgtggacgac acgcagttcg tgcggttcga cagcgacgcc     120
gcgagccaga ggatggagcc gcgggcgccg tggatagagc aggaggggcc ggagtattgg     180
gaccggaaca cacggaatgt gaaggccac tcacagactg accgagcgaa cctggggacc      240
ctgcgcggct gctacaacca gagcgaggac ggttctcaca ccatccagag gatgtatggc     300
tgcgacgtgg ggccggacgg gcgcttcctc cgcgggtacc agcaggacgc ttacgacggc     360
aaggattaca tcgccctgaa cgaggacctg cgctcttgga ccgcggcgga catggcggct     420
cagatcaccc agcgcaagtg ggagacggcc catgaggcgg agcagtggag agcctacctg     480
gagggccggt gcgtggagtg gctccgcaga tacctggaga acgggaagga gacgctgcag     540
cgcacggacg cccccaagac gcatatgact caccacgctg tctctgacca tgaggccacc     600
ctgaggtgct gggccctgag cttctaccct gcggagatca cactgacctg gcagcgggat     660
ggggaggacc agacccagga cacggagctc gtggagacca ggcctgcagg ggatgggacc     720
ttccagaagt gggcgtctgt ggtggtgcct tctggacagg agcagagata cacctgccat     780
gtgcagcatg agggtctgcc caagcccctc accctgagat gggagccg                 828

<210> SEQ ID NO 153
<211> LENGTH: 828
<212> TYPE: DNA
<213> ORGANISM: Homo sapiens

<400> SEQUENCE: 153
ggctcccact ccatgaggta tttcaccaca tccgtgtccc ggcccggccg cggggagccc      60
cgcttcatcg ccgtgggcta cgtggacgac acgcagttcg tgcggtttga cagcgacgcc     120
gcgagccaga ggatggagcc gcgggcaccg tggatagagc aggaggggcc ggagtattgg     180
gacctgcaga cacggaatgt gaaggccag tcacagactg accgagcgaa cctggggacc      240
ctgcgcggct gctacaacca gagcgaggcc ggttctcaca ccatccagat gatgtatggc     300
tgcgacgtgg ggtcggacgg gcgcttcctc cgcgggtacc␣gcaggacgc ctacgacggc     360 aaggattaca tcgccttgaa cgaggacctg cgctcttgga ccgcggcgga catggcggct     420
cagatcaccc agcgcaagtg ggaggcggcc cgtgtggcgg agcagttgag agcctacctg     480
gagggcacgt gcgtggagtg gctccgcaga tacctggaga acgggaagga gacgctgcag     540
cgcacggacg cccccaagac gcatatgact caccacgctg tctctgacca tgaggccacc     600
ctgaggtgct gggccctgag cttctaccct gcggagatca cactgacctg gcagcgggat     660
ggggaggacc agacccagga cacggagctt gtggagacca ggcctgcagg ggatggaacc     720
ttccagaagt gggcgtctgt ggtggtgcct tctggacagg agcagagata cacctgccat     780
gtgcagcatg agggtctgcc caagcccctc accctgagat gggagccg                 828

<210> SEQ ID NO 154
<211> LENGTH: 828
<212> TYPE: DNA
<213> ORGANISM: Homo sapiens

<400> SEQUENCE: 154
```

```
ggctcccact ccatgaggta tttctacacc tccatgtccc ggcccggccg cggggagccc      60
cgcttcatcg ccgtgggcta cgtggacgac acgcagttcg tgcggttcga cagcgacgcc     120
gcgagccaga ggatggagcc gcgggcgccg tggatagagc aggaggggcc ggagtattgg     180
gaccggaaca cacggaatgt gaaggcccag tcacagactg accgagtgga cctggggacc     240
ctgcgcggct gctacaacca gagcgaggcc ggttctcaca ccatccagag gatgtatggc     300
tgcgacgtgg ggccggacgg gcgcttcctc cgcgggtacc accagtacgc ctacgacggc     360
aaggattaca tcgccctgaa agaggacctg cgctcttgga ccgcggcgga catggcagct     420
cagaccacca agcacaagtg ggaggcggcc catgtggcgg agcagtggag agcctacctg     480
gagggcacgt gcgtggagtg gctccgcaga tacctggaga cgggaaggga gacgctgcag     540
cgcacggacg cccccaaaac gcatatgact caccacgctg tctctgacca tgaagccacc     600
ctgaggtgct gggccctgag cttctaccct gcggagatca cactgacctg gcagcgggat     660
ggggaggacc agacccagga cacggagctc gtggagacca ggcctgcagg ggatggaacc     720
ttccagaagt gggtggctgt ggtggtgcct tctggacagg agcagagata cacctgccat     780
gtgcagcatg agggtttgcc caagccccct accctgagat gggagccg                  828

<210> SEQ ID NO 155
<211> LENGTH: 828
<212> TYPE: DNA
<213> ORGANISM: Homo sapiens

<400> SEQUENCE: 155
ggctcccact ccatgaggta tttctacacc gccatgtccc ggcccggccg cggggagccc      60
cgcttcatca ccgtgggcta cgtggacgac acccagttcg tgaggttcga cagcgacgcc     120
acgagtccga ggatggcgcc ccgggcgcca tggatagagc aggaggggcc ggagtattgg     180
gaccgggaga cacagatctc caagaccaac acacagactt accgagagaa cctgcgcacc     240
gcgctccgct gctacaacca gagcgaggcc gggtctcaca cttggcagac gatgtatggc     300
tgcgacctgg ggccggacgg gcgcctcctc cgcgggcata accagttagc ctacgacggc     360
aaggattaca tcgccctgaa cgaggacctg agctcctgga ccgcggcgga caccgcggct     420
cagatcaccc agctcaagtg ggaggcggcc cgtgtggcgg agcagctgag agcctacctg     480
gagggcgagt gcgtggagtg gctccgcaga tacctggaga cgggaaggga cgcgctgcag     540
cgcgcggacc ccccaaagac acacgtgacc caccacccca tctctgacca tgaggccacc     600
ctgaggtgct gggccctggg cttctaccct gcggagatca cactgacctg gcagcgggat     660
ggcgaggacc aaactcagga cactgagctt gtggagacca gccagcagg agatagaacc      720 ttccagaagt gggcagctgt ggtggtgcct tctggagaag agcagagata cacatgccat     780
gtacagcatg aggggctgcc gaagcccctc accctgagat gggagcca                  828

<210> SEQ ID NO 156
<211> LENGTH: 828
<212> TYPE: DNA
<213> ORGANISM: Homo sapiens

<400> SEQUENCE: 156
ggctcccact ccatgaggta tttctacacc gccatgtccc ggcccggccg cggggagccc      60
cgcttcatcg cagtgggcta cgtggacgac acccagttcg tgaggttcga cagcgacgcc     120
gcgagtccga ggatggcgcc ccgggcgcca tggatagagc aggaggggcc ggagtattgg     180
gaccgggaga cacagatctc caagaccaac acacagactt accgagagag cctgcggaac     240
```

```
ctgcgcggct gctacaacca gagcgaggcc gggtctcaca ccctccagag catgtacggc    300
tgcgacgtgg ggccggacgg gcgcctcctc cgcgggcatg accagtccgc ctacgacggc    360
aaggattaca tcgccctgaa cgaggacctg agctcctgga ccgcggcgga cacggcggct    420
cagatcaccc agcgcaagtg ggaggcggcc cgtgaggcgg agcagtggag agcctacctg    480
gagggcctgt gcgtggagtg gctccgcaga tacctggaga cgggaaggga gacgctgcag    540
cgcgcggacc cccaaaagac acatgtgacc caccacccca tctctgacca tgaggccacc    600
ctgaggtgct gggccctggg cttctaccct gcggagatca cactgacctg gcagcgggat    660
ggcgaggacc aaaactcagga caccgagctt gtggagacca gccagcagg agatagaacc    720 ttccagaagt gggcagctgt ggtggtgcct tctggagaag agcagagata cacatgccat    780
gtacagcatg aggggctgcc gaagcccctc accctgagat gggagcca              828

<210> SEQ ID NO 157
<211> LENGTH: 828
<212> TYPE: DNA
<213> ORGANISM: Homo sapiens

<400> SEQUENCE: 157
ggctcccact ccatgaggta tttccacacc tccgtgtccc ggcccggccg cggggagccc     60
cgcttcatca ccgtgggcta cgtggacgac acgctgttcg tgaggttcga cagcgacgcc    120
gcgagtccga gagaggagcc gcgggcgccg tggatagagc aggaggggcc ggagtattgg    180
gaccgggaga cacagatctg caaggccaag gcacagactg accgagagga cctgcggacc    240
ctgctccgct gctacaacca gagcgaggcc gggtctcaca ccctccagaa tatgtatggc    300
tgcgacgtgg ggccggacgg gcgcctcctc cgcgggtacc accaggacgc ctacgacggc    360
aaggattaca tcgccctgaa cgaggacctg agctcctgga ccgccgcgga cacggcggct    420
cagatcaccc agcgcaagtg ggaggcggcc cgtgtggcgg agcagctgag agcctacctg    480
gagggcgagt gcgtggagtg gctccgcaga tacctggaga cgggaaggga gacgctgcag    540
cgcgcggacc cccaaaagac acacgtgacc caccacccca tctctgacca tgaggccacc    600
ctgaggtgct gggccctggg cttctaccct gcggagatca cactgacctg gcagcgggat    660
ggcgaggacc aaaactcagga cactgagctt gtggagacca gccagcagg agatagaacc    720 ttccagaagt gggcagctgt ggtggtgcct tctggagaag agcagagata cacatgccat    780
gtacagcatg aggggctgcc gaagcccctc accctgagat gggagccg              828

<210> SEQ ID NO 158
<211> LENGTH: 828
<212> TYPE: DNA
<213> ORGANISM: Homo sapiens

<400> SEQUENCE: 158
ggctcccact ccatgaggta tttctacacc gccatgtccc ggcccggccg cggggagccc     60
cgcttcatcg cagtgggcta cgtggacgac acccagttcg tgaggttcga cagcgacgcc    120
gcgagtccga ggacggagcc ccgggcgcca tggatagagc aggaggggcc ggagtattgg    180
gaccggaaca cacagatctt caagaccaac acacagactt accgagagag cctgcggaac    240
ctgcgcggct gctacaacca gagcgaggcc gggtctcaca tcatccagag gatgtatggc    300
tgcgacctgg ggcccgacgg gcgcctcctc cgcgggcatg accagttcgc ctacgacggc    360
aaggattaca tcgccctgaa cgaggacctg agctcctgga ccgcggcgga caccgcggct    420
```

| | |
|---|---|
| cagatcaccc agcgcaagtg ggaggcggcc cgtgtggcgg agcagctgag agcctacctg | 480 |
| gagggcctgt gcgtggagtg gctccgcaga tacctggaga acgggaagga gacgctgcag | 540 |
| cgcgcggacc ccccaaagac acacgtgacc caccaccccg tctctgacca tgaggccacc | 600 |
| ctgaggtgct gggccctggg cttctaccct gcggagatca cactgacctg gcagcgggat | 660 |
| ggcgaggacc aaactcagga cactgagctt gtggagacca gaccagcagg agatagaacc | 720 |
| ttccagaagt gggcagctgt ggtggtgcct tctggagaag agcagagata cacatgccat | 780 |
| gtacagcatg aggggctgcc gaagcccctc accctgagat gggagcca | 828 |

<210> SEQ ID NO 159
<211> LENGTH: 828
<212> TYPE: DNA
<213> ORGANISM: Homo sapiens

<400> SEQUENCE: 159

| | |
|---|---|
| ggctcccact ccatgaggta tttccacacc tccgtgtccc ggcccggccg cggggagccc | 60 |
| cgcttcatct cagtgggcta cgtggacgac acccagttcg tgaggttcga cagcgacgcc | 120 |
| gcgagtccga ggacggagcc ccgggcgccg tggatagagc aggaggggcc ggagtattgg | 180 |
| gaccgggaga cacagatctc caagaccaac acacagactt accgagagga cctgcggacc | 240 |
| ctgctccgct gctacaacca gagcgaggcc gggtctcaca ccatccagag gatgtctggc | 300 |
| tgcgacgtgg ggccggacgg gcgcctcctc cgcgggtata accagttcgc ctacgacggc | 360 |
| aaggattaca tcgccctgaa cgaggacctg agctcctgga ccgcggcgga caccgcggct | 420 |
| cagatcaccc agcgcaagtg ggaggcggcc cgtgtggcgg agcaggacag agcctacctg | 480 |
| gagggcacgt gcgtggagtg gctccgcaga tacctggaga acgggaagga gacgctgcag | 540 |
| cgcgcggacc ccccaaagac acatgtgacc caccaccccg tctctgacca tgaggccacc | 600 |
| ctgaggtgct gggccctggg cttctaccct gcggagatca cactgacctg gcagcgggat | 660 |
| ggcgaggacc aaactcagga caccgagctt gtggagacca gaccagcagg agatagaacc | 720 |
| ttccagaagt gggcagctgt ggtggtgcct tctggagaag agcagagata cacatgccat | 780 |
| gtacagcatg aggggctgcc gaagcccctc accctgagat gggagcca | 828 |

<210> SEQ ID NO 160
<211> LENGTH: 828
<212> TYPE: DNA
<213> ORGANISM: Homo sapiens

<400> SEQUENCE: 160

| | |
|---|---|
| ggctcccact ccatgaggta tttctacacc tccgtgtccc ggcccggccg cggggagccc | 60 |
| cgcttcatct cagtgggcta cgtggacgac acgcagttcg tgaggttcga cagcgacgcc | 120 |
| gcgagtccga gagaggagcc gcgggcgccg tggatagagc aggaggggcc ggaatattgg | 180 |
| gaccggaaca cacagatctg caagaccaac acacagactt accgagagaa cctgcggatc | 240 |
| gcgctccgct gctacaacca gagcgaggcc gggtctcaca ccctccagag gatgtacggc | 300 |
| tgcgacgtgg ggccggacgg gcgcctcctc cgcgggcata accagttcgc ctacgacggc | 360 |
| aaggattaca tcgccctgaa cgaggacctg agctcctgga ccgcggcgga caccgcggct | 420 |
| cagatcaccc agcgcaagtg ggaggcggcc cgtgtggcgg agcagctgag aacctacctg | 480 |
| gagggcacgt gcgtggagtg gctccgcaga tacctggaga acgggaagga gacgctgcag | 540 |
| cgcgcggacc ccccaaagac acatgtgacc caccaccccg tctctgacca tgaggccacc | 600 |
| ctgaggtgct gggccctggg cttctaccct gcggagatca cactgacctg gcagcgggat | 660 |

| | |
|---|---|
| ggcgaggacc aaaactcagga caccgagctt gtggagacca gaccagcagg agacagaacc | 720 |
| ttccagaagt gggcagctgt ggtggtgcct tctggagaag agcagagata cacatgccat | 780 |
| gtacagcatg aggggctgcc gaagcccctc accctgagat gggagcca | 828 |

<210> SEQ ID NO 161
<211> LENGTH: 828
<212> TYPE: DNA
<213> ORGANISM: Homo sapiens

<400> SEQUENCE: 161

| | |
|---|---|
| ggctcccact ccatgaggta tttccacacc gccatgtccc ggcccggccg cggggagccc | 60 |
| cgcttcatca ccgtgggcta cgtggacgac acgctgttcg tgaggttcga cagcgacgcc | 120 |
| acgagtccga ggaaggagcc gcgggcgcca tggatagagc aggaggggcc ggagtattgg | 180 |
| gaccgggaga cacagatctc caagaccaac acacagactt accgagagag cctgcggaac | 240 |
| ctgcgcggct gctacaacca gagcgaggcc ggtctcaca ccctccagag catgtacggc | 300 |
| tgcgacgtgg ggccggacgg gcgcctcctc cgcgggcata accagtacgc ctacgacggc | 360 |
| aaggattaca tcgccctgaa cgaggacctg cgctcctgga ccgcggcgga caccgcggct | 420 |
| cagatcaccc agcgcaagtg ggaggcggcc cgtgtggcgg agcaggacag agcctacctg | 480 |
| gagggcacgt gcgtggagtg gctccgcaga tacctggaga cgggaagga cacgctggag | 540 |
| cgcgcggacc ccccaaagac acacgtgacc caccacccca tctctgacca tgaggccacc | 600 |
| ctgaggtgct gggccctggg cttctaccct gcggagatca cactgacctg gcagcgggat | 660 |
| ggcgaggacc aaaactcagga cactgagctt gtggagacca gaccagcagg agatagaacc | 720 |
| ttccagaagt gggcagctgt ggtggtgcct tctggagaag agcagagata cacatgccat | 780 |
| gtacagcatg aggggctgcc gaagcccctc accctgagat gggagccg | 828 |

<210> SEQ ID NO 162
<211> LENGTH: 828
<212> TYPE: DNA
<213> ORGANISM: Homo sapiens

<400> SEQUENCE: 162

| | |
|---|---|
| ggctcccact ccatgaggta tttctacacc gccatgtccc ggcccggccg cggggagccc | 60 |
| cgcttcatca ccgtgggcta cgtggacgac acgctgttcg tgaggttcga cagcgacgcc | 120 |
| acgagtccga ggaaggagcc gcgggcgcca tggatagagc aggaggggcc ggagtattgg | 180 |
| gaccgggaga cacagatctc caagaccaac acacagactt accgagagaa cctgcgcacc | 240 |
| gcgctccgct gctacaacca gagcgaggcc gggtctcaca tcatccagag gatgtacggc | 300 |
| tgcgacgtgg ggccggacgg gcgcctcctc cgcgggtatg accagtacgc ctacgacggc | 360 |
| aaggattaca tcgccctgaa cgaggacctg agctcctgga ccgcggcgga caccgcggct | 420 |
| cagatcaccc agcgcaagtg ggaggcggcc cgtgtggcgg agcaggacag agcctacctg | 480 |
| gagggcctgt gcgtggagtc gctccgcaga tacctggaga cgggaagga cacgctgcag | 540 |
| cgcgcggacc ccccaaagac acatgtgacc caccacccca tctctgacca tgaggtcacc | 600 |
| ctgaggtgct gggccctggg cttctaccct gcggagatca cactgacctg gcagcgggat | 660 |
| ggcgaggacc aaaactcagga caccgagctt gtggagacca gaccagcagg agatagaacc | 720 |
| ttccagaagt gggcagctgt ggtggtgcct tctggagaag agcagagata cacatgccat | 780 |
| gtacagcatg aggggctgcc gaagcccctc accctgagat gggagccg | 828 |

<210> SEQ ID NO 163
<211> LENGTH: 828
<212> TYPE: DNA
<213> ORGANISM: Homo sapiens

<400> SEQUENCE: 163

| | | | | | | |
|---|---|---|---|---|---|---|
| ggctcccact | ccatgaggta | tttccacacc | gccatgtccc | ggcccggccg | cggggagccc | 60 |
| cgcttcatca | ccgtgggcta | cgtggacgac | acgctgttcg | tgaggttcga | cagcgacgcc | 120 |
| acgagtccga | ggaaggagcc | gcgggcgcca | tggatagagc | aggaggggcc | ggagtattgg | 180 |
| gaccgggaga | cacagatctc | caagaccaac | acacagactt | accgagagaa | cctgcggatc | 240 |
| gcgctccgct | gctacaacca | gagcgaggcc | gggtctcaca | cttggcagag | gatgtatggc | 300 |
| tgcgacctgg | ggcccgacgg | gcgcctcctc | cgcgggtata | accagttagc | ctacgacggc | 360 |
| aaggattaca | tcgccctgaa | cgaggacctg | agctcctgga | ccgcggcgga | caccgcggct | 420 |
| cagatcaccc | agcgcaagtg | ggaggcggcc | cgtgaggcgg | agcagctgag | agcctacctg | 480 |
| gagggcctgt | gcgtggagtg | gctccgcaga | tacctggaga | acgggaagga | gacgctgcag | 540 |
| cgcgcggacc | ccccaaagac | acatgtgacc | caccacccca | tctctgacca | tgaggccacc | 600 |
| ctgaggtgct | gggccctggg | cttctaccct | gcggagatca | cactgacctg | gcagcgggat | 660 |
| ggcgaggacc | aaactcagga | caccgagctt | gtggagacca | gaccagcagg | agatagaacc | 720 |
| ttccagaagt | gggcagctgt | ggtggtgcct | tctggagaag | agcagagata | cacatgccat | 780 |
| gtacagcatg | aggggctgcc | gaagcccctc | accctgagat | gggagcca | | 828 |

<210> SEQ ID NO 164
<211> LENGTH: 828
<212> TYPE: DNA
<213> ORGANISM: Homo sapiens

<400> SEQUENCE: 164

| | | | | | | |
|---|---|---|---|---|---|---|
| ggctcccact | ccatgaggta | tttctacacc | gccatgtccc | ggcccggccg | cggggagccc | 60 |
| cgcttcatcg | cagtgggcta | cgtggacgac | acccagttcg | tgaggttcga | cagcgacgcc | 120 |
| gcgagtccga | ggacggagcc | ccgggcgcca | tggatagagc | aggaggggcc | ggagtattgg | 180 |
| gaccgggaga | cacagatctc | caagaccaac | acacagactt | accgagagaa | cctgcggatc | 240 |
| gcgctccgct | gctacaacca | gagcgaggcc | gggtctcaca | cttggcagac | gatgtatggc | 300 |
| tgcgacgtgg | ggccggacgg | gcgcctcctc | cgcgggcata | accagtacgc | ctacgacggc | 360 |
| aaagattaca | tcgccctgaa | cgaggacctg | agctcctgga | ccgcggcgga | caccgcggct | 420 |
| cagatcaccc | agcgcaagtg | ggaggcggcc | cgtgaggcgg | agcagctgag | agcctacctg | 480 |
| gagggcctgt | gcgtggagtg | gctccgcaga | cacctggaga | acgggaagga | gacgctgcag | 540 |
| cgcgcggacc | ccccaaagac | acacgtgacc | caccacccg | tctctgacca | tgaggccacc | 600 |
| ctgaggtgct | gggccctggg | cttctaccct | gcggagatca | cactgacctg | gcagcgggat | 660 |
| ggcgaggacc | aaactcagga | cactgagctt | gtggagacca | gaccagcagg | agatagaacc | 720 |
| ttccagaagt | gggcagctgt | ggtggtgcct | tctggagaag | agcagagata | cacatgccat | 780 |
| gtacagcatg | aggggctgcc | gaagcccctc | accctgagat | gggagcca | | 828 |

<210> SEQ ID NO 165
<211> LENGTH: 828
<212> TYPE: DNA
<213> ORGANISM: Homo sapiens

<400> SEQUENCE: 165

```
ggctcccact ccatgaggta tttctacacc gccatgtccc ggcccggccg cggggagccc    60
cgcttcatcg cagtgggcta cgtggacgac acgcagttcg tgaggttcga cagcgacgcc   120
gcgagtccga gagaggagcc gcgggcgccg tggatagagc aggaggggcc ggagtattgg   180
gaccggaaca cacagatcta caaggcccag gcacagactg accgagagag cctgcggaac   240
ctgcgcggct gctacaacca gagcgaggcc gggtctcaca cttggcagac gatgtatggc   300
tgcgacctgg ggccgacgg gcgcctcctc cgcgggcata accagttagc ctacgacggc    360
aaggattaca tcgccctgaa cgaggacctg agctcctgga ccgcggcgga caccgcggct   420
cagatcaccc agcgcaagtg ggaggcggcc cgtgaggcgg agcagctgag agcctacctg   480
gagggcacgt gcgtggagtg gctccgcaga tacctggaga cgggaaggga gacgctgcag   540
cgcgcggacc ccccaaagac acacgtgacc caccaccccca tctctgacca tgaggccacc   600
ctgaggtgct gggccctggg cttctaccct gcggagatca cactgacctg gcagcgggat   660
ggcgaggacc aaactcagga cactgagctt gtggagacca gccagcagg agatagaacc   720 ttccagaagt gggcagctgt ggtggtgcct tctggagaag agcagagata cacatgccat   780
gtacagcatg aggggctgcc gaagcccctc accctgagat gggagcca               828
```

<210> SEQ ID NO 166
<211> LENGTH: 828
<212> TYPE: DNA
<213> ORGANISM: Homo sapiens

<400> SEQUENCE: 166

```
ggctcccact ccatgaggta tttctacacc gctgtgtccc ggcccggccg cggggagccc    60
cacttcatcg cagtgggcta cgtggacgac acgcagttcg tgcggttcga cagcgacgcc   120
gcgagtccga gagggagcc gcgggcgccg tgggtggagc aggaggggcc ggagtattgg   180
gaccgggaga cacagaagta caagcgccag gcacagactg accgagtgag cctgcggaac   240
ctgcgcggct gctacaacca gagcgaggcc aggtctcaca tcatccagag gatgtatggc   300
tgcgacgtgg ggcccgacgg gcgcctcctc cgcgggtatg accagtacgc ctacgacggc   360
aaggattaca tcgccctgaa cgaggatctg cgctcctgga ccgccgcgga cacggcggct   420
cagatcaccc agcgcaagtg ggaggcggcc cgtgaggcgg agcagctgag agcctacctg   480
gagggcctgt gcgtggagtg gctccgcaga tacctgaaga tgggaaggga gacgctgcag   540
cgcgcggaac acccaaagac acacgtgacc caccatcccg tctctgacca tgaggccacc   600
ctgaggtgct gggccctggg cttctaccct gcggagatca cactgacctg gcagtgggat   660
ggggaggacc aaactcagga cactgagctt gtggagacca ggccagcagg agatggaacc   720
ttccagaagt gggcagctgt ggtggtgcct tctggagaag agcagagata cacgtgccat   780
gtgcagcacg aggggctgcc ggagcccctc accctgagat gggagccg                828
```

<210> SEQ ID NO 167
<211> LENGTH: 828
<212> TYPE: DNA
<213> ORGANISM: Homo sapiens

<400> SEQUENCE: 167

```
tgctcccact ccatgaggta tttcgacacc gccgtgtccc ggcccggccg cggagagccc    60
cgcttcatct cagtgggcta cgtggacgac acgcagttcg tgcggttcga cagcgacgcc   120
gcgagtccga gagggagcc ccgggcgccg tgggtggagc aggaggggcc ggagtattgg   180
```

```
gaccgggaga cacagaagta caagcgccag gcacaggctg accgagtgag cctgcggaac    240
ctgcgcggct gctacaacca gagcgaggac gggtctcaca ccttccagag gatgtatggc    300
tgcgacctgg ggcccgacgg gcgcctcctc cgcgggtatg accagttcgc ctacgacggc    360
aaggattaca tcgccctgaa cgaggacctg cgctcctgga ccgccgcgga caccgcggct    420
cagatcaccc agcgcaagtt ggaggcggcc cgtgcggcgg agcaggacag agcctacctg    480
gagggcacgt gcgtggagtg gctccgcaga tacctggaga cgggaagaa gacgctgcag    540 cgcgcggaac ccccaaagac acacgtgacc caccacccc tctctgacca tgaggccacc    600
ctgaggtgct gggccctggg cttctaccct gcggagatca cactgacctg gcagcgggat    660
ggggaggacc agacccagga caccgagctt gtggagacca ggccagcagg agatggaacc    720
ttccagaagt gggcagctgt ggtggtgcct tctggacaag agcagagata cacgtgccat    780
atgcagcacg aggggctgca agagcccctc accctgagct gggagcca             828

<210> SEQ ID NO 168
<211> LENGTH: 828
<212> TYPE: DNA
<213> ORGANISM: Homo sapiens

<400> SEQUENCE: 168
tgctcccact ccatgaggta tttctacacc gccgtgtccc ggcccggccg cggagagccc     60
cgcttcatcg cagtgggcta cgtggacgac acgcagttcg tgcagttcga cagcgacgcc    120
gcgagtccaa gaggggagcc gcgggcgccg tgggtggagc aggaggggcc ggagtattgg    180
gaccgggaga cacagaagta caagcgccag gcacagactg accgagtgag cctgcggaac    240
ctgcgcggct gctacaacca gagcgaggcc gggtctcaca ccctccagag gatgtatggc    300
tgcgacctgg ggcccgacgg gcgcctcctc cgcgggtata accagttcgc ctacgacggc    360
aaggattaca tcgccctgaa tgaggacctg cgctcctgga ccgccgcgga caccgcggct    420
cagatcaccc agcgcaagtg ggaggcggcc cgtacggcgg agcagctgag agcctacctg    480
gagggcacgt gcgtggagtg gctccgcaga tacctggaga cgggaagaa gacgctgcag    540 cgcgcggaac acccaaagac acacgtgacc caccatcccg tctctgacca tgaggccacc    600
ctgaggtgct gggccctggg cttctaccct gcggagatca cactgacctg gcagcgggat    660
ggcgaggacc aaaactcagga caccgagctt gtggagacca ggccagcagg agatggaacc    720
ttccagaagt gggcagctgt ggtggtgcct tctggagaag agcagagata cacgtgccat    780
gtgcagcacg aggggctgcc agagcccctc accctgagat gggggcca             828

<210> SEQ ID NO 169
<211> LENGTH: 828
<212> TYPE: DNA
<213> ORGANISM: Homo sapiens

<400> SEQUENCE: 169
tgctcccact ccatgaggta tttctacacc gccgtgtccc ggcccggccg cggagagccc     60
cgcttcatcg cagtgggcta cgtggacgac acgcagttcg tgcagttcga cagcgacgcc    120
gcgagtccaa gaggggagcc gcgggcgccg tgggtggagc aggaggggcc ggagtattgg    180
gaccgggaga cacagaagta caagcgccag gcacagactg accgagtgag cctgcggaac    240
ctgcgcggct gctacaacca gagcgaggcc gggtctcaca ccctccagag gatgtatggc    300
tgcgacctgg ggcccgacgg gcgcctcctc cgcgggtata accagttcgc ctacgacggc    360
aaggattaca tcgccctgaa tgaggacctg cgctcctgga ccgccgcgga caaggcggct    420
```

| | |
|---|---|
| cagatcaccc agcgcaagtg ggaggcggcc cgtgaggcgg agcagcggag agcctacctg | 480 |
| gagggcacgt gcgtggagtg gctccgcaga tacctggaga cgggaagaa gacgctgcag | 540 |
| cgcgcggaac acccaaagac acacgtgacc caccatcccg tctctgacca tgaggccacc | 600 |
| ctgaggtgct gggccctggg cttctaccct gcggagatca cactgacctg gcagcgggat | 660 |
| ggcgaggacc aaactcagga caccgagctt gtggagacca ggccagcagg agatggaacc | 720 |
| ttccagaagt gggcagctgt ggtggtgcct tctggagaag agcagagata cacgtgccat | 780 |
| gtgcagcacg aggggctgcc agagcccctc accctgagat gggggcca | 828 |

<210> SEQ ID NO 170
<211> LENGTH: 828
<212> TYPE: DNA
<213> ORGANISM: Homo sapiens

<400> SEQUENCE: 170

| | |
|---|---|
| tgctcccact ccatgaggta tttctacacc gccgtgtccc ggcccggccg cggagagccc | 60 |
| cgcttcatcg cagtgggcta cgtggacgac acgcagttcg tgcggttcga cagcgacgcc | 120 |
| gcgagtccaa gaggggagcc gcgggcgccg tgggtggagc aggagggggcc ggagtattgg | 180 |
| gaccgggaga cacagaagta caagcgccag gcacaggctg accgagtgag cctgcggaac | 240 |
| ctgcgcggct gctacaacca gagcgaggcc gggtctcaca ccctccagag gatgtacggc | 300 |
| tgcgacctgg ggcccgacgg gcgcctcctc cgcgggtatg accagtccgc ctacgacggc | 360 |
| aaggattaca tcgccctgaa cgaggacctg cgctcctgga ccgctgcgga cacggcggct | 420 |
| cagatcaccc agcgcaagtg ggaggcggcc cgtgaggcgg agcagtggag agcctacctg | 480 |
| gagggcacgt gcgtggagtg gctccgcaga tacctggaga cgggaagga gacgctgcag | 540 |
| cgcgcggaac acccaaagac acacgtgacc caccatcccg tctctgacca tgaggccacc | 600 |
| ctgaggtgct gggccctggg cttctaccct gcggagatca cactgacctg gcagcgggat | 660 |
| ggcgaggacc aaactcagga caccgagctt gtggagacca ggccagcagg agatggaacc | 720 |
| ttccagaagt gggcagctgt ggtggtgcct tctggagaag agcagagata cacgtgccat | 780 |
| gtgcagcacg aggggctgcc ggagcccctc accctgagat gggagcca | 828 |

<210> SEQ ID NO 171
<211> LENGTH: 828
<212> TYPE: DNA
<213> ORGANISM: Homo sapiens

<400> SEQUENCE: 171

| | |
|---|---|
| tgctcccact ccatgaggta tttctacacc gccgtgtccc ggcccggccg cggagagccc | 60 |
| cgcttcatcg cagtgggcta cgtggacgac acgcagttcg tgcggttcga cagcgacgcc | 120 |
| gcgagtccaa gaggggagcc gcgggcgccg tgggtggagc aggagggggcc ggagtattgg | 180 |
| gaccgggaga cacagaagta caagcgccag gcacaggctg accgagtgag cctgcggaac | 240 |
| ctgcgcggct gctacaacca gagcgaggcc gggtctcaca ccctccagtg gatgtatggc | 300 |
| tgcgacctgg ggcccgacgg gcgcctcctc cgcgggtatg accagtccgc ctacgacggc | 360 |
| aaggattaca tcgccctgaa cgaggacctg cgctcctgga ctgccgcgga cacggcggct | 420 |
| cagatcaccc agcgcaagtg ggaggcggcc cgtgaggcgg agcagtggag agcctacctg | 480 |
| gagggcacgt gcgtggagtg gctccgcaga tacctggaga cgggaagga gacgctgcag | 540 |
| cgcgcggaac acccaaagac acacgtgacc caccatcccg tctctgacca tgaggccacc | 600 |

```
ctgaggtgct gggccctggg cttctaccct gcggagatca cactgacctg gcagcgggat    660
ggcgaggacc aaactcagga caccgagctt gtggagacca ggccagcagg agatggaacc    720
ttccagaagt gggcagctgt ggtggtgcct tctggagaag agcagagata cacgtgccat    780
gtgcagcacg aggggctgcc agagcccctc accctgagat gggagcca                 828
```

<210> SEQ ID NO 172
<211> LENGTH: 828
<212> TYPE: DNA
<213> ORGANISM: Homo sapiens

<400> SEQUENCE: 172

```
tgctcccact ccatgaggta tttctccaca tccgtgtccc ggcccggccg cggggagccc     60
cgcttcatcg cagtgggcta cgtggacgac acgcagttcg tgcggttcga cagcgacgcc    120
gcgagtccga gaggggagcc gcgggcgccg tgggtggagc aggaggggcc ggagtattgg    180
gaccgggaga cacagaagta caagcgccag gcacagactg accgagtgag cctgcggaac    240
ctgcgcggct gctacaacca gagcgaggcc gggtctcaca ccctccagtg gatgtttggc    300
tgcgacctgg ggcccgacgg gcgcctcctc cgcgggtatg accagtccgc ctacgacggc    360
aaggattaca tcgccctgaa cgaggatctg cgctcctgga ccgccgcgga cacggcggct    420
cagatcaccc agcgcaagtg ggaggcggcc cgtgaggcgg agcagcggag agcctacctg    480
gagggcacgt gcgtggagtg gctccgcaga tacctggaga cgggaagga gacgctgcag    540 cgcgcggaac acccaaagac acacgtgacc caccatcccg tctctgacca tgaggccacc    600
ctgaggtgct gggccctggg cttctaccct gcggagatca cactgacctg gcagtgggat    660
ggggaggacc aaactcagga caccgagctt gtggagacca ggccagcagg agatggaacc    720
ttccagaagt gggcagctgt ggtggtgcct tctggagaag agcagagata cacgtgccat    780
gtgcagcacg aggggctgcc ggagcccctc accctgagat gggagccg                 828
```

<210> SEQ ID NO 173
<211> LENGTH: 828
<212> TYPE: DNA
<213> ORGANISM: Homo sapiens

<400> SEQUENCE: 173

```
tgctcccact ccatgaggta tttctacacc gctgtgtccc ggcccggccg cggagagccc     60
cacttcatcg cagtgggcta cgtggacgac acgcagttcg tgcggttcga cagcgacgcc    120
gcgagtccaa gaggggagcc gcgggcgccg tgggtggagc aggaggggcc ggagtattgg    180
gaccgggaga cacagaacta caagcgccag gcacagactg accgagtgaa cctgcggaaa    240
ctgcgcggct gctacaacca gagcgaggcc gggtctcaca tcatccagag gatgtatggc    300
tgcgacctgg ggcccgacgg gcgcctcctc cgcgggcatg accagttagc ctacgacggc    360
aaggattaca tcgccctgaa cgaggacctg cgctcctgga ccgccgcgga cacggcggct    420
cagatcaccc agcgcaagtg ggaggcggcc cgtgaggcgg agcagctgag agcctacctg    480
gagggcacgt gcgtggagtg gctccgcaga tacctggaga cgggaagga gacgctgcag    540 cgcgcggaac acccaaagac acacgtgacc caccatcccg tctctgacca tgaggccacc    600
ctgaggtgct gggccctggg cttctaccct gcggagatca cactgacctg gcagcgggat    660
ggcgaggacc aaactcagga caccgagctt gtggagacca ggccagcagg agatggaacc    720
ttccagaagt gggcagctgt ggtggtgcct tctggagaag agcagagata cacgtgccat    780
gtgcagcacg aggggctgcc ggagcccctc accctgagat gggagcca                 828
```

<210> SEQ ID NO 174
<211> LENGTH: 828
<212> TYPE: DNA
<213> ORGANISM: Homo sapiens

<400> SEQUENCE: 174

```
ggctcccact ccatgaggta tttctacacc gccgtgtccc ggcccggccg cggagagccc      60
cgcttcatcg cagtgggcta cgtggacgac acgcagttcg tgcggttcga cagcgacgcc     120
gcgagtccga gaggggagcc gcgggcgccg tgggtggagc aggagggggcc ggagtattgg    180
gaccgggaga cacagaagta caagcgccag gcacaggctg accgagtgaa cctgcgaaa     240
ctgcgcggct gctacaacca gagcgaggcc ggttctcaca ccatccagag gatgtatggc    300
tgcgacctgg ggcccgacgg gcgcctcctc cgcgggtata accagttcgc ctacgacggc    360
aaggattaca tcgccctgaa cgaggacctg cgctcctgga ccgcggcgga cacggcggct    420
cagatctccc agcgcaagtt ggaggcgccc cgtgaggcgg agcagctgag agcctacctg    480
gagggcgagt gcgtggagtg gctccgcgga tacctggaga cgggaagga gacgctgcag    540
cgcgcggaac gcccaaagac acacgtgacc caccatcccg tctctgacca tgaggccacc    600
ctgaggtgct gggccctggg cttctaccct gcggagatca cactgacctg gcagcgggat    660
ggggaggacc aaactcagga caccgagctt gtggagacca ggccagcagg agatggaacc    720
ttccagaagt gggcagctgt ggtggtgcct tctggacaag aacagagata cacgtgccat    780
gtgcagcacg aggggctgca ggagccctgc accctgagat ggaagccg                   828
```

<210> SEQ ID NO 175
<211> LENGTH: 180
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 175

```
ggcagcggcg gcagcggggg ctccgccggc ggaggcctga cgacatctt cgaagcccag       60
aagatcgagt ggcacgaggg cggggagag aacctgtact ccagggcgg cagccaccac      120
catcaccacc atggcggcgg aagcggcggc gggtccggca gccaccatca ccatcaccat     180
```

<210> SEQ ID NO 176
<211> LENGTH: 60
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 176

Gly Ser Gly Gly Ser Gly Gly Ser Ala Gly Gly Gly Leu Asn Asp Ile
 1               5                  10                  15

Phe Glu Ala Gln Lys Ile Glu Trp His Glu Gly Gly Glu Asn Leu
                20                  25                  30

Tyr Phe Gln Gly Gly Ser His His His His His Gly Gly Gly Ser
            35                  40                  45

Gly Gly Gly Ser Gly Ser His His His His His
        50                  55                  60

<210> SEQ ID NO 177

```
<211> LENGTH: 78
<212> TYPE: DNA
<213> ORGANISM: Unknown
<220> FEATURE:
<223> OTHER INFORMATION: Description of Unknown: Signal sequence
      universal target sequence

<400> SEQUENCE: 177
atggcgacgg gttcaagaac ttccctactt cttgcatttg gcctgctttg tttgccgtgg    60
ttacaggagg gctcagca                                                  78

<210> SEQ ID NO 178
<211> LENGTH: 26
<212> TYPE: PRT
<213> ORGANISM: Unknown
<220> FEATURE:
<223> OTHER INFORMATION: Description of Unknown: Signal sequence
      universal target sequence

<400> SEQUENCE: 178

Met Ala Thr Gly Ser Arg Thr Ser Leu Leu Ala Phe Gly Leu Leu
1               5                   10                  15

Cys Leu Pro Trp Leu Gln Glu Gly Ser Ala
            20                  25

<210> SEQ ID NO 179
<211> LENGTH: 225
<212> TYPE: DNA
<213> ORGANISM: Bos taurus

<400> SEQUENCE: 179
tgtgccttct agttgccagc atctgttgt ttgcccctcc cccgtgcctt ccttgaccct     60
ggaaggtgcc actcccactg tcctttccta ataaaatgag gaaattgcat cgcattgtct   120
gagtaggtgt cattctattc tggggggtgg ggtggggcag acagcaagg gggaggattg    180 ggaagacaat agcaggcatg ctggggatgc ggtgggctct atggc                   225

<210> SEQ ID NO 180
<211> LENGTH: 131
<212> TYPE: DNA
<213> ORGANISM: Simian virus 40

<400> SEQUENCE: 180
acttgtttat tgcagcttat aatggttaca ataaagcaa tagcatcaca aatttcacaa     60
ataaagcatt ttttcactg cattctagtt gtggtttgtc caaactcatc aatgtatctt    120
atcatgtctg t                                                        131

<210> SEQ ID NO 181
<211> LENGTH: 479
<212> TYPE: DNA
<213> ORGANISM: Homo sapiens

<400> SEQUENCE: 181
acgggtggca tccctgtgac ccctccccag tgcctctcct ggccctggaa gttgccactc     60
cagtgcccac cagccttgtc ctaataaaat taagttgcat cattttgtct gactaggtgt   120
ccttctataa tattatgggg tgagggggg tggtatggag caaggggcaa gttgggaaga   180
caacctgtag ggcctgcggg gtctattggg aaccaagctg gagtgcagtg gcacaatctt   240
ggctcactgc aatctccgcc tcctgggttc aagcgattct cctgcctcag cctcccgagt   300
tgttgggatt ccaggcatgc atgaccaggc tcagctaatt tttgtttttt tggtagagac   360
```

```
ggggtttcac catattggcc aggctggtct ccaactccta atctcaggtg atctacccac    420
cttggcctcc caaattgctg ggattacagg cgtgaaccac tgctcccttc cctgtcctt     479
```

<210> SEQ ID NO 182
<211> LENGTH: 527
<212> TYPE: DNA
<213> ORGANISM: Unknown
<220> FEATURE:
<223> OTHER INFORMATION: Description of Unknown: rbGlob polyA sequence

<400> SEQUENCE: 182

```
ttcactcctc aggtgcaggc tgcctatcag aaggtggtgg ctggtgtggc caatgccctg    60
gctcacaaat accactgaga tcttttttcc tctgccaaaa attatgggga catcatgaag    120
ccccttgagc atctgacttc tggctaataa aggaaattta ttttcattgc aatagtgtgt    180
tggaattttt tgtgtctctc actcggaagg acatatggga gggcaaatca tttaaaacat    240
cagaatgagt atttggttta gagtttggca acatatgccc atatgctggc tgccatgaac    300
aaaggttggc tataaagagg tcatcagtat atgaaacagc ccctgctgtc cattccttat    360
tccatagaaa agccttgact tgaggttag atttttttta tatttgttt tgtgttattt     420 ttttctttaa catccctaaa attttcctta catgtttac tagccagatt tttcctcctc     480
tcctgactac tcccagtcat agctgtccct cttctcttat ggagatc                 527
```

<210> SEQ ID NO 183
<211> LENGTH: 6
<212> TYPE: PRT
<213> ORGANISM: Unknown
<220> FEATURE:
<223> OTHER INFORMATION: Description of Unknown: Thrombin cleavage site

<400> SEQUENCE: 183

Leu Val Pro Arg Gly Ser
1               5

<210> SEQ ID NO 184
<211> LENGTH: 18
<212> TYPE: DNA
<213> ORGANISM: Unknown
<220> FEATURE:
<223> OTHER INFORMATION: Description of Unknown: Thrombin cleavage site

<400> SEQUENCE: 184

```
ctggtgccgc gcggcagc                                                  18
```

<210> SEQ ID NO 185
<211> LENGTH: 4
<212> TYPE: PRT
<213> ORGANISM: Unknown
<220> FEATURE:
<223> OTHER INFORMATION: Description of Unknown: Factor Xa site

<400> SEQUENCE: 185

Ile Glu Gly Arg
1

<210> SEQ ID NO 186
<211> LENGTH: 12
<212> TYPE: DNA
<213> ORGANISM: Unknown
<220> FEATURE:
<223> OTHER INFORMATION: Description of Unknown: Factor Xa site

```
<400> SEQUENCE: 186
attgaaggcc gc                                                              12

<210> SEQ ID NO 187
<211> LENGTH: 8
<212> TYPE: PRT
<213> ORGANISM: Rhinovirus

<400> SEQUENCE: 187

Leu Glu Val Leu Phe Gln Gly Pro
1               5

<210> SEQ ID NO 188
<211> LENGTH: 24
<212> TYPE: DNA
<213> ORGANISM: Rhinovirus

<400> SEQUENCE: 188
ctggaagtgc tgtttcaggg cccg                                                 24

<210> SEQ ID NO 189
<211> LENGTH: 5
<212> TYPE: PRT
<213> ORGANISM: Unknown
<220> FEATURE:
<223> OTHER INFORMATION: Description of Unknown: Enterokinase site

<400> SEQUENCE: 189

Asp Asp Asp Asp Lys
1               5

<210> SEQ ID NO 190
<211> LENGTH: 15
<212> TYPE: DNA
<213> ORGANISM: Unknown
<220> FEATURE:
<223> OTHER INFORMATION: Description of Unknown: Enterokinase site

<400> SEQUENCE: 190
gatgatgatg ataaa                                                           15

<210> SEQ ID NO 191
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
gattacaagg atgacgacga taag                                                 24

<210> SEQ ID NO 192
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Asp Tyr Lys Asp Asp Asp Asp Lys
1               5

<210> SEQ ID NO 193
```

```
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
tacccatacg atgttccaga ttacgct                                          27

<210> SEQ ID NO 194
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Tyr Pro Tyr Asp Val Pro Asp Tyr Ala
1               5

<210> SEQ ID NO 195
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
gaacaaaaac ttatttctga agaagatctg                                       30

<210> SEQ ID NO 196
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Glu Gln Lys Leu Ile Ser Glu Glu Asp Leu
1               5                   10

<210> SEQ ID NO 197
<211> LENGTH: 549
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 197
cgcaagatcg tcgttgcagc catcgccgtt tccctgacca cggtctcgat tacggccagc      60
gcttcggcag acccctccaa ggactcgaag gcccaggtct cggccgccga ggccggcatc     120
accggcacct ggtacaacca gctcggctcg accttcatcg tgaccgcggg cgccgacggc     180
gccctgaccg gaacctacga gtcggccgtc ggcaacgccg agagccgcta cgtcctgacc     240
ggtcgttacg acagcgcccc ggccaccgac ggcagcggca ccgccctcgg ttggacggtg     300
gcctggaaga taactaccg caacgcccac tccgcgacca cgtggagcgg ccagtacgtc      360
ggcggcgccg aggcgaggat caacacccag tggctgctga cctccggcac caccgaggcc     420
aacgcctgga agtccacgct ggtcggccac gacaccttca ccaaggtgaa gccgtccgcc     480
```

```
gcctccatcg acgcggcgaa gaaggccggc gtcaacaacg gcaacccgct cgacgccgtt       540
cagcagtag                                                             549
```

<210> SEQ ID NO 198
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

```
Arg Lys Ile Val Val Ala Ala Ile Ala Val Ser Leu Thr Thr Val Ser
1               5                   10                  15

Ile Thr Ala Ser Ala Ser Ala Asp Pro Ser Lys Asp Ser Lys Ala Gln
            20                  25                  30

Val Ser Ala Ala Glu Ala Gly Ile Thr Gly Thr Trp Tyr Asn Gln Leu
        35                  40                  45

Gly Ser Thr Phe Ile Val Thr Ala Gly Ala Asp Gly Ala Leu Thr Gly
    50                  55                  60

Thr Tyr Glu Ser Ala Val Gly Asn Ala Glu Ser Arg Tyr Val Leu Thr
65                  70                  75                  80

Gly Arg Tyr Asp Ser Ala Pro Ala Thr Asp Gly Ser Gly Thr Ala Leu
                85                  90                  95

Gly Trp Thr Val Ala Trp Lys Asn Asn Tyr Arg Asn Ala His Ser Ala
            100                 105                 110

Thr Thr Trp Ser Gly Gln Tyr Val Gly Gly Ala Glu Ala Arg Ile Asn
        115                 120                 125

Thr Gln Trp Leu Leu Thr Ser Gly Thr Thr Glu Ala Asn Ala Trp Lys
    130                 135                 140

Ser Thr Leu Val Gly His Asp Thr Phe Thr Lys Val Lys Pro Ser Ala
145                 150                 155                 160

Ala Ser Ile Asp Ala Ala Lys Lys Ala Gly Val Asn Asn Gly Asn Pro
                165                 170                 175

Leu Asp Ala Val Gln Gln
            180
```

<210> SEQ ID NO 199
<211> LENGTH: 9
<212> TYPE: PRT
<213> ORGANISM: Unknown
<220> FEATURE:
<223> OTHER INFORMATION: Description of Unknown: Neo12 epitope sequence

<400> SEQUENCE: 199

```
Tyr Leu Tyr His Arg Val Asp Val Ile
1               5
```

<210> SEQ ID NO 200
<211> LENGTH: 10
<212> TYPE: PRT
<213> ORGANISM: Unknown
<220> FEATURE:
<223> OTHER INFORMATION: Description of Unknown: MART1 epitope sequence

<400> SEQUENCE: 200

```
Glu Leu Ala Gly Ile Gly Ile Leu Thr Val
1               5                   10
```

<210> SEQ ID NO 201

```
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25

<210> SEQ ID NO 202
<211> LENGTH: 1514
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 202
atggcgacgg gttcaagaac ttccctactt cttgcatttg gcctgctttg tttgccgtgg      60
ttacaggagg gctcagcatg actcgagata aatgtgaat aatgaggatg cggaggatcc     120
ggcggaggcg ggagcggagg cggagggtca tccagcgtac tccaaagatt caggtttact    180
cacgtcatcc agcagagaat ggaaagtcaa atttcctgaa ttgctatgtg tctgggtttc    240
atccatccga cattgaagtt gacttactga agaatggaga gagaattgaa aaagtggagc    300
attcagactt gtctttcagc aaggactggt ctttctatct cttgtactac actgaattca    360
cccccactga aaaagatgag tatgcctgcc gtgtgaacca tgtgactttg tcacagccca    420
agatagttaa gtgggatcga gacatggcg gaggcgggag cggcggaggc gggtccggcg    480
gaggcgggtc cggaggggga ggcagcggct ctcactccat gaggtatttc ttcacatccg    540
tgtcccggcc cggccgcggg gagccccgct tcatcgcagt gggctacgtg gacgacacgc    600
agttcgtgcg gttcgacagc gacgccgcga gccagaggat ggagccgcgg gcgccgtgga    660
tagagcagga gggtcccgag tattgggacg gggagacacg gaaagtgaag gcccactcac    720
agactcaccg agtggacctg gggaccctgc gcggctgcta caaccagagc gaggccggtt    780
ctcacaccgt ccagaggatg tatggctgcg acgtggggtc ggactggcgc ttcctccgcg    840 gtaccacca gtacgcctac gacggcaagg attacatcgc cctgaaagag gacctgcgct    900
cttggaccgc ggcggacatg gcagctcaga ccaccaagca aagtgggag gcggcccatg    960 tggcggagca gttgagagcc tacctggagg gcacgtgcgt ggagtggctc cgcagatacc   1020
tggagaacgg gaaggagacg ctgcagcgca cggacgcccc caaaacgcat atgactcacc   1080
acgctgtctc tgaccatgaa gccaccctga ggtgctgggc cctgagcttc tacccctgcgg   1140 agatcacact gacctggcag cgggatgggg aggaccagac ccaggacacg gagctcgtgg   1200
agaccaggcc tgcaggggat ggaaccttcc agaagtgggc ggctgtggtg gtgccttctg   1260
gacaggagca gagatacacc tgccatgtgc agcatgaggg tttgcccaag ccctcaccc    1320 tgagatggga gccggcagc ggcggcagcg ggggctccgc cggcggaggc ctgaacgaca    1380
tcttcgaagc ccagaagatc gagtggcacg agggcggggg agagaacctg tacttccagg    1440
gcggcagcca ccaccatcac caccatggcg gcggaagcgg cggcgggtcc ggcagccacc   1500
atcaccatca ccat                                                     1514
```

```
<210> SEQ ID NO 203
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Leu Glu Ile Lys Cys Glu
1               5

<210> SEQ ID NO 204
<211> LENGTH: 386
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Gly Cys Gly Gly Ser Gly Gly Gly Ser Gly Gly Gly Ser Ile
1               5                   10                  15

Gln Arg Thr Pro Lys Ile Gln Val Tyr Ser Arg His Pro Ala Glu Asn
            20                  25                  30

Gly Lys Ser Asn Phe Leu Asn Cys Tyr Val Ser Gly Phe His Pro Ser
        35                  40                  45

Asp Ile Glu Val Asp Leu Leu Lys Asn Gly Glu Arg Ile Glu Lys Val
    50                  55                  60

Glu His Ser Asp Leu Ser Phe Ser Lys Asp Trp Ser Phe Tyr Leu Leu
65                  70                  75                  80

Tyr Tyr Thr Glu Phe Thr Pro Thr Glu Lys Asp Glu Tyr Ala Cys Arg
                85                  90                  95

Val Asn His Val Thr Leu Ser Gln Pro Lys Ile Val Lys Trp Asp Arg
            100                 105                 110

Asp Met Arg Lys Val Lys Ala His Ser Gln Thr His Arg Val Asp Leu
        115                 120                 125

Gly Thr Leu Arg Gly Cys Tyr Asn Gln Ser Glu Ala Gly Ser His Thr
    130                 135                 140

Val Gln Arg Met Tyr Gly Cys Asp Val Gly Ser Asp Trp Arg Phe Leu
145                 150                 155                 160

Arg Gly Tyr His Gln Tyr Ala Tyr Asp Gly Lys Asp Tyr Ile Ala Leu
                165                 170                 175

Lys Glu Asp Leu Arg Ser Trp Thr Ala Ala Asp Met Ala Ala Gln Thr
            180                 185                 190

Thr Lys His Lys Trp Glu Ala Ala His Val Ala Glu Gln Leu Arg Ala
        195                 200                 205

Tyr Leu Glu Gly Thr Cys Val Glu Trp Leu Arg Arg Tyr Leu Glu Asn
    210                 215                 220

Gly Lys Glu Thr Leu Gln Arg Thr Asp Ala Pro Lys Thr His Met Thr
225                 230                 235                 240

His His Ala Val Ser Asp His Glu Ala Thr Leu Arg Cys Trp Ala Leu
                245                 250                 255

Ser Phe Tyr Pro Ala Glu Ile Thr Leu Thr Trp Gln Arg Asp Gly Glu
            260                 265                 270

Asp Gln Thr Gln Asp Thr Glu Leu Val Glu Thr Arg Pro Ala Gly Asp
        275                 280                 285

Gly Thr Phe Gln Lys Trp Ala Ala Val Val Val Pro Ser Gly Gln Glu
```

Gln Arg Tyr Thr Cys His Val Gln His Glu Gly Leu Pro Lys Pro Leu
                    305                 310                 315                 320

Thr Leu Arg Trp Glu Pro Gly Ser Gly Gly Ser Gly Gly Ser Ala Gly
                325                 330                 335

Gly Gly Leu Asn Asp Ile Phe Glu Ala Gln Lys Ile Glu Trp His Glu
            340                 345                 350

Gly Gly Gly Glu Asn Leu Tyr Phe Gln Gly Gly Ser His His His His
        355                 360                 365

His His Gly Gly Gly Ser Gly Gly Gly Ser His His His His
    370                 375                 380

His His
385

<210> SEQ ID NO 205
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Gly Gly Gly Ser
1

<210> SEQ ID NO 206
<211> LENGTH: 4
<212> TYPE: PRT
<213> ORGANISM: Unknown
<220> FEATURE:
<223> OTHER INFORMATION: Description of Unknown: Retention sequence

<400> SEQUENCE: 206

Lys Asp Glu Leu
1

<210> SEQ ID NO 207
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
ggagggctca gcatgactcg agataaaatg tgaataatga ggatgcggag gatccggcgg      60

<210> SEQ ID NO 208
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Gly Ser Gly Gly Ser Gly Gly Ala Gly Gly Leu Asn Asp Ile
1               5                   10                  15

Phe Glu Ala Gln Lys Ile Glu Trp His Glu Gly Gly Gly Glu Asn Leu
            20                  25                  30

Tyr Phe Gln Gly His His His His His His
        35                  40

<210> SEQ ID NO 209
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
tcagcatacc tgtaccaccg ggtggacgtg atcggatgcg gag                    43

<210> SEQ ID NO 210
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
gatccggcgg                                                         10

<210> SEQ ID NO 211
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
tgagccctcc                                                         10

<210> SEQ ID NO 212
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
gatcctccgc atccgatcac gtccacccgg tggtacaggt atgc                   44

<210> SEQ ID NO 213
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gly Gly Gly Leu Asn Asp Ile Phe Glu Ala Gln Lys Ile Glu Trp His
1               5                   10                  15

<210> SEQ ID NO 214
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, t, g, unknown or other

```
<220> FEATURE:
<221> NAME/KEY: misc_feature
<222> LOCATION: (1)..(3)
<223> OTHER INFORMATION: n is a, c, g, or t

<400> SEQUENCE: 214
nnngctcagc atacctgtac caccgggtgg acgtgatcgg aagcggagga tccggc      56

<210> SEQ ID NO 215
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: misc_feature
<222> LOCATION: (1)..(4)
<223> OTHER INFORMATION: n is a, c, g, or t

<400> SEQUENCE: 215
nnnngccggt acctccgctt cc                                           22

<210> SEQ ID NO 216
<211> LENGTH: 200
<212> TYPE: DNA
<213> ORGANISM: Unknown
<220> FEATURE:
<223> OTHER INFORMATION: Description of Unknown: MHC sequence

<400> SEQUENCE: 216
gtttaaactt aagcttgcgg ccgccatggc gacgggttca agaacttccc tacttcttgc   60
atttggcctg ctttgtttgc cgtggttaca ggagggctca gcatacctgt accaccgggt  120
ggacgtgatc ggatgcggag gatccggcgg aggcgggagc ggaggcggag ggtctatcca  180
gcgtactcca aagattcagg                                              200

<210> SEQ ID NO 217
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
tcagcatacc tgtaccaccg ggtggacgtg atcggatgcg gag                    43

<210> SEQ ID NO 218
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
gatcctccgc atccgatcac gtccacccgg tggtacaggt atgc                   44
```